United States Patent
Grammenos et al.

(10) Patent No.: US 10,696,634 B2
(45) Date of Patent: Jun. 30, 2020

(54) PYRIDINE COMPOUNDS AS FUNGICIDES

(71) Applicant: BASF SE, Ludwigshafen (DE)

(72) Inventors: Wassilios Grammenos, Ludwigshafen (DE); Christian Winter, Ludwigshafen (DE); Bernd Mueller, Frankenthal (DE); Antje Wolf, Ludwigshafen (DE); Ana Escribano Cuesta, Mannheim (DE); Erica Cambeis, Hessheim (DE); Jan Klaas Lohmann, Lambsheim (DE); Thomas Grote, Wachenheim (DE); Manuel Kretschmer, New York, NY (US); Nadine Riediger, Schifferstadt (DE); Ian Robert Craig, Ludwigshafen (DE); Christine Wiebe, Mannheim (DE); Violeta Terteryan-Seiser, Mannheim (DE); Andreas Koch, Birkenheide (DE); Marcus Fehr, Speyer (DE); Tobias Mentzel, Roemerberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/779,949

(22) PCT Filed: Nov. 24, 2016

(86) PCT No.: PCT/EP2016/078693
§ 371 (c)(1),
(2) Date: May 30, 2018

(87) PCT Pub. No.: WO2017/093120
PCT Pub. Date: Jun. 8, 2017

(65) Prior Publication Data
US 2018/0346423 A1    Dec. 6, 2018

(30) Foreign Application Priority Data

Dec. 1, 2015  (EP) .................................. 15197236

(51) Int. Cl.
| C07D 213/65 | (2006.01) |
| C07D 405/12 | (2006.01) |
| C07D 401/12 | (2006.01) |
| C07D 417/12 | (2006.01) |
| A01N 43/40  | (2006.01) |
| C07D 403/12 | (2006.01) |

(52) U.S. Cl.
CPC .......... *C07D 213/65* (2013.01); *A01N 43/40* (2013.01); *C07D 401/12* (2013.01); *C07D 403/12* (2013.01); *C07D 405/12* (2013.01); *C07D 417/12* (2013.01)

(58) Field of Classification Search
None
See application file for complete search history.

(56) References Cited

U.S. PATENT DOCUMENTS

| 8,772,200 B2 | 7/2014 | Shibayama et al. |
| 2018/0368403 A1* | 12/2018 | Grammenos ........ C07D 213/71 |

FOREIGN PATENT DOCUMENTS

| EP | 2522658 | 11/2012 |
| EP | 2762002 | 8/2014 |
| JP | 2010202530 | 9/2010 |
| JP | 2014166991 | 9/2014 |
| JP | 2014166991 A * | 9/2014 |
| WO | 2007117381 A2 | 10/2007 |
| WO | 2012037782 A1 | 3/2012 |
| WO | 2013007767 | 1/2013 |
| WO | 2011081174 | 5/2013 |
| WO | 2014082881 | 6/2014 |
| WO | 2015181035 | 12/2015 |
| WO | 2016156129 | 10/2016 |
| WO | 2017016915 | 2/2017 |
| WO | 2017060148 | 4/2017 |
| WO | 2017067784 | 4/2017 |
| WO | 2017093167 | 6/2017 |

OTHER PUBLICATIONS

Taygerly, et al., "Discovery of INT131: A selective PPARγ modulator that enhances insulin sensitivity", Bioorganic & Medicinal Chemistry, vol. 21, Issue 4, Feb. 15, 2013, pp. 979-992.
Betson et al., "Three Groups Good, Four Groups Bad? Atropisomerism in ortho-Substituted Diary! Ethers," Agnew. Chem. Int. Ed., vol. 45, (2006), pp. 5803-5807.
Search Report, issued in EP Application No. 15197236.1, dated Feb. 24, 2016.
International Search Report, issued in PCT/EP2016/078693, dated Jan. 9, 2017.
International Preliminary Report on Patentability, issued in PCT/EP2016/078693, dated Jun. 5, 2018.

* cited by examiner

*Primary Examiner* — Erin E Hirt
(74) *Attorney, Agent, or Firm* — Marshall, Gerstein & Borun LLP

(57) ABSTRACT

The present invention relates to compounds I

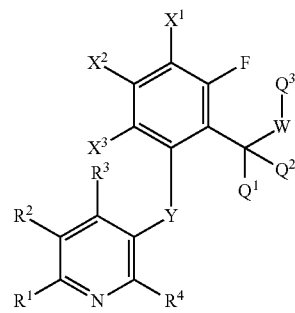

wherein the variables are defined as given in the description and claims. The invention further relates to uses, processes and intermediates for compounds I.

20 Claims, No Drawings

PYRIDINE COMPOUNDS AS FUNGICIDES

This application is a National Stage application of International Application No. PCT/EP2016/078693, filed Nov. 24, 2016. This application also claims priority under 35 U.S.C. § 119 to European Patent Application No. 15197236.1, filed Dec. 1, 2015.

The present invention relates to novel pyridine compounds and the N-oxides and the salts thereof, and to the use and methods for combating phytopathogenic fungi and to seeds coated with at least one such compound. The invention also relates to processes for preparing these compounds and to compositions comprising at least one compound I.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

Surprisingly, this objective is achieved by the use of the inventive pyridine compounds of formula I having favorable fungicidal activity against phytopathogenic fungi.

Accordingly, the present invention relates to the compounds of the formula I

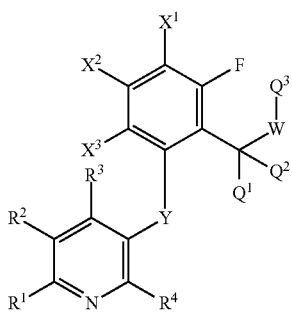

wherein
$R^1$ is $CH_3$;
$R^2$ is $CH_3$;
$R^3$ is selected from H, halogen, OH, CN, $NO_2$, SH, $NH_2$, $NH(C_1-C_4$-alkyl), $N(C_1-C_4$-alkyl$)_2$, $NH—SO_2—R^{31}$, $C_1-C_6$-alkyl, $C_2-C_6$-alkenyl, $C_2-C_6$-alkynyl, $C_1-C_6$-alkoxy, $C_3-C_6$-cycloalkyl, five- or six-membered heteroaryl and aryl; wherein the heteroaryl contains one, two or three heteroatoms selected from N, O and S; wherein
  $R^{31}$ is selected $C_1-C_4$-alkyl, $C_1-C_4$-halogenalkyl, aryl or heteroaryl that is unsubstituted or substituted by 1, 2, 3, 4 or 5 substituents $R^{311}$ independently selected from $C_1-C_4$-alkyl;
  and wherein the aliphatic moieties of $R^3$ are unsubstituted or substituted with identical or different groups $R^{3a}$ which independently of one another are selected from:
  $R^{3a}$ halogen, OH, CN, $C_1-C_6$-alkoxy, $C_3-C_6$-cycloalkyl, $C_3-C_6$-halogencycloalkyl, $C_1-C_4$-halogenalkoxy, $C_1-C_6$-alkylthio, phenyl and phenoxy, wherein the phenyl and phenoxy group is unsubstituted or carries 1, 2, 3, 4 or 5 substituents $R^{31a}$ selected from the group consisting of halogen, OH, $C_1-C_4$-alkyl, $C_1-C_4$-halogenalkyl, $C_1-C_4$-alkoxy and $C_1-C_4$-halogenalkoxy;
  and wherein the cycloalkyl, heteroaryl and aryl moieties of $R^3$ are unsubstituted or substituted with 1, 2, 3, 4, 5 or up to the maximum number of identical or different groups $R^{3b}$ which independently of one another are selected from:
  $R^{3b}$ halogen, OH, CN, $C_1-C_4$-alkyl, $C_1-C_4$-alkoxy, $C_1-C_4$-halogenalkyl, $C_3-C_6$-cycloalkyl, $C_3-C_6$-halogencycloalkyl, $C_1-C_4$-halogenalkoxy and $C_1-C_6$-alkylthio;
$R^4$ is selected from H, halogen, OH, CN, $NO_2$, SH, $NH_2$, $NH(C_1-C_4$-alkyl), $N(C_1-C_4$-alkyl$)_2$, $NH—SO_2—R^{41}$, $C_1-C_6$-alkyl, $C_2-C_6$-alkenyl, $C_2-C_6$-alkynyl, $C_1-C_6$-alkoxy, $C_3-C_6$-cycloalkyl, five- or six-membered heteroaryl and aryl; wherein the heteroaryl contains one, two or three heteroatoms selected from N, O and S; wherein
  $R^{41}$ is selected $C_1-C_4$-alkyl, $C_1-C_4$-halogenalkyl, aryl or heteroaryl that is unsubstituted or substituted by 1, 2, 3, 4 or 5 substituents $R^{411}$ independently selected from $C_1-C_4$-alkyl;
  and wherein the aliphatic moieties of $R^4$ are unsubstituted or substituted with identical or different groups $R^{4a}$ which independently of one another are selected from:
  $R^{4a}$ halogen, OH, CN, $C_1-C_6$-alkoxy, $C_3-C_6$-cycloalkyl, $C_3-C_6$-halogencycloalkyl, $C_1-C_4$-halogenalkoxy, $C_1-C_6$-alkylthio, phenyl and phenoxy, wherein the phenyl and phenoxy group is unsubstituted or carries 1, 2, 3, 4 or 5 substituents $R^{41a}$ selected from the group consisting of halogen, OH, $C_1-C_4$-alkyl, $C_1-C_4$-halogenalkyl, $C_1-C_4$-alkoxy and $C_1-C_4$-halogenalkoxy;
  and wherein the cycloalkyl, heteroaryl and aryl moieties of $R^4$ are unsubstituted or substituted with 1, 2, 3, 4, 5 or up to the maximum number of identical or different groups $R^{4b}$ which independently of one another are selected from:
  $R^{4b}$ halogen, OH, CN, $C_1-C_4$-alkyl, $C_1-C_4$-alkoxy, $C_1-C_4$-halogenalkyl, $C_3-C_6$-cycloalkyl, $C_3-C_6$-halogencycloalkyl, $C_1-C_4$-halogenalkoxy and $C_1-C_6$-alkylthio;
Y is O or S(O)n wherein
  n is 0, 1 or 2;
$Q^1$ is selected from $C_1-C_6$-alkyl, $C_2-C_6$-alkenyl, $C_2-C_6$-alkynyl, $C_3-C_6$-cycloalkyl, five- or six-membered heteroaryl and aryl; wherein the heteroaryl contains one, two or three heteroatoms selected from N, O and S;
  wherein the aliphatic moieties of $Q^1$ are unsubstituted or substituted with identical or different groups $Q^{1a}$ which independently of one another are selected from:
  $Q^{1a}$ halogen, OH, CN, $C_1-C_6$-alkoxy, $C_3-C_6$-cycloalkyl, $C_3-C_6$-halogencycloalkyl, $C_1-C_4$-halogenalkoxy, $C_1-C_6$-alkylthio, phenyl and phenoxy, wherein the phenyl and phenoxy group is unsubstituted or carries 1, 2, 3, 4 or 5 substituents $Q^{11a}$ selected from the group consisting of halogen, OH, $C_1-C_4$-alkyl, $C_1-C_4$-halogenalkyl, $C_1-C_4$-alkoxy and $C_1-C_4$-halogenalkoxy;
  wherein the cycloalkyl, heteroaryl and aryl moieties of $Q^1$ are unsubstituted or substituted with 1, 2, 3, 4, 5 or up to the maximum number of identical or different groups $Q^{1b}$ which independently of one another are selected from:
  $Q^{1b}$ halogen, OH, CN, $C_1-C_4$-alkyl, $C_1-C_4$-alkoxy, $C_1-C_4$-halogenalkyl, $C_3-C_6$-cycloalkyl, $C_3-C_6$-halogencycloalkyl, $C_1-C_4$-halogenalkoxy and $C_1-C_6$-alkylthio;
$Q^2$ is selected from H, $C_1-C_6$-alkyl, $C_2-C_6$-alkenyl, $C_2-C_6$-alkynyl, $C_3-C_6$-cycloalkyl, five- or six-membered heteroaryl and aryl; wherein the heteroaryl contains one, two or three heteroatoms selected from N, O and S;
  wherein the aliphatic moieties of $Q^2$ are unsubstituted or substituted with identical or different groups $Q^{2a}$ which independently of one another are selected from:
  $Q^{2a}$ halogen, OH, CN, $C_1-C_6$-alkoxy, $C_3-C_6$-cycloalkyl, $C_3-C_6$-halogencycloalkyl, $C_1-C_4$-halogenalkoxy, $C_1-C_6$-alkylthio, phenyl and phenoxy, wherein the phenyl and phenoxy group is unsubstituted or substituted with 1, 2, 3, 4 or 5 substituents $Q^{12}$ selected from the group consisting of halogen, OH, $C_1-C_4$-alkyl, $C_1-C_4$-halogenalkyl, $C_1-C_4$-alkoxy and $C_1-C_4$-halogenalkoxy;

wherein the cycloalkyl, heteroaryl and aryl moieties of $Q^2$ are unsubstituted or substituted with 1, 2, 3, 4, 5 or up to the maximum number of identical or different groups $Q^{2b}$ which independently of one another are selected from:

$Q^{2b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

$Q^1$ and $Q^2$ together with the carbon atoms to which they are bound form a three- to seven-membered saturated or partially unsaturated ring, wherein the ring may further contain 1, 2, 3 or 4 heteroatoms selected from N—$R^N$, O and S wherein $R^N$ is selected from H, $C_1$-$C_4$-alkyl and $SO_2R^Q$; wherein $R^Q$ is selected from $C_1$-$C_4$-alkyl, $C_1$-$C_4$-halogenalkyl, unsubstituted aryl or heteroaryl that is substituted by 1, 2, 3, 4 or 5 substituents $R^{Q1}$ independently selected from $C_1$-$C_4$-alkyl;

and wherein S may be in the form of its oxide SO or $SO_2$; and wherein in each case one or two $CH_2$ groups of the carbo- or heterocycle may be replaced by a group independently selected from C(=O) and C(=S);

and wherein the ring is unsubstituted or substituted with 1, 2, 3, 4, 5 or up to the maximum number of identical or different groups $R^{2R}$ which independently of one another are selected from:

$Q^{QR}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

$Q^3$ is selected from H, $C_1$-$C_6$-alkyl, $C_2$-$C_6$-alkenyl, $C_2$-$C_6$-alkynyl, $C_3$-$C_6$-cycloalkyl, five- or six-membered heteroaryl and aryl; wherein the heteroaryl contains one, two or three heteroatoms selected from N, O and S;

wherein the aliphatic moieties of $Q^3$ are unsubstituted or substituted with identical or different groups $Q^{3a}$ which independently of one another are selected from:

$Q^{3a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy and five- to ten-membered heterocycle, heteroaryl, heterocycloxy, heteryloxy; wherein the heterocycle or heteroaryl contains one, two or three heteroatoms selected from N, O and S; wherein the phenyl, phenoxy, heterocycle and heteroaryl groups are unsubstituted or substituted with 1, 2, 3, 4 or 5 substituents $Q^{13a}$ selected from the group consisting of halogen, OH, $C_1$-$C_4$-alkyl, $C_1$-$C_4$-halogenalkyl, $C_1$-$C_4$-alkoxy, $C_1$-$C_4$-halogenalkoxy, CR'=NOR''; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{113a}$ selected from the group consisting of halogen, OH, $C_1$-$C_4$-alkyl, $C_1$-$C_4$-halogenalkyl, $C_1$-$C_4$-alkoxy, CN, CR'=NOR'' and $C_1$-$C_4$-halogenalkoxy;

wherein the cycloalkyl, heteroaryl and aryl moieties of $Q^3$ are unsubstituted or substituted with 1, 2, 3, 4, 5 or up to the maximum number of identical or different groups $Q^{3b}$ which independently of one another are selected from:

$Q^{3b}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy and five- to ten-membered heterocycle, heteroaryl, heterocycloxy, heteryloxy; wherein the heterocycle or heteroaryl contains one, two or three heteroatoms selected from N, O and S; wherein the phenyl, phenoxy, heterocycle and heteroaryl groups are unsubstituted or substituted with 1, 2, 3, 4 or 5 substituents $Q^{13b}$ selected from the group consisting of halogen, OH, $C_1$-$C_4$-alkyl, $C_1$-$C_4$-halogenalkyl, $C_1$-$C_4$-alkoxy, $C_1$-$C_4$-halogenalkoxy, CR'=NOR''; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{113b}$ selected from the group consisting of halogen, OH, $C_1$-$C_4$-alkyl, $C_1$-$C_4$-halogenalkyl, $C_1$-$C_4$-alkoxy, CN, CR'=NOR'' and $C_1$-$C_4$-halogenalkoxy;

and wherein R' and R'' are independently unsubstituted or substituted by R''' which is independently selected from halogen, OH, CN, $NO_2$, SH, $NH_2$, $NH(C_1$-$C_4$-alkyl), $N(C_1$-$C_4$-alkyl$)_2$, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-cycloalkyl, $C_3$-$C_6$-halogencycloalkyl and phenyl;

W is O or S;

$X^1$ is selected from H, halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

$X^2$ is selected from H, halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

$X^3$ is selected from H, halogen, OH, CN, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

with the proviso that if $X^1$, $X^2$ and $X^3$ is H $Q^3$ is not H and $CH_3$ and the N-oxides and the agriculturally acceptable salts thereof.

Compounds of type I can be prepared by reacting compounds of type II with a suitable electrophile $Q^3$-LG in an organic solvent and in the presence of a base at temperatures between −20 and 100° C., most preferably between 0 and 40° C. LG represents a suitable leaving group, preferably a halogen or a sulfonate.

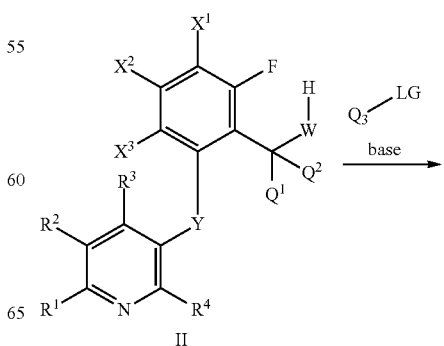

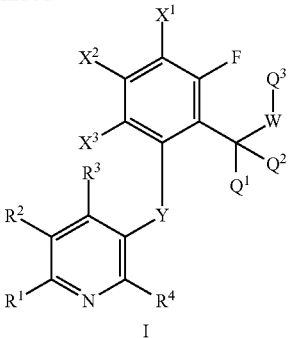
I

Alternatively compounds I can be accessed by reating compounds of type II* with reagents Q₃-W—H in the presence of a base using conditions already described for the reaction of compounds II with reagents of type Q₃-LG yielding compounds I.

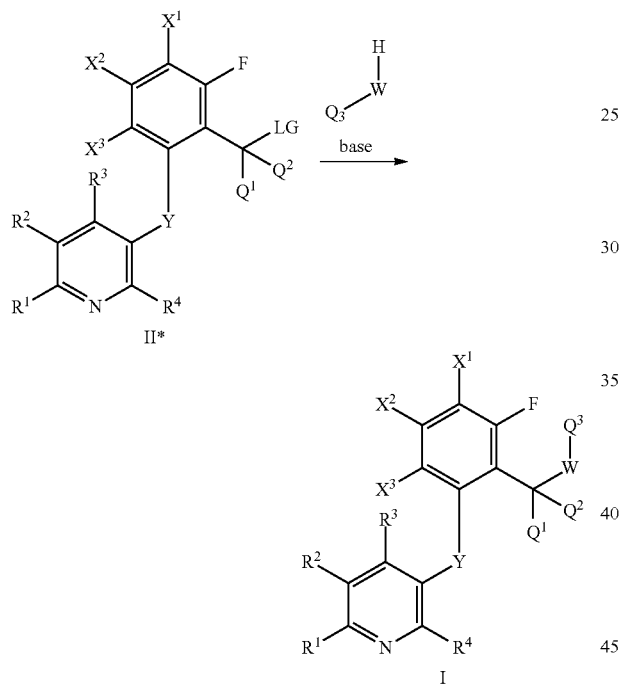

Compounds of type II may be accessed as described for example in JP2010/202530 or Angewandte Chemie, International Edition, 45(35), 5803-5807; 2006 and as outlined below. Compounds of type III (where Hal is a halogen, most preferably Br or I) can be metallated by treatment with an appropriate organometallic reagent [M] in an ethereal solvent at low temperatures. Preferably, an organolithium or organomagnesium compound is used and the reaction is best performed in THF and between −78° C. and 0° C. The intermediary organometallic species can be trapped with (thio)carbonyl compounds of type IV to furnish compounds of type II after aqueous workup.

To access compounds of type IIIa, it may be preferred to react compounds V in a nucleophilic aromatic substitution with compounds of type VIa which are either commercially available or can be prepared following procedures that are obvious to a person skilled in the art. LG represents a suitable leaving group, with special preference given to fluoride (for precedents see e.g. WO2007/117381, WO2012/037782, or Bioorganic & Medicinal Chemistry, 21(4), 979-992; 2013). The reaction is best carried out at temperatures between 0 and 100° C., preferably between room temperature and 80° C. Furthermore, it may be appropriate to perform the reaction in an organic solvent, preferably, but not limited to DMF or NMP and in the presence of a base, preferably, but not limited to potassium carbonate or sodium hydride.

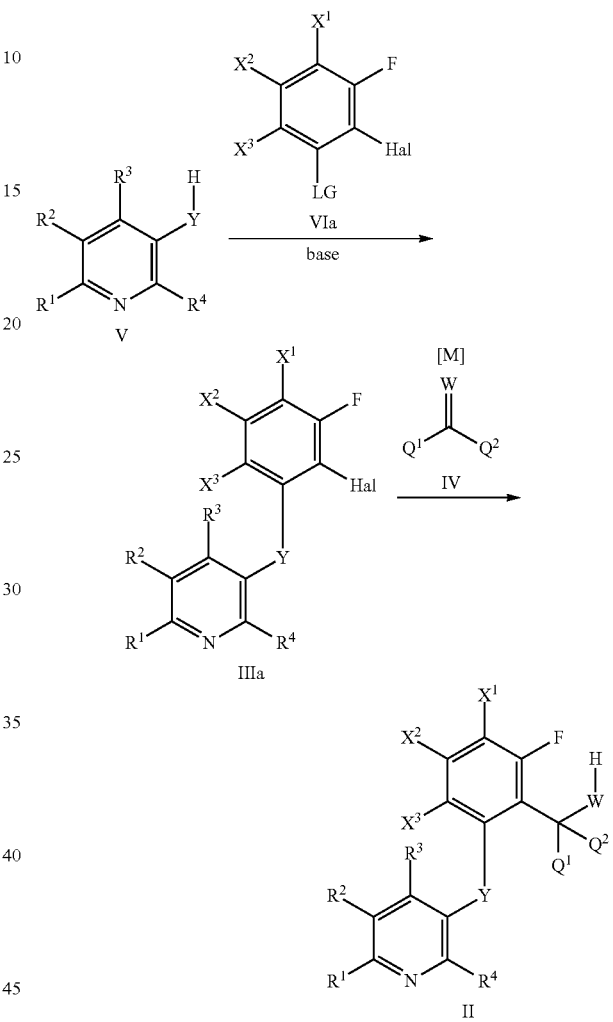

Alternatively compounds IIIa can be synthesized reacting compounds V* and VIa* applying conditions already described for the reaction of compounds V with compounds VIa

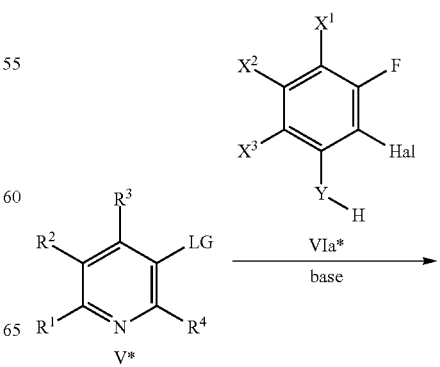

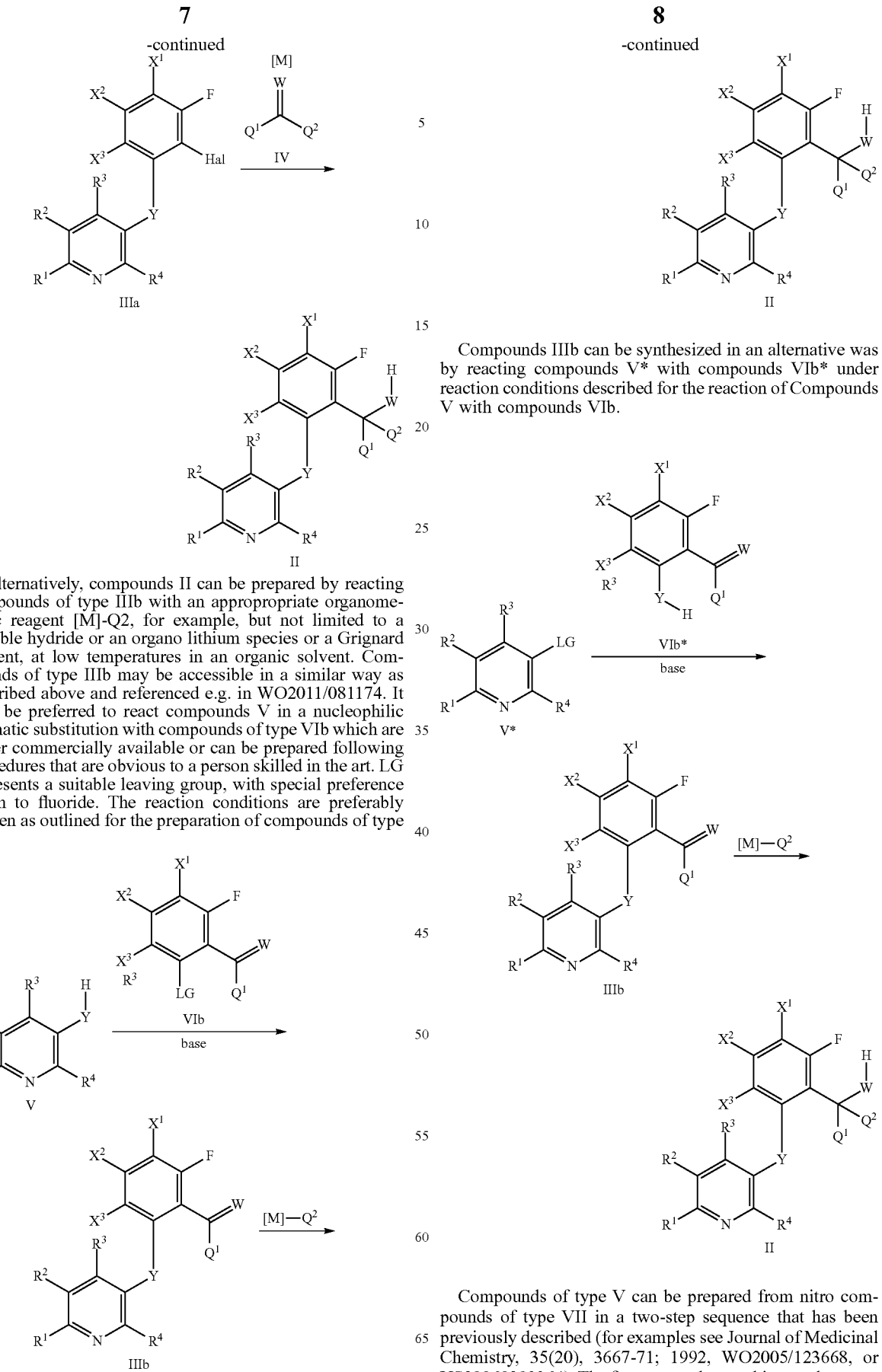

Alternatively, compounds II can be prepared by reacting compounds of type IIIb with an appropropriate organometallic reagent [M]-Q2, for example, but not limited to a suitable hydride or an organo lithium species or a Grignard reagent, at low temperatures in an organic solvent. Compounds of type IIIb may be accessible in a similar way as described above and referenced e.g. in WO2011/081174. It may be preferred to react compounds V in a nucleophilic aromatic substitution with compounds of type VIb which are either commercially available or can be prepared following procedures that are obvious to a person skilled in the art. LG represents a suitable leaving group, with special preference given to fluoride. The reaction conditions are preferably chosen as outlined for the preparation of compounds of type IIIa.

Compounds IIIb can be synthesized in an alternative was by reacting compounds V* with compounds VIb* under reaction conditions described for the reaction of Compounds V with compounds VIb.

Compounds of type V can be prepared from nitro compounds of type VII in a two-step sequence that has been previously described (for examples see Journal of Medicinal Chemistry, 35(20), 3667-71; 1992, WO2005/123668, or US20060293364). The first step seeks to achieve a chemoselective reduction of the nitro group to its amino congener by employing a suitable reducing agent, such as iron, zinc, or hydrogen in the presence of a transition metal catalyst such as palladium. Preferably, the reduction is performed in an organic solvent, more preferably in an alcoholic solvent, if appropriate at elevated temperatures and/or increased pressure. The respective amino compounds can be transformed into compounds of type V through a Sandmeyer reaction by reacting them first with a suitable nitrite source at low temperatures, preferably but not limited to sodium nitrite or t-BuONO. For the preparation of compounds in which Y is oxygen, the intermediary diazonium salt may be treated with a suitable acid, for example but not limited to HCl or $HBF_4$. It may be appropriate to increase the temperature upon addition of the acid. Compounds in which Y is S can be accessed by reacting said diazonium salt with a suitable sulfur source, preferably a alkali xanthate such as potassium xanthate, followed by base-mediated cleavage of the thioester. A precedent can be found for example in Journal of Medicinal Chemistry, 36(8), 953-66; 1993.

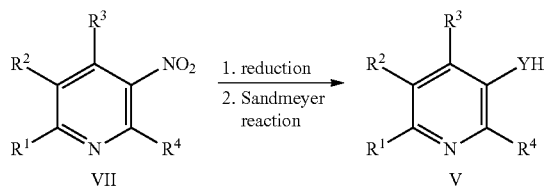

A person skilled in the art will realize that compounds of type VII are either commercially available or be able to prepare said compounds following standard procedures.

The N-oxides may be prepared from the inventive compounds according to conventional oxidation methods, e.g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (e.g. under the action of light, acids or bases). Such conversions may also take place after use, e.g. in the treatment of plants in the treated plant, or in the harmful fungus to be controlled.

In the following, the intermediate compounds are further described. A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

In the definitions of the variables given above, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methyl pentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl (n-propyl), 1-methylethyl (iso-propoyl), butyl, 1-methylpropyl (sec.-butyl), 2-methylpropyl (iso-butyl), 1,1-dimethylethyl (tert.-butyl).

The term "$C_1$-$C_6$-halogenalkyl" refers to an alkyl group having 1 or 6 carbon atoms as defined above, wherein some or all of the hydrogen atoms in these groups may be replaced by halogen atoms as mentioned above. Examples are "$C_1$-$C_2$-halogenalkyl" groups such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_1$-$C_6$-hydroxyalkyl" refers to an alkyl group having 1 or 6 carbon atoms as defined above, wherein some or all of the hydrogen atoms in these groups may be replaced by OH groups.

The term "$C_1$-$C_4$-alkoxy-$C_1$-$C_4$-alkyl" refers to alkyl having 1 to 4 carbon atoms (as defined above), wherein one hydrogen atom of the alkyl radical is replaced by a $C_1$-$C_4$-alkoxy group (as defined above). Likewise, the term "$C_1$-$C_6$-alkoxy-$C_1$-$C_4$-alkyl" refers to alkyl having 1 to 4 carbon atoms (as defined above), wherein one hydrogen atom of the alkyl radical is replaced by a $C_1$-$C_6$-alkoxy group (as defined above).

The term "$C_2$-$C_6$-alkenyl" refers to a straight-chain or branched unsaturated hydrocarbon radical having 2 to 6 carbon atoms and a double bond in any position. Examples are "$C_2$-$C_4$-alkenyl" groups, such as ethenyl, 1-propenyl, 2-propenyl (allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl.

The term "$C_2$-$C_6$-alkynyl" refers to a straight-chain or branched unsaturated hydrocarbon radical having 2 to 6 carbon atoms and containing at least one triple bond. Examples are "$C_2$-$C_4$-alkynyl" groups, such as ethynyl, prop-1-ynyl, prop-2-ynyl (propargyl), but-1-ynyl, but-2-ynyl, but-3-ynyl, 1-methyl-prop-2-ynyl.

The term "$C_1$-$C_6$-alkoxy" refers to a straight-chain or branched alkyl group having 1 to 6 carbon atoms which is bonded via an oxygen, at any position in the alkyl group. Examples are "$C_1$-$C_4$-alkoxy" groups, such as methoxy, ethoxy, n-propoxy, 1-methylethoxy, butoxy, 1-methyl¬propoxy, 2-methylpropoxy or 1,1-dimethylethoxy.

The term "$C_1$-$C_6$-halogenalkoxy" refers to a $C_1$-$C_6$-alkoxy radical as defined above, wherein some or all of the hydrogen atoms in these groups may be replaced by halogen atoms as mentioned above. Examples are "$C_1$-$C_4$-halogenalkoxy" groups, such as $OCH_2F$, $OCHF_2$, $OCF_3$, $OCH_2Cl$, $OCHCl_2$, $OCCl_3$ chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-tri-fluoroethoxy, 2-chloro-2-fluoroethoxy, 2-chloro-2,2-difluoroethoxy, 2,2-dichloro-2-fluoroethoxy, 2,2,2-trichloro‑ethoxy, $OC_2F_5$, 2-fluoropropoxy, 3-fluoropropoxy, 2,2-difluoropropoxy, 2,3-difluoro‑propoxy, 2 chloropropoxy, 3-chloropropoxy, 2,3-dichloropropoxy, 2-bromo‑propoxy, 3 bromopropoxy, 3,3,3-trifluoropropoxy, 3,3,3-trichloropropoxy, $OCH_2—C_2F_5$, $OCF_2—C_2F_5$, 1-fluoromethyl-2-fluoroethoxy, 1-chloromethyl-2-chloroethoxy, 1-bromomethyl-2-bromo‑ethoxy, 4-fluorobutoxy, 4-chlorobutoxy, 4-bromobutoxy or nonafluorobutoxy.

The term "$C_2$-$C_6$-alkenyloxy" refers to a straight-chain or branched alkenyl group having 2 to 6 carbon atoms which is bonded via an oxygen, at any position in the alkenyl group. Examples are "$C_2$-$C_4$-alkenyloxy" groups.

The term "$C_2$-$C_6$-alkynyloxy" refers to a straight-chain or branched alkynyl group having 2 to 6 carbon atoms which is bonded via an oxygen, at any position in the alkynyl group. Examples are "$C_2$-$C_4$-alkynyloxy" groups.

The term "$C_3$-$C_6$-cycloalkyl" refers to monocyclic saturated hydrocarbon radicals having 3 to 6 carbon ring members, such as cyclopropyl, cyclobutyl, cyclopentyl, cyclohexyl. Accordingly, a saturated three-, four-, five-, six-, seven-, eight-, nine or ten-membered carbocyclyl or carbocycle is a "$C_3$-$C_{10}$-cycloalkyl".

The term "$C_3$-$C_6$-cycloalkenyl" refers to a monocyclic partially unsaturated 3-, 4-5- or 6-membered carbocycle having 3 to 6 carbon ring members and at least one double bond, such as cyclopentenyl, cyclopentadienyl, cyclohexadienyl. Accordingly, a partially unsaturated three-, four-, five-, six-, seven-, eight-, nine or ten-membered carbocyclyl or carbocycle is a "$C_3$-$C_{10}$-cycloalkenyl".

The term "$C_3$-$C_6$-cycloalkynyl" refers to a monocyclic partially unsaturated 3-, 4-5- or 6-membered carbocycle having 3 to 6 carbon ring members and at least one triple bond.

The term "$C_1$-$C_6$-alkylthio" as used herein refers to straight-chain or branched alkyl groups having 1 to 6 carbon atoms (as defined above) bonded via a sulfur atom. Accordingly, the term "$C_1$-$C_6$-halogenalkylthio" as used herein refers to straight-chain or branched halogenalkyl group having 1 to 6 carbon atoms (as defined above) bonded through a sulfur atom, at any position in the halogenalkyl group.

The term "C(=O)—$C_1$-$C_6$-alkyl" refers to a radical which is attached through the carbon atom of the group C(=O) as indicated by the number valence of the carbon atom. The number of valence of carbon is 4, that of nitrogen is 3. Likewise the following terms are to be construed: NH($C_1$-$C_4$-alkyl), N($C_1$-$C_4$-alkyl)$_2$, NH($C_3$-$C_6$-cycloalkyl), N($C_3$-$C_6$-cycloalkyl)$_2$, C(=O)—NH($C_1$-$C_6$-alkyl), C(=O)—N($C_1$-$C_6$-alkyl)$_2$.

The term "saturated or partially unsaturated three-, four-, five-, six-, seven-, eight-, nine or ten-membered heterocyclyl or heterocycle, wherein the heterocyclyl or heterocycle contains 1, 2, 3 or 4 heteroatoms selected from N, O and S" is to be understood as meaning both saturated and partially unsaturated heterocycles, wherein the ring member atoms of the heterocycle include besides carbon atoms 1, 2, 3 or 4 heteroatoms independently selected from the group of O, N and S. For example:

a 3- or 4-membered saturated heterocycle which contains 1 or 2 heteroatoms from the group consisting of O, N and S as ring members such as oxirane, aziridine, thiirane, oxetane, azetidine, thiethane, [1,2]dioxetane, [1,2]dithietane, [1,2]diazetidine; and a 5- or 6-membered saturated or partially unsaturated heterocycle which contains 1, 2 or 3 heteroatoms from the group consisting of O, N and S as ring members such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl and also the corresponding-ylidene radicals; and a 7-membered saturated or partially unsaturated heterocycle such as tetra- and hexahydroazepinyl, such as 2,3,4,5-tetrahydro[1H]azepin-1-,-2-,-3-,-4-,-5-,-6- or -7-yl, 3,4,5,6-tetra-hydro[2H]azepin-2-,-3-,-4-,-5-,-6- or -7-yl, 2,3,4,7-tetrahydro[1H]azepin-1-,-2-,-3-,-4-,-5-,-6- or -7-yl, 2,3,6,7-tetrahydro[1H]azepin-1-,-2-,-3-,-4-,-5-,-6- or -7-yl, hexahydroazepin-1-,-2-,-3- or -4-yl, tetra- and hexahydrooxepinyl such as 2,3,4,5-tetrahydro[1H]oxepin-2-,-3-,-4-,-5-,-6- or -7-yl, 2,3,4,7-tetrahydro[1H]oxepin-2-,-3-,-4-,-5-,-6- or -7-yl, 2,3,6,7-tetrahydro[1H]oxepin-2-, -3-,-4-,-5-,-6- or -7-yl, hexahydroazepin-1-,-2-,-3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl and the corresponding -ylidene radicals.

The term "5- or 6-membered heteroaryl" refers to aromatic ring systems incuding besides carbon atoms, 1, 2, 3 or 4 heteroatoms independently selected from the group consisting of N, O and S, for example, a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol- 5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl; or a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

Agriculturally acceptable salts of the inventive compounds encompass especially the salts of those cations or the acid addition salts of those acids whose cations and anions, respectively, have no adverse effect on the fungicidal action of said compounds. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl) sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting such inventive compound with an acid of the corresponding anion, preferably of hydrochloric acid, hydrobromic acid, sulfuric acid, phosphoric acid or nitric acid.

The inventive compounds can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In the following, particular embodiments of the inventive compounds are described. Therein, specific meanings of the respective substituents are further detailed, wherein the meanings are in each case on their own but also in any combination with one another, particular embodiments of the present invention.

Furthermore, in respect of the variables, generally, the embodiments of the compounds I also apply to the intermediates.

$R^1$ according to the invention is $CH_3$.

$R^2$ according to the invention is $CH_3$.

$R^3$ according to the invention is in each case independently selected from H, halogen, OH, CN, $NO_2$, $SR^{31}$, $NH_2$, $NH(C_1$-$C_4$-alkyl), $N(C_1$-$C_4$-alkyl)$_2$, $NH$—$SO_2$—$R^{31}$, $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, five- or six-membered heteroaryl and aryl; wherein the heteroaryl contains one, two or three heteroatoms selected from N, O and S; wherein $R^{31}$ is selected from $C_1$-$C_4$-alkyl, $C_1$-$C_4$-halogenalkyl, aryl or heteroaryl that is unsubstituted or substituted by 1, 2, 3, 4 or 5 substituents $R^{311}$ independently selected from $C_1$-$C_4$-alkyl; and wherein the aliphatic moieties of $R^3$ are unsubstituted or substituted with identical or different groups $R^{3a}$ which independently of one another are selected from:

$R^{3a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl and phenoxy, wherein the phenyl and phenoxy group is unsubstituted or carries 1, 2, 3, 4 or 5 substituents $R^{31a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein the cycloalkyl, heteroaryl and aryl moieties of $R^3$ are unsubstituted or substituted with 1, 2, 3, 4, 5 or up to the maximum number of identical or different groups $R^{3b}$ which independently of one another are selected from:

$R^{3b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one specific embodiment, $R^3$ is H.

According to one specific embodiment, $R^3$ is halogen, in particular Br, F or Cl, more specifically F or Cl.

According to a further specific embodiment, $R^3$ is CN.

According to a further specific embodiment $R^3$ is $NH_2$, $NH(C_1$-$C_4$-alkyl), $N(C_1$-$C_4$-alkyl)$_2$ or $NH$—$SO_2$—$R^{31}$, wherein $R^{31}$ is $C_1$-$C_4$-alkyl, $C_1$-$C_4$-halogenalkyl, unsubstituted aryl or aryl that is substituted by one, two, three, four or five substituents $R^{311}$ independently selected from $C_1$-$C_4$-alkyl.

According to a further specific embodiment, $R^3$ is $C_1$-$C_6$-alkyl, in particular $C_1$-$C_4$-alkyl, such as $CH_3$.

According to a further specific embodiment, $R^3$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to still a further embodiment, $R^3$ is $C_2$-$C_6$-alkenyl or $C_2$-$C_6$-halogenalkenyl, in particular $C_2$-$C_4$-alkenyl or $C_2$-$C_4$-halogenalkenyl, such as CH=$CH_2$.

According to still a further embodiment, $R^3$ is $C_2$-$C_6$-alkynyl or $C_2$-$C_6$-halogenalkynyl, in particular $C_2$-$C_4$-alkynyl or $C_2$-$C_4$-halogenalkynyl, such as C≡CH.

According to a further specific embodiment, $R^3$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^3$ is $C_1$-$C_6$-halogenalkoxy, in particular $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment $R^3$ is $C_3$-$C_6$-cycloalkyl, in particular cyclopropyl.

In a further specific embodiment, $R^3$ is $C_3$-$C_6$-cycloalkyl, for example cyclopropyl, substituted by one, two, three or up to the maximum possible number of identical or different groups $R^{1b}$ as defined and preferably herein.

According to a specific embodiment $R^3$ is $C_3$-$C_6$-halogencycloalkyl. In a special embodiment $R^1$ is fully or partially halogenated cyclopropyl.

According to still a further specific embodiment, $R^3$ is unsubstituted aryl or aryl that is substituted by one, two, three or four $R^{3b}$, as defined herein. In particular, $R^3$ is unsubstituted phenyl or phenyl that is substituted by one, two, three or four $R^{3b}$, as defined herein.

According to still a further specific embodiment, $R^3$ is unsubstituted 5- or 6-membered heteroaryl. According to still a further embodiment, $R^3$ is 5- or 6-membered heteroaryl that is substituted by one, two or three $R^{3b}$, as defined herein.

According to one further embodiment $R^3$ is in each case independently selected from H, halogen, OH, CN, $NO_2$, $SR^{31}$, $NH_2$, $NH(C_1$-$C_4$-alkyl), $N(C_1$-$C_4$-alkyl)$_2$, $NH$—$SO_2$—$R^{31}$, $C_1$-$C_6$-alkyl, $C_2$-$C_6$-alkenyl, $C_2$-$C_6$-alkynyl, $C_1$-$C_6$-alkoxy and $C_3$-$C_6$-cycloalkyl; wherein the aliphatic moieties of $R^{3a}$ are not further substituted or carry one, two, three, four or five identical or different groups $R^{3a}$ as defined below and wherein the cycloalkyl moieties of $R^3$ are not further substituted or carry one, two, three, four or five identical or different groups $R^{3b}$ as defined below.

According to a further embodiment, $R^3$ is independently selected from H, halogen, OH, $C_1$-$C_6$-alkyl, $C_1$-$C_6$-halogenalkyl, $C_1$-$C_6$-alkoxy and $C_1$-$C_6$-halogenalkoxy, in particular independently selected from F, Cl, Br, CN, OH, $C_1$-$C_4$-alkyl, $C_1$-$C_4$-halogenalkyl, $C_1$-$C_4$-alkoxy and $C_1$-$C_4$-halogenalkoxy.

$R^{3a}$ are the possible substituents for the aliphatic moieties of $R^3$.

$R^{3a}$ according to the invention is independently selected from halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio and phenoxy, wherein the phenyl group is unsubstituted or carries one, two, three, four or five substituents $R^{31a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

According to one embodiment $R^{3a}$ is independently selected from halogen, OH, CN, $C_1$-$C_2$-alkoxy, $C_3$-$C_6$-cycloalkyl, $C_3$-$C_6$-halogencycloalkyl and $C_1$-$C_2$-halogenalkoxy. Specifically, $R^{3a}$ is independently selected from F, Cl, OH, CN, $C_1$-$C_2$-alkoxy, cyclopropyl, 1-F-cyclopropyl, 1-Cl-cyclopropyl and $C_1$-$C_2$-halogenalkoxy.

According to one particular embodiment $R^{3a}$ is independently selected from halogen, such as F, Cl, Br and I, more specifically F, Cl and Br.

According to a further embodiment, $R^{3a}$ is independently selected from OH, $C_3$-$C_6$-cycloalkyl, $C_3$-$C_6$-halogencycloalkyl and $C_1$-$C_2$-halogenalkoxy. Specifically, $R^{3a}$ is independently selected from OH, cyclopropyl and $C_1$-$C_2$-halogenalkoxy.

$R^{3b}$ are the possible substituents for the cycloalkyl, heteroaryl and aryl moieties of $R^3$.

$R^{3b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy.

According to one embodiment thereof $R^{3b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $R^{3b}$ is independently selected from F, Cl, OH, CN, $CH_3$, $OCH_3$, cyclopropyl, 1-F-cyclopropyl, 1-Cl-cyclopropyl and halogenmethoxy.

According to a further embodiment thereof $R^{3b}$ is independently selected from $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $R^{3b}$ is independently selected from OH, $CH_3$, $OCH_3$, cyclopropyl, 1-F-cyclopropyl, 1-Cl-cyclopropyl and halogenmethoxy, more specifically independently selected from OH, $CH_3$, $OCH_3$, cyclopropyl, 1-F-cyclopropyl, 1-Cl-cyclopropyl and $OCHF_2$.

$R^4$ according to the invention is in each case independently selected from H, halogen, OH, CN, $NO_2$, $SR^{41}$, $NH_2$, $NH(C_1$-$C_4$-alkyl), $N(C_1$-$C_4$-alkyl)$_2$, $NH$—$SO_2$—$R^{41}$, $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, five- or six-membered heteroaryl and aryl; wherein the heteroaryl contains one, two or three heteroatoms selected from N, O and S; wherein $R^{41}$ is selected from $C_1$-$C_4$-alkyl, $C_1$-$C_4$-halogenalkyl, aryl or heteroaryl that is unsubstituted or substituted by 1, 2, 3, 4 or 5 substituents $R^{411}$ independently selected from $C_1$-$C_4$-alkyl; and wherein the aliphatic moieties of $R^4$ are unsubstituted or substituted with identical or different groups $R^{4a}$ which independently of one another are selected from:

$R^{4a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl and phenoxy, wherein the phenyl and phenoxy group is unsubstituted or carries 1, 2, 3, 4 or 5 substituents $R^{41a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein the cycloalkyl, heteroaryl and aryl moieties of $R^4$ are unsubstituted or substituted with 1, 2, 3, 4, 5 or up to the maximum number of identical or different groups $R^{4b}$ which independently of one another are selected from:

$R^{4b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one specific embodiment, $R^4$ is H.

According to one specific embodiment, $R^4$ is halogen, in particular Br, F or Cl, more specifically F or Cl.

According to a further specific embodiment, $R^4$ is CN.

According to a further specific embodiment $R^4$ is $NH_2$, $NH(C_1$-$C_4$-alkyl), $N(C_1$-$C_4$-alkyl)$_2$ or $NH$—$O_2$—$R^{41}$, wherein $R^{41}$ is $C_1$-$C_4$-alkyl, $C_1$-$C_4$-halogenalkyl, unsubstituted aryl or aryl that is substituted by one, two, three, four or five substituents $R^{411}$ independently selected from $C_1$-$C_4$-alkyl.

According to a further specific embodiment, $R^4$ is $C_1$-$C_6$-alkyl, in particular $C_1$-$C_4$-alkyl, such as $CH_3$.

According to a further specific embodiment, $R^4$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to still a further embodiment, $R^4$ is $C_2$-$C_6$-alkenyl or $C_2$-$C_6$-halogenalkenyl, in particular $C_2$-$C_4$-alkenyl or $C_2$-$C_4$-halogenalkenyl, such as $CH=CH_2$.

According to still a further embodiment, $R^4$ is $C_2$-$C_6$-alkynyl or $C_2$-$C_6$-halogenalkynyl, in particular $C_2$-$C_4$-alkynyl or $C_2$-$C_4$-halogenalkynyl, such as $C\equiv CH$.

According to a further specific embodiment, $R^4$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $R^4$ is $C_1$-$C_6$-halogenalkoxy, in particular $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment $R^4$ is $C_3$-$C_6$-cycloalkyl, in particular cyclopropyl.

In a further specific embodiment, $R^4$ is $C_3$-$C_6$-cycloalkyl, for example cyclopropyl, substituted by one, two, three or up to the maximum possible number of identical or different groups $R^{1b}$ as defined and preferably herein.

According to a specific embodiment $R^4$ is $C_3$-$C_6$-halogencycloalkyl. In a special embodiment $R^1$ is fully or partially halogenated cyclopropyl.

According to still a further specific embodiment, $R^4$ is unsubstituted aryl or aryl that is substituted by one, two, three or four $R^{4b}$, as defined herein. In particular, $R^4$ is unsubstituted phenyl or phenyl that is substituted by one, two, three or four $R^{4b}$, as defined herein.

According to still a further specific embodiment, $R^4$ is unsubstituted 5- or 6-membered heteroaryl. According to still a further embodiment, $R^4$ is 5- or 6-membered heteroaryl that is substituted by one, two or three $R^{4b}$, as defined herein.

According to one further embodiment $R^4$ is in each case independently selected from H, halogen, OH, CN, $NO_2$, $SR^{41}$ $NH_2$, $NH(C_1-C_4$-alkyl), $N(C_1-C_4$-alkyl$)_2$, $NH-SO_2-R^{41}$, $C_1-C_6$-alkyl, $C_2-C_6$-alkenyl, $C_2-C_6$-alkynyl, $C_1-C_6$-alkoxy and $C_3-C_6$-cycloalkyl; wherein the aliphatic moieties of $R^4$ are not further substituted or carry one, two, three, four or five identical or different groups $R^{4a}$ as defined below and wherein the cycloalkyl moieties of $R^4$ are not further substituted or carry one, two, three, four or five identical or different groups $R^{4b}$ as defined below.

According to a further embodiment, $R^4$ is independently selected from H, halogen, OH, $C_1-C_6$-alkyl, $C_1-C_6$-halogenalkyl, $C_1-C_6$-alkoxy and $C_1-C_6$-halogenalkoxy, in particular independently selected from F, Cl, Br, CN, OH, $C_1-C_4$-alkyl, $C_1-C_4$-halogenalkyl, $C_1-C_4$-alkoxy and $C_1-C_4$-halogenalkoxy.

$R^{4a}$ are the possible substituents for the aliphatic moieties of $R^4$.

$R^{4a}$ according to the invention is independently selected from halogen, OH, CN, $C_1-C_6$-alkoxy, $C_3-C_6$-cycloalkyl, $C_3-C_6$-halogencycloalkyl, $C_1-C_4$-halogenalkoxy, $C_1-C_6$-alkylthio and phenoxy, wherein the phenyl group is unsubstituted or carries one, two, three, four or five substituents $R^{41a}$ selected from the group consisting of halogen, OH, $C_1-C_4$-alkyl, $C_1-C_4$-halogenalkyl, $C_1-C_4$-alkoxy and $C_1-C_4$-halogenalkoxy, in particular selected from halogen, $C_1-C_2$-alkyl, $C_1-C_2$-halogenalkyl, $C_1-C_2$-alkoxy and $C_1-C_2$-halogenalkoxy, more specifically selected from halogen, such as F, Cl and Br.

According to one embodiment $R^{4a}$ is independently selected from halogen, OH, CN, $C_1-C_2$-alkoxy, $C_3-C_6$-cycloalkyl, $C_3-C_6$-halogencycloalkyl and $C_1-C_2$-halogenalkoxy. Specifically, $R^{4a}$ is independently selected from F, Cl, OH, CN, $C_1-C_2$-alkoxy, cyclopropyl, 1-F-cyclopropyl, 1-Cl-cyclopropyl and $C_1-C_2$-halogenalkoxy.

According to one particular embodiment $R^{4a}$ is independently selected from halogen, such as F, Cl, Br and I, more specifically F, Cl and Br.

According to a further embodiment, $R^{4a}$ is independently selected from OH, $C_3-C_6$-cycloalkyl, $C_3-C_6$-halogencycloalkyl and $C_1-C_2$-halogenalkoxy. Specifically, $R^{4a}$ is independently selected from OH, cyclopropyl and $C_1-C_2$-halogenalkoxy.

$R^{4b}$ are the possible substituents for the cycloalkyl, heteroaryl and aryl moieties of $R^4$.

$R^{4b}$ according to the invention is independently selected from halogen, OH, CN, $C_1-C_4$-alkyl, $C_1-C_4$-alkoxy, $C_1-C_4$-halogenalkyl, $C_3-C_6$-cycloalkyl, $C_3-C_6$-halogencycloalkyl and $C_1-C_4$-halogenalkoxy.

According to one embodiment thereof $R^{4b}$ is independently selected from halogen, CN, $C_1-C_2$-alkyl, $C_1-C_2$-alkoxy, $C_1-C_2$-halogenalkyl, $C_3-C_6$-cycloalkyl, $C_3-C_6$-halogencycloalkyl and $C_1-C_2$-halogenalkoxy. Specifically, $R^{4b}$ is independently selected from F, Cl, OH, CN, $CH_3$, $OCH_3$, cyclopropyl, 1-F-cyclopropyl, 1-Cl-cyclopropyl and halogenmethoxy.

According to a further embodiment thereof $R^{4b}$ is independently selected from $C_1-C_2$-alkyl, $C_1-C_2$-alkoxy, $C_1-C_2$-halogenalkyl, $C_3-C_6$-cycloalkyl, $C_3-C_6$-halogencycloalkyl and $C_1-C_2$-halogenalkoxy. Specifically, $R^{4b}$ is independently selected from OH, $CH_3$, $OCH_3$, cyclopropyl, 1-F-cyclopropyl, 1-Cl-cyclopropyl and halogenmethoxy, more specifically independently selected from OH, $CH_3$, $OCH_3$, cyclopropyl, 1-F-cyclopropyl, 1-Cl-cyclopropyl and $OCHF_2$.

Y according to the invention is O.

According to a further embodiment thereof Y is S.

According to a further embodiment thereof Y is S(O).

According to a further embodiment thereof Y is $S(O)_2$.

$Q^1$ according to the invention is in each case independently selected from $C_1-C_6$-alkyl, $C_2-C_6$-alkenyl, $C_2-C_6$-alkynyl, $C_3-C_6$-cycloalkyl, five- or six-membered heteroaryl and aryl; wherein the heteroaryl contains one, two or three heteroatoms selected from N, O and S; and wherein the aliphatic moieties of $Q^1$ are unsubstituted or substituted with identical or different groups $Q^{1a}$ which independently of one another are selected from:

$Q^{1a}$ halogen, OH, CN, $C_1-C_6$-alkoxy, $C_3-C_6$-cycloalkyl, $C_3-C_6$-halogencycloalkyl, $C_1-C_4$-halogenalkoxy, $C_1-C_6$-alkylthio, phenyl and phenoxy, wherein the phenyl and phenoxy group is unsubstituted or carries 1, 2, 3, 4 or 5 substituents $Q^{11a}$ selected from the group consisting of halogen, OH, $C_1-C_4$-alkyl, $C_1-C_4$-halogenalkyl, $C_1-C_4$-alkoxy and $C_1-C_4$-halogenalkoxy; and wherein the cycloalkyl, heteroaryl and aryl moieties of $Q^1$ are unsubstituted or substituted with 1, 2, 3, 4, 5 or up to the maximum number of identical or different groups $Q^{1b}$ which independently of one another are selected from:

$Q^{1b}$ halogen, OH, CN, $C_1-C_4$-alkyl, $C_1-C_4$-alkoxy, $C_1-C_4$-halogenalkyl, $C_3-C_6$-cycloalkyl, $C_3-C_6$-halogencycloalkyl, $C_1-C_4$-halogenalkoxy and $C_1-C_6$-alkylthio.

According to a further specific embodiment, $Q^1$ is $C_1-C_6$-alkyl, in particular $C_1-C_4$-alkyl, such as $CH_3$.

According to a further specific embodiment, $Q^1$ is $C_1-C_6$-alkyl, in particular $C_1$-alkyl, substituted by phenyl which is unsubstitituted.

According to a further specific embodiment, $Q^1$ is $C_1-C_6$-alkyl, in particular $C_1$-alkyl, substituted by phenyl which carries 1, 2 or 3 halogen.

According to a further specific embodiment, $Q^1$ is $C_1-C_6$-alkyl, in particular $C_1$-alkyl, substituted by phenyl which carries 1, 2 or 3 $C_1-C_4$-alkoxy groups.

According to a further specific embodiment, $Q^1$ is $C_1-C_6$-alkyl, in particular $C_1$-alkyl, substituted by phenyl which carries 1, 2 or 3 $C_1-C_4$-alkyl groups.

According to a further specific embodiment, $Q^1$ is $C_1-C_6$-alkyl, in particular $C_1$-alkyl, substituted by phenyl which carries 1, 2 or 3 $C_1-C_4$-halogenalkyl groups.

According to a further specific embodiment, $Q^1$ is $C_1-C_6$-halogenalkyl, in particular $C_1-C_4$-halogenalkyl, such as $CF_3$, $CHF_2$, $CH_2F$, $CCl_3$, $CHCl_2$ or $CH_2Cl$.

According to still a further embodiment, $Q^1$ is $C_2-C_6$-alkenyl or $C_2-C_6$-halogenalkenyl, in particular $C_2-C_4$-alkenyl or $C_2-C_4$-halogenalkenyl, such as $CH=CH_2$.

According to still a further embodiment, $Q^1$ is $C_2-C_6$-alkynyl or $C_2-C_6$-halogenalkynyl, in particular $C_2-C_4$-alkynyl or $C_2-C_4$-halogenalkynyl, such as $C≡CH$.

According to a further specific embodiment $Q^1$ is $C_3-C_6$-cycloalkyl, in particular cyclopropyl.

In a further specific embodiment, $Q^1$ is $C_3-C_6$-cycloalkyl, for example cyclopropyl, substituted by one, two, three or up to the maximum possible number of identical or different groups $Q^{1b}$ as defined and preferably herein.

According to a specific embodiment $Q^1$ is $C_3-C_6$-halogencycloalkyl. In a special embodiment $Q^1$ is fully or partially halogenated cyclopropyl.

According to still a further specific embodiment, $Q^1$ is unsubstituted aryl or aryl that is substituted by one, two, three or four $Q^{1b}$, as defined herein. In particular, $Q^1$ is unsubstituted phenyl or phenyl that is substituted by one, two, three or four $Q^{1b}$, as defined herein.

According to still a further specific embodiment, $Q^1$ is unsubstituted 5- or 6-membered heteroaryl. According to still a further embodiment, $Q^1$ is 5- or 6-membered heteroaryl that is substituted by one, two or three $Q^{1b}$, as defined herein.

According to one further embodiment $Q^1$ according to the invention is in each case independently selected from $C_1$-$C_6$-alkyl, $C_2$-$C_6$-alkenyl, $C_2$-$C_6$-alkynyl, $C_3$-$C_6$-cycloalkyl, five- or six-membered heteroaryl and aryl; wherein the heteroaryl contains one, two or three heteroatoms selected from N, O and S; wherein $Q^{1a}$ is selected from halogen, $C_1$-$C_6$-alkoxy, $C_3$-$C_6$-halogencycloalkyl, phenyl that is unsubstituted or substituted by 1, 2, 3, 4 or 5 substituents $Q^{11a}$ independently selected from $C_1$-$C_4$-alkyl; and wherein the aliphatic moieties of $Q^1$ are unsubstituted or substituted with identical or different groups $Q^{1a}$ as defined below and wherein the cycloalkyl moieties of $Q^1$ are not further substituted or carry one, two, three, four or five identical or different groups $Q^{1b}$ as defined below.

According to a further embodiment, $Q^1$ is independently selected from halogen, OH, $C_1$-$C_6$-alkyl, $C_1$-$C_6$-halogenalkyl, $C_1$-$C_6$-alkoxy and $C_1$-$C_6$-halogenalkoxy, in particular independently selected from F, Cl, Br, CN, OH, $C_1$-$C_4$-alkyl, $C_1$-$C_4$-halogenalkyl, $C_1$-$C_4$-alkoxy and $C_1$-$C_4$-halogenalkoxy.

$Q^{1a}$ are the possible substituents for the aliphatic moieties of $Q^1$.

$Q^{1a}$ according to the invention is independently selected from halogen, $C_1$-$C_6$-alkoxy, $C_3$-$C_6$-halogencycloalkyl, phenoxy and phenyl, wherein the phenyl and phenoxy groups are unsubstituted or carries one, two, three, four or five substituents $R^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

According to one embodiment $Q^{1a}$ is independently selected from halogen, OH, CN, $C_1$-$C_2$-alkoxy, $C_3$-$C_6$-cycloalkyl, $C_3$-$C_6$-halogencycloalkyl and $C_1$-$C_2$-halogenalkoxy. Specifically, $Q^{1a}$ is independently selected from F, Cl, OH, CN, $C_1$-$C_2$-alkoxy, cyclopropyl, 1-F-cyclopropyl, 1-Cl-cyclopropyl and $C_1$-$C_2$-halogenalkoxy.

According to one particular embodiment $Q^{1a}$ is independently selected from halogen, such as F, Cl, Br and I, more specifically F, Cl and Br.

According to a further embodiment, $Q^{1a}$ is independently selected from OH, $C_3$-$C_6$-cycloalkyl, $C_3$-$C_6$-halogencycloalkyl and $C_1$-$C_2$-halogenalkoxy. Specifically, $Q^{1a}$ is independently selected from OH, cyclopropyl and $C_1$-$C_2$-halogenalkoxy.

$Q^{1b}$ are the possible substituents for the cycloalkyl, heteroaryl and aryl moieties of $Q^1$.

$Q^{1b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy.

According to one embodiment thereof $Q^{1b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $Q^{1b}$ is independently selected from F, Cl, OH, CN, $CH_3$, $OCH_3$, cyclopropyl, 1-F-cyclopropyl, 1-Cl-cyclopropyl and halogenmethoxy.

According to a further embodiment thereof $Q^{1b}$ is independently selected from $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $Q^{1b}$ is independently selected from OH, $CH_3$, $OCH_3$, cyclopropyl, 1-F-cyclopropyl, 1-Cl-cyclopropyl and halogenmethoxy, more specifically independently selected from OH, $CH_3$, $OCH_3$, cyclopropyl, 1-F-cyclopropyl, 1-Cl-cyclopropyl and $OCHF_2$.

$Q^2$ according to the invention is in each case independently selected from H, $C_1$-$C_6$-alkyl, $C_2$-$C_6$-alkenyl, $C_2$-$C_6$-alkynyl, $C_3$-$C_6$-cycloalkyl, five- or six-membered heteroaryl and aryl; wherein the heteroaryl contains one, two or three heteroatoms selected from N, O and S; and wherein the aliphatic moieties of $Q^2$ are unsubstituted or substituted with identical or different groups $Q^{2a}$ which independently of one another are selected from:

$Q^{2a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl and phenoxy, wherein the phenyl and phenoxy group is unsubstituted or carries 1, 2, 3, 4 or 5 substituents $Q^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein the cycloalkyl, heteroaryl and aryl moieties of $Q^2$ are unsubstituted or substituted with 1, 2, 3, 4, 5 or up to the maximum number of identical or different groups $Q^{2b}$ which independently of one another are selected from:

$Q^{2b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to a further specific embodiment, $Q^2$ is H.

According to a further specific embodiment, $Q^2$ is $C_1$-$C_6$-alkyl, in particular $C_1$-$C_4$-alkyl, such as $CH_3$.

According to a further specific embodiment, $Q^2$ is $C_1$-$C_6$-alkyl, in particular $C_1$-alkyl, substituted by phenyl which is unsubstititued.

According to a further specific embodiment, $Q^2$ is $C_1$-$C_6$-alkyl, in particular $C_1$-alkyl, substituted by phenyl which carries 1, 2 or 3 halogen.

According to a further specific embodiment, $Q^2$ is $C_1$-$C_6$-alkyl, in particular $C_1$alkyl, substituted by phenyl which carries 1, 2 or 3 $C_1$-$C_4$-alkoxy groups.

According to a further specific embodiment, $Q^2$ is $C_1$-$C_6$-alkyl, in particular $C_1$-alkyl, substituted by phenyl which carries 1, 2 or 3 $C_1$-$C_4$-alkyl groups.

According to a further specific embodiment, $Q^2$ is $C_1$-$C_6$-alkyl, in particular $C_1$-alkyl, substituted by phenyl which carries 1, 2 or 3 $C_1$-$C_4$-halogenalkyl groups.

According to a further specific embodiment, $Q^2$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to still a further embodiment, $Q^2$ is $C_2$-$C_6$-alkenyl or $C_2$-$C_6$-halogenalkenyl, in particular $C_2$-$C_4$-alkenyl or $C_2$-$C_4$-halogenalkenyl, such as $CH=CH_2$.

According to still a further embodiment, $Q^2$ is $C_2$-$C_6$-alkynyl or $C_2$-$C_6$-halogenalkynyl, in particular $C_2$-$C_4$-alkynyl or $C_2$-$C_4$-halogenalkynyl, such as $C\equiv CH$.

According to a further specific embodiment $Q^2$ is $C_3$-$C_6$-cycloalkyl, in particular cyclopropyl.

In a further specific embodiment, $Q^2$ is $C_3$-$C_6$-cycloalkyl, for example cyclopropyl, substituted by one, two, three or up to the maximum possible number of identical or different groups $Q^{2b}$ as defined and preferably herein.

According to a specific embodiment $Q^2$ is $C_3$-$C_6$-halogencycloalkyl. In a special embodiment $Q^1$ is fully or partially halogenated cyclopropyl.

According to still a further specific embodiment, $Q^2$ is unsubstituted aryl or aryl that is substituted by one, two, three or four $Q^{2b}$, as defined herein. In particular, $Q^2$ is unsubstituted phenyl or phenyl that is substituted by one, two, three or four $Q^{2b}$, as defined herein.

According to still a further specific embodiment, $Q^2$ is unsubstituted 5- or 6-membered heteroaryl. According to still a further embodiment, $Q^2$ is 5- or 6-membered heteroaryl that is substituted by one, two or three $Q^{2b}$, as defined herein.

According to one further embodiment $Q^2$ according to the invention is in each case independently selected from $C_1$-$C_6$-alkyl, $C_2$-$C_6$-alkenyl, $C_2$-$C_6$-alkynyl, $C_3$-$C_6$-cycloalkyl, five- or six-membered heteroaryl and aryl; wherein the heteroaryl contains one, two or three heteroatoms selected from N, O and S; and wherein the aliphatic moieties of $Q^2$ are unsubstituted or substituted with identical or different groups $Q^{2a}$ as defined below and wherein the cycloalkyl moieties of $Q^2$ are not further substituted or carry one, two, three, four or five identical or different groups $Q^{2b}$ as defined below.

According to a further embodiment, $Q^2$ is independently selected from halogen, OH, $C_1$-$C_6$-alkyl, $C_1$-$C_6$-halogenalkyl, $C_1$-$C_6$-alkoxy and $C_1$-$C_6$-halogenalkoxy, in particular independently selected from F, Cl, Br, CN, OH, $C_1$-$C_4$-alkyl, $C_1$-$C_4$-halogenalkyl, $C_1$-$C_4$-alkoxy and $C_1$-$C_4$-halogenalkoxy.

$Q^{2a}$ are the possible substituents for the aliphatic moieties of $Q^2$.

$Q^{2a}$ according to the invention is independently selected from halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio and phenoxy, wherein the phenyl group is unsubstituted or carries one, two, three, four or five substituents $Q^{2a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy, in particular selected from halogen, $C_1$-$C_2$-alkyl, $C_1$-$C_2$-halogenalkyl, $C_1$-$C_2$-alkoxy and $C_1$-$C_2$-halogenalkoxy, more specifically selected from halogen, such as F, Cl and Br.

According to one embodiment $Q^{2a}$ is independently selected from halogen, OH, CN, $C_1$-$C_2$-alkoxy, $C_3$-$C_6$-cycloalkyl, $C_3$-$C_6$-halogencycloalkyl and $C_1$-$C_2$-halogenalkoxy. Specifically, $Q^{2a}$ is independently selected from F, Cl, OH, CN, $C_1$-$C_2$-alkoxy, cyclopropyl, 1-F-cyclopropyl, 1-Cl-cyclopropyl and $C_1$-$C_2$-halogenalkoxy.

According to one particular embodiment $Q^{2a}$ is independently selected from halogen, such as F, Cl, Br and I, more specifically F, Cl and Br.

According to a further embodiment, $Q^{2a}$ is independently selected from OH, $C_3$-$C_6$-cycloalkyl, $C_3$-$C_6$-halogencycloalkyl and $C_1$-$C_2$-halogenalkoxy. Specifically, $Q^{2a}$ is independently selected from OH, cyclopropyl and $C_1$-$C_2$-halogenalkoxy.

$Q^{2b}$ are the possible substituents for the cycloalkyl, heteroaryl and aryl moieties of $Q^2$.

$Q^{2b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy.

According to one embodiment thereof $Q^{2b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $Q^{2b}$ is independently selected from F, Cl, OH, CN, $CH_3$, $OCH_3$, cyclopropyl, 1-F-cyclopropyl, 1-Cl-cyclopropyl and halogenmethoxy.

According to a further embodiment thereof $Q^{2b}$ is independently selected from $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $Q^{2b}$ is independently selected from OH, $CH_3$, $OCH_3$, cyclopropyl, 1-F-cyclopropyl, 1-Cl-cyclopropyl and halogenmethoxy, more specifically independently selected from OH, $CH_3$, $OCH_3$, cyclopropyl, 1-F-cyclopropyl, 1-Cl-cyclopropyl and $OCHF_2$.

$Q^1$ and $Q^2$ according to the present invention form, together with the carbon atom to which they are bound a three- to seven-membered saturated or partially unsaturated carbo- or heterocycle, wherein the ring may further contain 1, 2, 3 or 4 heteroatoms selected from N—$R^N$, O and S, wherein $R^N$ is selected from H, $C_1$-$C_4$-alkyl and $SO_2R^Q$; wherein $R^Q$ is selected from $C_1$-$C_4$-alkyl, $C_1$-$C_4$-halogenalkyl, unsubstituted aryl or heteroaryl that is substituted by 1, 2, 3, 4 or 5 substituents $R^{Q1}$ independently selected from $C_1$-$C_4$-alkyl; and wherein S may be in the form of its oxide SO or $SO_2$; and wherein in each case one or two $CH_2$ groups of the carbo- or heterocycle may be replaced by a group independently selected from C(=O) and C(=S);

and wherein the ring is unsubstituted or substituted with 1, 2, 3, 4, 5 or up to the maximum number of identical or different groups $R^{QR}$ which independently of one another are selected from:

$Q^{QR}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

According to one embodiment, the carbocycle formed by $Q^1$ and $Q^2$ is saturated.

According to a further embodiment, the carbocycle formed by $Q^1$ and $Q^2$ is a saturated unsubstituted or substituted carbocycle. According to one embodiment, this saturated carbocycle is unsubstituted. According to a further embodiment, the saturated carbocycle carries one, two, three or four substituents $Q^{QR}$. In one further particular embodiment, said carbocycle is cyclopropane. In one further particular embodiment, said carbocycle is cyclobutane. In one further particular embodiment, said carbocycle is cyclohexane. In one further particular embodiment, said carbocycle is cyclopentane. In one further particular embodiment, said carbocycle is cyclopropane substituted by halogene or $C_1$-$C_4$-alkyl. In one further particular embodiment, said carbocycle is cyclobutane substituted by halogene or $C_1$-$C_4$-alkyl. In one further particular embodiment, said carbocycle is cyclohexane substituted by halogene or $C_1$-$C_4$-alkyl. In one further particular embodiment, said carbocycle is cyclopentane substituted by halogene or $C_1$-$C_4$-alkyl.

According to a further embodiment, the unsubstituted or substituted and saturated or partially unsaturated heterocycle is three-, four-, five- or six-membered and contains one, two or three, more particularly one or two, heteroatoms selected from NH, $NR^N$, O, S, S(=O) and $S(=O)_2$, wherein $R^N$ is as defined above or preferably selected from $C_1$-$C_2$-alkyl, $C_1$-$C_2$-halogenalkyl and $SO_2Ph$, wherein Ph is unsubstituted phenyl or phenyl that is substituted by one $C_1$-$C_2$-alkyl. In one further particular embodiment, said heterocycle is four- or six-membered.

According to a further embodiment, the heterocycle formed by $Q^1$ and $Q^2$ contains one, two or three, more specifically one or two, heteroatoms selected from NH and $NR^N$, wherein $R^N$ is as defined and preferably defined below, more particularly selected from $C_1$-$C_2$-alkyl, $C_1$-$C_2$-halogenalkyl and $SO_2Ph$, wherein Ph is unsubstituted phenyl or phenyl that is substituted by one methyl. In one embodiment thereof, it contains one or two heteroatoms NH, in particular one NH. In another embodiment, it contains one or two heteroatoms $NR^N$, in particular one $NR^N$, wherein $R^N$ in each case is as defined and preferably defined above.

According to a further embodiment, the heterocycle formed by $Q^1$ and $Q^2$ contains one, two or three, more specifically one or two, in particular one, heteroatom(s) selected from S, S(=O) and S(=O)$_2$. In one embodiment thereof, it contains one or two heteroatoms S, in particular one S. In another embodiment, it contains one or two heteroatoms S(=O), in particular one S(=O). In still another embodiment, it contains one or two heteroatoms S(=O)$_2$, in particular one S(=O)$_2$.

According to a further embodiment, the heterocycle formed by $Q^1$ and $Q^2$ contains one or two heteroatoms O. In one embodiment thereof, it contains one heteroatom O. In another embodiment, it contains two heteroatoms O.

According to a further embodiment, the heterocycle formed by $Q^1$ and $Q^2$ is unsubstituted, i.e. it does not carry any substituent $Q^{QR}$. According to a further embodiment, it carries one, two, three or four $Q^{QR}$.

According to one particular embodiment, $Q^1$ and $Q^2$ together form a 4-membered saturated heterocycle which contains 1 or 2 heteroatoms, in particular 1 heteroatom, from the group consisting of NH, $NR^N$, O, S, S(=O) and S(=O)$_2$, as ring members, wherein $R^N$ is defined and preferably defined above. In one embodiment, the heterocycle contains one O as heteroatom. For example, the formed heterocycle is oxetane. According to one embodiment thereof, the heterocycle is unsubstituted, i.e. it does not carry any substituent $Q^{QR}$. According to a further embodiment, it carries one, two, three or four $Q^{QR}$.

According to a further particular embodiment, $Q^1$ and $Q^2$ together form a 5-membered saturated heterocycle which contains 1, 2 or 3, in particular 1 or 2, heteroatoms from the group consisting of NH, $NR^N$, O, S, S(=O) and S(=O)$_2$, as ring members, wherein $R^N$ is as defined and preferably defined above. According to one embodiment thereof, the heterocycle is unsubstituted, i.e. it does not carry any substituent $Q^{QR}$. According to a further embodiment, it carries one, two, three or four $Q^{QR}$.

According to a further particular embodiment, $Q^1$ and $Q^2$ together form a 6-membered saturated heterocycle which contains 1, 2 or 3, in particular 1 or 2, heteroatoms from the group consisting of NH, $NR^N$, O, S, S(=O) and S(=O)$_2$, as ring members, wherein $R^N$ is as defined and preferably defined below. According to one embodiment thereof, the heterocycle is unsubstituted, i.e. it does not carry any substituent $Q^{QR}$. According to a further embodiment, it carries one, two, three or four $Q^{QR}$. According to one specific embodiment thereof, said 6-membered saturated heterocycle contains 1 or 2 heteroatoms selected from NH and $NR^N$. According to a further specific embodiment thereof, said 6-membered saturated heterocycle contains 1 or 2 heteroatoms O. According to a further specific embodiment thereof, said 6-membered saturated heterocycle contains 1 or 2 heteroatoms selected from S, S(=O) and S(=O)$_2$. According to one embodiment thereof, the respective 6-membered heterocycle is unsubstituted, i.e. it does not carry any substituent $Q^{QR}$. According to a further embodiment, it carries one, two, three or four $Q^{QR}$.

$Q^{QR}$ are the possible substituents for the heterocycle formed by $Q^1$ and $Q^2$ and are independently selected from halogen, OH, CN, $NO_2$, SH, $NH_2$, $C_1$-$C_6$-alkyl, $C_1$-$C_6$-halogenalkyl, $C_1$-$C_6$-alkoxy, $C_1$-$C_6$-halogenalkoxy, $C_1$-$C_6$-alkylthio, $C_1$-$C_6$-halogenalkylthio, $C_1$-$C_4$-alkoxy-$C_1$-$C_4$-alkyl, phenyl and phenoxy, wherein the phenyl groups are unsubstituted or carry one, two, three, four or five substituents $Q^{QR}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein in each case one or two $CH_2$ groups of the carbo- or heterocycle may be replaced by a group independently selected from C(=O) and C(=S).

In one preferred embodiment, $Q^{QR}$ is in each case independently selected from halogen, OH, CN, SH, $C_1$-$C_6$-alkyl, $C_1$-$C_6$-halogenalkyl, $C_1$-$C_6$-alkoxy, $C_1$-$C_6$-halogenalkoxy and $C_1$-$C_6$-alkylthio. In one further preferred embodiment, $Q^{QR}$ is in each case independently selected from halogen, $C_1$-$C_6$-alkyl and $C_1$-$C_6$-halogenalkyl. In one further particular embodiment, $Q^{QR}$ is in each case independently selected from $C_1$-$C_6$-alkyl, such as methyl and ethyl.

$R^N$ is the substituent of the heteroatom $NR^N$ that is contained in the heterocycle formed by $Q^2$ and $Q^3$ in some of the inventive compounds. $R^N$ is selected from $C_1$-$C_4$-alkyl, $C_1$-$C_4$-halogenalk and $SO_2$Ph, wherein Ph is unsubstituted phenyl or phenyl that is substituted by one, two or three substituents selected from $C_1$-$C_4$-alkyl. In one preferred embodiment, $R^N$ is in each case independently selected from $C_1$-$C_2$-alkyl, $C_1$-$C_2$-halogenalkyl and $SO_2$Ph, wherein Ph is unsubstituted phenyl or phenyl that is substituted by one methyl substituents. In one particular embodiment, $R^N$ is in each case independently selected from $C_1$-$C_2$-alkyl, more particularly methyl. In one particular embodiment, $R^N$ is in each case independently selected from $SO_2$Ph, wherein Ph is unsubstituted phenyl or phenyl that is substituted by one methyl.

Particularly preferred embodiments of the heterocycles formed $Q^1$ and $Q^2$ and according to the invention are in Table P1 below, wherein each line of lines P3-1 to P3-15 corresponds to one particular embodiment of the invention, wherein P3-1 to P3-15 are also in any combination with one another a preferred embodiment of the present invention. The carbon atom, to which $Q^1$ and $Q^2$ are bound is marked with # in the drawings.

TABLE P1

| No. | heterocycle formed by $Q^1$ and $Q^2$ |
|---|---|
| P1-1 | △ (3-membered ring, #) |
| P1-2 | ◇ (4-membered ring, #) |
| P1-3 | ⬠ (5-membered ring, #) |
| P1-4 | ⬡ (6-membered ring, #) |
| P1-5 | 3-membered ring with $CH_3$, # |
| P1-6 | 3-membered ring with $H_3C$ and $CH_3$, # |
| P1-7 | 3-membered ring with two $CH_3$ groups, # |

TABLE P1-continued

| No. | heterocycle formed by Q¹ and Q² |
|---|---|
| P1-8 | 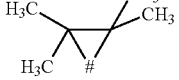 |
| P1-9 | 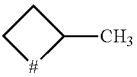 |
| P1-10 |  |
| P1-11 |  |
| P1-12 |  |
| P1-13 |  |
| P1-14 |  |
| P1-15 |  | is selected from H, $C_1$-$C_6$-alkyl, $C_2$-$C_6$-alkenyl, $C_2$-$C_6$-alkynyl, $C_3$-$C_6$-cycloalkyl, five- or six-membered heteroaryl and aryl; wherein the heteroaryl contains one, two or three heteroatoms selected from N, O and S;

wherein the aliphatic moieties of $Q^3$ are unsubstituted or substituted with identical or different groups $Q^{3a}$ which independently of one another are selected from:

$Q^{3a}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy and five- to ten-membered heterocycle, heteroaryl, heterocycloxy, heteryloxy; wherein the heterocycle or heteroaryl contains one, two or three heteroatoms selected from N, O and S; wherein the phenyl, phenoxy, heterocycle and heteroaryl groups are unsubstituted or substituted with 1, 2, 3, 4 or 5 substituents $Q^{13a}$ selected from the group consisting of halogen, OH, $C_1$-$C_4$-alkyl, $C_1$-$C_4$-halogenalkyl, $C_1$-$C_4$-alkoxy, $C_1$-$C_4$-halogenalkoxy, CR'=NOR"; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{113a}$ selected from the group consisting of halogen, OH, $C_1$-$C_4$-alkyl, $C_1$-$C_4$-halogenalkyl, $C_1$-$C_4$-alkoxy, CN, CR'=NOR" and $C_1$-$C_4$-halogenalkoxy;

wherein the cycloalkyl, heteroaryl and aryl moieties of $Q^3$ are unsubstituted or substituted with 1, 2, 3, 4, 5 or up to the maximum number of identical or different groups $Q^{3b}$ which independently of one another are selected from:

$Q^{3b}$ halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy and five- to ten-membered heterocycle, heteroaryl, heterocycloxy, heteryloxy; wherein the heterocycle or heteroaryl contains one, two or three heteroatoms selected from N, O and S; wherein the phenyl, phenoxy, heterocycle and heteroaryl groups are unsubstituted or substituted with 1, 2, 3, 4 or 5 substituents $Q^{13b}$ selected from the group consisting of halogen, OH, $C_1$-$C_4$-alkyl, $C_1$-$C_4$-halogenalkyl, $C_1$-$C_4$-alkoxy, $C_1$-$C_4$-halogenalkoxy, CR'=NOR"; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{113b}$ selected from the group consisting of halogen, OH, $C_1$-$C_4$-alkyl, $C_1$-$C_4$-halogenalkyl, $C_1$-$C_4$-alkoxy, CN, CR'=NOR" and $C_1$-$C_4$-halogenalkoxy;

and wherein R' and R" are independently unsubstituted or substituted by R''' which is independently selected from halogen, OH, CN, $NO_2$, SH, $NH_2$, $NH(C_1$-$C_4$-alkyl), $N(C_1$-$C_4$-alkyl$)_2$, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-cycloalkyl, $C_3$-$C_6$-halogencycloalkyl and phenyl.

According to a further specific embodiment, $Q^3$ is H.

According to a further specific embodiment, $Q^3$ is $C_1$-$C_6$-alkyl, in particular $C_1$-$C_4$-alkyl, such as $CH_3$.

According to a further specific embodiment, $Q^3$ is $C_1$-$C_6$-alkyl, in particular $C_1$alkyl, substituted by phenyl which is unsubstituted.

According to a further specific embodiment, $Q^3$ is $C_1$-$C_6$-alkyl, in particular $C_1$-alkyl, substituted by phenyl which carries 1, 2 or 3 halogen.

According to a further specific embodiment, $Q^3$ is $C_1$-$C_6$-alkyl, in particular $C_1$-alkyl, substituted by phenyl which carries 1, 2 or 3 $C_1$-$C_4$-alkoxy groups.

According to a further specific embodiment, $Q^3$ is $C_1$-$C_6$-alkyl, in particular $C_1$-alkyl, substituted by phenyl which carries 1, 2 or 3 $C_1$-$C_4$-alkyl groups.

According to a further specific embodiment, $Q^3$ is $C_1$-$C_6$-alkyl, in particular $C_1$alkyl, substituted by phenyl which carries 1, 2 or 3 $C_1$-$C_4$-halogenalkyl groups.

According to a further specific embodiment, $Q^3$ is $C_1$-$C_6$-alkyl, in particular $C_1$-alkyl, substituted by phenyl which carries a further phenyl group which can be unsubstituted or substituted by halogen or $C_1$-$C_4$-alkyl. In one embodiment the phenyl is attached to phenyl directly. In one further embodiment the phenyl is attached to the phenyl via O.

According to a further specific embodiment, $Q^3$ is $C_1$-$C_6$-alkyl, in particular $C_1$-alkyl, substituted by phenoxy which carries a phenyl group which can be unsubstituted or substituted by halogen or $C_1$-$C_4$-alkyl. In one embodiment the phenyl is attached to phenoxy directly. In one further embodiment the phenyl is attached to the phenyl via O.

According to a further specific embodiment of formula I, $Q^3$ is $C_1$-$C_6$-alkyl, especially $CH_2$ subsitited by a 5-membered saturated heteroaryl which contains 1, 2 or 3, in particular 1 or 2, heteroatoms from the group consisting of N, O and S as ring members.

According to a further specific embodiment of formula I, $Q^3$ is $C_1$-$C_6$-alkyl, especially $CH_2$ subsitited by a 5-membered saturated heteroaryl which contains one N as ring member. According to one embodiment thereof, the heteroaryl is unsubstituted, i.e. it does not carry any substituent $Q^{13a}$. According to still another embodiment of formula I, it is substituted by $Q^{13a}$.

According to a further specific embodiment of formula I, $Q^3$ is $C_1$-$C_6$-alkyl, especially $CH_2$ subsitited by a 5-membered saturated heteroaryl which contains two N as ring members.

According to one embodiment thereof, the heteroaryl is unsubstituted, i.e. it does not carry any substituent $Q^{13a}$. According to still another embodiment of formula I, it is substituted by $Q^{13a}$.

According to a further specific embodiment of formula I, $Q^3$ is $C_1$-$C_6$-alkyl, especially $CH_2$ subsitited by a 5-membered saturated heteroaryl which contains three N as ring members. According to one embodiment thereof, the heteroaryl is unsubstituted, i.e. it does not carry any substituent $Q^{13a}$. According to still another embodiment of formula I, it is substituted by $Q^{13a}$. According to one specific embodiment thereof, said 5-membered saturated heterocycle contains 1 or 2, in particular 1, heteroatom(s) O.

According to a further specific embodiment of formula I, $Q^3$ is $C_1$-$C_6$-alkyl, especially $CH_2$ subsitited by a 5-membered saturated heteroaryl which contains one S as ring member.

According to one embodiment thereof, the heteroaryl is unsubstituted, i.e. it does not carry any substituent $Q^{13a}$. According to still another embodiment of formula I, it is substituted by $Q^{13a}$.

According to a further specific embodiment of formula I, $Q^3$ is $C_1$-$C_6$-alkyl, especially $CH_2$ subsitited by a 5-membered saturated heteroaryl which contains one S and one N as ring members. According to one embodiment thereof, the heteroaryl is unsubstituted, i.e. it does not carry any substituent $Q^{13a}$. According to still another embodiment of formula I, it is substituted by $Q^{13a}$.

According to a further specific embodiment of formula I, $Q^3$ is $C_1$-$C_6$-alkyl, especially $CH_2$ subsitited by a 5-membered saturated heteroaryl which contains one S and two N as ring members. According to one embodiment thereof, the heteroaryl is unsubstituted, i.e. it does not carry any substituent $Q^{13a}$. According to still another embodiment of formula I, it is substituted by $Q^{13a}$.

According to a further specific embodiment of formula I, $Q^3$ is $C_1$-$C_6$-alkyl, especially $CH_2$ subsitited by a 5-membered saturated heteroaryl which contains one oxygen and one N as ring members. According to one embodiment thereof, the heteroaryl is unsubstituted, i.e. it does not carry any substituent $Q^{13a}$. According to still another embodiment of formula I, it is substituted by $Q^{13a}$.

According to a further specific embodiment of formula I, $Q^3$ is $C_1$-$C_6$-alkyl, especially $CH_2$ subsitited by a 5-membered saturated heteroaryl which contains one oxygen and two N as ring members. According to one embodiment thereof, the heteroaryl is unsubstituted, i.e. it does not carry any substituent $Q^{13a}$. According to still another embodiment of formula I, it is substituted by $Q^{13a}$.

According to a further specific embodiment of formula I, $Q^3$ is $C_1$-$C_6$-alkyl, especially $CH_2$ subsitited by a 6-membered saturated heteroaryl which contains 1, 2 or 3, in particular 1 or 2, heteroatoms from the group consisting of N, O and S as ring members. According to one embodiment thereof, the heteroaryl is unsubstituted, i.e. it does not carry any substituent $Q^{13a}$. According to still another embodiment of formula I, it is substituted by $Q^{13a}$.

According to a further specific embodiment of formula I, $Q^3$ is $C_1$-$C_6$-alkyl, especially $CH_2$ subsitited by a 6-membered saturated heteroaryl which one N as ring member. According to one embodiment thereof, the heteroaryl is unsubstituted, i.e. it does not carry any substituent $Q^{13a}$. According to still another embodiment of formula I, it is substituted by $Q^{13a}$.

According to a further specific embodiment of formula I, $Q^3$ is $C_1$-$C_6$-alkyl, especially $CH_2$ subsitited by a 6-membered saturated heteroaryl which two N as ring members. According to one embodiment thereof, the heteroaryl is unsubstituted, i.e. it does not carry any substituent $Q^{13a}$. According to still another embodiment of formula I, it is substituted by $Q^{13a}$.

According to a further specific embodiment of formula I, $Q^3$ is $C_1$-$C_6$-alkyl, especially $CH_2$ subsitited by a 10-membered saturated heteroaryl which contains 1, 2 or 3, in particular 1 or 2, heteroatoms from the group consisting of N, O and S as ring members. According to one embodiment thereof, the heteroaryl is unsubstituted, i.e. it does not carry any substituent $Q^{13a}$. According to still another embodiment of formula I, it is substituted by $Q^{13a}$. According to one specific embodiment thereof, said 10-membered saturated heterocycle contains 1 or 2, in particular 1, heteroatom(s) N.

According to a further specific embodiment of formula I, $Q^3$ is $C_1$-$C_6$-alkyl, especially $CH_2$ subsitited by a 10-membered saturated heteroaryl which one N as ring members. According to one embodiment thereof, the heteroaryl is unsubstituted, i.e. it does not carry any substituent $Q^{13a}$. According to still another embodiment of formula I, it is substituted by $Q^{13a}$.

According to still another embodiment of formula I, $Q^3$ is $CH_2$ substituted by a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl.

According to still another embodiment of formula I, $Q^3$ is $CH_2$ substituted by a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

According to a further specific embodiment, $Q^3$ is $C_1$-$C_6$-alkyl, in particular $CH(CH_3)$, substituted by phenyl which is unsubstitituted.

According to a further specific embodiment, $Q^3$ is $C_1$-$C_6$-alkyl, in particular $CH(CH_3)$, substituted by phenyl which carries 1, 2 or 3 halogen.

According to a further specific embodiment, $Q^3$ is $C_1$-$C_6$-alkyl, in particular $CH(CH_3)$, substituted by phenyl which carries 1, 2 or 3 $C_1$-$C_4$-alkoxy groups.

According to a further specific embodiment, $Q^3$ is $C_1$-$C_6$-alkyl, in particular $CH(CH_3)$, substituted by phenyl which carries 1, 2 or 3 $C_1$-$C_4$-alkyl groups.

According to a further specific embodiment, $Q^3$ is $C_1$-$C_6$-alkyl, in particular $CH(CH_3)$, substituted by phenyl which carries 1, 2 or 3 $C_1$-$C_4$-halogenalkyl groups.

According to a further specific embodiment, $Q^3$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to still a further embodiment, $Q^3$ is $C_2$-$C_6$-alkenyl or $C_2$-$C_6$-halogenalkenyl, in particular $C_2$-$C_4$-alkenyl or $C_2$-$C_4$-halogenalkenyl, such as $CH=CH_2$.

According to still a further embodiment, $Q^3$ is $C_2$-$C_6$-alkynyl or $C_2$-$C_6$-halogenalkynyl, in particular $C_2$-$C_4$-alkynyl or $C_2$-$C_4$-halogenalkynyl, such as $C\equiv CH$.

According to a further specific embodiment $Q^3$ is $C_3$-$C_6$-cycloalkyl, in particular cyclopropyl.

In a further specific embodiment, $Q^3$ is $C_3$-$C_6$-cycloalkyl, for example cyclopropyl, substituted by one, two, three or up to the maximum possible number of identical or different groups $Q^{1b}$ as defined and preferably herein.

According to a specific embodiment $Q^3$ is $C_3$-$C_6$-halogencycloalkyl. In a special embodiment $Q^1$ is fully or partially halogenated cyclopropyl.

According to still a further specific embodiment, $Q^3$ is unsubstituted aryl or aryl that is substituted by one, two, three or four $Q^{3b}$, as defined herein. In particular, $Q^3$ is unsubstituted phenyl or phenyl that is substituted by one, two, three or four $Q^{3b}$, as defined herein.

According to still a further specific embodiment, $Q^3$ is unsubstituted 5- or 6-membered heteroaryl. According to still a further embodiment, $Q^3$ is 5- or 6-membered heteroaryl that is substituted by one, two or three $Q^{3b}$, as defined herein.

According to a further specific embodiment, $Q^3$ is $C_1$-$C_6$-alkyl, in particular $C_1$-alkyl, substituted by phenyl which carries a further phenyl group which can be unsubstituted or substituted by halogen or $C_1$-$C_4$-alkyl. In one embodiment the phenyl is attached to phenyl directly. In one further embodiment the phenyl is attached to the phenyl via O.

According to a further specific embodiment, $Q^3$ is $C_1$-$C_6$-alkyl, in particular $C_1$-alkyl, substituted by phenoxy which carries a phenyl group which can be unsubstituted or substituted by halogen or $C_1$-$C_4$-alkyl. In one embodiment the phenyl is attached to phenoxy directly. In one further embodiment the phenyl is attached to the phenyl via O.

According to a further specific embodiment of formula I, $Q^3$ is $C_1$-$C_6$-alkyl, especially $CH_2$ subsitited by a 5-membered saturated heteroaryl which contains 1, 2 or 3, in particular 1 or 2, heteroatoms from the group consisting of N, O and S as ring members.

According to a further specific embodiment of formula I, $Q^3$ is $C_1$-$C_6$-alkyl, especially $CH_2$ subsitited by a 5-membered saturated heteroaryl which contains one N as ring member. According to one embodiment thereof, the heteroaryl is unsubstituted, i.e. it does not carry any substituent $Q^{13b}$. According to still another embodiment of formula I, it is substituted by $Q^{13b}$.

According to a further specific embodiment of formula I, $Q^3$ is $C_1$-$C_6$-alkyl, especially $CH_2$ subsitited by a 5-membered saturated heteroaryl which contains two N as ring members. According to one embodiment thereof, the heteroaryl is unsubstituted, i.e. it does not carry any substituent $Q^{13b}$. According to still another embodiment of formula I, it is substituted by $Q^{13b}$.

According to a further specific embodiment of formula I, $Q^3$ is $C_1$-$C_6$-alkyl, especially $CH_2$ subsitited by a 5-membered saturated heteroaryl which contains three N as ring members. According to one embodiment thereof, the heteroaryl is unsubstituted, i.e. it does not carry any substituent $Q^{13b}$. According to still another embodiment of formula I, it is substituted by $Q^{13b}$. According to one specific embodiment thereof, said 5-membered saturated heterocycle contains 1 or 2, in particular 1, heteroatom(s) O.

According to a further specific embodiment of formula I, $Q^3$ is $C_1$-$C_6$-alkyl, especially $CH_2$ subsitited by a 5-membered saturated heteroaryl which contains one S as ring member. According to one embodiment thereof, the heteroaryl is unsubstituted, i.e. it does not carry any substituent $Q^{13b}$. According to still another embodiment of formula I, it is substituted by $Q^{13b}$.

According to a further specific embodiment of formula I, $Q^3$ is $C_1$-$C_6$-alkyl, especially $CH_2$ subsitited by a 5-membered saturated heteroaryl which contains one S and one N as ring members. According to one embodiment thereof, the heteroaryl is unsubstituted, i.e. it does not carry any substituent $Q^{13b}$. According to still another embodiment of formula I, it is substituted by $Q^{13b}$.

According to a further specific embodiment of formula I, $Q^3$ is $C_1$-$C_6$-alkyl, especially $CH_2$ subsitited by a 5-membered saturated heteroaryl which contains one S and two N as ring members. According to one embodiment thereof, the heteroaryl is unsubstituted, i.e. it does not carry any substituent $Q^{13b}$. According to still another embodiment of formula I, it is substituted by $Q^{13b}$.

According to a further specific embodiment of formula I, $Q^3$ is $C_1$-$C_6$-alkyl, especially $CH_2$ subsitited by a 5-membered saturated heteroaryl which contains one oxygen and one N as ring members. According to one embodiment thereof, the heteroaryl is unsubstituted, i.e. it does not carry any substituent $Q^{13b}$. According to still another embodiment of formula I, it is substituted by $Q^{13b}$.

According to a further specific embodiment of formula I, $Q^3$ is $C_1$-$C_6$-alkyl, especially $CH_2$ subsitited by a 5-membered saturated heteroaryl which contains one oxygen and two N as ring members. According to one embodiment thereof, the heteroaryl is unsubstituted, i.e. it does not carry any substituent $Q^{13b}$. According to still another embodiment of formula I, it is substituted by $Q^{13b}$.

According to a further specific embodiment of formula I, $Q^3$ is $C_1$-$C_6$-alkyl, especially $CH_2$ subsitited by a 6-membered saturated heteroaryl which contains 1, 2 or 3, in particular 1 or 2, heteroatoms from the group consisting of N, O and S as ring members. According to one embodiment thereof, the heteroaryl is unsubstituted, i.e. it does not carry any substituent $Q^{13b}$. According to still another embodiment of formula I, it is substituted by $Q^{13b}$.

According to a further specific embodiment of formula I, $Q^3$ is $C_1$-$C_6$-alkyl, especially $CH_2$ subsitited by a 6-membered saturated heteroaryl which one N as ring member. According to one embodiment thereof, the heteroaryl is unsubstituted, i.e. it does not carry any substituent $Q^{13b}$. According to still another embodiment of formula I, it is substituted by $Q^{13b}$.

According to a further specific embodiment of formula I, $Q^3$ is $C_1$-$C_6$-alkyl, especially $CH_2$ subsitited by a 6-membered saturated heteroaryl which two N as ring members. According to one embodiment thereof, the heteroaryl is unsubstituted, i.e. it does not carry any substituent $Q^{13b}$. According to still another embodiment of formula I, it is substituted by $Q^{13b}$.

According to a further specific embodiment of formula I, $Q^3$ is $C_1$-$C_6$-alkyl, especially $CH_2$ subsitited by a 10-membered saturated heteroaryl which contains 1, 2 or 3, in particular 1 or 2, heteroatoms from the group consisting of N, O and S as ring members. According to one embodiment thereof, the heteroaryl is unsubstituted, i.e. it does not carry any substituent $Q^{13b}$. According to still another embodiment of formula I, it is substituted by $Q^{13b}$. According to one specific embodiment thereof, said 10-membered saturated heterocycle contains 1 or 2, in particular 1, heteroatom(s) N.

According to a further specific embodiment of formula I, $Q^3$ is $C_1$-$C_6$-alkyl, especially $CH_2$ subsitited by a 10-membered saturated heteroaryl which one N as ring members. According to one embodiment thereof, the heteroaryl is unsubstituted, i.e. it does not carry any substituent $Q^{13b}$. According to still another embodiment of formula I, it is substituted by $Q^{13b}$.

According to still another embodiment of formula I, $Q^3$ is $CH_2$ substituted by a 5-membered heteroaryl such as pyrrol-1-yl, pyrrol-2-yl, pyrrol-3-yl, thien-2-yl, thien-3-yl, furan-2-yl, furan-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-triazolyl-1-yl, 1,2,4-triazol-3-yl 1,2,4-triazol-5-yl, 1,2,4-oxadiazol-3-yl, 1,2,4-oxadiazol-5-yl and 1,2,4-thiadiazol-3-yl, 1,2,4-thiadiazol-5-yl.

According to still another embodiment of formula I, $Q^3$ is $CH_2$ substituted by a 6-membered heteroaryl, such as pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and 1,3,5-triazin-2-yl and 1,2,4-triazin-3-yl.

$^{bb}Q^{3a}$ are the possible substituents for the aliphatic moieties of $Q^3$.

$Q^{3a}$ according to the invention is independently selected from halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy and five- to ten-membered heterocycle, heteroaryl, heterocycloxy, heteryloxy; wherein the heterocycle or heteroaryl contains one, two or three heteroatoms selected from N, O and S; wherein the phenyl, phenoxy, heterocycle and heteroaryl groups are unsubstituted or substituted with 1, 2, 3, 4 or 5 substituents $Q^{13a}$ selected from the group consisting of halogen, OH, $C_1$-$C_4$-alkyl, $C_1$-$C_4$-halogenalkyl, $C_1$-$C_4$-alkoxy, $C_1$-$C_4$-halogenalkoxy, CR'=NOR"; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups are unsubstituted or substituted with 1, 2, 3, 4 or 5 substituents $Q^{113a}$ selected from the group consisting of halogen, OH, $C_1$-$C_4$-alkyl, $C_1$-$C_4$-halogenalkyl, $C_1$-$C_4$-alkoxy, CN, CR'=NOR" and $C_1$-$C_4$-halogenalkoxy.

In particular $Q^{3a}$ is selected from halogen, $C_1$-$C_2$-alkyl, $C_1$-$C_2$-halogenalkyl, $C_1$-$C_2$-alkoxy and $C_1$-$C_2$-halogenalkoxy, phenyl, phenoxy and five- to ten-membered heterocycle and heteroaryl. According to one embodiment $Q^{3a}$ is independently selected from halogen, OH, CN, $C_1$-$C_2$-alkoxy, $C_3$-$C_6$-cycloalkyl, $C_3$-$C_6$-halogencycloalkyl and $C_1$-$C_2$-halogenalkoxy. Specifically, $Q^{3a}$ is independently selected from F, Cl, OH, CN, $C_1$-$C_2$-alkoxy, cyclopropyl, 1-F-cyclopropyl, 1-Cl-cyclopropyl, $C_1$-$C_2$-halogenalkoxy, phenyl and five- to ten-membered heterocycle and heteroaryl.

According to one particular embodiment $Q^{3a}$ is independently selected from halogen, such as F, Cl, Br and I, more specifically F, Cl and Br.

According to a further embodiment, $Q^{3a}$ is independently selected from OH, $C_3$-$C_6$-cycloalkyl, $C_3$-$C_6$-halogencycloalkyl, $C_1$-$C_2$-halogenalkoxy, phenyl and five- to ten-membered heterocycle and heteroaryl. Specifically, $Q^{3a}$ is independently selected from OH, cyclopropyl and $C_1$-$C_2$-halogenalkoxy.

According to one embodiment $Q^{3a}$ is independently selected from halogen, OH, CN, $C_1$-$C_2$-alkoxy, $C_3$-$C_6$-cycloalkyl, $C_3$-$C_6$-halogencycloalkyl and $C_1$-$C_2$-halogenalkoxy. Specifically, $Q^{3a}$ is independently selected from F, Cl, OH, CN, $C_1$-$C_2$-alkoxy, cyclopropyl, 1-F-cyclopropyl, 1-Cl-cyclopropyl, $C_1$-$C_2$-halogenalkoxy, phenyl, five- and sex-membered heteroaryl.

According to one embodiment $Q^{3a}$ is independently selected from halogen, OH, CN, $C_1$-$C_2$-alkoxy, $C_3$-$C_6$-cycloalkyl, $C_3$-$C_6$-halogencycloalkyl, $C_1$-$C_2$-halogenalkoxy, phenyl and five- to ten-membered heterocycle and heteroaryl. Specifically, $Q^{3a}$ is independently selected from F, Cl, OH, CN, $C_1$-$C_2$-alkoxy, cyclopropyl, 1-F-cyclopropyl, 1-Cl-cyclopropyl, $C_1$-$C_2$-halogenalkoxy, phenyl, five- and sex-membered heteroaryl.

In the embodiments in which $Q^{3a}$ phenyl, phenoxy, heterocycle and heteroaryl groups, these groups are unsubstituted or substituted with 1, 2, 3, 4 or 5 substituents $Q^{13a}$ selected from the group consisting of halogen, OH, $C_1$-$C_4$-alkyl, $C_1$-$C_4$-halogenalkyl, $C_1$-$C_4$-alkoxy, $C_1$-$C_4$-halogenalkoxy; phenyl, phenoxy and five- to ten-membered heterocycle and heteroaryl; wherein the heterocycle or heteroaryl contains one, two or three heteroatoms selected from N, O and S; and wherein the phenyl, phenoxy, heterocycle and heteroaryl groups can be attached directly to $Q^{3a}$ or via O; and wherein the phenyl, phenoxy, heterocycle and heteroaryl groups are unsubstituted or substituted with 1, 2, 3, 4 or 5 substituents $Q^{113a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy.

$Q^{3b}$ are the possible substituents for the cycloalkyl, heteroaryl and aryl moieties of $Q^3$.

$Q^{3b}$ according to the invention is independently selected from halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl and $C_1$-$C_4$-halogenalkoxy.

According to one embodiment thereof $Q^{3b}$ is independently selected from halogen, CN, $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $Q^{3b}$ is independently selected from F, Cl, OH, CN, $CH_3$, $OCH_3$, cyclopropyl, 1-F-cyclopropyl, 1-Cl-cyclopropyl and halogenmethoxy.

According to a further embodiment thereof $Q^{3b}$ is independently selected from $C_1$-$C_2$-alkyl, $C_1$-$C_2$-alkoxy, $C_1$-$C_2$-halogenalkyl, $C_3$-$C_6$-cycloalkyl, $C_3$-$C_6$-halogencycloalkyl and $C_1$-$C_2$-halogenalkoxy. Specifically, $Q^{3b}$ is independently selected from OH, $CH_3$, $OCH_3$, cyclopropyl, 1-F-cyclopropyl, 1-Cl-cyclopropyl and halogenmethoxy, more specifically independently selected from OH, $CH_3$, $OCH_3$, cyclopropyl, 1-F-cyclopropyl, 1-Cl-cyclopropyl and $OCHF_2$.

Particularly preferred embodiments of $Q^3$ according to the invention are in Table P4 below, wherein each line of lines Q3-1 to Q3-180 corresponds to one particular embodiment of the invention, wherein Q3-1 to Q3-180 are also in any combination with one another a preferred embodiment of the present invention. The connection point to the W group, to which $Q^3$ is bound is marked with "#" in the drawings.

TABLE Q3

| No. | $Q^3$ |
|---|---|
| Q3-1 | $CH_3$ |
| Q3-2 | $CF_3$ |
| Q3-3 | $CH_2F$ |
| Q3-4 | $CH_2Cl$ |

TABLE Q3-continued

| No. | Q³ |
|---|---|
| Q3-5 | CHF₂ |
| Q3-6 | CHCl₂ |
| Q3-7 | CH₂CF₃ |
| Q3-8 | CH₂CCl₃ |
| Q3-9 | CF₂CHF₂ |
| Q3-10 | CH₂OCH₃ |
| Q3-11 | CH₂OCH₂F |
| Q3-12 | CH₂OCHF₂ |
| Q3-13 | CH₂OCF₃ |
| Q3-14 | CH₂OCF₂CHF₂ |
| Q3-15 | CH₂CH₃ |
| Q3-16 | oxetan-3-yl |
| Q3-17 | tetrahydrofuran-3-yl |
| Q3-18 | tetrahydro-2H-pyran-4-yl |
| Q3-19 | cyclopropyl |
| Q3-20 | 2,2-dichlorocyclopropyl |
| Q3-21 | 2,2-difluorocyclopropyl |
| Q3-22 | cyclobutyl |
| Q3-23 | cyclopentyl |
| Q3-24 | cyclohexyl |
| Q3-25 | (pyrrolidin-1-yl)methyl |
| Q3-26 | (2-oxopyrrolidin-1-yl)methyl |
| Q3-27 | (2,5-dioxopyrrolidin-1-yl)methyl |
| Q3-28 | CH₂CH=CCl₂ |
| Q3-29 | CH₂CH₂CH=CCl₂ |
| Q3-30 | CH₂CH=CF₂ |
| Q3-31 | CH₂C(F)=CF₂ |
| Q3-32 | CH=CF₂ |
| Q3-33 | CF=CF₂ |
| Q3-34 | C(CH₃)=CH₂ |
| Q3-35 | CH₂C≡CH |
| Q3-36 | CH₂C≡CCl |
| Q3-37 | CH₂C≡CCH₃ |
| Q3-38 | CH₂C≡C-cyclopropyl |
| Q3-39 | CH₂C≡CCF₃ |
| Q3-40 | C≡CH |
| Q3-41 | C≡CCl |
| Q3-42 | C≡CCH₃ |
| Q3-43 | C≡C-cyclopropyl |

TABLE Q3-continued

| No. | Q³ |
|---|---|
| Q3-44 | #—≡—CF₃ |
| Q3-45 | C₆H₅ |
| Q3-46 | 4-Cl—C₆H₄ |
| Q3-47 | 3-Cl—C₆H₄ |
| Q3-48 | 2-Cl—C₆H₄ |
| Q3-49 | 2,4-Cl₂—C₆H₃ |
| Q3-50 | 4-F—C₆H₄ |
| Q3-51 | 3-F—C₆H₄ |
| Q3-52 | 2-F—C₆H₄ |
| Q3-53 | 2,4-F₂—C₆H₃ |
| Q3-54 | 4-MeO—C₆H₄ |
| Q3-55 | 3-MeO—C₆H₄ |
| Q3-56 | 2-MeO—C₆H₄ |
| Q3-57 | 4-MeO₂S—C₆H₄ |
| Q3-58 | 3-MeO₂S—C₆H₄ |
| Q3-59 | 2-MeO₂S—C₆H₄ |
| Q3-60 | —CH₂—C₆H₅ |
| Q3-61 | —CH₂—C₆H₄-4-F |
| Q3-62 | —CH₂—C₆H₄-3-F |
| Q3-63 | —CH₂—C₆H₄-2-F |
| Q3-64 | —CH₂—C₆H₄-4-Cl |
| Q3-65 | —CH₂—C₆H₄-3-Cl |
| Q3-66 | —CH₂—C₆H₄-2-Cl |
| Q3-67 | —CH₂—C₆H₄-4-OCH₃ |
| Q3-68 | —CH₂—C₆H₄-3-OCH₃ |
| Q3-69 | —CH₂—C₆H₄-2-OCH₃ |
| Q3-70 | —CH₂—C₆H₄-4-CN |
| Q3-71 | —CH₂—C₆H₄-3-CN |
| Q3-72 | —CH₂—C₆H₄-2-CN |
| Q3-73 | —CH₂—C₆H₄-4-SO₂Me |
| Q3-74 | 3-py |
| Q3-75 | 2-py |
| Q3-76 | 4-py |
| Q3-77 | 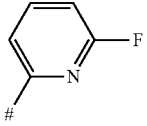 |
| Q3-78 | 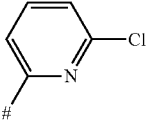 |
| Q3-79 | 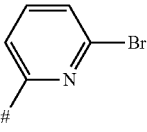 |
| Q3-80 | 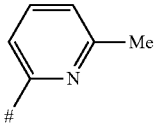 |
| Q3-81 | 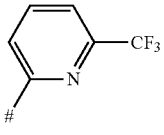 |
| Q3-82 | 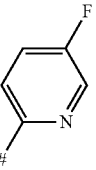 |
| Q3-83 | 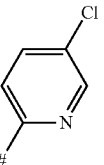 |
| Q3-84 | 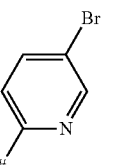 |
| Q3-85 | 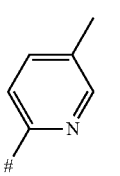 |
| Q3-86 | 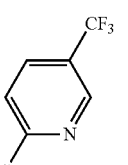 |
| Q3-87 | 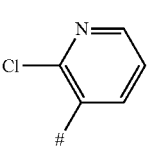 |
| Q3-88 | 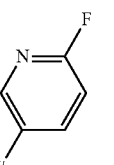 |
| Q3-89 | 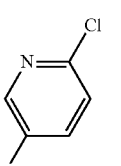 |
| Q3-90 | 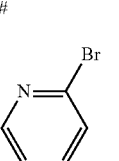 |
| Q3-91 | 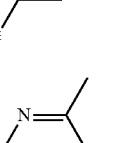 |

TABLE Q3-continued
| No. | Q³ |
|---|---|
| Q3-92 |  |
| Q3-93 |  |
| Q3-94 |  |
| Q3-95 |  |
| Q3-96 |  |
| Q3-97 |  |
| Q3-98 |  |
| Q3-99 |  |
| Q3-100 |  |
| Q3-101 | 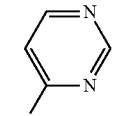 |
| Q3-102 | 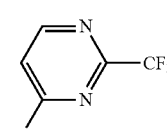 |
| Q3-103 | 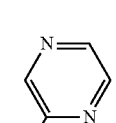 |
| Q3-104 | 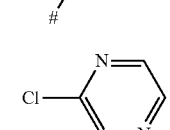 |
| Q3-105 | 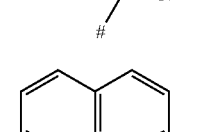 |
| Q3-106 | 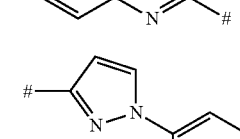 |
| Q3-107 | 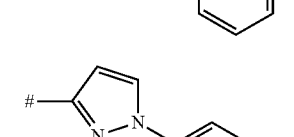 |
| Q3-108 | 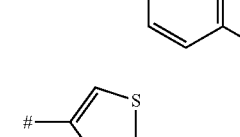 |
| Q3-109 | 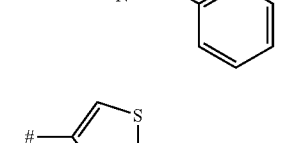 |
| Q3-110 | 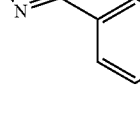 |
| Q3-111 | 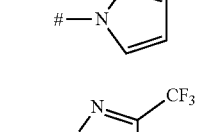 |

TABLE Q3-continued

| No. | Q³ |
|---|---|
| Q3-112 | (1H-1,2,4-triazol-1-yl, #-N) |
| Q3-113 | (1-methyl-1H-pyrazol-3-yl) |
| Q3-114 | (5-CF₃-1-methyl-1H-pyrazol-3-yl) |
| Q3-115 | (1H-1,2,4-triazol-1-yl) |
| Q3-116 | (3-CF₃-1H-1,2,4-triazol-1-yl) |
| Q3-117 | (thiazol-2-yl) |
| Q3-118 | (oxazol-2-yl) |
| Q3-119 | (thiophen-2-yl) |
| Q3-120 | (5-Cl-thiophen-2-yl) |
| Q3-121 | (1,2,4-oxadiazol-3-yl) |
| Q3-122 | (5-CF₃-1,2,4-oxadiazol-3-yl) |
| Q3-123 | (pyridin-2-ylmethyl) |
| Q3-124 | (5-F-pyridin-2-ylmethyl) |
| Q3-125 | (6-Cl-pyridin-2-ylmethyl) |
| Q3-126 | (6-Br-pyridin-2-ylmethyl) |
| Q3-127 | (6-methyl-pyridin-2-ylmethyl) |
| Q3-128 | (6-CF₃-pyridin-2-ylmethyl) |
| Q3-129 | (5-F-pyridin-2-ylmethyl) |
| Q3-130 | (5-Cl-pyridin-2-ylmethyl) |
| Q3-131 | (5-Br-pyridin-2-ylmethyl) |
| Q3-132 | (5-methyl-pyridin-2-ylmethyl) |
| Q3-133 | (5-CF₃-pyridin-2-ylmethyl) |
| Q3-134 | (pyridin-3-ylmethyl) |

TABLE Q3-continued
| No. | Q³ |
|---|---|
| Q3-135 | 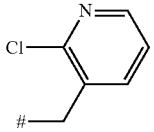 |
| Q3-136 | 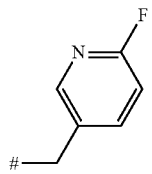 |
| Q3-137 | 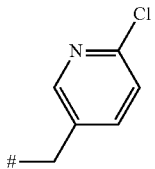 |
| Q3-138 | 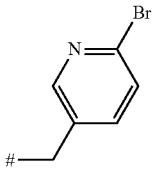 |
| Q3-139 | 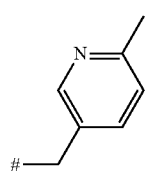 |
| Q3-140 | 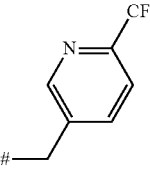 |
| Q3-141 | 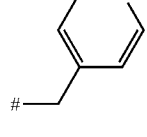 |
| Q3-142 | 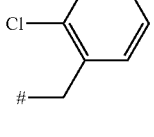 |
| Q3-143 | 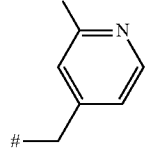 |
| Q3-144 | 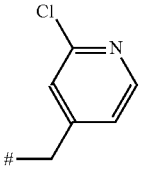 |
| Q3-145 |  |
| Q3-146 | 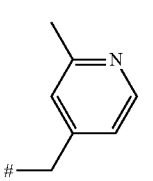 |
| Q3-147 |  |
| Q3-148 | 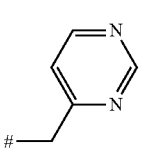 |
| Q3-149 | 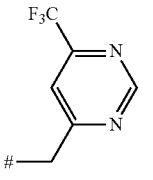 |
| Q3-150 | 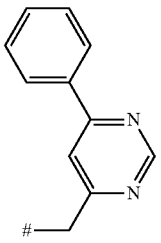 |
| Q3-151 | 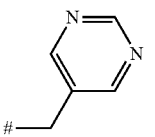 |

TABLE Q3-continued

| No. | Q³ |
|---|---|
| Q3-152 | 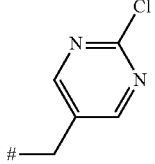 |
| Q3-153 | 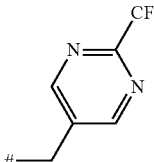 |
| Q3-154 | 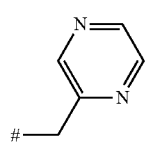 |
| Q3-155 | 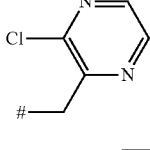 |
| Q3-156 | 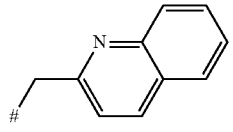 |
| Q3-157 | 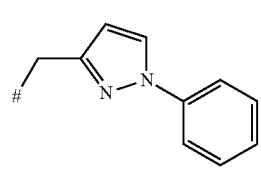 |
| Q3-158 | 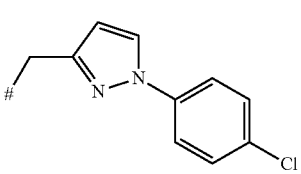 |
| Q3-159 | 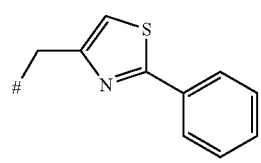 |
| Q3-160 | 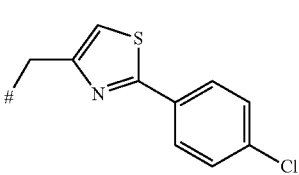 |
| Q3-161 | 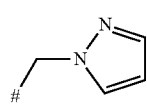 |

TABLE Q3-continued

| No. | Q³ |
|---|---|
| Q3-162 | 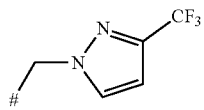 |
| Q3-163 | 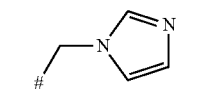 |
| Q3-164 | 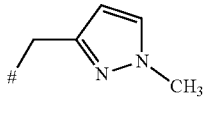 |
| Q3-165 | 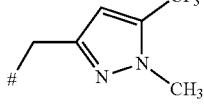 |
| Q3-166 | 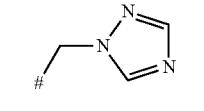 |
| Q3-167 | 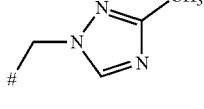 |
| Q3-168 | 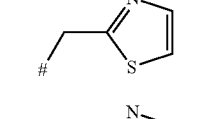 |
| Q3-169 | 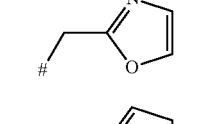 |
| Q3-170 | 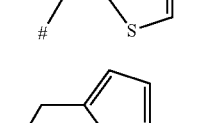 |
| Q3-171 | 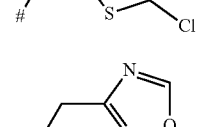 |
| Q3-172 | 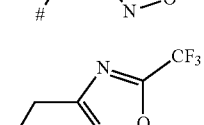 |
| Q3-173 | 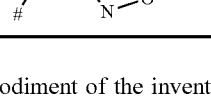 |

According to one embodiment of the invention W is O.

According to one further embodiment of the invention W is S.

$X^1$ according to the invention is is in each case independently selected from H, halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

$X^1$ according to the invention is in each case independently selected from H, halogen, CN, $C_1$-$C_4$-alkyl, $C_1$-$C_4$-halogenalkyl.

According to one specific embodiment, $X^1$ ist H.

According to a further specific embodiment $X^1$ is halogen, in particular Br, F or Cl, more specifically F or Cl.

According to a further specific embodiment, $X^1$ is CN.

According to a further specific embodiment, $X^1$ is $C_1$-$C_6$-alkyl, in particular $C_1$-$C_4$-alkyl, such as $CH_3$.

According to a further specific embodiment, $X^1$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $X^1$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to a further specific embodiment $X^1$ is $C_3$-$C_6$-cycloalkyl, in particular cyclopropyl.

In a further specific embodiment, $X^1$ is $C_3$-$C_6$-cycloalkyl, for example cyclopropyl, substituted by one, two, three or up to the maximum possible number of identical or different groups $R^{1b}$ as defined and preferably herein.

According to a specific embodiment $X^1$ is $C_3$-$C_6$-halogencycloalkyl. In a special embodiment $R^1$ is fully or partially halogenated cyclopropyl.

According to a further specific embodiment, $X^1$ is $C_1$-$C_6$-halogenalkoxy, in particular $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment, $X^1$ is selected from H, F, Cl, CN, $CH_3$, $CF_3$.

$X^2$ according to the invention is is in each case independently selected from H, halogen, OH, CN, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

$X^2$ according to the invention is in each case independently selected from H, halogen, CN, $C_1$-$C_4$-alkyl, $C_1$-$C_4$-halogenalkyl.

According to one specific embodiment, $X^2$ ist H.

According to a further specific embodiment $X^2$ is halogen, in particular Br, F or Cl, more specifically F or Cl.

According to a further specific embodiment, $X^2$ is CN.

According to a further specific embodiment, $X^2$ is $C_1$-$C_6$-alkyl, in particular $C_1$-$C_4$-alkyl, such as $CH_3$.

According to a further specific embodiment, $X^2$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $X^2$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to a further specific embodiment $X^2$ is $C_3$-$C_6$-cycloalkyl, in particular cyclopropyl.

In a further specific embodiment, $X^2$ is $C_3$-$C_6$-cycloalkyl, for example cyclopropyl, substituted by one, two, three or up to the maximum possible number of identical or different groups $R^{1b}$ as defined and preferably herein.

According to a specific embodiment $X^2$ is $C_3$-$C_6$-halogencycloalkyl. In a special embodiment $R^1$ is fully or partially halogenated cyclopropyl.

According to a further specific embodiment, $X^2$ is $C_1$-$C_6$-halogenalkoxy, in particular $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, $OCCl_3$ or $OCHCl_2$.

According to a further specific embodiment, $X^1$ is selected from H, F, Cl, CN, $CH_3$, $CF_3$.

$X^3$ according to the invention is is in each case independently selected from H, halogen, OH, CN, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio.

$X^3$ according to the invention is in each case independently selected from H, halogen, CN, $C_1$-$C_4$-alkyl, $C_1$-$C_4$-halogenalkyl.

According to one specific embodiment, $X^3$ ist H.

According to a further specific embodiment $X^3$ is halogen, in particular Br, F or Cl, more specifically F or Cl.

According to a further specific embodiment, $X^3$ is CN.

According to a further specific embodiment, $X^3$ is $C_1$-$C_6$-alkyl, in particular $C_1$-$C_4$-alkyl, such as $CH_3$.

According to a further specific embodiment, $X^3$ is $C_1$-$C_6$-alkoxy, in particular $C_1$-$C_4$-alkoxy, more specifically $C_1$-$C_2$-alkoxy such as $OCH_3$ or $OCH_2CH_3$.

According to a further specific embodiment, $X^3$ is $C_1$-$C_6$-halogenalkyl, in particular $C_1$-$C_4$-halogenalkyl, such as $CF_3$, $CHF_2$, $CH_2F$, $CCl_3$, $CHCl_2$ or $CH_2Cl$.

According to a further specific embodiment, $X^3$ is $C_3$-$C_6$-cycloalkyl, in particular cyclopropyl.

In a further specific embodiment, $X^3$ is $C_3$-$C_6$-cycloalkyl, for example cyclopropyl, substituted by one, two, three or up to the maximum possible number of identical or different groups $R^{1b}$ as defined and preferably herein.

According to a specific embodiment $X^3$ is $C_3$-$C_6$-halogencycloalkyl. In a special embodiment $R^1$ is fully or partially halogenated cyclopropyl.

According to a further specific embodiment, $X^3$ is $C_1$-$C_6$-halogenalkoxy, in particular $C_1$-$C_4$-halogenalkoxy, more specifically $C_1$-$C_2$-halogenalkoxy such as $OCF_3$, $OCHF_2$, $OCH_2F$, $OCCl_3$, $OCHCl_2$ or $OCH_2Cl$, in particular $OCF_3$, $OCHF_2$, or $OCHCl_2$.

According to a further specific embodiment, $X^3$ is selected from H, F, Cl, CN, $CH_3$, $CF_3$.

According to the invention if $X^1$, $X^2$ and $X^3$ is H $Q^3$ is not H and $CH_3$.

In a one specific embodiment if $X^1$, $X^2$ and $X^3$ is H $Q^3$ is not H and $C_1$-$C_6$-alkyl.

Preferred embodiments of the present invention are the following compounds I.A, I.B, I.C, I.D, I.E, I.F, I.G and I.H In these formulae, the substituents $R^1$, $R^2$, $R^3$, $R^4$, $Q^3$, X and n are independently as defined or preferably defined herein:

I.A

-continued
I.B
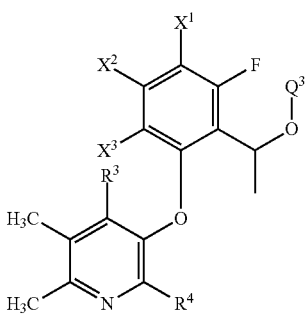
I.C
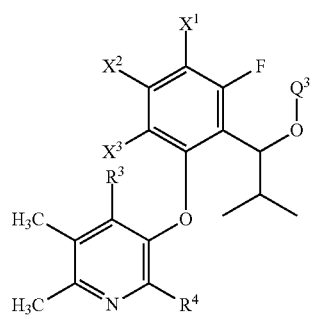
I.D
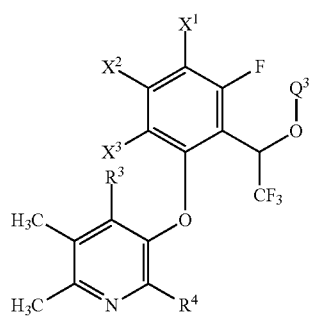
I.E
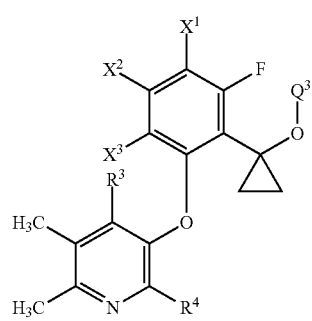
I.F
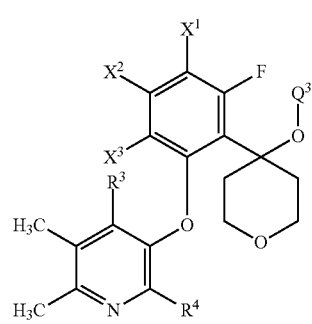
-continued
I.G
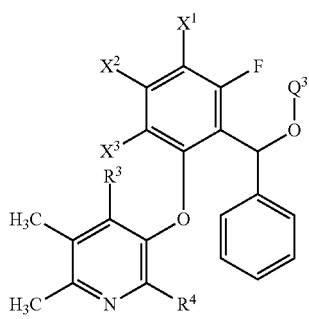
I.H
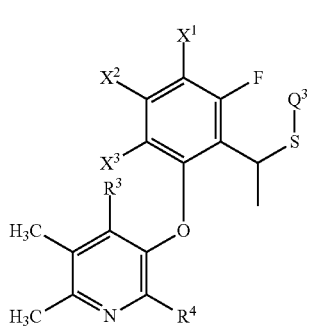
Preferred embodiments of the present invention are the following compounds I.A-1 to I.A-6, I.B-1 to I.B-6, I.C-1 to I.C-6, I.D-1 to I.D-6, I.E-1 to I.E-6, I.F-1 to I.F-6, I.G-1 to I.G-6, I.H-1 to I.H-6. In these formulae, the substituents $R^1$, $R^2$, $R^3$, $R^4$, $Q^3$, X and n are independently as defined or preferably defined herein:
I.A-1
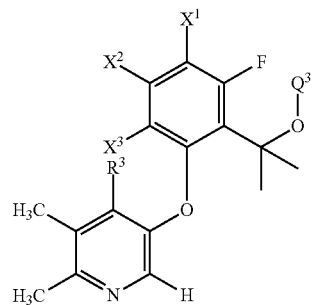
I.B-1
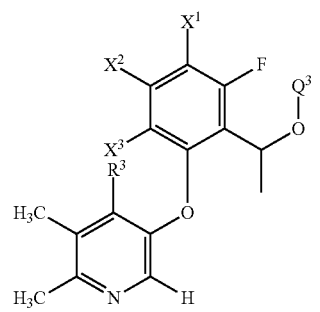

-continued
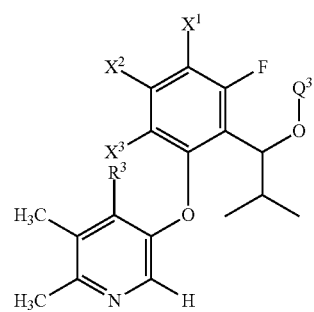
I.C-1
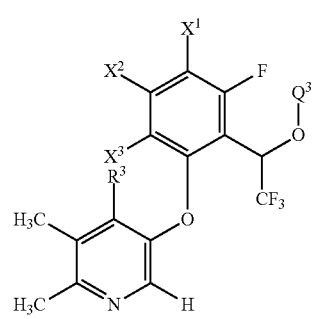
I.D-1
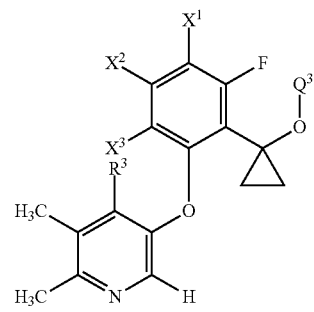
I.E-1
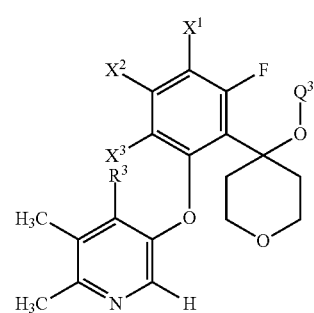
I.F-1
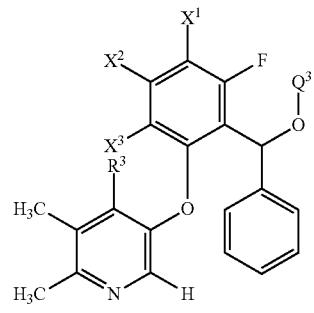
I.G-1
-continued
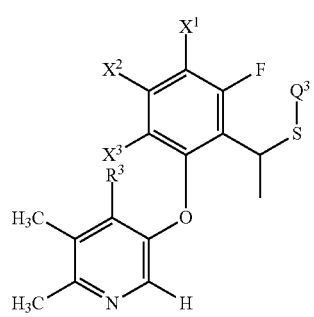
I.H-1
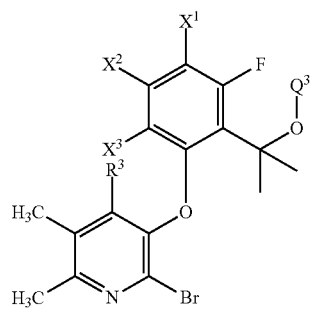
I.A-2
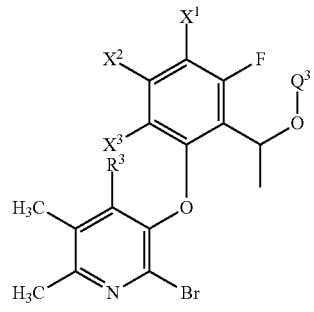
I.B-2
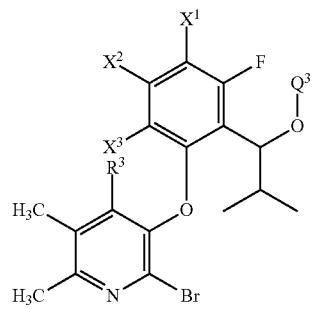
I.C-2
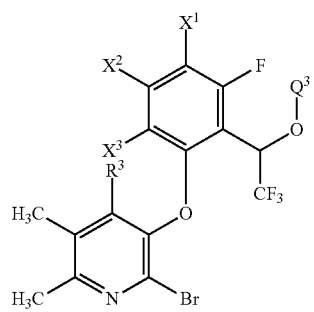
I.D-2

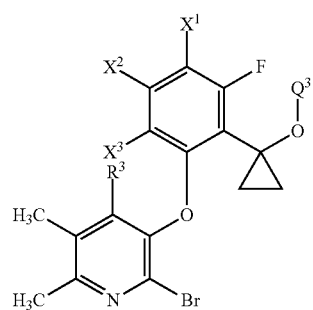 I.E-2
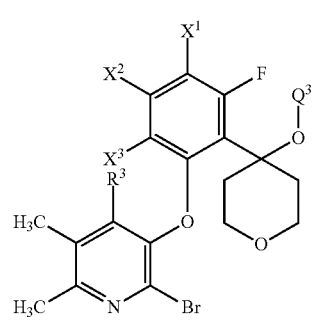 I.F-2
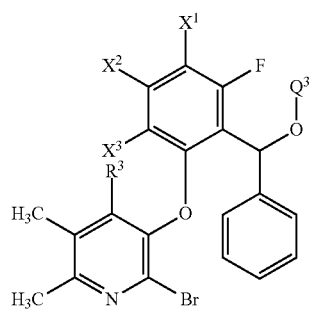 I.G-2
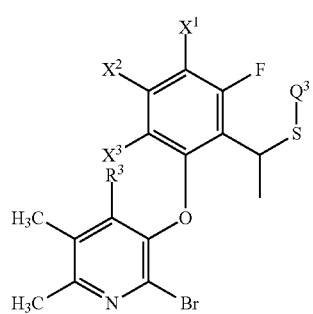 I.H-2
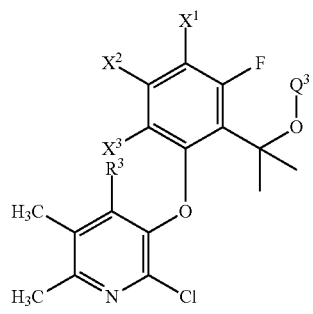 I.A-3
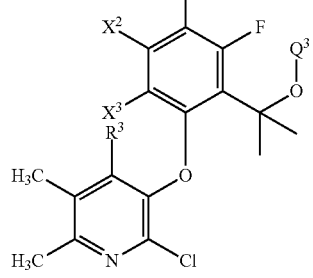 I.B-3
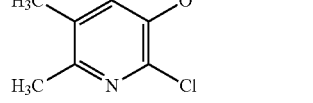 I.C-3
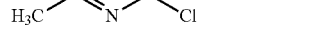 I.D-3
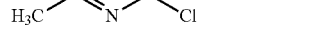 I.E-3
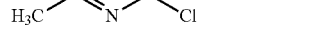 I.F-3

I.G-3
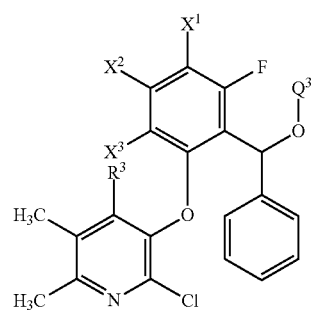
I.H-3
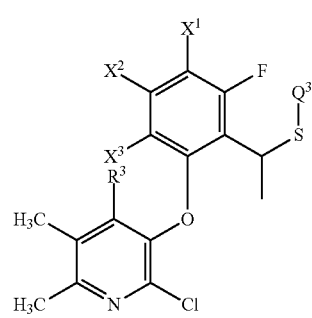
I.A-4
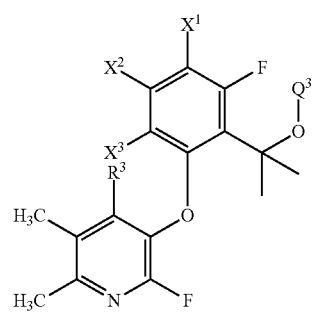
I.B-4
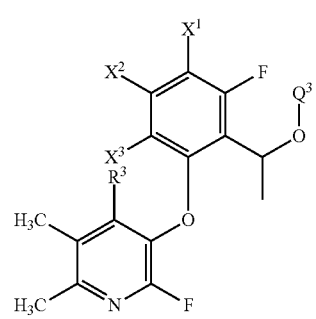
I.C-4
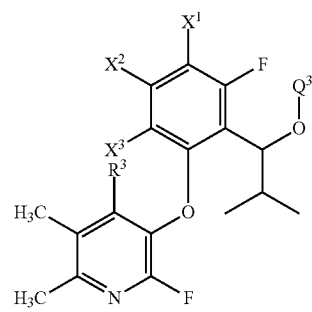
I.D-4
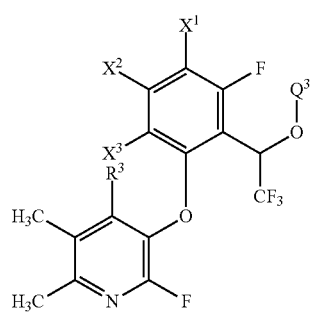
I.E-4
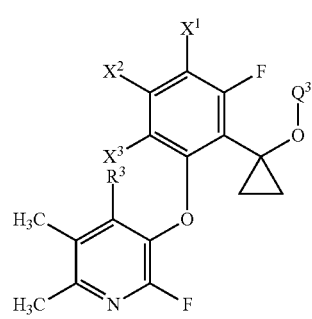
I.F-4
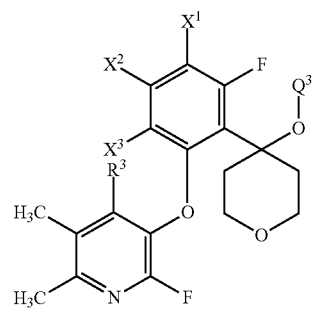
I.G-4
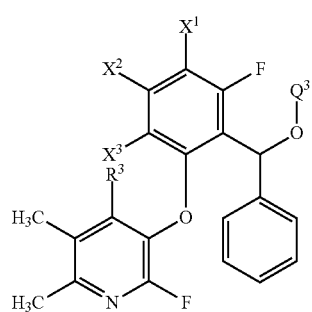
I.H-4
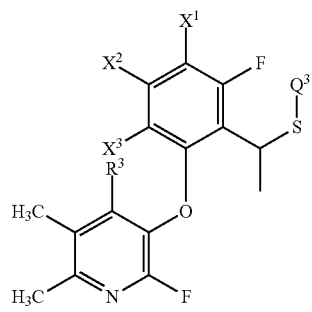

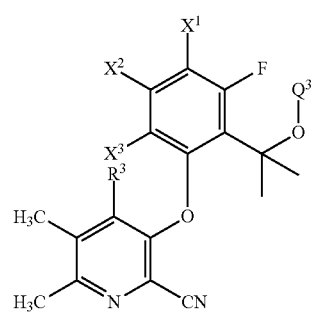
I.A-5
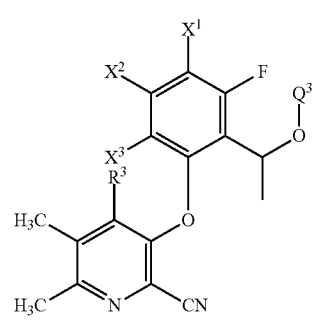
I.B-5
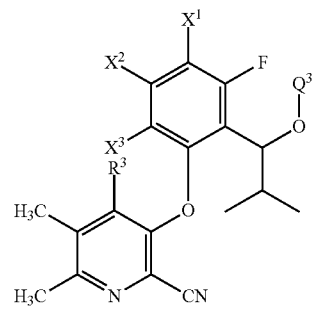
I.C-5
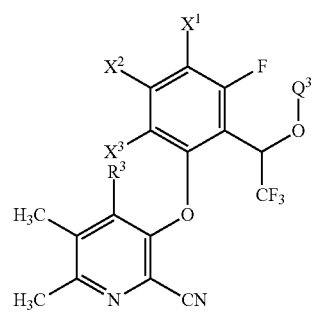
I.D-5
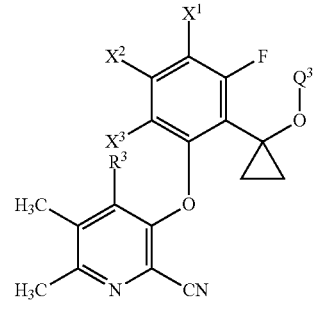
I.E-5
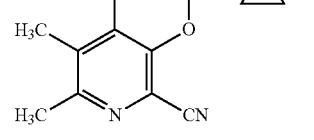
I.F-5
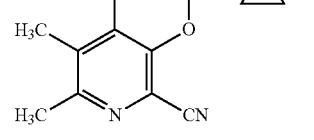
I.G-5
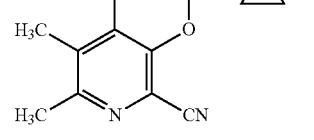
I.H-5
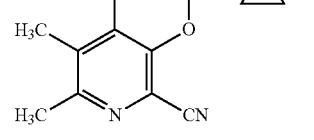
I.A-6
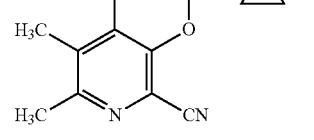
I.B-6

I.C-6

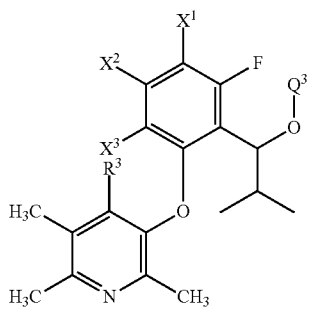

I.D-6

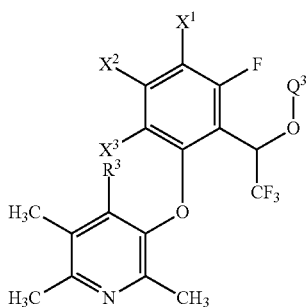

I.E-6

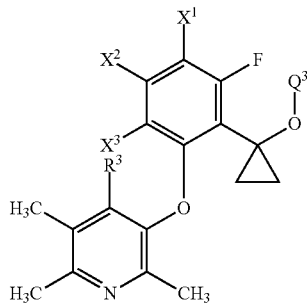

I.F-6

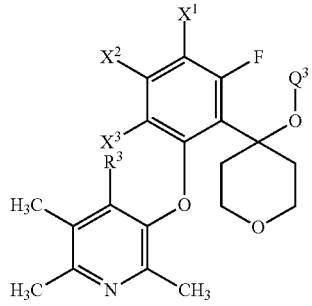

I.G-6

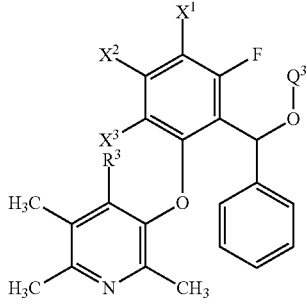

I.H-6

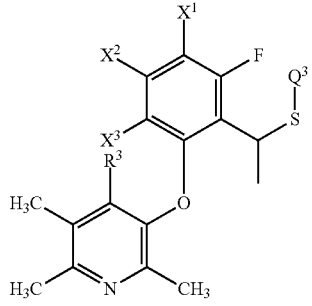

In particular with a view to their use, according to one embodiment, preference is given to the compounds of the formula I.A-1 to I.A-6, I.B-1 to I.B-6, I.C-1 to I.C-6, I.D-1 to I.D-6, I.E-1 to I.E-6, I.F-1 to I.F-6, I.G-1 to I.G-6 and I.H-1 to I.H-6 that are compiled in the Tables 1a to 41a. Each of the groups mentioned for a substituent in the tables is furthermore per se, independently of the combination in which it is mentioned, a particularly preferred aspect of the substituent in question.

Table 1a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-1 of Table X and the meaning for the combination of $X^1$, $X^2$, $X^3$ and $R^3$ for each individual compound corresponds in each case to one line of Table A (compounds I.A-1.X-1.A-1 to I.A-1.X-1.A-750; compounds I.B-1.X-1.A-1 to I.B-1.X-1.A-750; compounds I.C-1.X-1.A-1 to I.C-1.X-1.A-750; compounds I.D-1.X-1.A-1 to I.D-1.X-1.A-750; compounds I.E-1.X-1.A-1 to I.E-1.X-1.A-750; compounds I.F-1.X-1.A-1 to I.F-1.X-1.A-750; compounds I.G-1.X-1.A-1 to I.G-1.X-1.A-750; compounds I.H-1.X-1.A-1 to I.H-1.X-1.A-750;

compounds I.A-2.X-1.A-1 to I.A-2.X-1.A-750; compounds I.B-2.X-1.A-1 to I.B-2.X-1.A-750; compounds I.C-2.X-1.A-1 to I.C-2.X-1.A-750; compounds I.D-2.X-1.A-1 to I.D-2.X-1.A-750; compounds I.E-2.X-1.A-1 to I.E-2.X-1.A-750; compounds I.F-2.X-1.A-1 to I.F-2.X-1.A-750; compounds I.G-2.X-1.A-1 to I.G-2.X-1.A-750; compounds I.H-2.X-1.A-1 to I.H-2.X-1.A-750;

compounds I.A-3.X-1.A-1 to I.A-3.X-1.A-750; compounds I.B-3.X-1.A-1 to I.B-3.X-1.A-750; compounds I.C-3.X-1.A-1 to I.C-3.X-1.A-750; compounds I.D-3.X-1.A-1 to I.D-3.X-1.A-750; compounds I.E-3.X-1.A-1 to I.E-3.X-1.A-750; compounds I.F-3.X-1.A-1 to I.F-3.X-1.A-750; compounds I.G-3.X-1.A-1 to I.G-3.X-1.A-750; compounds I.H-3.X-1.A-1 to I.H-3.X-1.A-750;

compounds I.A-4.X-1.A-1 to I.A-4.X-1.A-750; compounds I.B-4.X-1.A-1 to I.B-4.X-1.A-750; compounds I.C-4.X-1.A-1 to I.C-4.X-1.A-750; compounds I.D-4.X-1.A-1 to I.D-4.X-1.A-750; compounds I.E-4.X-1.A-1 to I.E-4.X-1.A-750; compounds I.F-4.X-1.A-1 to I.F-4.X-1.A-750; compounds I.G-4.X-1.A-1 to I.G-4.X-1.A-750; compounds I.H-4.X-1.A-1 to I.H-4.X-1.A-750;

compounds I.A-5.X-1.A-1 to I.A-5.X-1.A-750; compounds I.B-5.X-1.A-1 to I.B-5.X-1.A-750; compounds I.C-5.X-1.A-1 to I.C-5.X-1.A-750; compounds I.D-5.X-1.A-1 to I.D-5.X-1.A-750; compounds I.E-5.X-1.A-1 to I.E-5.X-1.A-

750; compounds I.F-5.X-1.A-1 to I.F-5.X-1.A-750; compounds I.G-5.X-1.A-1 to I.G-5.X-1.A-750; compounds I.H-5.X-1.A-1 to I.H-5.X-1.A-750;

compounds I.A-6.X-1.A-1 to I.A-6.X-1.A-750; compounds I.B-6.X-1.A-1 to I.B-6.X-1.A-750; compounds I.C-6.X-1.A-1 to I.C-6.X-1.A-750; compounds I.D-6.X-1.A-1 to I.D-6.X-1.A-750; compounds I.E-6.X-1.A-1 to I.E-6.X-1.A-750; compounds I.F-6.X-1.A-1 to I.F-6.X-1.A-750; compounds I.G-6.X-1.A-1 to I.G-6.X-1.A-750; compounds I.H-6.X-1.A-1 to I.H-6.X-1.A-750).

Table 2a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-2 of Table X and the meaning for the combination of $X^1$, $X^2$, $X^3$ and $R^3$ for each individual compound corresponds in each case to one line of Table A (compounds I.A-1.X-2.A-1 to I.A-1.X-2.A-750; compounds I.B-1.X-2.A-1 to I.B-1.X-2.A-750; compounds I.C-1.X-2.A-1 to I.C-1.X-2.A-750; compounds I.D-1.X-2.A-1 to I.D-1.X-2.A-750; compounds I.E-1.X-2.A-1 to I.E-1.X-2.A-750; compounds I.F-1.X-2.A-1 to I.F-1.X-2.A-750; compounds I.G-1.X-2.A-1 to I.G-1.X-2.A-750; compounds I.H-1.X-2.A-1 to I.H-1.X-2.A-750;

compounds I.A-2.X-2.A-1 to I.A-2.X-2.A-750; compounds I.B-2.X-2.A-1 to I.B-2.X-2.A-750; compounds I.C-2.X-2.A-1 to I.C-2.X-2.A-750; compounds I.D-2.X-2.A-1 to I.D-2.X-2.A-750; compounds I.E-2.X-2.A-1 to I.E-2.X-2.A-750; compounds I.F-2.X-2.A-1 to I.F-2.X-2.A-750; compounds I.G-2.X-2.A-1 to I.G-2.X-2.A-750; compounds I.H-2.X-2.A-1 to I.H-2.X-2.A-750;

compounds I.A-3.X-2.A-1 to I.A-3.X-2.A-750; compounds I.B-3.X-2.A-1 to I.B-3.X-2.A-750; compounds I.C-3.X-2.A-1 to I.C-3.X-2.A-750; compounds I.D-3.X-2.A-1 to I.D-3.X-2.A-750; compounds I.E-3.X-2.A-1 to I.E-3.X-2.A-750; compounds I.F-3.X-2.A-1 to I.F-3.X-2.A-750; compounds I.G-3.X-2.A-1 to I.G-3.X-2.A-750; compounds I.H-3.X-2.A-1 to I.H-3.X-2.A-750;

compounds I.A-4.X-2.A-1 to I.A-4.X-2.A-750; compounds I.B-4.X-2.A-1 to I.B-4.X-2.A-750; compounds I.C-4.X-2.A-1 to I.C-4.X-2.A-750; compounds I.D-4.X-2.A-1 to I.D-4.X-2.A-750; compounds I.E-4.X-2.A-1 to I.E-4.X-2.A-750; compounds I.F-4.X-2.A-1 to I.F-4.X-2.A-750; compounds I.G-4.X-2.A-1 to I.G-4.X-2.A-750; compounds I.H-4.X-2.A-1 to I.H-4.X-2.A-750;

compounds I.A-5.X-2.A-1 to I.A-5.X-2.A-750; compounds I.B-5.X-2.A-1 to I.B-5.X-2.A-750; compounds I.C-5.X-2.A-1 to I.C-5.X-2.A-750; compounds I.D-5.X-2.A-1 to I.D-5.X-2.A-750; compounds I.E-5.X-2.A-1 to I.E-5.X-2.A-750; compounds I.F-5.X-2.A-1 to I.F-5.X-2.A-750; compounds I.G-5.X-2.A-1 to I.G-5.X-2.A-750; compounds I.H-5.X-2.A-1 to I.H-5.X-2.A-750;

compounds I.A-6.X-2.A-1 to I.A-6.X-2.A-750; compounds I.B-6.X-2.A-1 to I.B-6.X-2.A-750; compounds I.C-6.X-2.A-1 to I.C-6.X-2.A-750; compounds I.D-6.X-2.A-1 to I.D-6.X-2.A-750; compounds I.E-6.X-2.A-1 to I.E-6.X-2.A-750; compounds I.F-6.X-2.A-1 to I.F-6.X-2.A-750; compounds I.G-6.X-2.A-1 to I.G-6.X-2.A-750; compounds I.H-6.X-2.A-1 to I.H-6.X-2.A-750).

Table 3a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2,1-H.2; I.A-3, I.B-3, I.C-3, I.D-3, I.E-3, I.F-3, I.G-3,1-H.3; I.A-4, I.B-4, I.C-4, I.D-4, I.E-4, I.F-4, I.G-4, 1-H.4; I.A-5, I.B-5, I.C-5, I.D-5, I.E-5, I.F-5, I.G-5,1-H.5; I.A-6, I.B-6, I.C-6, I.D-6, I.E-6, I.F-6, I.G-6,1-H.6;

in which $Q^3$ is as defined in line X-3 of Table X and the meaning for the combination of $X^1$, $X^2$, $X^3$ and $R^3$ for each individual compound corresponds in each case to one line of Table A (compounds I.A-1.X-3.A-1 to I.A-1.X-3.A-750; compounds I.B-1.X-3.A-1 to I.B-1.X-3.A-750; compounds I.C-1.X-3.A-1 to I.C-1.X-3.A-750; compounds I.D-1.X-3.A-1 to I.D-1.X-3.A-750; compounds I.E-1.X-3.A-1 to I.E-1.X-3.A-750; compounds I.F-1.X-3.A-1 to I.F-1.X-3.A-750; compounds I.G-1.X-3.A-1 to I.G-1.X-3.A-750; compounds I.H-1.X-3.A-1 to I.H-1.X-3.A-750;

compounds I.A-2.X-3.A-1 to I.A-2.X-3.A-750; compounds I.B-2.X-3.A-1 to I.B-2.X-3.A-750; compounds I.C-2.X-3.A-1 to I.C-2.X-3.A-750; compounds I.D-2.X-3.A-1 to I.D-2.X-3.A-750; compounds I.E-2.X-3.A-1 to I.E-2.X-3.A-750; compounds I.F-2.X-3.A-1 to I.F-2.X-3.A-750; compounds I.G-2.X-3.A-1 to I.G-2.X-3.A-750; compounds I.H-2.X-3.A-1 to I.H-2.X-3.A-750;

compounds I.A-3.X-3.A-1 to I.A-3.X-3.A-750; compounds I.B-3.X-3.A-1 to I.B-3.X-3.A-750; compounds I.C-3.X-3.A-1 to I.C-3.X-3.A-750; compounds I.D-3.X-3.A-1 to I.D-3.X-3.A-750; compounds I.E-3.X-3.A-1 to I.E-3.X-3.A-750; compounds I.F-3.X-3.A-1 to I.F-3.X-3.A-750; compounds I.G-3.X-3.A-1 to I.G-3.X-3.A-750; compounds I.H-3.X-3.A-1 to I.H-3.X-3.A-750;

compounds I.A-4.X-3.A-1 to I.A-4.X-3.A-750; compounds I.B-4.X-3.A-1 to I.B-4.X-3.A-750; compounds I.C-4.X-3.A-1 to I.C-4.X-3.A-750; compounds I.D-4.X-3.A-1 to I.D-4.X-3.A-750; compounds I.E-4.X-3.A-1 to I.E-4.X-3.A-750; compounds I.F-4.X-3.A-1 to I.F-4.X-3.A-750; compounds I.G-4.X-3.A-1 to I.G-4.X-3.A-750; compounds I.H-4.X-3.A-1 to I.H-4.X-3.A-750;

compounds I.A-5.X-3.A-1 to I.A-5.X-3.A-750; compounds I.B-5.X-3.A-1 to I.B-5.X-3.A-750; compounds I.C-5.X-3.A-1 to I.C-5.X-3.A-750; compounds I.D-5.X-3.A-1 to I.D-5.X-3.A-750; compounds I.E-5.X-3.A-1 to I.E-5.X-3.A-750; compounds I.F-5.X-3.A-1 to I.F-5.X-3.A-750; compounds I.G-5.X-3.A-1 to I.G-5.X-3.A-750; compounds I.H-5.X-3.A-1 to I.H-5.X-3.A-750;

compounds I.A-6.X-3.A-1 to I.A-6.X-3.A-750; compounds I.B-6.X-3.A-1 to I.B-6.X-3.A-750; compounds I.C-6.X-3.A-1 to I.C-6.X-3.A-750; compounds I.D-6.X-3.A-1 to I.D-6.X-3.A-750; compounds I.E-6.X-3.A-1 to I.E-6.X-3.A-750; compounds I.F-6.X-3.A-1 to I.F-6.X-3.A-750; compounds I.G-6.X-3.A-1 to I.G-6.X-3.A-750; compounds I.H-6.X-3.A-1 to I.H-6.X-3.A-750).

Table 4a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-4 of Table X and the meaning for the combination of $X^1$, $X^2$, $X^3$ and $R^3$ for each individual compound corresponds in each case to one line of Table A (compounds I.A-1.X-4.A-1 to I.A-1.X-4.A-750; compounds I.B-1.X-4.A-1 to I.B-1.X-4.A-750; compounds I.C-1.X-4.A-1 to I.C-1.X-4.A-750; compounds I.D-1.X-4.A-1 to I.D-1.X-4.A-750; compounds I.E-1.X-4.A-1 to I.E-1.X-4.A-750; compounds I.F-1.X-4.A-1 to I.F-1.X-4.A-750; compounds I.G-1.X-4.A-1 to I.G-1.X-4.A-750; compounds I.H-1.X-4.A-1 to I.H-1.X-4.A-750;

compounds I.A-2.X-4.A-1 to I.A-2.X-4.A-750; compounds I.B-2.X-4.A-1 to I.B-2.X-4.A-750; compounds I.C-2.X-4.A-1 to I.C-2.X-4.A-750; compounds I.D-2.X-4.A-1 to I.D-2.X-4.A-750; compounds I.E-2.X-4.A-1 to I.E-2.X-4.A-750; compounds I.F-2.X-4.A-1 to I.F-2.X-4.A-750; compounds I.G-2.X-4.A-1 to I.G-2.X-4.A-750; compounds I.H-2.X-4.A-1 to I.H-2.X-4.A-750;

compounds I.A-3.X-4.A-1 to I.A-3.X-4.A-750; compounds I.B-3.X-4.A-1 to I.B-3.X-4.A-750; compounds I.C-3.X-4.A-1 to I.C-3.X-4.A-750; compounds I.D-3.X-4.A-1 to I.D-3.X-4.A-750; compounds I.E-3.X-4.A-1 to I.E-3.X-4.A-750; compounds I.F-3.X-4.A-1 to I.F-3.X-4.A-750; compounds I.G-3.X-4.A-1 to I.G-3.X-4.A-750; compounds I.H-3.X-4.A-1 to I.H-3.X-4.A-750;

compounds I.A-4.X-4.A-1 to I.A-4.X-4.A-750; compounds I.B-4.X-4.A-1 to I.B-4.X-4.A-750; compounds I.C-4.X-4.A-1 to I.C-4.X-4.A-750; compounds I.D-4.X-4.A-1 to I.D-4.X-4.A-750; compounds I.E-4.X-4.A-1 to I.E-4.X-4.A-750; compounds I.F-4.X-4.A-1 to I.F-4.X-4.A-750; compounds I.G-4.X-4.A-1 to I.G-4.X-4.A-750; compounds I.H-4.X-4.A-1 to I.H-4.X-4.A-750;

compounds I.A-5.X-4.A-1 to I.A-5.X-4.A-750; compounds I.B-5.X-4.A-1 to I.B-5.X-4.A-750; compounds I.C-5.X-4.A-1 to I.C-5.X-4.A-750; compounds I.D-5.X-4.A-1 to I.D-5.X-4.A-750; compounds I.E-5.X-4.A-1 to I.E-5.X-4.A-750; compounds I.F-5.X-4.A-1 to I.F-5.X-4.A-750; compounds I.G-5.X-4.A-1 to I.G-5.X-4.A-750; compounds I.H-5.X-4.A-1 to I.H-5.X-4.A-750;

compounds I.A-6.X-4.A-1 to I.A-6.X-4.A-750; compounds I.B-6.X-4.A-1 to I.B-6.X-4.A-750; compounds I.C-6.X-4.A-1 to I.C-6.X-4.A-750; compounds I.D-6.X-4.A-1 to I.D-6.X-4.A-750; compounds I.E-6.X-4.A-1 to I.E-6.X-4.A-750; compounds I.F-6.X-4.A-1 to I.F-6.X-4.A-750; compounds I.G-6.X-4.A-1 to I.G-6.X-4.A-750; compounds I.H-6.X-4.A-1 to I.H-6.X-4.A-750).

Table 5a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-5 of Table X and the meaning for the combination of $X^1$, $X^2$, $X^3$ and $R^3$ for each individual compound corresponds in each case to one line of Table A (compounds I.A-1.X-5.A-1 to I.A-1.X-5.A-750; compounds I.B-1.X-5.A-1 to I.B-1.X-5.A-750; compounds I.C-1.X-5.A-1 to I.C-1.X-5.A-750; compounds I.D-1.X-5.A-1 to I.D-1.X-5.A-750; compounds I.E-1.X-5.A-1 to I.E-1.X-5.A-750; compounds I.F-1.X-5.A-1 to I.F-1.X-5.A-750; compounds I.G-1.X-5.A-1 to I.G-1.X-5.A-750; compounds I.H-1.X-5.A-1 to I.H-1.X-5.A-750;

compounds I.A-2.X-5.A-1 to I.A-2.X-5.A-750; compounds I.B-2.X-5.A-1 to I.B-2.X-5.A-750; compounds I.C-2.X-5.A-1 to I.C-2.X-5.A-750; compounds I.D-2.X-5.A-1 to I.D-2.X-5.A-750; compounds I.E-2.X-5.A-1 to I.E-2.X-5.A-750; compounds I.F-2.X-5.A-1 to I.F-2.X-5.A-750; compounds I.G-2.X-5.A-1 to I.G-2.X-5.A-750; compounds I.H-2.X-5.A-1 to I.H-2.X-5.A-750;

compounds I.A-3.X-5.A-1 to I.A-3.X-5.A-750; compounds I.B-3.X-5.A-1 to I.B-3.X-5.A-750; compounds I.C-3.X-5.A-1 to I.C-3.X-5.A-750; compounds I.D-3.X-5.A-1 to I.D-3.X-5.A-750; compounds I.E-3.X-5.A-1 to I.E-3.X-5.A-750; compounds I.F-3.X-5.A-1 to I.F-3.X-5.A-750; compounds I.G-3.X-5.A-1 to I.G-3.X-5.A-750; compounds I.H-3.X-5.A-1 to I.H-3.X-5.A-750;

compounds I.A-4.X-5.A-1 to I.A-4.X-5.A-750; compounds I.B-4.X-5.A-1 to I.B-4.X-5.A-750; compounds I.C-4.X-5.A-1 to I.C-4.X-5.A-750; compounds I.D-4.X-5.A-1 to I.D-4.X-5.A-750; compounds I.E-4.X-5.A-1 to I.E-4.X-5.A-750; compounds I.F-4.X-5.A-1 to I.F-4.X-5.A-750; compounds I.G-4.X-5.A-1 to I.G-4.X-5.A-750; compounds I.H-4.X-5.A-1 to I.H-4.X-5.A-750;

compounds I.A-5.X-5.A-1 to I.A-5.X-5.A-750; compounds I.B-5.X-5.A-1 to I.B-5.X-5.A-750; compounds I.C-5.X-5.A-1 to I.C-5.X-5.A-750; compounds I.D-5.X-5.A-1 to I.D-5.X-5.A-750; compounds I.E-5.X-5.A-1 to I.E-5.X-5.A-750; compounds I.F-5.X-5.A-1 to I.F-5.X-5.A-750; compounds I.G-5.X-5.A-1 to I.G-5.X-5.A-750; compounds I.H-5.X-5.A-1 to I.H-5.X-5.A-750;

compounds I.A-6.X-5.A-1 to I.A-6.X-5.A-750; compounds I.B-6.X-5.A-1 to I.B-6.X-5.A-750; compounds I.C-6.X-5.A-1 to I.C-6.X-5.A-750; compounds I.D-6.X-5.A-1 to I.D-6.X-5.A-750; compounds I.E-6.X-5.A-1 to I.E-6.X-5.A-750; compounds I.F-6.X-5.A-1 to I.F-6.X-5.A-750; compounds I.G-6.X-5.A-1 to I.G-6.X-5.A-750; compounds I.H-6.X-5.A-1 to I.H-6.X-5.A-750).

Table 6a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-6 of Table X and the meaning for the combination of $X^1$, $X^2$, $X^3$ and $R^3$ for each individual compound corresponds in each case to one line of Table A (compounds I.A-1.X-6.A-1 to I.A-1.X-6.A-750; compounds I.B-1.X-6.A-1 to I.B-1.X-6.A-750; compounds I.C-1.X-6.A-1 to I.C-1.X-6.A-750; compounds I.D-1.X-6.A-1 to I.D-1.X-6.A-750; compounds I.E-1.X-6.A-1 to I.E-1.X-6.A-750; compounds I.F-1.X-6.A-1 to I.F-1.X-6.A-750; compounds I.G-1.X-6.A-1 to I.G-1.X-6.A-750; compounds I.H-1.X-6.A-1 to I.H-1.X-6.A-750;

compounds I.A-2.X-6.A-1 to I.A-2.X-6.A-750; compounds I.B-2.X-6.A-1 to I.B-2.X-6.A-750; compounds I.C-2.X-6.A-1 to I.C-2.X-6.A-750; compounds I.D-2.X-6.A-1 to I.D-2.X-6.A-750; compounds I.E-2.X-6.A-1 to I.E-2.X-6.A-750; compounds I.F-2.X-6.A-1 to I.F-2.X-6.A-750; compounds I.G-2.X-6.A-1 to I.G-2.X-6.A-750; compounds I.H-2.X-6.A-1 to I.H-2.X-6.A-750;

compounds I.A-3.X-6.A-1 to I.A-3.X-6.A-750; compounds I.B-3.X-6.A-1 to I.B-3.X-6.A-750; compounds I.C-3.X-6.A-1 to I.C-3.X-6.A-750; compounds I.D-3.X-6.A-1 to I.D-3.X-6.A-750; compounds I.E-3.X-6.A-1 to I.E-3.X-6.A-750; compounds I.F-3.X-6.A-1 to I.F-3.X-6.A-750; compounds I.G-3.X-6.A-1 to I.G-3.X-6.A-750; compounds I.H-3.X-6.A-1 to I.H-3.X-6.A-750;

compounds I.A-4.X-6.A-1 to I.A-4.X-6.A-750; compounds I.B-4.X-6.A-1 to I.B-4.X-6.A-750; compounds I.C-4.X-6.A-1 to I.C-4.X-6.A-750; compounds I.D-4.X-6.A-1 to I.D-4.X-6.A-750; compounds I.E-4.X-6.A-1 to I.E-4.X-6.A-750; compounds I.F-4.X-6.A-1 to I.F-4.X-6.A-750; compounds I.G-4.X-6.A-1 to I.G-4.X-6.A-750; compounds I.H-4.X-6.A-1 to I.H-4.X-6.A-750;

compounds I.A-5.X-6.A-1 to I.A-5.X-6.A-750; compounds I.B-5.X-6.A-1 to I.B-5.X-6.A-750; compounds I.C-5.X-6.A-1 to I.C-5.X-6.A-750; compounds I.D-5.X-6.A-1 to I.D-5.X-6.A-750; compounds I.E-5.X-6.A-1 to I.E-5.X-6.A-750; compounds I.F-5.X-6.A-1 to I.F-5.X-6.A-750; compounds I.G-5.X-6.A-1 to I.G-5.X-6.A-750; compounds I.H-5.X-6.A-1 to I.H-5.X-6.A-750;

compounds I.A-6.X-6.A-1 to I.A-6.X-6.A-750; compounds I.B-6.X-6.A-1 to I.B-6.X-6.A-750; compounds I.C-6.X-6.A-1 to I.C-6.X-6.A-750; compounds I.D-6.X-6.A-1 to I.D-6.X-6.A-750; compounds I.E-6.X-6.A-1 to I.E-6.X-6.A-750; compounds I.F-6.X-6.A-1 to I.F-6.X-6.A-750; compounds I.G-6.X-6.A-1 to I.G-6.X-6.A-750; compounds I.H-6.X-6.A-1 to I.H-6.X-6.A-750).

Table 7a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-7 of Table X and the meaning for the combination of $X^1$, $X^2$, $X^3$ and $R^3$ for each individual compound corresponds in each case to one line of Table A (compounds I.A-1.X-7.A-1 to I.A-1.X-7.A-750; compounds I.B-1.X-7.A-1 to I.B-1.X-7.A-750; compounds I.C-1.X-7.A-1 to I.C-1.X-7.A-750; compounds I.D-1.X-7.A-1 to I.D-1.X-7.A-750; compounds I.E-1.X-7.A-1 to I.E-1.X-7.A-750; compounds I.F-1.X-7.A-1 to I.F-1.X-7.A-750; compounds I.G-1.X-7.A-1 to I.G-1.X-7.A-750; compounds I.H-1.X-7.A-1 to I.H-1.X-7.A-750;

compounds I.A-2.X-7.A-1 to I.A-2.X-7.A-750; compounds I.B-2.X-7.A-1 to I.B-2.X-7.A-750; compounds I.C-2.X-7.A-1 to I.C-2.X-7.A-750; compounds I.D-2.X-7.A-1 to I.D-2.X-7.A-750; compounds I.E-2.X-7.A-1 to I.E-2.X-7.A-750; compounds I.F-2.X-7.A-1 to I.F-2.X-7.A-750; compounds I.G-2.X-7.A-1 to I.G-2.X-7.A-750; compounds I.H-2.X-7.A-1 to I.H-2.X-7.A-750;

compounds I.A-3.X-7.A-1 to I.A-3.X-7.A-750; compounds I.B-3.X-7.A-1 to I.B-3.X-7.A-750; compounds I.C-3.X-7.A-1 to I.C-3.X-7.A-750; compounds I.D-3.X-7.A-1 to I.D-3.X-7.A-750; compounds I.E-3.X-7.A-1 to I.E-3.X-7.A-750; compounds I.F-3.X-7.A-1 to I.F-3.X-7.A-750; compounds I.G-3.X-7.A-1 to I.G-3.X-7.A-750; compounds I.H-3.X-7.A-1 to I.H-3.X-7.A-750;

compounds I.A-4.X-7.A-1 to I.A-4.X-7.A-750; compounds I.B-4.X-7.A-1 to I.B-4.X-7.A-750; compounds I.C-4.X-7.A-1 to I.C-4.X-7.A-750; compounds I.D-4.X-7.A-1 to I.D-4.X-7.A-750; compounds I.E-4.X-7.A-1 to I.E-4.X-7.A-750; compounds I.F-4.X-7.A-1 to I.F-4.X-7.A-750; compounds I.G-4.X-7.A-1 to I.G-4.X-7.A-750; compounds I.H-4.X-7.A-1 to I.H-4.X-7.A-750;

compounds I.A-5.X-7.A-1 to I.A-5.X-7.A-750; compounds I.B-5.X-7.A-1 to I.B-5.X-7.A-750; compounds I.C-5.X-7.A-1 to I.C-5.X-7.A-750; compounds I.D-5.X-7.A-1 to I.D-5.X-7.A-750; compounds I.E-5.X-7.A-1 to I.E-5.X-7.A-750; compounds I.F-5.X-7.A-1 to I.F-5.X-7.A-750; compounds I.G-5.X-7.A-1 to I.G-5.X-7.A-750; compounds I.H-5.X-7.A-1 to I.H-5.X-7.A-750;

compounds I.A-6.X-7.A-1 to I.A-6.X-7.A-750; compounds I.B-6.X-7.A-1 to I.B-6.X-7.A-750; compounds I.C-6.X-7.A-1 to I.C-6.X-7.A-750; compounds I.D-6.X-7.A-1 to I.D-6.X-7.A-750; compounds I.E-6.X-7.A-1 to I.E-6.X-7.A-750; compounds I.F-6.X-7.A-1 to I.F-6.X-7.A-750; compounds I.G-6.X-7.A-1 to I.G-6.X-7.A-750; compounds I.H-6.X-7.A-1 to I.H-6.X-7.A-750).

Table 8a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-8 of Table X and the meaning for the combination of $X^1$, $X^2$, $X^3$ and $R^3$ for each individual compound corresponds in each case to one line of Table A (compounds I.A-1.X-8.A-1 to I.A-1.X-8.A-750; compounds I.B-1.X-8.A-1 to I.B-1.X-8.A-750; compounds I.C-1.X-8.A-1 to I.C-1.X-8.A-750; compounds I.D-1.X-8.A-1 to I.D-1.X-8.A-750; compounds I.E-1.X-8.A-1 to I.E-1.X-8.A-750; compounds I.F-1.X-8.A-1 to I.F-1.X-8.A-750; compounds I.G-1.X-8.A-1 to I.G-1.X-8.A-750; compounds I.H-1.X-8.A-1 to I.H-1.X-8.A-750;

compounds I.A-2.X-8.A-1 to I.A-2.X-8.A-750; compounds I.B-2.X-8.A-1 to I.B-2.X-8.A-750; compounds I.C-2.X-8.A-1 to I.C-2.X-8.A-750; compounds I.D-2.X-8.A-1 to I.D-2.X-8.A-750; compounds I.E-2.X-8.A-1 to I.E-2.X-8.A-750; compounds I.F-2.X-8.A-1 to I.F-2.X-8.A-750; compounds I.G-2.X-8.A-1 to I.G-2.X-8.A-750; compounds I.H-2.X-8.A-1 to I.H-2.X-8.A-750;

compounds I.A-3.X-8.A-1 to I.A-3.X-8.A-750; compounds I.B-3.X-8.A-1 to I.B-3.X-8.A-750; compounds I.C-3.X-8.A-1 to I.C-3.X-8.A-750; compounds I.D-3.X-8.A-1 to I.D-3.X-8.A-750; compounds I.E-3.X-8.A-1 to I.E-3.X-8.A-750; compounds I.F-3.X-8.A-1 to I.F-3.X-8.A-750; compounds I.G-3.X-8.A-1 to I.G-3.X-8.A-750; compounds I.H-3.X-8.A-1 to I.H-3.X-8.A-750;

compounds I.A-4.X-8.A-1 to I.A-4.X-8.A-750; compounds I.B-4.X-8.A-1 to I.B-4.X-8.A-750; compounds I.C-4.X-8.A-1 to I.C-4.X-8.A-750; compounds I.D-4.X-8.A-1 to I.D-4.X-8.A-750; compounds I.E-4.X-8.A-1 to I.E-4.X-8.A-750; compounds I.F-4.X-8.A-1 to I.F-4.X-8.A-750; compounds I.G-4.X-8.A-1 to I.G-4.X-8.A-750; compounds I.H-4.X-8.A-1 to I.H-4.X-8.A-750;

compounds I.A-5.X-8.A-1 to I.A-5.X-8.A-750; compounds I.B-5.X-8.A-1 to I.B-5.X-8.A-750; compounds I.C-5.X-8.A-1 to I.C-5.X-8.A-750; compounds I.D-5.X-8.A-1 to I.D-5.X-8.A-750; compounds I.E-5.X-8.A-1 to I.E-5.X-8.A-750; compounds I.F-5.X-8.A-1 to I.F-5.X-8.A-750; compounds I.G-5.X-8.A-1 to I.G-5.X-8.A-750; compounds I.H-5.X-8.A-1 to I.H-5.X-8.A-750;

compounds I.A-6.X-8.A-1 to I.A-6.X-8.A-750; compounds I.B-6.X-8.A-1 to I.B-6.X-8.A-750; compounds I.C-6.X-8.A-1 to I.C-6.X-8.A-750; compounds I.D-6.X-8.A-1 to I.D-6.X-8.A-750; compounds I.E-6.X-8.A-1 to I.E-6.X-8.A-750; compounds I.F-6.X-8.A-1 to I.F-6.X-8.A-750; compounds I.G-6.X-8.A-1 to I.G-6.X-8.A-750; compounds I.H-6.X-8.A-1 to I.H-6.X-8.A-750).

Table 9a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-9 of Table X and the meaning for the combination of $X^1$, $X^2$, $X^3$ and $R^3$ for each individual compound corresponds in each case to one line of Table A (compounds I.A-1.X-9.A-1 to I.A-1.X-9.A-750; compounds I.B-1.X-9.A-1 to I.B-1.X-9.A-750; compounds I.C-1.X-9.A-1 to I.C-1.X-9.A-750; compounds I.D-1.X-9.A-1 to I.D-1.X-9.A-750; compounds I.E-1.X-9.A-1 to I.E-1.X-9.A-750; compounds I.F-1.X-9.A-1 to I.F-1.X-9.A-750; compounds I.G-1.X-9.A-1 to I.G-1.X-9.A-750; compounds I.H-1.X-9.A-1 to I.H-1.X-9.A-750;

compounds I.A-2.X-9.A-1 to I.A-2.X-9.A-750; compounds I.B-2.X-9.A-1 to I.B-2.X-9.A-750; compounds I.C-2.X-9.A-1 to I.C-2.X-9.A-750; compounds I.D-2.X-9.A-1 to I.D-2.X-9.A-750; compounds I.E-2.X-9.A-1 to I.E-2.X-9.A-750; compounds I.F-2.X-9.A-1 to I.F-2.X-9.A-750; compounds I.G-2.X-9.A-1 to I.G-2.X-9.A-750; compounds I.H-2.X-9.A-1 to I.H-2.X-9.A-750;

compounds I.A-3.X-9.A-1 to I.A-3.X-9.A-750; compounds I.B-3.X-9.A-1 to I.B-3.X-9.A-750; compounds I.C-3.X-9.A-1 to I.C-3.X-9.A-750; compounds I.D-3.X-9.A-1 to I.D-3.X-9.A-750; compounds I.E-3.X-9.A-1 to I.E-3.X-9.A-750; compounds I.F-3.X-9.A-1 to I.F-3.X-9.A-750; compounds I.G-3.X-9.A-1 to I.G-3.X-9.A-750; compounds I.H-3.X-9.A-1 to I.H-3.X-9.A-750;

compounds I.A-4.X-9.A-1 to I.A-4.X-9.A-750; compounds I.B-4.X-9.A-1 to I.B-4.X-9.A-750; compounds I.C-4.X-9.A-1 to I.C-4.X-9.A-750; compounds I.D-4.X-9.A-1 to I.D-4.X-9.A-750; compounds I.E-4.X-9.A-1 to I.E-4.X-9.A-750; compounds I.F-4.X-9.A-1 to I.F-4.X-9.A-750; compounds I.G-4.X-9.A-1 to I.G-4.X-9.A-750; compounds I.H-4.X-9.A-1 to I.H-4.X-9.A-750;

compounds I.A-5.X-9.A-1 to I.A-5.X-9.A-750; compounds I.B-5.X-9.A-1 to I.B-5.X-9.A-750; compounds I.C-5.X-9.A-1 to I.C-5.X-9.A-750; compounds I.D-5.X-9.A-1 to I.D-5.X-9.A-750; compounds I.E-5.X-9.A-1 to I.E-5.X-9.A-750; compounds I.F-5.X-9.A-1 to I.F-5.X-9.A-750; compounds I.G-5.X-9.A-1 to I.G-5.X-9.A-750; compounds I.H-5.X-9.A-1 to I.H-5.X-9.A-750;

compounds I.A-6.X-9.A-1 to I.A-6.X-9.A-750; compounds I.B-6.X-9.A-1 to I.B-6.X-9.A-750; compounds I.C-6.X-9.A-1 to I.C-6.X-9.A-750; compounds I.D-6.X-9.A-1 to I.D-6.X-9.A-750; compounds I.E-6.X-9.A-1 to I.E-6.X-9.A-750; compounds I.F-6.X-9.A-1 to I.F-6.X-9.A-750; compounds I.G-6.X-9.A-1 to I.G-6.X-9.A-750; compounds I.H-6.X-9.A-1 to I.H-6.X-9.A-750).

Table 10a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I.H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-10 of Table X and the meaning for the combination of $X^1$, $X^2$, $X^3$ and $R^3$ for each individual compound corresponds in each case to one line of Table A (compounds I.A-1.X-10.A-1 to I.A-1.X-10.A-750; compounds I.B-1.X-10.A-1 to I.B-1.X-10.A-750; compounds I.C-1.X-10.A-1 to I.C-1.X-10.A-750; compounds I.D-1.X-10.A-1 to I.D-1.X-10.A-750; compounds I.E-1.X-10.A-1 to I.E-1.X-10.A-750; compounds I.F-1.X-10.A-1 to I.F-1.X-10.A-750; compounds I.G-1.X-10.A-1 to I.G-1.X-10.A-750; compounds I.H-1.X-10.A-1 to I.H-1.X-10.A-750;

compounds I.A-2.X-10.A-1 to I.A-2.X-10.A-750; compounds I.B-2.X-10.A-1 to I.B-2.X-10.A-750; compounds I.C-2.X-10.A-1 to I.C-2.X-10.A-750; compounds I.D-2.X-10.A-1 to I.D-2.X-10.A-750; compounds I.E-2.X-10.A-1 to I.E-2.X-10.A-750; compounds I.F-2.X-10.A-1 to I.F-2.X-10.A-750; compounds I.G-2.X-10.A-1 to I.G-2.X-10.A-750; compounds I.H-2.X-10.A-1 to I.H-2.X-10.A-750;

compounds I.A-3.X-10.A-1 to I.A-3.X-10.A-750; compounds I.B-3.X-10.A-1 to I.B-3.X-10.A-750; compounds I.C-3.X-10.A-1 to I.C-3.X-10.A-750; compounds I.D-3.X-10.A-1 to I.D-3.X-10.A-750; compounds I.E-3.X-10.A-1 to I.E-3.X-10.A-750; compounds I.F-3.X-10.A-1 to I.F-3.X-10.A-750; compounds I.G-3.X-10.A-1 to I.G-3.X-10.A-750; compounds I.H-3.X-10.A-1 to I.H-3.X-10.A-750;

compounds I.A-4.X-10.A-1 to I.A-4.X-10.A-750; compounds I.B-4.X-10.A-1 to I.B-4.X-10.A-750; compounds I.C-4.X-10.A-1 to I.C-4.X-10.A-750; compounds I.D-4.X-10.A-1 to I.D-4.X-10.A-750; compounds I.E-4.X-10.A-1 to I.E-4.X-10.A-750; compounds I.F-4.X-10.A-1 to I.F-4.X-10.A-750; compounds I.G-4.X-10.A-1 to I.G-4.X-10.A-750; compounds I.H-4.X-10.A-1 to I.H-4.X-10.A-750;

compounds I.A-5.X-10.A-1 to I.A-5.X-10.A-750; compounds I.B-5.X-10.A-1 to I.B-5.X-10.A-750; compounds I.C-5.X-10.A-1 to I.C-5.X-10.A-750; compounds I.D-5.X-10.A-1 to I.D-5.X-10.A-750; compounds I.E-5.X-10.A-1 to I.E-5.X-10.A-750; compounds I.F-5.X-10.A-1 to I.F-5.X-10.A-750; compounds I.G-5.X-10.A-1 to I.G-5.X-10.A-750; compounds I.H-5.X-10.A-1 to I.H-5.X-10.A-750;

compounds I.A-6.X-10.A-1 to I.A-6.X-10.A-750; compounds I.B-6.X-10.A-1 to I.B-6.X-10.A-750; compounds I.C-6.X-10.A-1 to I.C-6.X-10.A-750; compounds I.D-6.X-10.A-1 to I.D-6.X-10.A-750; compounds I.E-6.X-10.A-1 to I.E-6.X-10.A-750; compounds I.F-6.X-10.A-1 to I.F-6.X-10.A-750; compounds I.G-6.X-10.A-1 to I.G-6.X-10.A-750; compounds I.H-6.X-10.A-1 to I.H-6.X-10.A-750).

Table 11a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I.H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-11 of Table X and the meaning for the combination of $X^1$, $X^2$, $X^3$ and $R^3$ for each individual compound corresponds in each case to one line of Table A (compounds I.A-1.X-11.A-1 to I.A-1.X-11.A-750; compounds I.B-1.X-11.A-1 to I.B-1.X-11.A-750; compounds I.C-1.X-11.A-1 to I.C-1.X-11.A-750; compounds I.D-1.X-11.A-1 to I.D-1.X-11.A-750; compounds I.E-1.X-11.A-1 to I.E-1.X-11.A-750; compounds I.F-1.X-11.A-1 to I.F-1.X-11.A-750; compounds I.G-1.X-11.A-1 to I.G-1.X-11.A-750; compounds I.H-1.X-11.A-1 to I.H-1.X-11.A-750;

compounds I.A-2.X-11.A-1 to I.A-2.X-11.A-750; compounds I.B-2.X-11.A-1 to I.B-2.X-11.A-750; compounds I.C-2.X-11.A-1 to I.C-2.X-11.A-750; compounds I.D-2.X-11.A-1 to I.D-2.X-11.A-750; compounds I.E-2.X-11.A-1 to I.E-2.X-11.A-750; compounds I.F-2.X-11.A-1 to I.F-2.X-11.A-750; compounds I.G-2.X-11.A-1 to I.G-2.X-11.A-750; compounds I.H-2.X-11.A-1 to I.H-2.X-11.A-750;

compounds I.A-3.X-11.A-1 to I.A-3.X-11.A-750; compounds I.B-3.X-11.A-1 to I.B-3.X-11.A-750; compounds I.C-3.X-11.A-1 to I.C-3.X-11.A-750; compounds I.D-3.X-11.A-1 to I.D-3.X-11.A-750; compounds I.E-3.X-11.A-1 to I.E-3.X-11.A-750; compounds I.F-3.X-11.A-1 to I.F-3.X-11.A-750; compounds I.G-3.X-11.A-1 to I.G-3.X-11.A-750; compounds I.H-3.X-11.A-1 to I.H-3.X-11.A-750;

compounds I.A-4.X-11.A-1 to I.A-4.X-11.A-750; compounds I.B-4.X-11.A-1 to I.B-4.X-11.A-750; compounds I.C-4.X-11.A-1 to I.C-4.X-11.A-750; compounds I.D-4.X-11.A-1 to I.D-4.X-11.A-750; compounds I.E-4.X-11.A-1 to I.E-4.X-11.A-750; compounds I.F-4.X-11.A-1 to I.F-4.X-11.A-750; compounds I.G-4.X-11.A-1 to I.G-4.X-11.A-750; compounds I.H-4.X-11.A-1 to I.H-4.X-11.A-750;

compounds I.A-5.X-11.A-1 to I.A-5.X-11.A-750; compounds I.B-5.X-11.A-1 to I.B-5.X-11.A-750; compounds I.C-5.X-11.A-1 to I.C-5.X-11.A-750; compounds I.D-5.X-11.A-1 to I.D-5.X-11.A-750; compounds I.E-5.X-11.A-1 to I.E-5.X-11.A-750; compounds I.F-5.X-11.A-1 to I.F-5.X-11.A-750; compounds I.G-5.X-11.A-1 to I.G-5.X-11.A-750; compounds I.H-5.X-11.A-1 to I.H-5.X-11.A-750;

compounds I.A-6.X-11.A-1 to I.A-6.X-11.A-750; compounds I.B-6.X-11.A-1 to I.B-6.X-11.A-750; compounds I.C-6.X-11.A-1 to I.C-6.X-11.A-750; compounds I.D-6.X-

11.A-1 to I.D-6.X-11.A-750; compounds I.E-6.X-11.A-1 to I.E-6.X-11.A-750; compounds I.F-6.X-11.A-1 to I.F-6.X-11.A-750; compounds I.G-6.X-11.A-1 to I.G-6.X-11.A-750; compounds I.H-6.X-11.A-1 to I.H-6.X-11.A-750).

Table 12a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-12 of Table X and the meaning for the combination of $X^1$, $X^2$, $X^3$ and $R^3$ for each individual compound corresponds in each case to one line of Table A (compounds I.A-1.X-12.A-1 to I.A-1.X-12.A-750; compounds I.B-1.X-12.A-1 to I.B-1.X-12.A-750; compounds I.C-1.X-12.A-1 to I.C-1.X-12.A-750; compounds I.D-1.X-12.A-1 to I.D-1.X-12.A-750; compounds I.E-1.X-12.A-1 to I.E-1.X-12.A-750; compounds I.F-1.X-12.A-1 to I.F-1.X-12.A-750; compounds I.G-1.X-12.A-1 to I.G-1.X-12.A-750; compounds I.H-1.X-12.A-1 to I.H-1.X-12.A-750;

compounds I.A-2.X-12.A-1 to I.A-2.X-12.A-750; compounds I.B-2.X-12.A-1 to I.B-2.X-12.A-750; compounds I.C-2.X-12.A-1 to I.C-2.X-12.A-750; compounds I.D-2.X-12.A-1 to I.D-2.X-12.A-750; compounds I.E-2.X-12.A-1 to I.E-2.X-12.A-750; compounds I.F-2.X-12.A-1 to I.F-2.X-12.A-750; compounds I.G-2.X-12.A-1 to I.G-2.X-12.A-750; compounds I.H-2.X-12.A-1 to I.H-2.X-12.A-750;

compounds I.A-3.X-12.A-1 to I.A-3.X-12.A-750; compounds I.B-3.X-12.A-1 to I.B-3.X-12.A-750; compounds I.C-3.X-12.A-1 to I.C-3.X-12.A-750; compounds I.D-3.X-12.A-1 to I.D-3.X-12.A-750; compounds I.E-3.X-12.A-1 to I.E-3.X-12.A-750; compounds I.F-3.X-12.A-1 to I.F-3.X-12.A-750; compounds I.G-3.X-12.A-1 to I.G-3.X-12.A-750; compounds I.H-3.X-12.A-1 to I.H-3.X-12.A-750;

compounds I.A-4.X-12.A-1 to I.A-4.X-12.A-750; compounds I.B-4.X-12.A-1 to I.B-4.X-12.A-750; compounds I.C-4.X-12.A-1 to I.C-4.X-12.A-750; compounds I.D-4.X-12.A-1 to I.D-4.X-12.A-750; compounds I.E-4.X-12.A-1 to I.E-4.X-12.A-750; compounds I.F-4.X-12.A-1 to I.F-4.X-12.A-750; compounds I.G-4.X-12.A-1 to I.G-4.X-12.A-750; compounds I.H-4.X-12.A-1 to I.H-4.X-12.A-750;

compounds I.A-5.X-12.A-1 to I.A-5.X-12.A-750; compounds I.B-5.X-12.A-1 to I.B-5.X-12.A-750; compounds I.C-5.X-12.A-1 to I.C-5.X-12.A-750; compounds I.D-5.X-12.A-1 to I.D-5.X-12.A-750; compounds I.E-5.X-12.A-1 to I.E-5.X-12.A-750; compounds I.F-5.X-12.A-1 to I.F-5.X-12.A-750; compounds I.G-5.X-12.A-1 to I.G-5.X-12.A-750; compounds I.H-5.X-12.A-1 to I.H-5.X-12.A-750;

compounds I.A-6.X-12.A-1 to I.A-6.X-12.A-750; compounds I.B-6.X-12.A-1 to I.B-6.X-12.A-750; compounds I.C-6.X-12.A-1 to I.C-6.X-12.A-750; compounds I.D-6.X-12.A-1 to I.D-6.X-12.A-750; compounds I.E-6.X-12.A-1 to I.E-6.X-12.A-750; compounds I.F-6.X-12.A-1 to I.F-6.X-12.A-750; compounds I.G-6.X-12.A-1 to I.G-6.X-12.A-750; compounds I.H-6.X-12.A-1 to I.H-6.X-12.A-750).

Table 13a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-13 of Table X and the meaning for the combination of $X^1$, $X^2$, $X^3$ and $R^3$ for each individual compound corresponds in each case to one line of Table A (compounds I.A-1.X-13.A-1 to I.A-1.X-13.A-750; compounds I.B-1.X-13.A-1 to I.B-1.X-13.A-750; compounds I.C-1.X-13.A-1 to I.C-1.X-13.A-750; compounds I.D-1.X-13.A-1 to I.D-1.X-13.A-750; compounds I.E-1.X-13.A-1 to I.E-1.X-13.A-750; compounds I.F-1.X-13.A-1 to I.F-1.X-13.A-750; compounds I.G-1.X-13.A-1 to I.G-1.X-13.A-750; compounds I.H-1.X-13.A-1 to I.H-1.X-13.A-750;

compounds I.A-2.X-13.A-1 to I.A-2.X-13.A-750; compounds I.B-2.X-13.A-1 to I.B-2.X-13.A-750; compounds I.C-2.X-13.A-1 to I.C-2.X-13.A-750; compounds I.D-2.X-13.A-1 to I.D-2.X-13.A-750; compounds I.E-2.X-13.A-1 to I.E-2.X-13.A-750; compounds I.F-2.X-13.A-1 to I.F-2.X-13.A-750; compounds I.G-2.X-13.A-1 to I.G-2.X-13.A-750; compounds I.H-2.X-13.A-1 to I.H-2.X-13.A-750;

compounds I.A-3.X-13.A-1 to I.A-3.X-13.A-750; compounds I.B-3.X-13.A-1 to I.B-3.X-13.A-750; compounds I.C-3.X-13.A-1 to I.C-3.X-13.A-750; compounds I.D-3.X-13.A-1 to I.D-3.X-13.A-750; compounds I.E-3.X-13.A-1 to I.E-3.X-13.A-750; compounds I.F-3.X-13.A-1 to I.F-3.X-13.A-750; compounds I.G-3.X-13.A-1 to I.G-3.X-13.A-750; compounds I.H-3.X-13.A-1 to I.H-3.X-13.A-750;

compounds I.A-4.X-13.A-1 to I.A-4.X-13.A-750; compounds I.B-4.X-13.A-1 to I.B-4.X-13.A-750; compounds I.C-4.X-13.A-1 to I.C-4.X-13.A-750; compounds I.D-4.X-13.A-1 to I.D-4.X-13.A-750; compounds I.E-4.X-13.A-1 to I.E-4.X-13.A-750; compounds I.F-4.X-13.A-1 to I.F-4.X-13.A-750; compounds I.G-4.X-13.A-1 to I.G-4.X-13.A-750; compounds I.H-4.X-13.A-1 to I.H-4.X-13.A-750;

compounds I.A-5.X-13.A-1 to I.A-5.X-13.A-750; compounds I.B-5.X-13.A-1 to I.B-5.X-13.A-750; compounds I.C-5.X-13.A-1 to I.C-5.X-13.A-750; compounds I.D-5.X-13.A-1 to I.D-5.X-13.A-750; compounds I.E-5.X-13.A-1 to I.E-5.X-13.A-750; compounds I.F-5.X-13.A-1 to I.F-5.X-13.A-750; compounds I.G-5.X-13.A-1 to I.G-5.X-13.A-750; compounds I.H-5.X-13.A-1 to I.H-5.X-13.A-750;

compounds I.A-6.X-13.A-1 to I.A-6.X-13.A-750; compounds I.B-6.X-13.A-1 to I.B-6.X-13.A-750; compounds I.C-6.X-13.A-1 to I.C-6.X-13.A-750; compounds I.D-6.X-13.A-1 to I.D-6.X-13.A-750; compounds I.E-6.X-13.A-1 to I.E-6.X-13.A-750; compounds I.F-6.X-13.A-1 to I.F-6.X-13.A-750; compounds I.G-6.X-13.A-1 to I.G-6.X-13.A-750; compounds I.H-6.X-13.A-1 to I.H-6.X-13.A-750).

Table 14a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-14 of Table X and the meaning for the combination of $X^1$, $X^2$, $X^3$ and $R^3$ for each individual compound corresponds in each case to one line of Table A (compounds I.A-1.X-14.A-1 to I.A-1.X-14.A-750; compounds I.B-1.X-14.A-1 to I.B-1.X-14.A-750; compounds I.C-1.X-14.A-1 to I.C-1.X-14.A-750; compounds I.D-1.X-14.A-1 to I.D-1.X-14.A-750; compounds I.E-1.X-14.A-1 to I.E-1.X-14.A-750; compounds I.F-1.X-14.A-1 to I.F-1.X-14.A-750; compounds I.G-1.X-14.A-1 to I.G-1.X-14.A-750; compounds I.H-1.X-14.A-1 to I.H-1.X-14.A-750;

compounds I.A-2.X-14.A-1 to I.A-2.X-14.A-750; compounds I.B-2.X-14.A-1 to I.B-2.X-14.A-750; compounds I.C-2.X-14.A-1 to I.C-2.X-14.A-750; compounds I.D-2.X-

14.A-1 to I.D-2.X-14.A-750; compounds I.E-2.X-14.A-1 to I.E-2.X-14.A-750; compounds I.F-2.X-14.A-1 to I.F-2.X-14.A-750; compounds I.G-2.X-14.A-1 to I.G-2.X-14.A-750; compounds I.H-2.X-14.A-1 to I.H-2.X-14.A-750;

compounds I.A-3.X-14.A-1 to I.A-3.X-14.A-750; compounds I.B-3.X-14.A-1 to I.B-3.X-14.A-750; compounds I.C-3.X-14.A-1 to I.C-3.X-14.A-750; compounds I.D-3.X-14.A-1 to I.D-3.X-14.A-750; compounds I.E-3.X-14.A-1 to I.E-3.X-14.A-750; compounds I.F-3.X-14.A-1 to I.F-3.X-14.A-750; compounds I.G-3.X-14.A-1 to I.G-3.X-14.A-750; compounds I.H-3.X-14.A-1 to I.H-3.X-14.A-750;

compounds I.A-4.X-14.A-1 to I.A-4.X-14.A-750; compounds I.B-4.X-14.A-1 to I.B-4.X-14.A-750; compounds I.C-4.X-14.A-1 to I.C-4.X-14.A-750; compounds I.D-4.X-14.A-1 to I.D-4.X-14.A-750; compounds I.E-4.X-14.A-1 to I.E-4.X-14.A-750; compounds I.F-4.X-14.A-1 to I.F-4.X-14.A-750; compounds I.G-4.X-14.A-1 to I.G-4.X-14.A-750; compounds I.H-4.X-14.A-1 to I.H-4.X-14.A-750;

compounds I.A-5.X-14.A-1 to I.A-5.X-14.A-750; compounds I.B-5.X-14.A-1 to I.B-5.X-14.A-750; compounds I.C-5.X-14.A-1 to I.C-5.X-14.A-750; compounds I.D-5.X-14.A-1 to I.D-5.X-14.A-750; compounds I.E-5.X-14.A-1 to I.E-5.X-14.A-750; compounds I.F-5.X-14.A-1 to I.F-5.X-14.A-750; compounds I.G-5.X-14.A-1 to I.G-5.X-14.A-750; compounds I.H-5.X-14.A-1 to I.H-5.X-14.A-750;

compounds I.A-6.X-14.A-1 to I.A-6.X-14.A-750; compounds I.B-6.X-14.A-1 to I.B-6.X-14.A-750; compounds I.C-6.X-14.A-1 to I.C-6.X-14.A-750; compounds I.D-6.X-14.A-1 to I.D-6.X-14.A-750; compounds I.E-6.X-14.A-1 to I.E-6.X-14.A-750; compounds I.F-6.X-14.A-1 to I.F-6.X-14.A-750; compounds I.G-6.X-14.A-1 to I.G-6.X-14.A-750; compounds I.H-6.X-14.A-1 to I.H-6.X-14.A-750).

Table 15a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I.H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-15 of Table X and the meaning for the combination of $X^1$, $X^2$, $X^3$ and $R^3$ for each individual compound corresponds in each case to one line of Table A (compounds I.A-1.X-15.A-1 to I.A-1.X-15.A-750; compounds I.B-1.X-15.A-1 to I.B-1.X-15.A-750; compounds I.C-1.X-15.A-1 to I.C-1.X-15.A-750; compounds I.D-1.X-15.A-1 to I.D-1.X-15.A-750; compounds I.E-1.X-15.A-1 to I.E-1.X-15.A-750; compounds I.F-1.X-15.A-1 to I.F-1.X-15.A-750; compounds I.G-1.X-15.A-1 to I.G-1.X-15.A-750; compounds I.H-1.X-15.A-1 to I.H-1.X-15.A-750;

compounds I.A-2.X-15.A-1 to I.A-2.X-15.A-750; compounds I.B-2.X-15.A-1 to I.B-2.X-15.A-750; compounds I.C-2.X-15.A-1 to I.C-2.X-15.A-750; compounds I.D-2.X-15.A-1 to I.D-2.X-15.A-750; compounds I.E-2.X-15.A-1 to I.E-2.X-15.A-750; compounds I.F-2.X-15.A-1 to I.F-2.X-15.A-750; compounds I.G-2.X-15.A-1 to I.G-2.X-15.A-750; compounds I.H-2.X-15.A-1 to I.H-2.X-15.A-750;

compounds I.A-3.X-15.A-1 to I.A-3.X-15.A-750; compounds I.B-3.X-15.A-1 to I.B-3.X-15.A-750; compounds I.C-3.X-15.A-1 to I.C-3.X-15.A-750; compounds I.D-3.X-15.A-1 to I.D-3.X-15.A-750; compounds I.E-3.X-15.A-1 to I.E-3.X-15.A-750; compounds I.F-3.X-15.A-1 to I.F-3.X-15.A-750; compounds I.G-3.X-15.A-1 to I.G-3.X-15.A-750; compounds I.H-3.X-15.A-1 to I.H-3.X-15.A-750;

compounds I.A-4.X-15.A-1 to I.A-4.X-15.A-750; compounds I.B-4.X-15.A-1 to I.B-4.X-15.A-750; compounds I.C-4.X-15.A-1 to I.C-4.X-15.A-750; compounds I.D-4.X-15.A-1 to I.D-4.X-15.A-750; compounds I.E-4.X-15.A-1 to I.E-4.X-15.A-750; compounds I.F-4.X-15.A-1 to I.F-4.X-15.A-750; compounds I.G-4.X-15.A-1 to I.G-4.X-15.A-750; compounds I.H-4.X-15.A-1 to I.H-4.X-15.A-750;

compounds I.A-5.X-15.A-1 to I.A-5.X-15.A-750; compounds I.B-5.X-15.A-1 to I.B-5.X-15.A-750; compounds I.C-5.X-15.A-1 to I.C-5.X-15.A-750; compounds I.D-5.X-15.A-1 to I.D-5.X-15.A-750; compounds I.E-5.X-15.A-1 to I.E-5.X-15.A-750; compounds I.F-5.X-15.A-1 to I.F-5.X-15.A-750; compounds I.G-5.X-15.A-1 to I.G-5.X-15.A-750; compounds I.H-5.X-15.A-1 to I.H-5.X-15.A-750;

compounds I.A-6.X-15.A-1 to I.A-6.X-15.A-750; compounds I.B-6.X-15.A-1 to I.B-6.X-15.A-750; compounds I.C-6.X-15.A-1 to I.C-6.X-15.A-750; compounds I.D-6.X-15.A-1 to I.D-6.X-15.A-750; compounds I.E-6.X-15.A-1 to I.E-6.X-15.A-750; compounds I.F-6.X-15.A-1 to I.F-6.X-15.A-750; compounds I.G-6.X-15.A-1 to I.G-6.X-15.A-750; compounds I.H-6.X-15.A-1 to I.H-6.X-15.A-750).

Table 16a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I.H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-16 of Table X and the meaning for the combination of $X^1$, $X^2$, $X^3$ and $R^3$ for each individual compound corresponds in each case to one line of Table A (compounds I.A-1.X-16.A-1 to I.A-1.X-16.A-750; compounds I.B-1.X-16.A-1 to I.B-1.X-16.A-750; compounds I.C-1.X-16.A-1 to I.C-1.X-16.A-750; compounds I.D-1.X-16.A-1 to I.D-1.X-16.A-750; compounds I.E-1.X-16.A-1 to I.E-1.X-16.A-750; compounds I.F-1.X-16.A-1 to I.F-1.X-16.A-750; compounds I.G-1.X-16.A-1 to I.G-1.X-16.A-750; compounds I.H-1.X-16.A-1 to I.H-1.X-16.A-750;

compounds I.A-2.X-16.A-1 to I.A-2.X-16.A-750; compounds I.B-2.X-16.A-1 to I.B-2.X-16.A-750; compounds I.C-2.X-16.A-1 to I.C-2.X-16.A-750; compounds I.D-2.X-16.A-1 to I.D-2.X-16.A-750; compounds I.E-2.X-16.A-1 to I.E-2.X-16.A-750; compounds I.F-2.X-16.A-1 to I.F-2.X-16.A-750; compounds I.G-2.X-16.A-1 to I.G-2.X-16.A-750; compounds I.H-2.X-16.A-1 to I.H-2.X-16.A-750;

compounds I.A-3.X-16.A-1 to I.A-3.X-16.A-750; compounds I.B-3.X-16.A-1 to I.B-3.X-16.A-750; compounds I.C-3.X-16.A-1 to I.C-3.X-16.A-750; compounds I.D-3.X-16.A-1 to I.D-3.X-16.A-750; compounds I.E-3.X-16.A-1 to I.E-3.X-16.A-750; compounds I.F-3.X-16.A-1 to I.F-3.X-16.A-750; compounds I.G-3.X-16.A-1 to I.G-3.X-16.A-750; compounds I.H-3.X-16.A-1 to I.H-3.X-16.A-750;

compounds I.A-4.X-16.A-1 to I.A-4.X-16.A-750; compounds I.B-4.X-16.A-1 to I.B-4.X-16.A-750; compounds I.C-4.X-16.A-1 to I.C-4.X-16.A-750; compounds I.D-4.X-16.A-1 to I.D-4.X-16.A-750; compounds I.E-4.X-16.A-1 to I.E-4.X-16.A-750; compounds I.F-4.X-16.A-1 to I.F-4.X-16.A-750; compounds I.G-4.X-16.A-1 to I.G-4.X-16.A-750; compounds I.H-4.X-16.A-1 to I.H-4.X-16.A-750;

compounds I.A-5.X-16.A-1 to I.A-5.X-16.A-750; compounds I.B-5.X-16.A-1 to I.B-5.X-16.A-750; compounds I.C-5.X-16.A-1 to I.C-5.X-16.A-750; compounds I.D-5.X-16.A-1 to I.D-5.X-16.A-750; compounds I.E-5.X-16.A-1 to I.E-5.X-16.A-750; compounds I.F-5.X-16.A-1 to I.F-5.X-16.A-750; compounds I.G-5.X-16.A-1 to I.G-5.X-16.A-750; compounds I.H-5.X-16.A-1 to I.H-5.X-16.A-750;

compounds I.A-6.X-16.A-1 to I.A-6.X-16.A-750; compounds I.B-6.X-16.A-1 to I.B-6.X-16.A-750; compounds I.C-6.X-16.A-1 to I.C-6.X-16.A-750; compounds I.D-6.X-

16.A-1 to I.D-6.X-16.A-750; compounds I.E-6.X-16.A-1 to I.E-6.X-16.A-750; compounds I.F-6.X-16.A-1 to I.F-6.X-16.A-750; compounds I.G-6.X-16.A-1 to I.G-6.X-16.A-750; compounds I.H-6.X-16.A-1 to I.H-6.X-16.A-750).

Table 17a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-17 of Table X and the meaning for the combination of $X^1$, $X^2$, $X^3$ and $R^3$ for each individual compound corresponds in each case to one line of Table A (compounds I.A-1.X-17.A-1 to I.A-1.X-17.A-750; compounds I.B-1.X-17.A-1 to I.B-1.X-17.A-750; compounds I.C-1.X-17.A-1 to I.C-1.X-17.A-750; compounds I.D-1.X-17.A-1 to I.D-1.X-17.A-750; compounds I.E-1.X-17.A-1 to I.E-1.X-17.A-750; compounds I.F-1.X-17.A-1 to I.F-1.X-17.A-750; compounds I.G-1.X-17.A-1 to I.G-1.X-17.A-750; compounds I.H-1.X-17.A-1 to I.H-1.X-17.A-750;

compounds I.A-2.X-17.A-1 to I.A-2.X-17.A-750; compounds I.B-2.X-17.A-1 to I.B-2.X-17.A-750; compounds I.C-2.X-17.A-1 to I.C-2.X-17.A-750; compounds I.D-2.X-17.A-1 to I.D-2.X-17.A-750; compounds I.E-2.X-17.A-1 to I.E-2.X-17.A-750; compounds I.F-2.X-17.A-1 to I.F-2.X-17.A-750; compounds I.G-2.X-17.A-1 to I.G-2.X-17.A-750; compounds I.H-2.X-17.A-1 to I.H-2.X-17.A-750;

compounds I.A-3.X-17.A-1 to I.A-3.X-17.A-750; compounds I.B-3.X-17.A-1 to I.B-3.X-17.A-750; compounds I.C-3.X-17.A-1 to I.C-3.X-17.A-750; compounds I.D-3.X-17.A-1 to I.D-3.X-17.A-750; compounds I.E-3.X-17.A-1 to I.E-3.X-17.A-750; compounds I.F-3.X-17.A-1 to I.F-3.X-17.A-750; compounds I.G-3.X-17.A-1 to I.G-3.X-17.A-750; compounds I.H-3.X-17.A-1 to I.H-3.X-17.A-750;

compounds I.A-4.X-17.A-1 to I.A-4.X-17.A-750; compounds I.B-4.X-17.A-1 to I.B-4.X-17.A-750; compounds I.C-4.X-17.A-1 to I.C-4.X-17.A-750; compounds I.D-4.X-17.A-1 to I.D-4.X-17.A-750; compounds I.E-4.X-17.A-1 to I.E-4.X-17.A-750; compounds I.F-4.X-17.A-1 to I.F-4.X-17.A-750; compounds I.G-4.X-17.A-1 to I.G-4.X-17.A-750; compounds I.H-4.X-17.A-1 to I.H-4.X-17.A-750;

compounds I.A-5.X-17.A-1 to I.A-5.X-17.A-750; compounds I.B-5.X-17.A-1 to I.B-5.X-17.A-750; compounds I.C-5.X-17.A-1 to I.C-5.X-17.A-750; compounds I.D-5.X-17.A-1 to I.D-5.X-17.A-750; compounds I.E-5.X-17.A-1 to I.E-5.X-17.A-750; compounds I.F-5.X-17.A-1 to I.F-5.X-17.A-750; compounds I.G-5.X-17.A-1 to I.G-5.X-17.A-750; compounds I.H-5.X-17.A-1 to I.H-5.X-17.A-750;

compounds I.A-6.X-17.A-1 to I.A-6.X-17.A-750; compounds I.B-6.X-17.A-1 to I.B-6.X-17.A-750; compounds I.C-6.X-17.A-1 to I.C-6.X-17.A-750; compounds I.D-6.X-17.A-1 to I.D-6.X-17.A-750; compounds I.E-6.X-17.A-1 to I.E-6.X-17.A-750; compounds I.F-6.X-17.A-1 to I.F-6.X-17.A-750; compounds I.G-6.X-17.A-1 to I.G-6.X-17.A-750; compounds I.H-6.X-17.A-1 to I.H-6.X-17.A-750).

Table 18a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-18 of Table X and the meaning for the combination of $X^1$, $X^2$, $X^3$ and $R^3$ for each individual compound corresponds in each case to one line of Table A (compounds I.A-1.X-18.A-1 to I.A-1.X-18.A-750; compounds I.B-1.X-18.A-1 to I.B-1.X-18.A-750; compounds I.C-1.X-18.A-1 to I.C-1.X-18.A-750; compounds I.D-1.X-18.A-1 to I.D-1.X-18.A-750; compounds I.E-1.X-18.A-1 to I.E-1.X-18.A-750; compounds I.F-1.X-18.A-1 to I.F-1.X-18.A-750; compounds I.G-1.X-18.A-1 to I.G-1.X-18.A-750; compounds I.H-1.X-18.A-1 to I.H-1.X-18.A-750;

compounds I.A-2.X-18.A-1 to I.A-2.X-18.A-750; compounds I.B-2.X-18.A-1 to I.B-2.X-18.A-750; compounds I.C-2.X-18.A-1 to I.C-2.X-18.A-750; compounds I.D-2.X-18.A-1 to I.D-2.X-18.A-750; compounds I.E-2.X-18.A-1 to I.E-2.X-18.A-750; compounds I.F-2.X-18.A-1 to I.F-2.X-18.A-750; compounds I.G-2.X-18.A-1 to I.G-2.X-18.A-750; compounds I.H-2.X-18.A-1 to I.H-2.X-18.A-750;

compounds I.A-3.X-18.A-1 to I.A-3.X-18.A-750; compounds I.B-3.X-18.A-1 to I.B-3.X-18.A-750; compounds I.C-3.X-18.A-1 to I.C-3.X-18.A-750; compounds I.D-3.X-18.A-1 to I.D-3.X-18.A-750; compounds I.E-3.X-18.A-1 to I.E-3.X-18.A-750; compounds I.F-3.X-18.A-1 to I.F-3.X-18.A-750; compounds I.G-3.X-18.A-1 to I.G-3.X-18.A-750; compounds I.H-3.X-18.A-1 to I.H-3.X-18.A-750;

compounds I.A-4.X-18.A-1 to I.A-4.X-18.A-750; compounds I.B-4.X-18.A-1 to I.B-4.X-18.A-750; compounds I.C-4.X-18.A-1 to I.C-4.X-18.A-750; compounds I.D-4.X-18.A-1 to I.D-4.X-18.A-750; compounds I.E-4.X-18.A-1 to I.E-4.X-18.A-750; compounds I.F-4.X-18.A-1 to I.F-4.X-18.A-750; compounds I.G-4.X-18.A-1 to I.G-4.X-18.A-750; compounds I.H-4.X-18.A-1 to I.H-4.X-18.A-750;

compounds I.A-5.X-18.A-1 to I.A-5.X-18.A-750; compounds I.B-5.X-18.A-1 to I.B-5.X-18.A-750; compounds I.C-5.X-18.A-1 to I.C-5.X-18.A-750; compounds I.D-5.X-18.A-1 to I.D-5.X-18.A-750; compounds I.E-5.X-18.A-1 to I.E-5.X-18.A-750; compounds I.F-5.X-18.A-1 to I.F-5.X-18.A-750; compounds I.G-5.X-18.A-1 to I.G-5.X-18.A-750; compounds I.H-5.X-18.A-1 to I.H-5.X-18.A-750;

compounds I.A-6.X-18.A-1 to I.A-6.X-18.A-750; compounds I.B-6.X-18.A-1 to I.B-6.X-18.A-750; compounds I.C-6.X-18.A-1 to I.C-6.X-18.A-750; compounds I.D-6.X-18.A-1 to I.D-6.X-18.A-750; compounds I.E-6.X-18.A-1 to I.E-6.X-18.A-750; compounds I.F-6.X-18.A-1 to I.F-6.X-18.A-750; compounds I.G-6.X-18.A-1 to I.G-6.X-18.A-750; compounds I.H-6.X-18.A-1 to I.H-6.X-18.A-750).

Table 19a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q^3$ is as defined in line X-19 of Table X and the meaning for the combination of $X^1$, $X^2$, $X^3$ and $R^3$ for each individual compound corresponds in each case to one line of Table A (compounds I.A-1.X-19.A-1 to I.A-1.X-19.A-750; compounds I.B-1.X-19.A-1 to I.B-1.X-19.A-750; compounds I.C-1.X-19.A-1 to I.C-1.X-19.A-750; compounds I.D-1.X-19.A-1 to I.D-1.X-19.A-750; compounds I.E-1.X-19.A-1 to I.E-1.X-19.A-750; compounds I.F-1.X-19.A-1 to I.F-1.X-19.A-750; compounds I.G-1.X-19.A-1 to I.G-1.X-19.A-750; compounds I.H-1.X-19.A-1 to I.H-1.X-19.A-750;

compounds I.A-2.X-19.A-1 to I.A-2.X-19.A-750; compounds I.B-2.X-19.A-1 to I.B-2.X-19.A-750; compounds I.C-2.X-19.A-1 to I.C-2.X-19.A-750; compounds I.D-2.X-

19.A-1 to I.D-2.X-19.A-750; compounds I.E-2.X-19.A-1 to I.E-2.X-19.A-750; compounds I.F-2.X-19.A-1 to I.F-2.X-19.A-750; compounds I.G-2.X-19.A-1 to I.G-2.X-19.A-750; compounds I.H-2.X-19.A-1 to I.H-2.X-19.A-750;

compounds I.A-3.X-19.A-1 to I.A-3.X-19.A-750; compounds I.B-3.X-19.A-1 to I.B-3.X-19.A-750; compounds I.C-3.X-19.A-1 to I.C-3.X-19.A-750; compounds I.D-3.X-19.A-1 to I.D-3.X-19.A-750; compounds I.E-3.X-19.A-1 to I.E-3.X-19.A-750; compounds I.F-3.X-19.A-1 to I.F-3.X-19.A-750; compounds I.G-3.X-19.A-1 to I.G-3.X-19.A-750; compounds I.H-3.X-19.A-1 to I.H-3.X-19.A-750;

compounds I.A-4.X-19.A-1 to I.A-4.X-19.A-750; compounds I.B-4.X-19.A-1 to I.B-4.X-19.A-750; compounds I.C-4.X-19.A-1 to I.C-4.X-19.A-750; compounds I.D-4.X-19.A-1 to I.D-4.X-19.A-750; compounds I.E-4.X-19.A-1 to I.E-4.X-19.A-750; compounds I.F-4.X-19.A-1 to I.F-4.X-19.A-750; compounds I.G-4.X-19.A-1 to I.G-4.X-19.A-750; compounds I.H-4.X-19.A-1 to I.H-4.X-19.A-750;

compounds I.A-5.X-19.A-1 to I.A-5.X-19.A-750; compounds I.B-5.X-19.A-1 to I.B-5.X-19.A-750; compounds I.C-5.X-19.A-1 to I.C-5.X-19.A-750; compounds I.D-5.X-19.A-1 to I.D-5.X-19.A-750; compounds I.E-5.X-19.A-1 to I.E-5.X-19.A-750; compounds I.F-5.X-19.A-1 to I.F-5.X-19.A-750; compounds I.G-5.X-19.A-1 to I.G-5.X-19.A-750; compounds I.H-5.X-19.A-1 to I.H-5.X-19.A-750;

compounds I.A-6.X-19.A-1 to I.A-6.X-19.A-750; compounds I.B-6.X-19.A-1 to I.B-6.X-19.A-750; compounds I.C-6.X-19.A-1 to I.C-6.X-19.A-750; compounds I.D-6.X-19.A-1 to I.D-6.X-19.A-750; compounds I.E-6.X-19.A-1 to I.E-6.X-19.A-750; compounds I.F-6.X-19.A-1 to I.F-6.X-19.A-750; compounds I.G-6.X-19.A-1 to I.G-6.X-19.A-750; compounds I.H-6.X-19.A-1 to I.H-6.X-19.A-750).

Table 20a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-20 of Table X and the meaning for the combination of $X^1$, $X^2$, $X^3$ and $R^3$ for each individual compound corresponds in each case to one line of Table A (compounds I.A-1.X-20.A-1 to I.A-1.X-20.A-750; compounds I.B-1.X-20.A-1 to I.B-1.X-20.A-750; compounds I.C-1.X-20.A-1 to I.C-1.X-20.A-750; compounds I.D-1.X-20.A-1 to I.D-1.X-20.A-750; compounds I.E-1.X-20.A-1 to I.E-1.X-20.A-750; compounds I.F-1.X-20.A-1 to I.F-1.X-20.A-750; compounds I.G-1.X-20.A-1 to I.G-1.X-20.A-750; compounds I.H-1.X-20.A-1 to I.H-1.X-20.A-750;

compounds I.A-2.X-20.A-1 to I.A-2.X-20.A-750; compounds I.B-2.X-20.A-1 to I.B-2.X-20.A-750; compounds I.C-2.X-20.A-1 to I.C-2.X-20.A-750; compounds I.D-2.X-20.A-1 to I.D-2.X-20.A-750; compounds I.E-2.X-20.A-1 to I.E-2.X-20.A-750; compounds I.F-2.X-20.A-1 to I.F-2.X-20.A-750; compounds I.G-2.X-20.A-1 to I.G-2.X-20.A-750; compounds I.H-2.X-20.A-1 to I.H-2.X-20.A-750;

compounds I.A-3.X-20.A-1 to I.A-3.X-20.A-750; compounds I.B-3.X-20.A-1 to I.B-3.X-20.A-750; compounds I.C-3.X-20.A-1 to I.C-3.X-20.A-750; compounds I.D-3.X-20.A-1 to I.D-3.X-20.A-750; compounds I.E-3.X-20.A-1 to I.E-3.X-20.A-750; compounds I.F-3.X-20.A-1 to I.F-3.X-20.A-750; compounds I.G-3.X-20.A-1 to I.G-3.X-20.A-750; compounds I.H-3.X-20.A-1 to I.H-3.X-20.A-750;

compounds I.A-4.X-20.A-1 to I.A-4.X-20.A-750; compounds I.B-4.X-20.A-1 to I.B-4.X-20.A-750; compounds I.C-4.X-20.A-1 to I.C-4.X-20.A-750; compounds I.D-4.X-20.A-1 to I.D-4.X-20.A-750; compounds I.E-4.X-20.A-1 to I.E-4.X-20.A-750; compounds I.F-4.X-20.A-1 to I.F-4.X-20.A-750; compounds I.G-4.X-20.A-1 to I.G-4.X-20.A-750; compounds I.H-4.X-20.A-1 to I.H-4.X-20.A-750;

compounds I.A-5.X-20.A-1 to I.A-5.X-20.A-750; compounds I.B-5.X-20.A-1 to I.B-5.X-20.A-750; compounds I.C-5.X-20.A-1 to I.C-5.X-20.A-750; compounds I.D-5.X-20.A-1 to I.D-5.X-20.A-750; compounds I.E-5.X-20.A-1 to I.E-5.X-20.A-750; compounds I.F-5.X-20.A-1 to I.F-5.X-20.A-750; compounds I.G-5.X-20.A-1 to I.G-5.X-20.A-750; compounds I.H-5.X-20.A-1 to I.H-5.X-20.A-750;

compounds I.A-6.X-20.A-1 to I.A-6.X-20.A-750; compounds I.B-6.X-20.A-1 to I.B-6.X-20.A-750; compounds I.C-6.X-20.A-1 to I.C-6.X-20.A-750; compounds I.D-6.X-20.A-1 to I.D-6.X-20.A-750; compounds I.E-6.X-20.A-1 to I.E-6.X-20.A-750; compounds I.F-6.X-20.A-1 to I.F-6.X-20.A-750; compounds I.G-6.X-20.A-1 to I.G-6.X-20.A-750; compounds I.H-6.X-20.A-1 to I.H-6.X-20.A-750).

Table 21a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-21 of Table X and the meaning for the combination of $X^1$, $X^2$, $X^3$ and $R^3$ for each individual compound corresponds in each case to one line of Table A (compounds I.A-1.X-21.A-1 to I.A-1.X-21.A-750; compounds I.B-1.X-21.A-1 to I.B-1.X-21.A-750; compounds I.C-1.X-21.A-1 to I.C-1.X-21.A-750; compounds I.D-1.X-21.A-1 to I.D-1.X-21.A-750; compounds I.E-1.X-21.A-1 to I.E-1.X-21.A-750; compounds I.F-1.X-21.A-1 to I.F-1.X-21.A-750; compounds I.G-1.X-21.A-1 to I.G-1.X-21.A-750; compounds I.H-1.X-21.A-1 to I.H-1.X-21.A-750;

compounds I.A-2.X-21.A-1 to I.A-2.X-21.A-750; compounds I.B-2.X-21.A-1 to I.B-2.X-21.A-750; compounds I.C-2.X-21.A-1 to I.C-2.X-21.A-750; compounds I.D-2.X-21.A-1 to I.D-2.X-21.A-750; compounds I.E-2.X-21.A-1 to I.E-2.X-21.A-750; compounds I.F-2.X-21.A-1 to I.F-2.X-21.A-750; compounds I.G-2.X-21.A-1 to I.G-2.X-21.A-750; compounds I.H-2.X-21.A-1 to I.H-2.X-21.A-750;

compounds I.A-3.X-21.A-1 to I.A-3.X-21.A-750; compounds I.B-3.X-21.A-1 to I.B-3.X-21.A-750; compounds I.C-3.X-21.A-1 to I.C-3.X-21.A-750; compounds I.D-3.X-21.A-1 to I.D-3.X-21.A-750; compounds I.E-3.X-21.A-1 to I.E-3.X-21.A-750; compounds I.F-3.X-21.A-1 to I.F-3.X-21.A-750; compounds I.G-3.X-21.A-1 to I.G-3.X-21.A-750; compounds I.H-3.X-21.A-1 to I.H-3.X-21.A-750;

compounds I.A-4.X-21.A-1 to I.A-4.X-21.A-750; compounds I.B-4.X-21.A-1 to I.B-4.X-21.A-750; compounds I.C-4.X-21.A-1 to I.C-4.X-21.A-750; compounds I.D-4.X-21.A-1 to I.D-4.X-21.A-750; compounds I.E-4.X-21.A-1 to I.E-4.X-21.A-750; compounds I.F-4.X-21.A-1 to I.F-4.X-21.A-750; compounds I.G-4.X-21.A-1 to I.G-4.X-21.A-750; compounds I.H-4.X-21.A-1 to I.H-4.X-21.A-750;

compounds I.A-5.X-21.A-1 to I.A-5.X-21.A-750; compounds I.B-5.X-21.A-1 to I.B-5.X-21.A-750; compounds I.C-5.X-21.A-1 to I.C-5.X-21.A-750; compounds I.D-5.X-21.A-1 to I.D-5.X-21.A-750; compounds I.E-5.X-21.A-1 to I.E-5.X-21.A-750; compounds I.F-5.X-21.A-1 to I.F-5.X-21.A-750; compounds I.G-5.X-21.A-1 to I.G-5.X-21.A-750; compounds I.H-5.X-21.A-1 to I.H-5.X-21.A-750;

compounds I.A-6.X-21.A-1 to I.A-6.X-21.A-750; compounds I.B-6.X-21.A-1 to I.B-6.X-21.A-750; compounds I.C-6.X-21.A-1 to I.C-6.X-21.A-750; compounds I.D-6.X-

21.A-1 to I.D-6.X-21.A-750; compounds I.E-6.X-21.A-1 to I.E-6.X-21.A-750; compounds I.F-6.X-21.A-1 to I.F-6.X-21.A-750; compounds I.G-6.X-21.A-1 to I.G-6.X-21.A-750; compounds I.H-6.X-21.A-1 to I.H-6.X-21.A-750).

Table 22a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-22 of Table X and the meaning for the combination of $X^1$, $X^2$, $X^3$ and $R^3$ for each individual compound corresponds in each case to one line of Table A (compounds I.A-1.X-22.A-1 to I.A-1.X-22.A-750; compounds I.B-1.X-22.A-1 to I.B-1.X-22.A-750; compounds I.C-1.X-22.A-1 to I.C-1.X-22.A-750; compounds I.D-1.X-22.A-1 to I.D-1.X-22.A-750; compounds I.E-1.X-22.A-1 to I.E-1.X-22.A-750; compounds I.F-1.X-22.A-1 to I.F-1.X-22.A-750; compounds I.G-1.X-22.A-1 to I.G-1.X-22.A-750; compounds I.H-1.X-22.A-1 to I.H-1.X-22.A-750;

compounds I.A-2.X-22.A-1 to I.A-2.X-22.A-750; compounds I.B-2.X-22.A-1 to I.B-2.X-22.A-750; compounds I.C-2.X-22.A-1 to I.C-2.X-22.A-750; compounds I.D-2.X-22.A-1 to I.D-2.X-22.A-750; compounds I.E-2.X-22.A-1 to I.E-2.X-22.A-750; compounds I.F-2.X-22.A-1 to I.F-2.X-22.A-750; compounds I.G-2.X-22.A-1 to I.G-2.X-22.A-750; compounds I.H-2.X-22.A-1 to I.H-2.X-22.A-750;

compounds I.A-3.X-22.A-1 to I.A-3.X-22.A-750; compounds I.B-3.X-22.A-1 to I.B-3.X-22.A-750; compounds I.C-3.X-22.A-1 to I.C-3.X-22.A-750; compounds I.D-3.X-22.A-1 to I.D-3.X-22.A-750; compounds I.E-3.X-22.A-1 to I.E-3.X-22.A-750; compounds I.F-3.X-22.A-1 to I.F-3.X-22.A-750; compounds I.G-3.X-22.A-1 to I.G-3.X-22.A-750; compounds I.H-3.X-22.A-1 to I.H-3.X-22.A-750;

compounds I.A-4.X-22.A-1 to I.A-4.X-22.A-750; compounds I.B-4.X-22.A-1 to I.B-4.X-22.A-750; compounds I.C-4.X-22.A-1 to I.C-4.X-22.A-750; compounds I.D-4.X-22.A-1 to I.D-4.X-22.A-750; compounds I.E-4.X-22.A-1 to I.E-4.X-22.A-750; compounds I.F-4.X-22.A-1 to I.F-4.X-22.A-750; compounds I.G-4.X-22.A-1 to I.G-4.X-22.A-750; compounds I.H-4.X-22.A-1 to I.H-4.X-22.A-750;

compounds I.A-5.X-22.A-1 to I.A-5.X-22.A-750; compounds I.B-5.X-22.A-1 to I.B-5.X-22.A-750; compounds I.C-5.X-22.A-1 to I.C-5.X-22.A-750; compounds I.D-5.X-22.A-1 to I.D-5.X-22.A-750; compounds I.E-5.X-22.A-1 to I.E-5.X-22.A-750; compounds I.F-5.X-22.A-1 to I.F-5.X-22.A-750; compounds I.G-5.X-22.A-1 to I.G-5.X-22.A-750; compounds I.H-5.X-22.A-1 to I.H-5.X-22.A-750;

compounds I.A-6.X-22.A-1 to I.A-6.X-22.A-750; compounds I.B-6.X-22.A-1 to I.B-6.X-22.A-750; compounds I.C-6.X-22.A-1 to I.C-6.X-22.A-750; compounds I.D-6.X-22.A-1 to I.D-6.X-22.A-750; compounds I.E-6.X-22.A-1 to I.E-6.X-22.A-750; compounds I.F-6.X-22.A-1 to I.F-6.X-22.A-750; compounds I.G-6.X-22.A-1 to I.G-6.X-22.A-750; compounds I.H-6.X-22.A-1 to I.H-6.X-22.A-750).

Table 23a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-23 of Table X and the meaning for the combination of $X^1$, $X^2$, $X^3$ and $R^3$ for each individual compound corresponds in each case to one line of Table A (compounds I.A-1.X-23.A-1 to I.A-1.X-23.A-750; compounds I.B-1.X-23.A-1 to I.B-1.X-23.A-750; compounds I.C-1.X-23.A-1 to I.C-1.X-23.A-750; compounds I.D-1.X-23.A-1 to I.D-1.X-23.A-750; compounds I.E-1.X-23.A-1 to I.E-1.X-23.A-750; compounds I.F-1.X-23.A-1 to I.F-1.X-23.A-750; compounds I.G-1.X-23.A-1 to I.G-1.X-23.A-750; compounds I.H-1.X-23.A-1 to I.H-1.X-23.A-750;

compounds I.A-2.X-23.A-1 to I.A-2.X-23.A-750; compounds I.B-2.X-23.A-1 to I.B-2.X-23.A-750; compounds I.C-2.X-23.A-1 to I.C-2.X-23.A-750; compounds I.D-2.X-23.A-1 to I.D-2.X-23.A-750; compounds I.E-2.X-23.A-1 to I.E-2.X-23.A-750; compounds I.F-2.X-23.A-1 to I.F-2.X-23.A-750; compounds I.G-2.X-23.A-1 to I.G-2.X-23.A-750; compounds I.H-2.X-23.A-1 to I.H-2.X-23.A-750;

compounds I.A-3.X-23.A-1 to I.A-3.X-23.A-750; compounds I.B-3.X-23.A-1 to I.B-3.X-23.A-750; compounds I.C-3.X-23.A-1 to I.C-3.X-23.A-750; compounds I.D-3.X-23.A-1 to I.D-3.X-23.A-750; compounds I.E-3.X-23.A-1 to I.E-3.X-23.A-750; compounds I.F-3.X-23.A-1 to I.F-3.X-23.A-750; compounds I.G-3.X-23.A-1 to I.G-3.X-23.A-750; compounds I.H-3.X-23.A-1 to I.H-3.X-23.A-750;

compounds I.A-4.X-23.A-1 to I.A-4.X-23.A-750; compounds I.B-4.X-23.A-1 to I.B-4.X-23.A-750; compounds I.C-4.X-23.A-1 to I.C-4.X-23.A-750; compounds I.D-4.X-23.A-1 to I.D-4.X-23.A-750; compounds I.E-4.X-23.A-1 to I.E-4.X-23.A-750; compounds I.F-4.X-23.A-1 to I.F-4.X-23.A-750; compounds I.G-4.X-23.A-1 to I.G-4.X-23.A-750; compounds I.H-4.X-23.A-1 to I.H-4.X-23.A-750;

compounds I.A-5.X-23.A-1 to I.A-5.X-23.A-750; compounds I.B-5.X-23.A-1 to I.B-5.X-23.A-750; compounds I.C-5.X-23.A-1 to I.C-5.X-23.A-750; compounds I.D-5.X-23.A-1 to I.D-5.X-23.A-750; compounds I.E-5.X-23.A-1 to I.E-5.X-23.A-750; compounds I.F-5.X-23.A-1 to I.F-5.X-23.A-750; compounds I.G-5.X-23.A-1 to I.G-5.X-23.A-750; compounds I.H-5.X-23.A-1 to I.H-5.X-23.A-750;

compounds I.A-6.X-23.A-1 to I.A-6.X-23.A-750; compounds I.B-6.X-23.A-1 to I.B-6.X-23.A-750; compounds I.C-6.X-23.A-1 to I.C-6.X-23.A-750; compounds I.D-6.X-23.A-1 to I.D-6.X-23.A-750; compounds I.E-6.X-23.A-1 to I.E-6.X-23.A-750; compounds I.F-6.X-23.A-1 to I.F-6.X-23.A-750; compounds I.G-6.X-23.A-1 to I.G-6.X-23.A-750; compounds I.H-6.X-23.A-1 to I.H-6.X-23.A-750).

Table 24a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-24 of Table X and the meaning for the combination of $X^1$, $X^2$, $X^3$ and $R^3$ for each individual compound corresponds in each case to one line of Table A (compounds I.A-1.X-24.A-1 to I.A-1.X-24.A-750; compounds I.B-1.X-24.A-1 to I.B-1.X-24.A-750; compounds I.C-1.X-24.A-1 to I.C-1.X-24.A-750; compounds I.D-1.X-24.A-1 to I.D-1.X-24.A-750; compounds I.E-1.X-24.A-1 to I.E-1.X-24.A-750; compounds I.F-1.X-24.A-1 to I.F-1.X-24.A-750; compounds I.G-1.X-24.A-1 to I.G-1.X-24.A-750; compounds I.H-1.X-24.A-1 to I.H-1.X-24.A-750;

compounds I.A-2.X-24.A-1 to I.A-2.X-24.A-750; compounds I.B-2.X-24.A-1 to I.B-2.X-24.A-750; compounds I.C-2.X-24.A-1 to I.C-2.X-24.A-750; compounds I.D-2.X-

24.A-1 to I.D-2.X-24.A-750; compounds I.E-2.X-24.A-1 to I.E-2.X-24.A-750; compounds I.F-2.X-24.A-1 to I.F-2.X-24.A-750; compounds I.G-2.X-24.A-1 to I.G-2.X-24.A-750; compounds I.H-2.X-24.A-1 to I.H-2.X-24.A-750;

compounds I.A-3.X-24.A-1 to I.A-3.X-24.A-750; compounds I.B-3.X-24.A-1 to I.B-3.X-24.A-750; compounds I.C-3.X-24.A-1 to I.C-3.X-24.A-750; compounds I.D-3.X-24.A-1 to I.D-3.X-24.A-750; compounds I.E-3.X-24.A-1 to I.E-3.X-24.A-750; compounds I.F-3.X-24.A-1 to I.F-3.X-24.A-750; compounds I.G-3.X-24.A-1 to I.G-3.X-24.A-750; compounds I.H-3.X-24.A-1 to I.H-3.X-24.A-750;

compounds I.A-4.X-24.A-1 to I.A-4.X-24.A-750; compounds I.B-4.X-24.A-1 to I.B-4.X-24.A-750; compounds I.C-4.X-24.A-1 to I.C-4.X-24.A-750; compounds I.D-4.X-24.A-1 to I.D-4.X-24.A-750; compounds I.E-4.X-24.A-1 to I.E-4.X-24.A-750; compounds I.F-4.X-24.A-1 to I.F-4.X-24.A-750; compounds I.G-4.X-24.A-1 to I.G-4.X-24.A-750; compounds I.H-4.X-24.A-1 to I.H-4.X-24.A-750;

compounds I.A-5.X-24.A-1 to I.A-5.X-24.A-750; compounds I.B-5.X-24.A-1 to I.B-5.X-24.A-750; compounds I.C-5.X-24.A-1 to I.C-5.X-24.A-750; compounds I.D-5.X-24.A-1 to I.D-5.X-24.A-750; compounds I.E-5.X-24.A-1 to I.E-5.X-24.A-750; compounds I.F-5.X-24.A-1 to I.F-5.X-24.A-750; compounds I.G-5.X-24.A-1 to I.G-5.X-24.A-750; compounds I.H-5.X-24.A-1 to I.H-5.X-24.A-750;

compounds I.A-6.X-24.A-1 to I.A-6.X-24.A-750; compounds I.B-6.X-24.A-1 to I.B-6.X-24.A-750; compounds I.C-6.X-24.A-1 to I.C-6.X-24.A-750; compounds I.D-6.X-24.A-1 to I.D-6.X-24.A-750; compounds I.E-6.X-24.A-1 to I.E-6.X-24.A-750; compounds I.F-6.X-24.A-1 to I.F-6.X-24.A-750; compounds I.G-6.X-24.A-1 to I.G-6.X-24.A-750; compounds I.H-6.X-24.A-1 to I.H-6.X-24.A-750).

Table 25a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-25 of Table X and the meaning for the combination of $X^1$, $X^2$, $X^3$ and $R^3$ for each individual compound corresponds in each case to one line of Table A (compounds I.A-1.X-25.A-1 to I.A-1.X-25.A-750; compounds I.B-1.X-25.A-1 to I.B-1.X-25.A-750; compounds I.C-1.X-25.A-1 to I.C-1.X-25.A-750; compounds I.D-1.X-25.A-1 to I.D-1.X-25.A-750; compounds I.E-1.X-25.A-1 to I.E-1.X-25.A-750; compounds I.F-1.X-25.A-1 to I.F-1.X-25.A-750; compounds I.G-1.X-25.A-1 to I.G-1.X-25.A-750; compounds I.H-1.X-25.A-1 to I.H-1.X-25.A-750;

compounds I.A-2.X-25.A-1 to I.A-2.X-25.A-750; compounds I.B-2.X-25.A-1 to I.B-2.X-25.A-750; compounds I.C-2.X-25.A-1 to I.C-2.X-25.A-750; compounds I.D-2.X-25.A-1 to I.D-2.X-25.A-750; compounds I.E-2.X-25.A-1 to I.E-2.X-25.A-750; compounds I.F-2.X-25.A-1 to I.F-2.X-25.A-750; compounds I.G-2.X-25.A-1 to I.G-2.X-25.A-750; compounds I.H-2.X-25.A-1 to I.H-2.X-25.A-750;

compounds I.A-3.X-25.A-1 to I.A-3.X-25.A-750; compounds I.B-3.X-25.A-1 to I.B-3.X-25.A-750; compounds I.C-3.X-25.A-1 to I.C-3.X-25.A-750; compounds I.D-3.X-25.A-1 to I.D-3.X-25.A-750; compounds I.E-3.X-25.A-1 to I.E-3.X-25.A-750; compounds I.F-3.X-25.A-1 to I.F-3.X-25.A-750; compounds I.G-3.X-25.A-1 to I.G-3.X-25.A-750; compounds I.H-3.X-25.A-1 to I.H-3.X-25.A-750;

compounds I.A-4.X-25.A-1 to I.A-4.X-25.A-750; compounds I.B-4.X-25.A-1 to I.B-4.X-25.A-750; compounds I.C-4.X-25.A-1 to I.C-4.X-25.A-750; compounds I.D-4.X-25.A-1 to I.D-4.X-25.A-750; compounds I.E-4.X-25.A-1 to I.E-4.X-25.A-750; compounds I.F-4.X-25.A-1 to I.F-4.X-25.A-750; compounds I.G-4.X-25.A-1 to I.G-4.X-25.A-750; compounds I.H-4.X-25.A-1 to I.H-4.X-25.A-750;

compounds I.A-5.X-25.A-1 to I.A-5.X-25.A-750; compounds I.B-5.X-25.A-1 to I.B-5.X-25.A-750; compounds I.C-5.X-25.A-1 to I.C-5.X-25.A-750; compounds I.D-5.X-25.A-1 to I.D-5.X-25.A-750; compounds I.E-5.X-25.A-1 to I.E-5.X-25.A-750; compounds I.F-5.X-25.A-1 to I.F-5.X-25.A-750; compounds I.G-5.X-25.A-1 to I.G-5.X-25.A-750; compounds I.H-5.X-25.A-1 to I.H-5.X-25.A-750;

compounds I.A-6.X-25.A-1 to I.A-6.X-25.A-750; compounds I.B-6.X-25.A-1 to I.B-6.X-25.A-750; compounds I.C-6.X-25.A-1 to I.C-6.X-25.A-750; compounds I.D-6.X-25.A-1 to I.D-6.X-25.A-750; compounds I.E-6.X-25.A-1 to I.E-6.X-25.A-750; compounds I.F-6.X-25.A-1 to I.F-6.X-25.A-750; compounds I.G-6.X-25.A-1 to I.G-6.X-25.A-750; compounds I.H-6.X-25.A-1 to I.H-6.X-25.A-750).

Table 26a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-26 of Table X and the meaning for the combination of $X^1$, $X^2$, $X^3$ and $R^3$ for each individual compound corresponds in each case to one line of Table A (compounds I.A-1.X-26.A-1 to I.A-1.X-26.A-750; compounds I.B-1.X-26.A-1 to I.B-1.X-26.A-750; compounds I.C-1.X-26.A-1 to I.C-1.X-26.A-750; compounds I.D-1.X-26.A-1 to I.D-1.X-26.A-750; compounds I.E-1.X-26.A-1 to I.E-1.X-26.A-750; compounds I.F-1.X-26.A-1 to I.F-1.X-26.A-750; compounds I.G-1.X-26.A-1 to I.G-1.X-26.A-750; compounds I.H-1.X-26.A-1 to I.H-1.X-26.A-750;

compounds I.A-2.X-26.A-1 to I.A-2.X-26.A-750; compounds I.B-2.X-26.A-1 to I.B-2.X-26.A-750; compounds I.C-2.X-26.A-1 to I.C-2.X-26.A-750; compounds I.D-2.X-26.A-1 to I.D-2.X-26.A-750; compounds I.E-2.X-26.A-1 to I.E-2.X-26.A-750; compounds I.F-2.X-26.A-1 to I.F-2.X-26.A-750; compounds I.G-2.X-26.A-1 to I.G-2.X-26.A-750; compounds I.H-2.X-26.A-1 to I.H-2.X-26.A-750;

compounds I.A-3.X-26.A-1 to I.A-3.X-26.A-750; compounds I.B-3.X-26.A-1 to I.B-3.X-26.A-750; compounds I.C-3.X-26.A-1 to I.C-3.X-26.A-750; compounds I.D-3.X-26.A-1 to I.D-3.X-26.A-750; compounds I.E-3.X-26.A-1 to I.E-3.X-26.A-750; compounds I.F-3.X-26.A-1 to I.F-3.X-26.A-750; compounds I.G-3.X-26.A-1 to I.G-3.X-26.A-750; compounds I.H-3.X-26.A-1 to I.H-3.X-26.A-750;

compounds I.A-4.X-26.A-1 to I.A-4.X-26.A-750; compounds I.B-4.X-26.A-1 to I.B-4.X-26.A-750; compounds I.C-4.X-26.A-1 to I.C-4.X-26.A-750; compounds I.D-4.X-26.A-1 to I.D-4.X-26.A-750; compounds I.E-4.X-26.A-1 to I.E-4.X-26.A-750; compounds I.F-4.X-26.A-1 to I.F-4.X-26.A-750; compounds I.G-4.X-26.A-1 to I.G-4.X-26.A-750; compounds I.H-4.X-26.A-1 to I.H-4.X-26.A-750;

compounds I.A-5.X-26.A-1 to I.A-5.X-26.A-750; compounds I.B-5.X-26.A-1 to I.B-5.X-26.A-750; compounds I.C-5.X-26.A-1 to I.C-5.X-26.A-750; compounds I.D-5.X-26.A-1 to I.D-5.X-26.A-750; compounds I.E-5.X-26.A-1 to I.E-5.X-26.A-750; compounds I.F-5.X-26.A-1 to I.F-5.X-26.A-750; compounds I.G-5.X-26.A-1 to I.G-5.X-26.A-750; compounds I.H-5.X-26.A-1 to I.H-5.X-26.A-750;

compounds I.A-6.X-26.A-1 to I.A-6.X-26.A-750; compounds I.B-6.X-26.A-1 to I.B-6.X-26.A-750; compounds I.C-6.X-26.A-1 to I.C-6.X-26.A-750; compounds I.D-6.X-

26.A-1 to I.D-6.X-26.A-750; compounds I.E-6.X-26.A-1 to I.E-6.X-26.A-750; compounds I.F-6.X-26.A-1 to I.F-6.X-26.A-750; compounds I.G-6.X-26.A-1 to I.G-6.X-26.A-750; compounds I.H-6.X-26.A-1 to I.H-6.X-26.A-750).

Table 27a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-27 of Table X and the meaning for the combination of $X^1$, $X^2$, $X^3$ and $R^3$ for each individual compound corresponds in each case to one line of Table A (compounds I.A-1.X-27.A-1 to I.A-1.X-27.A-750; compounds I.B-1.X-27.A-1 to I.B-1.X-27.A-750; compounds I.C-1.X-27.A-1 to I.C-1.X-27.A-750; compounds I.D-1.X-27.A-1 to I.D-1.X-27.A-750; compounds I.E-1.X-27.A-1 to I.E-1.X-27.A-750; compounds I.F-1.X-27.A-1 to I.F-1.X-27.A-750; compounds I.G-1.X-27.A-1 to I.G-1.X-27.A-750; compounds I.H-1.X-27.A-1 to I.H-1.X-27.A-750;

compounds I.A-2.X-27.A-1 to I.A-2.X-27.A-750; compounds I.B-2.X-27.A-1 to I.B-2.X-27.A-750; compounds I.C-2.X-27.A-1 to I.C-2.X-27.A-750; compounds I.D-2.X-27.A-1 to I.D-2.X-27.A-750; compounds I.E-2.X-27.A-1 to I.E-2.X-27.A-750; compounds I.F-2.X-27.A-1 to I.F-2.X-27.A-750; compounds I.G-2.X-27.A-1 to I.G-2.X-27.A-750; compounds I.H-2.X-27.A-1 to I.H-2.X-27.A-750;

compounds I.A-3.X-27.A-1 to I.A-3.X-27.A-750; compounds I.B-3.X-27.A-1 to I.B-3.X-27.A-750; compounds I.C-3.X-27.A-1 to I.C-3.X-27.A-750; compounds I.D-3.X-27.A-1 to I.D-3.X-27.A-750; compounds I.E-3.X-27.A-1 to I.E-3.X-27.A-750; compounds I.F-3.X-27.A-1 to I.F-3.X-27.A-750; compounds I.G-3.X-27.A-1 to I.G-3.X-27.A-750; compounds I.H-3.X-27.A-1 to I.H-3.X-27.A-750;

compounds I.A-4.X-27.A-1 to I.A-4.X-27.A-750; compounds I.B-4.X-27.A-1 to I.B-4.X-27.A-750; compounds I.C-4.X-27.A-1 to I.C-4.X-27.A-750; compounds I.D-4.X-27.A-1 to I.D-4.X-27.A-750; compounds I.E-4.X-27.A-1 to I.E-4.X-27.A-750; compounds I.F-4.X-27.A-1 to I.F-4.X-27.A-750; compounds I.G-4.X-27.A-1 to I.G-4.X-27.A-750; compounds I.H-4.X-27.A-1 to I.H-4.X-27.A-750;

compounds I.A-5.X-27.A-1 to I.A-5.X-27.A-750; compounds I.B-5.X-27.A-1 to I.B-5.X-27.A-750; compounds I.C-5.X-27.A-1 to I.C-5.X-27.A-750; compounds I.D-5.X-27.A-1 to I.D-5.X-27.A-750; compounds I.E-5.X-27.A-1 to I.E-5.X-27.A-750; compounds I.F-5.X-27.A-1 to I.F-5.X-27.A-750; compounds I.G-5.X-27.A-1 to I.G-5.X-27.A-750; compounds I.H-5.X-27.A-1 to I.H-5.X-27.A-750;

compounds I.A-6.X-27.A-1 to I.A-6.X-27.A-750; compounds I.B-6.X-27.A-1 to I.B-6.X-27.A-750; compounds I.C-6.X-27.A-1 to I.C-6.X-27.A-750; compounds I.D-6.X-27.A-1 to I.D-6.X-27.A-750; compounds I.E-6.X-27.A-1 to I.E-6.X-27.A-750; compounds I.F-6.X-27.A-1 to I.F-6.X-27.A-750; compounds I.G-6.X-27.A-1 to I.G-6.X-27.A-750; compounds I.H-6.X-27.A-1 to I.H-6.X-27.A-750).

Table 28a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-28 of Table X and the meaning for the combination of $X^1$, $X^2$, $X^3$ and $R^3$ for each individual compound corresponds in each case to one line of Table A (compounds I.A-1.X-28.A-1 to I.A-1.X-28.A-750; compounds I.B-1.X-28.A-1 to I.B-1.X-28.A-750; compounds I.C-1.X-28.A-1 to I.C-1.X-28.A-750; compounds I.D-1.X-28.A-1 to I.D-1.X-28.A-750; compounds I.E-1.X-28.A-1 to I.E-1.X-28.A-750; compounds I.F-1.X-28.A-1 to I.F-1.X-28.A-750; compounds I.G-1.X-28.A-1 to I.G-1.X-28.A-750; compounds I.H-1.X-28.A-1 to I.H-1.X-28.A-750;

compounds I.A-2.X-28.A-1 to I.A-2.X-28.A-750; compounds I.B-2.X-28.A-1 to I.B-2.X-28.A-750; compounds I.C-2.X-28.A-1 to I.C-2.X-28.A-750; compounds I.D-2.X-28.A-1 to I.D-2.X-28.A-750; compounds I.E-2.X-28.A-1 to I.E-2.X-28.A-750; compounds I.F-2.X-28.A-1 to I.F-2.X-28.A-750; compounds I.G-2.X-28.A-1 to I.G-2.X-28.A-750; compounds I.H-2.X-28.A-1 to I.H-2.X-28.A-750;

compounds I.A-3.X-28.A-1 to I.A-3.X-28.A-750; compounds I.B-3.X-28.A-1 to I.B-3.X-28.A-750; compounds I.C-3.X-28.A-1 to I.C-3.X-28.A-750; compounds I.D-3.X-28.A-1 to I.D-3.X-28.A-750; compounds I.E-3.X-28.A-1 to I.E-3.X-28.A-750; compounds I.F-3.X-28.A-1 to I.F-3.X-28.A-750; compounds I.G-3.X-28.A-1 to I.G-3.X-28.A-750; compounds I.H-3.X-28.A-1 to I.H-3.X-28.A-750;

compounds I.A-4.X-28.A-1 to I.A-4.X-28.A-750; compounds I.B-4.X-28.A-1 to I.B-4.X-28.A-750; compounds I.C-4.X-28.A-1 to I.C-4.X-28.A-750; compounds I.D-4.X-28.A-1 to I.D-4.X-28.A-750; compounds I.E-4.X-28.A-1 to I.E-4.X-28.A-750; compounds I.F-4.X-28.A-1 to I.F-4.X-28.A-750; compounds I.G-4.X-28.A-1 to I.G-4.X-28.A-750; compounds I.H-4.X-28.A-1 to I.H-4.X-28.A-750;

compounds I.A-5.X-28.A-1 to I.A-5.X-28.A-750; compounds I.B-5.X-28.A-1 to I.B-5.X-28.A-750; compounds I.C-5.X-28.A-1 to I.C-5.X-28.A-750; compounds I.D-5.X-28.A-1 to I.D-5.X-28.A-750; compounds I.E-5.X-28.A-1 to I.E-5.X-28.A-750; compounds I.F-5.X-28.A-1 to I.F-5.X-28.A-750; compounds I.G-5.X-28.A-1 to I.G-5.X-28.A-750; compounds I.H-5.X-28.A-1 to I.H-5.X-28.A-750;

compounds I.A-6.X-28.A-1 to I.A-6.X-28.A-750; compounds I.B-6.X-28.A-1 to I.B-6.X-28.A-750; compounds I.C-6.X-28.A-1 to I.C-6.X-28.A-750; compounds I.D-6.X-28.A-1 to I.D-6.X-28.A-750; compounds I.E-6.X-28.A-1 to I.E-6.X-28.A-750; compounds I.F-6.X-28.A-1 to I.F-6.X-28.A-750; compounds I.G-6.X-28.A-1 to I.G-6.X-28.A-750; compounds I.H-6.X-28.A-1 to I.H-6.X-28.A-750).

Table 29a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-29 of Table X and the meaning for the combination of $X^1$, $X^2$, $X^3$ and $R^3$ for each individual compound corresponds in each case to one line of Table A (compounds I.A-1.X-29.A-1 to I.A-1.X-29.A-750; compounds I.B-1.X-29.A-1 to I.B-1.X-29.A-750; compounds I.C-1.X-29.A-1 to I.C-1.X-29.A-750; compounds I.D-1.X-29.A-1 to I.D-1.X-29.A-750; compounds I.E-1.X-29.A-1 to I.E-1.X-29.A-750; compounds I.F-1.X-29.A-1 to I.F-1.X-29.A-750; compounds I.G-1.X-29.A-1 to I.G-1.X-29.A-750; compounds I.H-1.X-29.A-1 to I.H-1.X-29.A-750;

compounds I.A-2.X-29.A-1 to I.A-2.X-29.A-750; compounds I.B-2.X-29.A-1 to I.B-2.X-29.A-750; compounds I.C-2.X-29.A-1 to I.C-2.X-29.A-750; compounds I.D-2.X-

29.A-1 to I.D-2.X-29.A-750; compounds I.E-2.X-29.A-1 to I.E-2.X-29.A-750; compounds I.F-2.X-29.A-1 to I.F-2.X-29.A-750; compounds I.G-2.X-29.A-1 to I.G-2.X-29.A-750; compounds I.H-2.X-29.A-1 to I.H-2.X-29.A-750;

compounds I.A-3.X-29.A-1 to I.A-3.X-29.A-750; compounds I.B-3.X-29.A-1 to I.B-3.X-29.A-750; compounds I.C-3.X-29.A-1 to I.C-3.X-29.A-750; compounds I.D-3.X-29.A-1 to I.D-3.X-29.A-750; compounds I.E-3.X-29.A-1 to I.E-3.X-29.A-750; compounds I.F-3.X-29.A-1 to I.F-3.X-29.A-750; compounds I.G-3.X-29.A-1 to I.G-3.X-29.A-750; compounds I.H-3.X-29.A-1 to I.H-3.X-29.A-750;

compounds I.A-4.X-29.A-1 to I.A-4.X-29.A-750; compounds I.B-4.X-29.A-1 to I.B-4.X-29.A-750; compounds I.C-4.X-29.A-1 to I.C-4.X-29.A-750; compounds I.D-4.X-29.A-1 to I.D-4.X-29.A-750; compounds I.E-4.X-29.A-1 to I.E-4.X-29.A-750; compounds I.F-4.X-29.A-1 to I.F-4.X-29.A-750; compounds I.G-4.X-29.A-1 to I.G-4.X-29.A-750; compounds I.H-4.X-29.A-1 to I.H-4.X-29.A-750;

compounds I.A-5.X-29.A-1 to I.A-5.X-29.A-750; compounds I.B-5.X-29.A-1 to I.B-5.X-29.A-750; compounds I.C-5.X-29.A-1 to I.C-5.X-29.A-750; compounds I.D-5.X-29.A-1 to I.D-5.X-29.A-750; compounds I.E-5.X-29.A-1 to I.E-5.X-29.A-750; compounds I.F-5.X-29.A-1 to I.F-5.X-29.A-750; compounds I.G-5.X-29.A-1 to I.G-5.X-29.A-750; compounds I.H-5.X-29.A-1 to I.H-5.X-29.A-750;

compounds I.A-6.X-29.A-1 to I.A-6.X-29.A-750; compounds I.B-6.X-29.A-1 to I.B-6.X-29.A-750; compounds I.C-6.X-29.A-1 to I.C-6.X-29.A-750; compounds I.D-6.X-29.A-1 to I.D-6.X-29.A-750; compounds I.E-6.X-29.A-1 to I.E-6.X-29.A-750; compounds I.F-6.X-29.A-1 to I.F-6.X-29.A-750; compounds I.G-6.X-29.A-1 to I.G-6.X-29.A-750; compounds I.H-6.X-29.A-1 to I.H-6.X-29.A-750).

Table 30a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-30 of Table X and the meaning for the combination of $X^1$, $X^2$, $X^3$ and $R^3$ for each individual compound corresponds in each case to one line of Table A (compounds I.A-1.X-30.A-1 to I.A-1.X-30.A-750; compounds I.B-1.X-30.A-1 to I.B-1.X-30.A-750; compounds I.C-1.X-30.A-1 to I.C-1.X-30.A-750; compounds I.D-1.X-30.A-1 to I.D-1.X-30.A-750; compounds I.E-1.X-30.A-1 to I.E-1.X-30.A-750; compounds I.F-1.X-30.A-1 to I.F-1.X-30.A-750; compounds I.G-1.X-30.A-1 to I.G-1.X-30.A-750; compounds I.H-1.X-30.A-1 to I.H-1.X-30.A-750;

compounds I.A-2.X-30.A-1 to I.A-2.X-30.A-750; compounds I.B-2.X-30.A-1 to I.B-2.X-30.A-750; compounds I.C-2.X-30.A-1 to I.C-2.X-30.A-750; compounds I.D-2.X-30.A-1 to I.D-2.X-30.A-750; compounds I.E-2.X-30.A-1 to I.E-2.X-30.A-750; compounds I.F-2.X-30.A-1 to I.F-2.X-30.A-750; compounds I.G-2.X-30.A-1 to I.G-2.X-30.A-750; compounds I.H-2.X-30.A-1 to I.H-2.X-30.A-750;

compounds I.A-3.X-30.A-1 to I.A-3.X-30.A-750; compounds I.B-3.X-30.A-1 to I.B-3.X-30.A-750; compounds I.C-3.X-30.A-1 to I.C-3.X-30.A-750; compounds I.D-3.X-30.A-1 to I.D-3.X-30.A-750; compounds I.E-3.X-30.A-1 to I.E-3.X-30.A-750; compounds I.F-3.X-30.A-1 to I.F-3.X-30.A-750; compounds I.G-3.X-30.A-1 to I.G-3.X-30.A-750; compounds I.H-3.X-30.A-1 to I.H-3.X-30.A-750;

compounds I.A-4.X-30.A-1 to I.A-4.X-30.A-750; compounds I.B-4.X-30.A-1 to I.B-4.X-30.A-750; compounds I.C-4.X-30.A-1 to I.C-4.X-30.A-750; compounds I.D-4.X-30.A-1 to I.D-4.X-30.A-750; compounds I.E-4.X-30.A-1 to I.E-4.X-30.A-750; compounds I.F-4.X-30.A-1 to I.F-4.X-30.A-750; compounds I.G-4.X-30.A-1 to I.G-4.X-30.A-750; compounds I.H-4.X-30.A-1 to I.H-4.X-30.A-750;

compounds I.A-5.X-30.A-1 to I.A-5.X-30.A-750; compounds I.B-5.X-30.A-1 to I.B-5.X-30.A-750; compounds I.C-5.X-30.A-1 to I.C-5.X-30.A-750; compounds I.D-5.X-30.A-1 to I.D-5.X-30.A-750; compounds I.E-5.X-30.A-1 to I.E-5.X-30.A-750; compounds I.F-5.X-30.A-1 to I.F-5.X-30.A-750; compounds I.G-5.X-30.A-1 to I.G-5.X-30.A-750; compounds I.H-5.X-30.A-1 to I.H-5.X-30.A-750;

compounds I.A-6.X-30.A-1 to I.A-6.X-30.A-750; compounds I.B-6.X-30.A-1 to I.B-6.X-30.A-750; compounds I.C-6.X-30.A-1 to I.C-6.X-30.A-750; compounds I.D-6.X-30.A-1 to I.D-6.X-30.A-750; compounds I.E-6.X-30.A-1 to I.E-6.X-30.A-750; compounds I.F-6.X-30.A-1 to I.F-6.X-30.A-750; compounds I.G-6.X-30.A-1 to I.G-6.X-30.A-750; compounds I.H-6.X-30.A-1 to I.H-6.X-30.A-750).

Table 31a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-31 of Table X and the meaning for the combination of $X^1$, $X^2$, $X^3$ and $R^3$ for each individual compound corresponds in each case to one line of Table A (compounds I.A-1.X-31.A-1 to I.A-1.X-31.A-750; compounds I.B-1.X-31.A-1 to I.B-1.X-31.A-750; compounds I.C-1.X-31.A-1 to I.C-1.X-31.A-750; compounds I.D-1.X-31.A-1 to I.D-1.X-31.A-750; compounds I.E-1.X-31.A-1 to I.E-1.X-31.A-750; compounds I.F-1.X-31.A-1 to I.F-1.X-31.A-750; compounds I.G-1.X-31.A-1 to I.G-1.X-31.A-750; compounds I.H-1.X-31.A-1 to I.H-1.X-31.A-750;

compounds I.A-2.X-31.A-1 to I.A-2.X-31.A-750; compounds I.B-2.X-31.A-1 to I.B-2.X-31.A-750; compounds I.C-2.X-31.A-1 to I.C-2.X-31.A-750; compounds I.D-2.X-31.A-1 to I.D-2.X-31.A-750; compounds I.E-2.X-31.A-1 to I.E-2.X-31.A-750; compounds I.F-2.X-31.A-1 to I.F-2.X-31.A-750; compounds I.G-2.X-31.A-1 to I.G-2.X-31.A-750; compounds I.H-2.X-31.A-1 to I.H-2.X-31.A-750;

compounds I.A-3.X-31.A-1 to I.A-3.X-31.A-750; compounds I.B-3.X-31.A-1 to I.B-3.X-31.A-750; compounds I.C-3.X-31.A-1 to I.C-3.X-31.A-750; compounds I.D-3.X-31.A-1 to I.D-3.X-31.A-750; compounds I.E-3.X-31.A-1 to I.E-3.X-31.A-750; compounds I.F-3.X-31.A-1 to I.F-3.X-31.A-750; compounds I.G-3.X-31.A-1 to I.G-3.X-31.A-750; compounds I.H-3.X-31.A-1 to I.H-3.X-31.A-750;

compounds I.A-4.X-31.A-1 to I.A-4.X-31.A-750; compounds I.B-4.X-31.A-1 to I.B-4.X-31.A-750; compounds I.C-4.X-31.A-1 to I.C-4.X-31.A-750; compounds I.D-4.X-31.A-1 to I.D-4.X-31.A-750; compounds I.E-4.X-31.A-1 to I.E-4.X-31.A-750; compounds I.F-4.X-31.A-1 to I.F-4.X-31.A-750; compounds I.G-4.X-31.A-1 to I.G-4.X-31.A-750; compounds I.H-4.X-31.A-1 to I.H-4.X-31.A-750;

compounds I.A-5.X-31.A-1 to I.A-5.X-31.A-750; compounds I.B-5.X-31.A-1 to I.B-5.X-31.A-750; compounds I.C-5.X-31.A-1 to I.C-5.X-31.A-750; compounds I.D-5.X-31.A-1 to I.D-5.X-31.A-750; compounds I.E-5.X-31.A-1 to I.E-5.X-31.A-750; compounds I.F-5.X-31.A-1 to I.F-5.X-31.A-750; compounds I.G-5.X-31.A-1 to I.G-5.X-31.A-750; compounds I.H-5.X-31.A-1 to I.H-5.X-31.A-750;

compounds I.A-6.X-31.A-1 to I.A-6.X-31.A-750; compounds I.B-6.X-31.A-1 to I.B-6.X-31.A-750; compounds I.C-6.X-31.A-1 to I.C-6.X-31.A-750; compounds I.D-6.X-

31.A-1 to I.D-6.X-31.A-750; compounds I.E-6.X-31.A-1 to I.E-6.X-31.A-750; compounds I.F-6.X-31.A-1 to I.F-6.X-31.A-750; compounds I.G-6.X-31.A-1 to I.G-6.X-31.A-750; compounds I.H-6.X-31.A-1 to I.H-6.X-31.A-750).

Table 32a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-32 of Table X and the meaning for the combination of $X^1$, $X^2$, $X^3$ and $R^3$ for each individual compound corresponds in each case to one line of Table A (compounds I.A-1.X-32.A-1 to I.A-1.X-32.A-750; compounds I.B-1.X-32.A-1 to I.B-1.X-32.A-750; compounds I.C-1.X-32.A-1 to I.C-1.X-32.A-750; compounds I.D-1.X-32.A-1 to I.D-1.X-32.A-750; compounds I.E-1.X-32.A-1 to I.E-1.X-32.A-750; compounds I.F-1.X-32.A-1 to I.F-1.X-32.A-750; compounds I.G-1.X-32.A-1 to I.G-1.X-32.A-750; compounds I.H-1.X-32.A-1 to I.H-1.X-32.A-750;

compounds I.A-2.X-32.A-1 to I.A-2.X-32.A-750; compounds I.B-2.X-32.A-1 to I.B-2.X-32.A-750; compounds I.C-2.X-32.A-1 to I.C-2.X-32.A-750; compounds I.D-2.X-32.A-1 to I.D-2.X-32.A-750; compounds I.E-2.X-32.A-1 to I.E-2.X-32.A-750; compounds I.F-2.X-32.A-1 to I.F-2.X-32.A-750; compounds I.G-2.X-32.A-1 to I.G-2.X-32.A-750; compounds I.H-2.X-32.A-1 to I.H-2.X-32.A-750;

compounds I.A-3.X-32.A-1 to I.A-3.X-32.A-750; compounds I.B-3.X-32.A-1 to I.B-3.X-32.A-750; compounds I.C-3.X-32.A-1 to I.C-3.X-32.A-750; compounds I.D-3.X-32.A-1 to I.D-3.X-32.A-750; compounds I.E-3.X-32.A-1 to I.E-3.X-32.A-750; compounds I.F-3.X-32.A-1 to I.F-3.X-32.A-750; compounds I.G-3.X-32.A-1 to I.G-3.X-32.A-750; compounds I.H-3.X-32.A-1 to I.H-3.X-32.A-750;

compounds I.A-4.X-32.A-1 to I.A-4.X-32.A-750; compounds I.B-4.X-32.A-1 to I.B-4.X-32.A-750; compounds I.C-4.X-32.A-1 to I.C-4.X-32.A-750; compounds I.D-4.X-32.A-1 to I.D-4.X-32.A-750; compounds I.E-4.X-32.A-1 to I.E-4.X-32.A-750; compounds I.F-4.X-32.A-1 to I.F-4.X-32.A-750; compounds I.G-4.X-32.A-1 to I.G-4.X-32.A-750; compounds I.H-4.X-32.A-1 to I.H-4.X-32.A-750;

compounds I.A-5.X-32.A-1 to I.A-5.X-32.A-750; compounds I.B-5.X-32.A-1 to I.B-5.X-32.A-750; compounds I.C-5.X-32.A-1 to I.C-5.X-32.A-750; compounds I.D-5.X-32.A-1 to I.D-5.X-32.A-750; compounds I.E-5.X-32.A-1 to I.E-5.X-32.A-750; compounds I.F-5.X-32.A-1 to I.F-5.X-32.A-750; compounds I.G-5.X-32.A-1 to I.G-5.X-32.A-750; compounds I.H-5.X-32.A-1 to I.H-5.X-32.A-750;

compounds I.A-6.X-32.A-1 to I.A-6.X-32.A-750; compounds I.B-6.X-32.A-1 to I.B-6.X-32.A-750; compounds I.C-6.X-32.A-1 to I.C-6.X-32.A-750; compounds I.D-6.X-32.A-1 to I.D-6.X-32.A-750; compounds I.E-6.X-32.A-1 to I.E-6.X-32.A-750; compounds I.F-6.X-32.A-1 to I.F-6.X-32.A-750; compounds I.G-6.X-32.A-1 to I.G-6.X-32.A-750; compounds I.H-6.X-32.A-1 to I.H-6.X-32.A-750).

Table 33a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-33 of Table X and the meaning for the combination of $X^1$, $X^2$, $X^3$ and $R^3$ for each individual compound corresponds in each case to one line of Table A (compounds I.A-1.X-33.A-1 to I.A-1.X-33.A-750; compounds I.B-1.X-33.A-1 to I.B-1.X-33.A-750; compounds I.C-1.X-33.A-1 to I.C-1.X-33.A-750; compounds I.D-1.X-33.A-1 to I.D-1.X-33.A-750; compounds I.E-1.X-33.A-1 to I.E-1.X-33.A-750; compounds I.F-1.X-33.A-1 to I.F-1.X-33.A-750; compounds I.G-1.X-33.A-1 to I.G-1.X-33.A-750; compounds I.H-1.X-33.A-1 to I.H-1.X-33.A-750;

compounds I.A-2.X-33.A-1 to I.A-2.X-33.A-750; compounds I.B-2.X-33.A-1 to I.B-2.X-33.A-750; compounds I.C-2.X-33.A-1 to I.C-2.X-33.A-750; compounds I.D-2.X-33.A-1 to I.D-2.X-33.A-750; compounds I.E-2.X-33.A-1 to I.E-2.X-33.A-750; compounds I.F-2.X-33.A-1 to I.F-2.X-33.A-750; compounds I.G-2.X-33.A-1 to I.G-2.X-33.A-750; compounds I.H-2.X-33.A-1 to I.H-2.X-33.A-750;

compounds I.A-3.X-33.A-1 to I.A-3.X-33.A-750; compounds I.B-3.X-33.A-1 to I.B-3.X-33.A-750; compounds I.C-3.X-33.A-1 to I.C-3.X-33.A-750; compounds I.D-3.X-33.A-1 to I.D-3.X-33.A-750; compounds I.E-3.X-33.A-1 to I.E-3.X-33.A-750; compounds I.F-3.X-33.A-1 to I.F-3.X-33.A-750; compounds I.G-3.X-33.A-1 to I.G-3.X-33.A-750; compounds I.H-3.X-33.A-1 to I.H-3.X-33.A-750;

compounds I.A-4.X-33.A-1 to I.A-4.X-33.A-750; compounds I.B-4.X-33.A-1 to I.B-4.X-33.A-750; compounds I.C-4.X-33.A-1 to I.C-4.X-33.A-750; compounds I.D-4.X-33.A-1 to I.D-4.X-33.A-750; compounds I.E-4.X-33.A-1 to I.E-4.X-33.A-750; compounds I.F-4.X-33.A-1 to I.F-4.X-33.A-750; compounds I.G-4.X-33.A-1 to I.G-4.X-33.A-750; compounds I.H-4.X-33.A-1 to I.H-4.X-33.A-750;

compounds I.A-5.X-33.A-1 to I.A-5.X-33.A-750; compounds I.B-5.X-33.A-1 to I.B-5.X-33.A-750; compounds I.C-5.X-33.A-1 to I.C-5.X-33.A-750; compounds I.D-5.X-33.A-1 to I.D-5.X-33.A-750; compounds I.E-5.X-33.A-1 to I.E-5.X-33.A-750; compounds I.F-5.X-33.A-1 to I.F-5.X-33.A-750; compounds I.G-5.X-33.A-1 to I.G-5.X-33.A-750; compounds I.H-5.X-33.A-1 to I.H-5.X-33.A-750;

compounds I.A-6.X-33.A-1 to I.A-6.X-33.A-750; compounds I.B-6.X-33.A-1 to I.B-6.X-33.A-750; compounds I.C-6.X-33.A-1 to I.C-6.X-33.A-750; compounds I.D-6.X-33.A-1 to I.D-6.X-33.A-750; compounds I.E-6.X-33.A-1 to I.E-6.X-33.A-750; compounds I.F-6.X-33.A-1 to I.F-6.X-33.A-750; compounds I.G-6.X-33.A-1 to I.G-6.X-33.A-750; compounds I.H-6.X-33.A-1 to I.H-6.X-33.A-750).

Table 34a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-34 of Table X and the meaning for the combination of $X^1$, $X^2$, $X^3$ and $R^3$ for each individual compound corresponds in each case to one line of Table A (compounds I.A-1.X-34.A-1 to I.A-1.X-34.A-750; compounds I.B-1.X-34.A-1 to I.B-1.X-34.A-750; compounds I.C-1.X-34.A-1 to I.C-1.X-34.A-750; compounds I.D-1.X-34.A-1 to I.D-1.X-34.A-750; compounds I.E-1.X-34.A-1 to I.E-1.X-34.A-750; compounds I.F-1.X-34.A-1 to I.F-1.X-34.A-750; compounds I.G-1.X-34.A-1 to I.G-1.X-34.A-750; compounds I.H-1.X-34.A-1 to I.H-1.X-34.A-750;

compounds I.A-2.X-34.A-1 to I.A-2.X-34.A-750; compounds I.B-2.X-34.A-1 to I.B-2.X-34.A-750; compounds I.C-2.X-34.A-1 to I.C-2.X-34.A-750; compounds I.D-2.X-

34.A-1 to I.D-2.X-34.A-750; compounds I.E-2.X-34.A-1 to I.E-2.X-34.A-750; compounds I.F-2.X-34.A-1 to I.F-2.X-34.A-750; compounds I.G-2.X-34.A-1 to I.G-2.X-34.A-750; compounds I.H-2.X-34.A-1 to I.H-2.X-34.A-750;

compounds I.A-3.X-34.A-1 to I.A-3.X-34.A-750; compounds I.B-3.X-34.A-1 to I.B-3.X-34.A-750; compounds I.C-3.X-34.A-1 to I.C-3.X-34.A-750; compounds I.D-3.X-34.A-1 to I.D-3.X-34.A-750; compounds I.E-3.X-34.A-1 to I.E-3.X-34.A-750; compounds I.F-3.X-34.A-1 to I.F-3.X-34.A-750; compounds I.G-3.X-34.A-1 to I.G-3.X-34.A-750; compounds I.H-3.X-34.A-1 to I.H-3.X-34.A-750;

compounds I.A-4.X-34.A-1 to I.A-4.X-34.A-750; compounds I.B-4.X-34.A-1 to I.B-4.X-34.A-750; compounds I.C-4.X-34.A-1 to I.C-4.X-34.A-750; compounds I.D-4.X-34.A-1 to I.D-4.X-34.A-750; compounds I.E-4.X-34.A-1 to I.E-4.X-34.A-750; compounds I.F-4.X-34.A-1 to I.F-4.X-34.A-750; compounds I.G-4.X-34.A-1 to I.G-4.X-34.A-750; compounds I.H-4.X-34.A-1 to I.H-4.X-34.A-750;

compounds I.A-5.X-34.A-1 to I.A-5.X-34.A-750; compounds I.B-5.X-34.A-1 to I.B-5.X-34.A-750; compounds I.C-5.X-34.A-1 to I.C-5.X-34.A-750; compounds I.D-5.X-34.A-1 to I.D-5.X-34.A-750; compounds I.E-5.X-34.A-1 to I.E-5.X-34.A-750; compounds I.F-5.X-34.A-1 to I.F-5.X-34.A-750; compounds I.G-5.X-34.A-1 to I.G-5.X-34.A-750; compounds I.H-5.X-34.A-1 to I.H-5.X-34.A-750;

compounds I.A-6.X-34.A-1 to I.A-6.X-34.A-750; compounds I.B-6.X-34.A-1 to I.B-6.X-34.A-750; compounds I.C-6.X-34.A-1 to I.C-6.X-34.A-750; compounds I.D-6.X-34.A-1 to I.D-6.X-34.A-750; compounds I.E-6.X-34.A-1 to I.E-6.X-34.A-750; compounds I.F-6.X-34.A-1 to I.F-6.X-34.A-750; compounds I.G-6.X-34.A-1 to I.G-6.X-34.A-750; compounds I.H-6.X-34.A-1 to I.H-6.X-34.A-750).

Table 35a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-35 of Table X and the meaning for the combination of $X^1$, $X^2$, $X^3$ and $R^3$ for each individual compound corresponds in each case to one line of Table A (compounds I.A-1.X-35.A-1 to I.A-1.X-35.A-750; compounds I.B-1.X-35.A-1 to I.B-1.X-35.A-750; compounds I.C-1.X-35.A-1 to I.C-1.X-35.A-750; compounds I.D-1.X-35.A-1 to I.D-1.X-35.A-750; compounds I.E-1.X-35.A-1 to I.E-1.X-35.A-750; compounds I.F-1.X-35.A-1 to I.F-1.X-35.A-750; compounds I.G-1.X-35.A-1 to I.G-1.X-35.A-750; compounds I.H-1.X-35.A-1 to I.H-1.X-35.A-750;

compounds I.A-2.X-35.A-1 to I.A-2.X-35.A-750; compounds I.B-2.X-35.A-1 to I.B-2.X-35.A-750; compounds I.C-2.X-35.A-1 to I.C-2.X-35.A-750; compounds I.D-2.X-35.A-1 to I.D-2.X-35.A-750; compounds I.E-2.X-35.A-1 to I.E-2.X-35.A-750; compounds I.F-2.X-35.A-1 to I.F-2.X-35.A-750; compounds I.G-2.X-35.A-1 to I.G-2.X-35.A-750; compounds I.H-2.X-35.A-1 to I.H-2.X-35.A-750;

compounds I.A-3.X-35.A-1 to I.A-3.X-35.A-750; compounds I.B-3.X-35.A-1 to I.B-3.X-35.A-750; compounds I.C-3.X-35.A-1 to I.C-3.X-35.A-750; compounds I.D-3.X-35.A-1 to I.D-3.X-35.A-750; compounds I.E-3.X-35.A-1 to I.E-3.X-35.A-750; compounds I.F-3.X-35.A-1 to I.F-3.X-35.A-750; compounds I.G-3.X-35.A-1 to I.G-3.X-35.A-750; compounds I.H-3.X-35.A-1 to I.H-3.X-35.A-750;

compounds I.A-4.X-35.A-1 to I.A-4.X-35.A-750; compounds I.B-4.X-35.A-1 to I.B-4.X-35.A-750; compounds I.C-4.X-35.A-1 to I.C-4.X-35.A-750; compounds I.D-4.X-35.A-1 to I.D-4.X-35.A-750; compounds I.E-4.X-35.A-1 to I.E-4.X-35.A-750; compounds I.F-4.X-35.A-1 to I.F-4.X-35.A-750; compounds I.G-4.X-35.A-1 to I.G-4.X-35.A-750; compounds I.H-4.X-35.A-1 to I.H-4.X-35.A-750;

compounds I.A-5.X-35.A-1 to I.A-5.X-35.A-750; compounds I.B-5.X-35.A-1 to I.B-5.X-35.A-750; compounds I.C-5.X-35.A-1 to I.C-5.X-35.A-750; compounds I.D-5.X-35.A-1 to I.D-5.X-35.A-750; compounds I.E-5.X-35.A-1 to I.E-5.X-35.A-750; compounds I.F-5.X-35.A-1 to I.F-5.X-35.A-750; compounds I.G-5.X-35.A-1 to I.G-5.X-35.A-750; compounds I.H-5.X-35.A-1 to I.H-5.X-35.A-750;

compounds I.A-6.X-35.A-1 to I.A-6.X-35.A-750; compounds I.B-6.X-35.A-1 to I.B-6.X-35.A-750; compounds I.C-6.X-35.A-1 to I.C-6.X-35.A-750; compounds I.D-6.X-35.A-1 to I.D-6.X-35.A-750; compounds I.E-6.X-35.A-1 to I.E-6.X-35.A-750; compounds I.F-6.X-35.A-1 to I.F-6.X-35.A-750; compounds I.G-6.X-35.A-1 to I.G-6.X-35.A-750; compounds I.H-6.X-35.A-1 to I.H-6.X-35.A-750).

Table 36a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-36 of Table X and the meaning for the combination of $X^1$, $X^2$, $X^3$ and $R^3$ for each individual compound corresponds in each case to one line of Table A (compounds I.A-1.X-36.A-1 to I.A-1.X-36.A-750; compounds I.B-1.X-36.A-1 to I.B-1.X-36.A-750; compounds I.C-1.X-36.A-1 to I.C-1.X-36.A-750; compounds I.D-1.X-36.A-1 to I.D-1.X-36.A-750; compounds I.E-1.X-36.A-1 to I.E-1.X-36.A-750; compounds I.F-1.X-36.A-1 to I.F-1.X-36.A-750; compounds I.G-1.X-36.A-1 to I.G-1.X-36.A-750; compounds I.H-1.X-36.A-1 to I.H-1.X-36.A-750;

compounds I.A-2.X-36.A-1 to I.A-2.X-36.A-750; compounds I.B-2.X-36.A-1 to I.B-2.X-36.A-750; compounds I.C-2.X-36.A-1 to I.C-2.X-36.A-750; compounds I.D-2.X-36.A-1 to I.D-2.X-36.A-750; compounds I.E-2.X-36.A-1 to I.E-2.X-36.A-750; compounds I.F-2.X-36.A-1 to I.F-2.X-36.A-750; compounds I.G-2.X-36.A-1 to I.G-2.X-36.A-750; compounds I.H-2.X-36.A-1 to I.H-2.X-36.A-750;

compounds I.A-3.X-36.A-1 to I.A-3.X-36.A-750; compounds I.B-3.X-36.A-1 to I.B-3.X-36.A-750; compounds I.C-3.X-36.A-1 to I.C-3.X-36.A-750; compounds I.D-3.X-36.A-1 to I.D-3.X-36.A-750; compounds I.E-3.X-36.A-1 to I.E-3.X-36.A-750; compounds I.F-3.X-36.A-1 to I.F-3.X-36.A-750; compounds I.G-3.X-36.A-1 to I.G-3.X-36.A-750; compounds I.H-3.X-36.A-1 to I.H-3.X-36.A-750;

compounds I.A-4.X-36.A-1 to I.A-4.X-36.A-750; compounds I.B-4.X-36.A-1 to I.B-4.X-36.A-750; compounds I.C-4.X-36.A-1 to I.C-4.X-36.A-750; compounds I.D-4.X-36.A-1 to I.D-4.X-36.A-750; compounds I.E-4.X-36.A-1 to I.E-4.X-36.A-750; compounds I.F-4.X-36.A-1 to I.F-4.X-36.A-750; compounds I.G-4.X-36.A-1 to I.G-4.X-36.A-750; compounds I.H-4.X-36.A-1 to I.H-4.X-36.A-750;

compounds I.A-5.X-36.A-1 to I.A-5.X-36.A-750; compounds I.B-5.X-36.A-1 to I.B-5.X-36.A-750; compounds I.C-5.X-36.A-1 to I.C-5.X-36.A-750; compounds I.D-5.X-36.A-1 to I.D-5.X-36.A-750; compounds I.E-5.X-36.A-1 to I.E-5.X-36.A-750; compounds I.F-5.X-36.A-1 to I.F-5.X-36.A-750; compounds I.G-5.X-36.A-1 to I.G-5.X-36.A-750; compounds I.H-5.X-36.A-1 to I.H-5.X-36.A-750;

compounds I.A-6.X-36.A-1 to I.A-6.X-36.A-750; compounds I.B-6.X-36.A-1 to I.B-6.X-36.A-750; compounds I.C-6.X-36.A-1 to I.C-6.X-36.A-750; compounds I.D-6.X-

36.A-1 to I.D-6.X-36.A-750; compounds I.E-6.X-36.A-1 to I.E-6.X-36.A-750; compounds I.F-6.X-36.A-1 to I.F-6.X-36.A-750; compounds I.G-6.X-36.A-1 to I.G-6.X-36.A-750; compounds I.H-6.X-36.A-1 to I.H-6.X-36.A-750).

Table 37a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-37 of Table X and the meaning for the combination of $X^1$, $X^2$, $X^3$ and $R^3$ for each individual compound corresponds in each case to one line of Table A (compounds I.A-1.X-37.A-1 to I.A-1.X-37.A-750; compounds I.B-1.X-37.A-1 to I.B-1.X-37.A-750; compounds I.C-1.X-37.A-1 to I.C-1.X-37.A-750; compounds I.D-1.X-37.A-1 to I.D-1.X-37.A-750; compounds I.E-1.X-37.A-1 to I.E-1.X-37.A-750; compounds I.F-1.X-37.A-1 to I.F-1.X-37.A-750; compounds I.G-1.X-37.A-1 to I.G-1.X-37.A-750; compounds I.H-1.X-37.A-1 to I.H-1.X-37.A-750;

compounds I.A-2.X-37.A-1 to I.A-2.X-37.A-750; compounds I.B-2.X-37.A-1 to I.B-2.X-37.A-750; compounds I.C-2.X-37.A-1 to I.C-2.X-37.A-750; compounds I.D-2.X-37.A-1 to I.D-2.X-37.A-750; compounds I.E-2.X-37.A-1 to I.E-2.X-37.A-750; compounds I.F-2.X-37.A-1 to I.F-2.X-37.A-750; compounds I.G-2.X-37.A-1 to I.G-2.X-37.A-750; compounds I.H-2.X-37.A-1 to I.H-2.X-37.A-750;

compounds I.A-3.X-37.A-1 to I.A-3.X-37.A-750; compounds I.B-3.X-37.A-1 to I.B-3.X-37.A-750; compounds I.C-3.X-37.A-1 to I.C-3.X-37.A-750; compounds I.D-3.X-37.A-1 to I.D-3.X-37.A-750; compounds I.E-3.X-37.A-1 to I.E-3.X-37.A-750; compounds I.F-3.X-37.A-1 to I.F-3.X-37.A-750; compounds I.G-3.X-37.A-1 to I.G-3.X-37.A-750; compounds I.H-3.X-37.A-1 to I.H-3.X-37.A-750;

compounds I.A-4.X-37.A-1 to I.A-4.X-37.A-750; compounds I.B-4.X-37.A-1 to I.B-4.X-37.A-750; compounds I.C-4.X-37.A-1 to I.C-4.X-37.A-750; compounds I.D-4.X-37.A-1 to I.D-4.X-37.A-750; compounds I.E-4.X-37.A-1 to I.E-4.X-37.A-750; compounds I.F-4.X-37.A-1 to I.F-4.X-37.A-750; compounds I.G-4.X-37.A-1 to I.G-4.X-37.A-750; compounds I.H-4.X-37.A-1 to I.H-4.X-37.A-750;

compounds I.A-5.X-37.A-1 to I.A-5.X-37.A-750; compounds I.B-5.X-37.A-1 to I.B-5.X-37.A-750; compounds I.C-5.X-37.A-1 to I.C-5.X-37.A-750; compounds I.D-5.X-37.A-1 to I.D-5.X-37.A-750; compounds I.E-5.X-37.A-1 to I.E-5.X-37.A-750; compounds I.F-5.X-37.A-1 to I.F-5.X-37.A-750; compounds I.G-5.X-37.A-1 to I.G-5.X-37.A-750; compounds I.H-5.X-37.A-1 to I.H-5.X-37.A-750;

compounds I.A-6.X-37.A-1 to I.A-6.X-37.A-750; compounds I.B-6.X-37.A-1 to I.B-6.X-37.A-750; compounds I.C-6.X-37.A-1 to I.C-6.X-37.A-750; compounds I.D-6.X-37.A-1 to I.D-6.X-37.A-750; compounds I.E-6.X-37.A-1 to I.E-6.X-37.A-750; compounds I.F-6.X-37.A-1 to I.F-6.X-37.A-750; compounds I.G-6.X-37.A-1 to I.G-6.X-37.A-750; compounds I.H-6.X-37.A-1 to I.H-6.X-37.A-750).

Table 38a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-38 of Table X and the meaning for the combination of $X^1$, $X^2$, $X^3$ and $R^3$ for each individual compound corresponds in each case to one line of Table A (compounds I.A-1.X-38.A-1 to I.A-1.X-38.A-750; compounds I.B-1.X-38.A-1 to I.B-1.X-38.A-750; compounds I.C-1.X-38.A-1 to I.C-1.X-38.A-750; compounds I.D-1.X-38.A-1 to I.D-1.X-38.A-750; compounds I.E-1.X-38.A-1 to I.E-1.X-38.A-750; compounds I.F-1.X-38.A-1 to I.F-1.X-38.A-750; compounds I.G-1.X-38.A-1 to I.G-1.X-38.A-750; compounds I.H-1.X-38.A-1 to I.H-1.X-38.A-750;

compounds I.A-2.X-38.A-1 to I.A-2.X-38.A-750; compounds I.B-2.X-38.A-1 to I.B-2.X-38.A-750; compounds I.C-2.X-38.A-1 to I.C-2.X-38.A-750; compounds I.D-2.X-38.A-1 to I.D-2.X-38.A-750; compounds I.E-2.X-38.A-1 to I.E-2.X-38.A-750; compounds I.F-2.X-38.A-1 to I.F-2.X-38.A-750; compounds I.G-2.X-38.A-1 to I.G-2.X-38.A-750; compounds I.H-2.X-38.A-1 to I.H-2.X-38.A-750;

compounds I.A-3.X-38.A-1 to I.A-3.X-38.A-750; compounds I.B-3.X-38.A-1 to I.B-3.X-38.A-750; compounds I.C-3.X-38.A-1 to I.C-3.X-38.A-750; compounds I.D-3.X-38.A-1 to I.D-3.X-38.A-750; compounds I.E-3.X-38.A-1 to I.E-3.X-38.A-750; compounds I.F-3.X-38.A-1 to I.F-3.X-38.A-750; compounds I.G-3.X-38.A-1 to I.G-3.X-38.A-750; compounds I.H-3.X-38.A-1 to I.H-3.X-38.A-750;

compounds I.A-4.X-38.A-1 to I.A-4.X-38.A-750; compounds I.B-4.X-38.A-1 to I.B-4.X-38.A-750; compounds I.C-4.X-38.A-1 to I.C-4.X-38.A-750; compounds I.D-4.X-38.A-1 to I.D-4.X-38.A-750; compounds I.E-4.X-38.A-1 to I.E-4.X-38.A-750; compounds I.F-4.X-38.A-1 to I.F-4.X-38.A-750; compounds I.G-4.X-38.A-1 to I.G-4.X-38.A-750; compounds I.H-4.X-38.A-1 to I.H-4.X-38.A-750;

compounds I.A-5.X-38.A-1 to I.A-5.X-38.A-750; compounds I.B-5.X-38.A-1 to I.B-5.X-38.A-750; compounds I.C-5.X-38.A-1 to I.C-5.X-38.A-750; compounds I.D-5.X-38.A-1 to I.D-5.X-38.A-750; compounds I.E-5.X-38.A-1 to I.E-5.X-38.A-750; compounds I.F-5.X-38.A-1 to I.F-5.X-38.A-750; compounds I.G-5.X-38.A-1 to I.G-5.X-38.A-750; compounds I.H-5.X-38.A-1 to I.H-5.X-38.A-750;

compounds I.A-6.X-38.A-1 to I.A-6.X-38.A-750; compounds I.B-6.X-38.A-1 to I.B-6.X-38.A-750; compounds I.C-6.X-38.A-1 to I.C-6.X-38.A-750; compounds I.D-6.X-38.A-1 to I.D-6.X-38.A-750; compounds I.E-6.X-38.A-1 to I.E-6.X-38.A-750; compounds I.F-6.X-38.A-1 to I.F-6.X-38.A-750; compounds I.G-6.X-38.A-1 to I.G-6.X-38.A-750; compounds I.H-6.X-38.A-1 to I.H-6.X-38.A-750).

Table 39a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-39 of Table X and the meaning for the combination of $X^1$, $X^2$, $X^3$ and $R^3$ for each individual compound corresponds in each case to one line of Table A (compounds I.A-1.X-39.A-1 to I.A-1.X-39.A-750; compounds I.B-1.X-39.A-1 to I.B-1.X-39.A-750; compounds I.C-1.X-39.A-1 to I.C-1.X-39.A-750; compounds I.D-1.X-39.A-1 to I.D-1.X-39.A-750; compounds I.E-1.X-39.A-1 to I.E-1.X-39.A-750; compounds I.F-1.X-39.A-1 to I.F-1.X-39.A-750; compounds I.G-1.X-39.A-1 to I.G-1.X-39.A-750; compounds I.H-1.X-39.A-1 to I.H-1.X-39.A-750;

compounds I.A-2.X-39.A-1 to I.A-2.X-39.A-750; compounds I.B-2.X-39.A-1 to I.B-2.X-39.A-750; compounds I.C-2.X-39.A-1 to I.C-2.X-39.A-750; compounds I.D-2.X-

39.A-1 to I.D-2.X-39.A-750; compounds I.E-2.X-39.A-1 to I.E-2.X-39.A-750; compounds I.F-2.X-39.A-1 to I.F-2.X-39.A-750; compounds I.G-2.X-39.A-1 to I.G-2.X-39.A-750; compounds I.H-2.X-39.A-1 to I.H-2.X-39.A-750;

compounds I.A-3.X-39.A-1 to I.A-3.X-39.A-750; compounds I.B-3.X-39.A-1 to I.B-3.X-39.A-750; compounds I.C-3.X-39.A-1 to I.C-3.X-39.A-750; compounds I.D-3.X-39.A-1 to I.D-3.X-39.A-750; compounds I.E-3.X-39.A-1 to I.E-3.X-39.A-750; compounds I.F-3.X-39.A-1 to I.F-3.X-39.A-750; compounds I.G-3.X-39.A-1 to I.G-3.X-39.A-750; compounds I.H-3.X-39.A-1 to I.H-3.X-39.A-750;

compounds I.A-4.X-39.A-1 to I.A-4.X-39.A-750; compounds I.B-4.X-39.A-1 to I.B-4.X-39.A-750; compounds I.C-4.X-39.A-1 to I.C-4.X-39.A-750; compounds I.D-4.X-39.A-1 to I.D-4.X-39.A-750; compounds I.E-4.X-39.A-1 to I.E-4.X-39.A-750; compounds I.F-4.X-39.A-1 to I.F-4.X-39.A-750; compounds I.G-4.X-39.A-1 to I.G-4.X-39.A-750; compounds I.H-4.X-39.A-1 to I.H-4.X-39.A-750;

compounds I.A-5.X-39.A-1 to I.A-5.X-39.A-750; compounds I.B-5.X-39.A-1 to I.B-5.X-39.A-750; compounds I.C-5.X-39.A-1 to I.C-5.X-39.A-750; compounds I.D-5.X-39.A-1 to I.D-5.X-39.A-750; compounds I.E-5.X-39.A-1 to I.E-5.X-39.A-750; compounds I.F-5.X-39.A-1 to I.F-5.X-39.A-750; compounds I.G-5.X-39.A-1 to I.G-5.X-39.A-750; compounds I.H-5.X-39.A-1 to I.H-5.X-39.A-750;

compounds I.A-6.X-39.A-1 to I.A-6.X-39.A-750; compounds I.B-6.X-39.A-1 to I.B-6.X-39.A-750; compounds I.C-6.X-39.A-1 to I.C-6.X-39.A-750; compounds I.D-6.X-39.A-1 to I.D-6.X-39.A-750; compounds I.E-6.X-39.A-1 to I.E-6.X-39.A-750; compounds I.F-6.X-39.A-1 to I.F-6.X-39.A-750; compounds I.G-6.X-39.A-1 to I.G-6.X-39.A-750; compounds I.H-6.X-39.A-1 to I.H-6.X-39.A-750).

Table 40a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-40 of Table X and the meaning for the combination of $X^1$, $X^2$, $X^3$ and $R^3$ for each individual compound corresponds in each case to one line of Table A (compounds I.A-1.X-40.A-1 to I.A-1.X-40.A-750; compounds I.B-1.X-40.A-1 to I.B-1.X-40.A-750; compounds I.C-1.X-40.A-1 to I.C-1.X-40.A-750; compounds I.D-1.X-40.A-1 to I.D-1.X-40.A-750; compounds I.E-1.X-40.A-1 to I.E-1.X-40.A-750; compounds I.F-1.X-40.A-1 to I.F-1.X-40.A-750; compounds I.G-1.X-40.A-1 to I.G-1.X-40.A-750; compounds I.H-1.X-40.A-1 to I.H-1.X-40.A-750;

compounds I.A-2.X-40.A-1 to I.A-2.X-40.A-750; compounds I.B-2.X-40.A-1 to I.B-2.X-40.A-750; compounds I.C-2.X-40.A-1 to I.C-2.X-40.A-750; compounds I.D-2.X-40.A-1 to I.D-2.X-40.A-750; compounds I.E-2.X-40.A-1 to I.E-2.X-40.A-750; compounds I.F-2.X-40.A-1 to I.F-2.X-40.A-750; compounds I.G-2.X-40.A-1 to I.G-2.X-40.A-750; compounds I.H-2.X-40.A-1 to I.H-2.X-40.A-750;

compounds I.A-3.X-40.A-1 to I.A-3.X-40.A-750; compounds I.B-3.X-40.A-1 to I.B-3.X-40.A-750; compounds I.C-3.X-40.A-1 to I.C-3.X-40.A-750; compounds I.D-3.X-40.A-1 to I.D-3.X-40.A-750; compounds I.E-3.X-40.A-1 to I.E-3.X-40.A-750; compounds I.F-3.X-40.A-1 to I.F-3.X-40.A-750; compounds I.G-3.X-40.A-1 to I.G-3.X-40.A-750; compounds I.H-3.X-40.A-1 to I.H-3.X-40.A-750;

compounds I.A-4.X-40.A-1 to I.A-4.X-40.A-750; compounds I.B-4.X-40.A-1 to I.B-4.X-40.A-750; compounds I.C-4.X-40.A-1 to I.C-4.X-40.A-750; compounds I.D-4.X-40.A-1 to I.D-4.X-40.A-750; compounds I.E-4.X-40.A-1 to I.E-4.X-40.A-750; compounds I.F-4.X-40.A-1 to I.F-4.X-40.A-750; compounds I.G-4.X-40.A-1 to I.G-4.X-40.A-750; compounds I.H-4.X-40.A-1 to I.H-4.X-40.A-750;

compounds I.A-5.X-40.A-1 to I.A-5.X-40.A-750; compounds I.B-5.X-40.A-1 to I.B-5.X-40.A-750; compounds I.C-5.X-40.A-1 to I.C-5.X-40.A-750; compounds I.D-5.X-40.A-1 to I.D-5.X-40.A-750; compounds I.E-5.X-40.A-1 to I.E-5.X-40.A-750; compounds I.F-5.X-40.A-1 to I.F-5.X-40.A-750; compounds I.G-5.X-40.A-1 to I.G-5.X-40.A-750; compounds I.H-5.X-40.A-1 to I.H-5.X-40.A-750;

compounds I.A-6.X-40.A-1 to I.A-6.X-40.A-750; compounds I.B-6.X-40.A-1 to I.B-6.X-40.A-750; compounds I.C-6.X-40.A-1 to I.C-6.X-40.A-750; compounds I.D-6.X-40.A-1 to I.D-6.X-40.A-750; compounds I.E-6.X-40.A-1 to I.E-6.X-40.A-750; compounds I.F-6.X-40.A-1 to I.F-6.X-40.A-750; compounds I.G-6.X-40.A-1 to I.G-6.X-40.A-750; compounds I.H-6.X-40.A-1 to I.H-6.X-40.A-750).

Table 41a

Compounds of the formula I.A-1, I.B-1, I.C-1, I.D-1, I.E-1, I.F-1, I.G-1, I.H-1; I.A-2, I.B-2, I.C-2, I.D-2, I.E-2, I.F-2, I.G-2, I-H.2; I.A-3, I.B-3, I.C-3, I.D-3, I.E-3, I.F-3, I.G-3, I-H.3; I.A-4, I.B-4, I.C-4, I.D-4, I.E-4, I.F-4, I.G-4, I-H.4; I.A-5, I.B-5, I.C-5, I.D-5, I.E-5, I.F-5, I.G-5, I-H.5; I.A-6, I.B-6, I.C-6, I.D-6, I.E-6, I.F-6, I.G-6, I-H.6;

in which $Q_3$ is as defined in line X-41 of Table X and the meaning for the combination of $X^1$, $X^2$, $X^3$ and $R^3$ for each individual compound corresponds in each case to one line of Table A (compounds I.A-1.X-41.A-1 to I.A-1.X-41.A-750; compounds I.B-1.X-41.A-1 to I.B-1.X-41.A-750; compounds I.C-1.X-41.A-1 to I.C-1.X-41.A-750; compounds I.D-1.X-41.A-1 to I.D-1.X-41.A-750; compounds I.E-1.X-41.A-1 to I.E-1.X-41.A-750; compounds I.F-1.X-41.A-1 to I.F-1.X-41.A-750; compounds I.G-1.X-41.A-1 to I.G-1.X-41.A-750; compounds I.H-1.X-41.A-1 to I.H-1.X-41.A-750;

compounds I.A-2.X-41.A-1 to I.A-2.X-41.A-750; compounds I.B-2.X-41.A-1 to I.B-2.X-41.A-750; compounds I.C-2.X-41.A-1 to I.C-2.X-41.A-750; compounds I.D-2.X-41.A-1 to I.D-2.X-41.A-750; compounds I.E-2.X-41.A-1 to I.E-2.X-41.A-750; compounds I.F-2.X-41.A-1 to I.F-2.X-41.A-750; compounds I.G-2.X-41.A-1 to I.G-2.X-41.A-750; compounds I.H-2.X-41.A-1 to I.H-2.X-41.A-750;

compounds I.A-3.X-41.A-1 to I.A-3.X-41.A-750; compounds I.B-3.X-41.A-1 to I.B-3.X-41.A-750; compounds I.C-3.X-41.A-1 to I.C-3.X-41.A-750; compounds I.D-3.X-41.A-1 to I.D-3.X-41.A-750; compounds I.E-3.X-41.A-1 to I.E-3.X-41.A-750; compounds I.F-3.X-41.A-1 to I.F-3.X-41.A-750; compounds I.G-3.X-41.A-1 to I.G-3.X-41.A-750; compounds I.H-3.X-41.A-1 to I.H-3.X-41.A-750;

compounds I.A-4.X-41.A-1 to I.A-4.X-41.A-750; compounds I.B-4.X-41.A-1 to I.B-4.X-41.A-750; compounds I.C-4.X-41.A-1 to I.C-4.X-41.A-750; compounds I.D-4.X-41.A-1 to I.D-4.X-41.A-750; compounds I.E-4.X-41.A-1 to I.E-4.X-41.A-750; compounds I.F-4.X-41.A-1 to I.F-4.X-41.A-750; compounds I.G-4.X-41.A-1 to I.G-4.X-41.A-750; compounds I.H-4.X-41.A-1 to I.H-4.X-41.A-750;

compounds I.A-5.X-41.A-1 to I.A-5.X-41.A-750; compounds I.B-5.X-41.A-1 to I.B-5.X-41.A-750; compounds I.C-5.X-41.A-1 to I.C-5.X-41.A-750; compounds I.D-5.X-41.A-1 to I.D-5.X-41.A-750; compounds I.E-5.X-41.A-1 to I.E-5.X-41.A-750; compounds I.F-5.X-41.A-1 to I.F-5.X-41.A-750; compounds I.G-5.X-41.A-1 to I.G-5.X-41.A-750; compounds I.H-5.X-41.A-1 to I.H-5.X-41.A-750;

compounds I.A-6.X-41.A-1 to I.A-6.X-41.A-750; compounds I.B-6.X-41.A-1 to I.B-6.X-41.A-750; compounds I.C-6.X-41.A-1 to I.C-6.X-41.A-750; compounds I.D-6.X-

41.A-1 to I.D-6.X-41.A-750; compounds I.E-6.X-41.A-1 to I.E-6.X-41.A-750; compounds I.F-6.X-41.A-1 to I.F-6.X-41.A-750; compounds I.G-6.X-41.A-1 to I.G-6.X-41.A-750; compounds I.H-6.X-41.A-1 to I.H-6.X-41.A-750).

TABLE X

| line | Q³ |
|---|---|
| X-1 | H |
| X-2 | CH₃ |
| X-3 | C₂H₅ |
| X-4 | CH(CH₃)₂ |
| X-5 | CHF₂ |
| X-6 | CF₃ |
| X-7 | cyclopropylmethyl |
| X-8 | CH₂CH=CH₂ |
| X-9 | CH₂C≡CH |
| X-10 | benzyl |
| X-11 | 2-fluorobenzyl |
| X-12 | 3-fluorobenzyl |
| X-13 | 4-fluorobenzyl |
| X-14 | 2-chlorobenzyl |
| X-15 | 3-chlorobenzyl |
| X-16 | 4-chlorobenzyl |
| X-17 | 2-methylbenzyl |
| X-18 | 3-methylbenzyl |
| X-19 | 4-methylbenzyl |
| X-20 | 2-t-butylbenzyl |
| X-21 | 3-t-butylbenzyl |
| X-22 | 4-t-butylbenzyl |
| X-23 | 2-(trifluoromethyl)benzyl |
| X-24 | 3-(trifluoromethyl)benzyl |
| X-25 | 4-(trifluoromethyl)benzyl |

TABLE X-continued

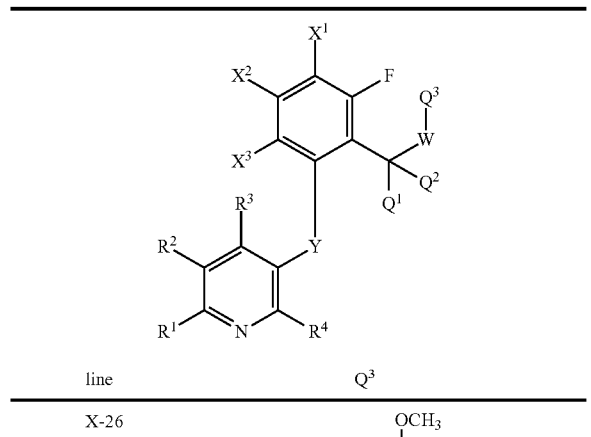

| line | Q³ |
|---|---|
| X-26 | 2-methoxybenzyl |
| X-27 | 3-methoxybenzyl |
| X-28 | 4-methoxybenzyl |
| X-29 | 2-(trifluoromethoxy)benzyl |
| X-30 | 3-(difluoromethoxy)benzyl |
| X-31 | 4-(difluoromethoxy)benzyl |
| X-32 | 1-phenylethyl |
| X-33 | 1-(2-fluorophenyl)ethyl |
| X-34 | 1-(3-fluorophenyl)ethyl |

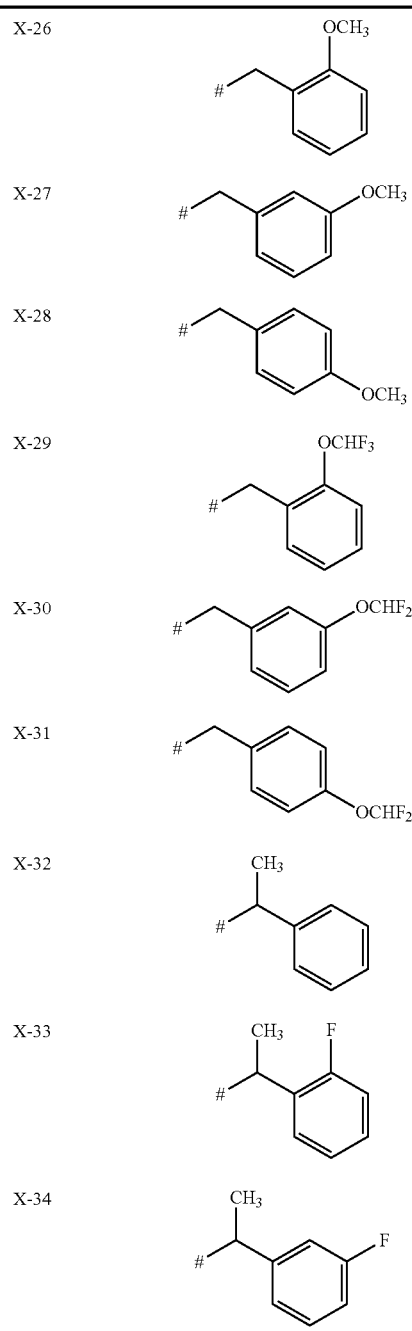

TABLE X-continued

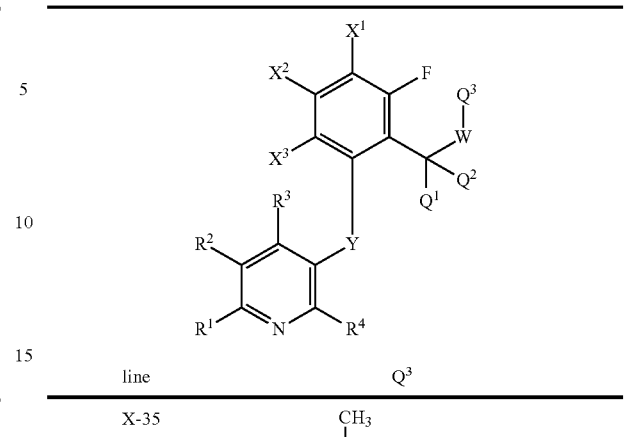

| line | Q³ |
|---|---|
| X-35 | 1-(4-fluorophenyl)ethyl |
| X-36 | 1-(2-methylphenyl)ethyl |
| X-37 | 1-(3-methylphenyl)ethyl |
| X-38 | 1-(4-methylphenyl)ethyl |
| X-39 | 1-(2-methoxyphenyl)ethyl |
| X-40 | 1-(3-methoxyphenyl)ethyl |
| X-41 | 1-(4-methoxyphenyl)ethyl |

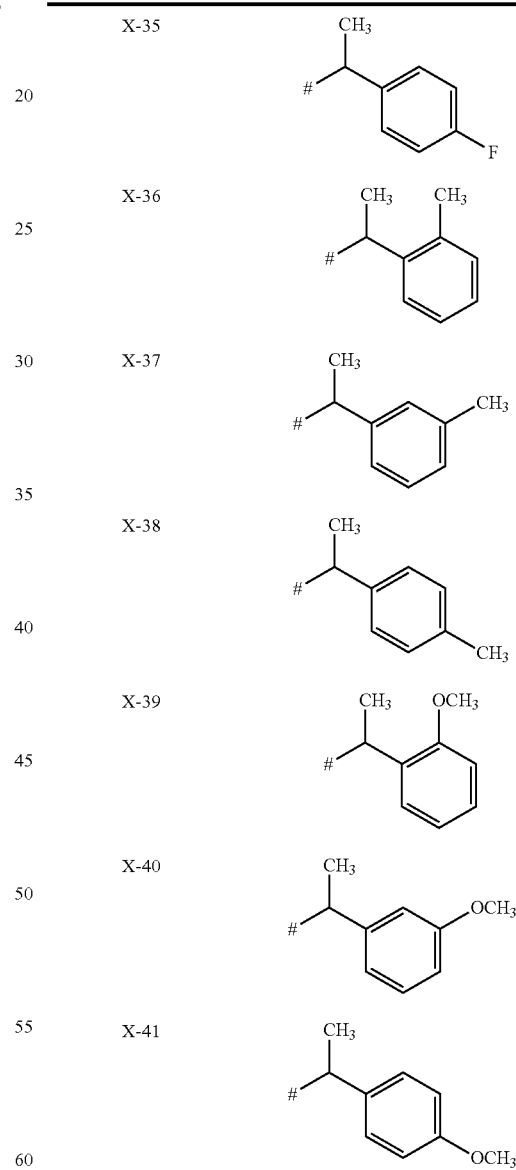

TABLE A

| Line | X¹ | X² | X³ | R³ |
|---|---|---|---|---|
| A-1 | H | H | H | H |
| A-2 | F | H | H | H |

TABLE A-continued

| Line | $X^1$ | $X^2$ | $X^3$ | $R^3$ |
|---|---|---|---|---|
| A-3 | Cl | H | H | H |
| A-4 | $CF_3$ | H | H | H |
| A-5 | CN | H | H | H |
| A-6 | H | F | H | H |
| A-7 | F | F | H | H |
| A-8 | Cl | F | H | H |
| A-9 | $CF_3$ | F | H | H |
| A-10 | CN | F | H | H |
| A-11 | H | Cl | H | H |
| A-12 | F | Cl | H | H |
| A-13 | Cl | Cl | H | H |
| A-14 | $CF_3$ | Cl | H | H |
| A-15 | CN | Cl | H | H |
| A-16 | H | $CF_3$ | H | H |
| A-17 | F | $CF_3$ | H | H |
| A-18 | Cl | $CF_3$ | H | H |
| A-19 | $CF_3$ | $CF_3$ | H | H |
| A-20 | CN | $CF_3$ | H | H |
| A-21 | H | CN | H | H |
| A-22 | F | CN | H | H |
| A-23 | Cl | CN | H | H |
| A-24 | $CF_3$ | CN | H | H |
| A-25 | CN | CN | H | H |
| A-26 | H | H | F | H |
| A-27 | F | H | F | H |
| A-28 | Cl | H | F | H |
| A-29 | $CF_3$ | H | F | H |
| A-30 | CN | H | F | H |
| A-31 | H | F | F | H |
| A-32 | F | F | F | H |
| A-33 | Cl | F | F | H |
| A-34 | $CF_3$ | F | F | H |
| A-35 | CN | F | F | H |
| A-36 | H | Cl | F | H |
| A-37 | F | Cl | F | H |
| A-38 | Cl | Cl | F | H |
| A-39 | $CF_3$ | Cl | F | H |
| A-40 | CN | Cl | F | H |
| A-41 | H | $CF_3$ | F | H |
| A-42 | F | $CF_3$ | F | H |
| A-43 | Cl | $CF_3$ | F | H |
| A-44 | $CF_3$ | $CF_3$ | F | H |
| A-45 | CN | $CF_3$ | F | H |
| A-46 | H | CN | F | H |
| A-47 | F | CN | F | H |
| A-48 | Cl | CN | F | H |
| A-49 | $CF_3$ | CN | F | H |
| A-50 | CN | CN | F | H |
| A-51 | H | H | Cl | H |
| A-52 | F | H | Cl | H |
| A-53 | Cl | H | Cl | H |
| A-54 | $CF_3$ | H | Cl | H |
| A-55 | CN | H | Cl | H |
| A-56 | H | F | Cl | H |
| A-57 | F | F | Cl | H |
| A-58 | Cl | F | Cl | H |
| A-59 | $CF_3$ | F | Cl | H |
| A-60 | CN | F | Cl | H |
| A-61 | H | Cl | Cl | H |
| A-62 | F | Cl | Cl | H |
| A-63 | Cl | Cl | Cl | H |
| A-64 | $CF_3$ | Cl | Cl | H |
| A-65 | CN | Cl | Cl | H |
| A-66 | H | $CF_3$ | Cl | H |
| A-67 | F | $CF_3$ | Cl | H |
| A-68 | Cl | $CF_3$ | Cl | H |
| A-69 | $CF_3$ | $CF_3$ | Cl | H |
| A-70 | CN | $CF_3$ | Cl | H |
| A-71 | H | CN | Cl | H |
| A-72 | F | CN | Cl | H |
| A-73 | Cl | CN | Cl | H |
| A-74 | $CF_3$ | CN | Cl | H |
| A-75 | CN | CN | Cl | H |
| A-76 | H | H | $CF_3$ | H |
| A-77 | F | H | $CF_3$ | H |
| A-78 | Cl | H | $CF_3$ | H |
| A-79 | $CF_3$ | H | $CF_3$ | H |
| A-80 | CN | H | $CF_3$ | H |
| A-81 | H | F | $CF_3$ | H |
| A-82 | F | F | $CF_3$ | H |
| A-83 | Cl | F | $CF_3$ | H |
| A-84 | $CF_3$ | F | $CF_3$ | H |
| A-85 | CN | F | $CF_3$ | H |
| A-86 | H | Cl | $CF_3$ | H |
| A-87 | F | Cl | $CF_3$ | H |
| A-88 | Cl | Cl | $CF_3$ | H |
| A-89 | $CF_3$ | Cl | $CF_3$ | H |
| A-90 | CN | Cl | $CF_3$ | H |
| A-91 | H | $CF_3$ | $CF_3$ | H |
| A-92 | F | $CF_3$ | $CF_3$ | H |
| A-93 | Cl | $CF_3$ | $CF_3$ | H |
| A-94 | $CF_3$ | $CF_3$ | $CF_3$ | H |
| A-95 | CN | $CF_3$ | $CF_3$ | H |
| A-96 | H | CN | $CF_3$ | H |
| A-97 | F | CN | $CF_3$ | H |
| A-98 | Cl | CN | $CF_3$ | H |
| A-99 | $CF_3$ | CN | $CF_3$ | H |
| A-100 | CN | CN | $CF_3$ | H |
| A-101 | H | H | CN | H |
| A-102 | F | H | CN | H |
| A-103 | Cl | H | CN | H |
| A-104 | $CF_3$ | H | CN | H |
| A-105 | CN | H | CN | H |
| A-106 | H | F | CN | H |
| A-107 | F | F | CN | H |
| A-108 | Cl | F | CN | H |
| A-109 | $CF_3$ | F | CN | H |
| A-110 | CN | F | CN | H |
| A-111 | H | Cl | CN | H |
| A-112 | F | Cl | CN | H |
| A-113 | Cl | Cl | CN | H |
| A-114 | $CF_3$ | Cl | CN | H |
| A-115 | CN | Cl | CN | H |
| A-116 | H | $CF_3$ | CN | H |
| A-117 | F | $CF_3$ | CN | H |
| A-118 | Cl | $CF_3$ | CN | H |
| A-119 | $CF_3$ | $CF_3$ | CN | H |
| A-120 | CN | $CF_3$ | CN | H |
| A-121 | H | CN | CN | H |
| A-122 | F | CN | CN | H |
| A-123 | Cl | CN | CN | H |
| A-124 | $CF_3$ | CN | CN | H |
| A-125 | CN | CN | CN | H |
| A-126 | H | H | H | F |
| A-127 | F | H | H | F |
| A-128 | Cl | H | H | F |
| A-129 | $CF_3$ | H | H | F |
| A-130 | CN | H | H | F |
| A-131 | H | F | H | F |
| A-132 | F | F | H | F |
| A-133 | Cl | F | H | F |
| A-134 | $CF_3$ | F | H | F |
| A-135 | CN | F | H | F |
| A-136 | H | Cl | H | F |
| A-137 | F | Cl | H | F |
| A-138 | Cl | Cl | H | F |
| A-139 | $CF_3$ | Cl | H | F |
| A-140 | CN | Cl | H | F |
| A-141 | H | $CF_3$ | H | F |
| A-142 | F | $CF_3$ | H | F |
| A-143 | Cl | $CF_3$ | H | F |
| A-144 | $CF_3$ | $CF_3$ | H | F |
| A-145 | CN | $CF_3$ | H | F |
| A-146 | H | CN | H | F |
| A-147 | F | CN | H | F |
| A-148 | Cl | CN | H | F |
| A-149 | $CF_3$ | CN | H | F |
| A-150 | CN | CN | H | F |
| A-151 | H | H | F | F |
| A-152 | F | H | F | F |
| A-153 | Cl | H | F | F |
| A-154 | $CF_3$ | H | F | F |
| A-155 | CN | H | F | F |
| A-156 | H | F | F | F |
| A-157 | F | F | F | F |
| A-158 | Cl | F | F | F |

TABLE A-continued

| Line | $X^1$ | $X^2$ | $X^3$ | $R^3$ |
| --- | --- | --- | --- | --- |
| A-159 | $CF_3$ | F | F | F |
| A-160 | CN | F | F | F |
| A-161 | H | Cl | F | F |
| A-162 | F | Cl | F | F |
| A-163 | Cl | Cl | F | F |
| A-164 | $CF_3$ | Cl | F | F |
| A-165 | CN | Cl | F | F |
| A-166 | H | $CF_3$ | F | F |
| A-167 | F | $CF_3$ | F | F |
| A-168 | Cl | $CF_3$ | F | F |
| A-169 | $CF_3$ | $CF_3$ | F | F |
| A-170 | CN | $CF_3$ | F | F |
| A-171 | H | CN | F | F |
| A-172 | F | CN | F | F |
| A-173 | Cl | CN | F | F |
| A-174 | $CF_3$ | CN | F | F |
| A-175 | CN | CN | F | F |
| A-176 | H | H | Cl | F |
| A-177 | F | H | Cl | F |
| A-178 | Cl | H | Cl | F |
| A-179 | $CF_3$ | H | Cl | F |
| A-180 | CN | H | Cl | F |
| A-181 | H | F | Cl | F |
| A-182 | F | F | Cl | F |
| A-183 | Cl | F | Cl | F |
| A-184 | $CF_3$ | F | Cl | F |
| A-185 | CN | F | Cl | F |
| A-186 | H | Cl | Cl | F |
| A-187 | F | Cl | Cl | F |
| A-188 | Cl | Cl | Cl | F |
| A-189 | $CF_3$ | Cl | Cl | F |
| A-190 | CN | Cl | Cl | F |
| A-191 | H | $CF_3$ | Cl | F |
| A-192 | F | $CF_3$ | Cl | F |
| A-193 | Cl | $CF_3$ | Cl | F |
| A-194 | $CF_3$ | $CF_3$ | Cl | F |
| A-195 | CN | $CF_3$ | Cl | F |
| A-196 | H | CN | Cl | F |
| A-197 | F | CN | Cl | F |
| A-198 | Cl | CN | Cl | F |
| A-199 | $CF_3$ | CN | Cl | F |
| A-200 | CN | CN | Cl | F |
| A-201 | H | H | $CF_3$ | F |
| A-202 | F | H | $CF_3$ | F |
| A-203 | Cl | H | $CF_3$ | F |
| A-204 | $CF_3$ | H | $CF_3$ | F |
| A-205 | CN | H | $CF_3$ | F |
| A-206 | H | F | $CF_3$ | F |
| A-207 | F | F | $CF_3$ | F |
| A-208 | Cl | F | $CF_3$ | F |
| A-209 | $CF_3$ | F | $CF_3$ | F |
| A-210 | CN | F | $CF_3$ | F |
| A-211 | H | Cl | $CF_3$ | F |
| A-212 | F | Cl | $CF_3$ | F |
| A-213 | Cl | Cl | $CF_3$ | F |
| A-214 | $CF_3$ | Cl | $CF_3$ | F |
| A-215 | CN | Cl | $CF_3$ | F |
| A-216 | H | $CF_3$ | $CF_3$ | F |
| A-217 | F | $CF_3$ | $CF_3$ | F |
| A-218 | Cl | $CF_3$ | $CF_3$ | F |
| A-219 | $CF_3$ | $CF_3$ | $CF_3$ | F |
| A-220 | CN | $CF_3$ | $CF_3$ | F |
| A-221 | H | CN | $CF_3$ | F |
| A-222 | F | CN | $CF_3$ | F |
| A-223 | Cl | CN | $CF_3$ | F |
| A-224 | $CF_3$ | CN | $CF_3$ | F |
| A-225 | CN | CN | $CF_3$ | F |
| A-226 | H | H | CN | F |
| A-227 | F | H | CN | F |
| A-228 | Cl | H | CN | F |
| A-229 | $CF_3$ | H | CN | F |
| A-230 | CN | H | CN | F |
| A-231 | H | F | CN | F |
| A-232 | F | F | CN | F |
| A-233 | Cl | F | CN | F |
| A-234 | $CF_3$ | F | CN | F |
| A-235 | CN | F | CN | F |
| A-236 | H | Cl | CN | F |
| A-237 | F | Cl | CN | F |
| A-238 | Cl | Cl | CN | F |
| A-239 | $CF_3$ | Cl | CN | F |
| A-240 | CN | Cl | CN | F |
| A-241 | H | $CF_3$ | CN | F |
| A-242 | F | $CF_3$ | CN | F |
| A-243 | Cl | $CF_3$ | CN | F |
| A-244 | $CF_3$ | $CF_3$ | CN | F |
| A-245 | CN | $CF_3$ | CN | F |
| A-246 | H | CN | CN | F |
| A-247 | F | CN | CN | F |
| A-248 | Cl | CN | CN | F |
| A-249 | $CF_3$ | CN | CN | F |
| A-250 | CN | CN | CN | F |
| A-251 | H | H | H | Cl |
| A-252 | F | H | H | Cl |
| A-253 | Cl | H | H | Cl |
| A-254 | $CF_3$ | H | H | Cl |
| A-255 | CN | H | H | Cl |
| A-256 | H | F | H | Cl |
| A-257 | F | F | H | Cl |
| A-258 | Cl | F | H | Cl |
| A-259 | $CF_3$ | F | H | Cl |
| A-260 | CN | F | H | Cl |
| A-261 | H | Cl | H | Cl |
| A-262 | F | Cl | H | Cl |
| A-263 | Cl | Cl | H | Cl |
| A-264 | $CF_3$ | Cl | H | Cl |
| A-265 | CN | Cl | H | Cl |
| A-266 | H | $CF_3$ | H | Cl |
| A-267 | F | $CF_3$ | H | Cl |
| A-268 | Cl | $CF_3$ | H | Cl |
| A-269 | $CF_3$ | $CF_3$ | H | Cl |
| A-270 | CN | $CF_3$ | H | Cl |
| A-271 | H | CN | H | Cl |
| A-272 | F | CN | H | Cl |
| A-273 | Cl | CN | H | Cl |
| A-274 | $CF_3$ | CN | H | Cl |
| A-275 | CN | CN | H | Cl |
| A-276 | H | H | F | Cl |
| A-277 | F | H | F | Cl |
| A-278 | Cl | H | F | Cl |
| A-279 | $CF_3$ | H | F | Cl |
| A-280 | CN | H | F | Cl |
| A-281 | H | F | F | Cl |
| A-282 | F | F | F | Cl |
| A-283 | Cl | F | F | Cl |
| A-284 | $CF_3$ | F | F | Cl |
| A-285 | CN | F | F | Cl |
| A-286 | H | Cl | F | Cl |
| A-287 | F | Cl | F | Cl |
| A-288 | Cl | Cl | F | Cl |
| A-289 | $CF_3$ | Cl | F | Cl |
| A-290 | CN | Cl | F | Cl |
| A-291 | H | $CF_3$ | F | Cl |
| A-292 | F | $CF_3$ | F | Cl |
| A-293 | Cl | $CF_3$ | F | Cl |
| A-294 | $CF_3$ | $CF_3$ | F | Cl |
| A-295 | CN | $CF_3$ | F | Cl |
| A-296 | H | CN | F | Cl |
| A-297 | F | CN | F | Cl |
| A-298 | Cl | CN | F | Cl |
| A-299 | $CF_3$ | CN | F | Cl |
| A-300 | CN | CN | F | Cl |
| A-301 | H | H | Cl | Cl |
| A-302 | F | H | Cl | Cl |
| A-303 | Cl | H | Cl | Cl |
| A-304 | $CF_3$ | H | Cl | Cl |
| A-305 | CN | H | Cl | Cl |
| A-306 | H | F | Cl | Cl |
| A-307 | F | F | Cl | Cl |
| A-308 | Cl | F | Cl | Cl |
| A-309 | $CF_3$ | F | Cl | Cl |
| A-310 | CN | F | Cl | Cl |
| A-311 | H | Cl | Cl | Cl |
| A-312 | F | Cl | Cl | Cl |
| A-313 | Cl | Cl | Cl | Cl |
| A-314 | $CF_3$ | Cl | Cl | Cl |

TABLE A-continued

| Line | X¹ | X² | X³ | R³ |
|---|---|---|---|---|
| A-315 | CN | Cl | Cl | Cl |
| A-316 | H | CF₃ | Cl | Cl |
| A-317 | F | CF₃ | Cl | Cl |
| A-318 | Cl | CF₃ | Cl | Cl |
| A-319 | CF₃ | CF₃ | Cl | Cl |
| A-320 | CN | CF₃ | Cl | Cl |
| A-321 | H | CN | Cl | Cl |
| A-322 | F | CN | Cl | Cl |
| A-323 | Cl | CN | Cl | Cl |
| A-324 | CF₃ | CN | Cl | Cl |
| A-325 | CN | CN | Cl | Cl |
| A-326 | H | H | CF₃ | Cl |
| A-327 | F | H | CF₃ | Cl |
| A-328 | Cl | H | CF₃ | Cl |
| A-329 | CF₃ | H | CF₃ | Cl |
| A-330 | CN | H | CF₃ | Cl |
| A-331 | H | F | CF₃ | Cl |
| A-332 | F | F | CF₃ | Cl |
| A-333 | Cl | F | CF₃ | Cl |
| A-334 | CF₃ | F | CF₃ | Cl |
| A-335 | CN | F | CF₃ | Cl |
| A-336 | H | Cl | CF₃ | Cl |
| A-337 | F | Cl | CF₃ | Cl |
| A-338 | Cl | Cl | CF₃ | Cl |
| A-339 | CF₃ | Cl | CF₃ | Cl |
| A-340 | CN | Cl | CF₃ | Cl |
| A-341 | H | CF₃ | CF₃ | Cl |
| A-342 | F | CF₃ | CF₃ | Cl |
| A-343 | Cl | CF₃ | CF₃ | Cl |
| A-344 | CF₃ | CF₃ | CF₃ | Cl |
| A-345 | CN | CF₃ | CF₃ | Cl |
| A-346 | H | CN | CF₃ | Cl |
| A-347 | F | CN | CF₃ | Cl |
| A-348 | Cl | CN | CF₃ | Cl |
| A-349 | CF₃ | CN | CF₃ | Cl |
| A-350 | CN | CN | CF₃ | Cl |
| A-351 | H | H | CN | Cl |
| A-352 | F | H | CN | Cl |
| A-353 | Cl | H | CN | Cl |
| A-354 | CF₃ | H | CN | Cl |
| A-355 | CN | H | CN | Cl |
| A-356 | H | F | CN | Cl |
| A-357 | F | F | CN | Cl |
| A-358 | Cl | F | CN | Cl |
| A-359 | CF₃ | F | CN | Cl |
| A-360 | CN | F | CN | Cl |
| A-361 | H | Cl | CN | Cl |
| A-362 | F | Cl | CN | Cl |
| A-363 | Cl | Cl | CN | Cl |
| A-364 | CF₃ | Cl | CN | Cl |
| A-365 | CN | Cl | CN | Cl |
| A-366 | H | CF₃ | CN | Cl |
| A-367 | F | CF₃ | CN | Cl |
| A-368 | Cl | CF₃ | CN | Cl |
| A-369 | CF₃ | CF₃ | CN | Cl |
| A-370 | CN | CF₃ | CN | Cl |
| A-371 | H | CN | CN | Cl |
| A-372 | F | CN | CN | Cl |
| A-373 | Cl | CN | CN | Cl |
| A-374 | CF₃ | CN | CN | Cl |
| A-375 | CN | CN | CN | Cl |
| A-376 | H | H | H | Br |
| A-377 | F | H | H | Br |
| A-378 | Cl | H | H | Br |
| A-379 | CF₃ | H | H | Br |
| A-380 | CN | H | H | Br |
| A-381 | H | F | H | Br |
| A-382 | F | F | H | Br |
| A-383 | Cl | F | H | Br |
| A-384 | CF₃ | F | H | Br |
| A-385 | CN | F | H | Br |
| A-386 | H | Cl | H | Br |
| A-387 | F | Cl | H | Br |
| A-388 | Cl | Cl | H | Br |
| A-389 | CF₃ | Cl | H | Br |
| A-390 | CN | Cl | H | Br |
| A-391 | H | CF₃ | H | Br |
| A-392 | F | CF₃ | H | Br |
| A-393 | Cl | CF₃ | H | Br |
| A-394 | CF₃ | CF₃ | H | Br |
| A-395 | CN | CF₃ | H | Br |
| A-396 | H | CN | H | Br |
| A-397 | F | CN | H | Br |
| A-398 | Cl | CN | H | Br |
| A-399 | CF₃ | CN | H | Br |
| A-400 | CN | CN | H | Br |
| A-401 | H | H | F | Br |
| A-402 | F | H | F | Br |
| A-403 | Cl | H | F | Br |
| A-404 | CF₃ | H | F | Br |
| A-405 | CN | H | F | Br |
| A-406 | H | F | F | Br |
| A-407 | F | F | F | Br |
| A-408 | Cl | F | F | Br |
| A-409 | CF₃ | F | F | Br |
| A-410 | CN | F | F | Br |
| A-411 | H | Cl | F | Br |
| A-412 | F | Cl | F | Br |
| A-413 | Cl | Cl | F | Br |
| A-414 | CF₃ | Cl | F | Br |
| A-415 | CN | Cl | F | Br |
| A-416 | H | CF₃ | F | Br |
| A-417 | F | CF₃ | F | Br |
| A-418 | Cl | CF₃ | F | Br |
| A-419 | CF₃ | CF₃ | F | Br |
| A-420 | CN | CF₃ | F | Br |
| A-421 | H | CN | F | Br |
| A-422 | F | CN | F | Br |
| A-423 | Cl | CN | F | Br |
| A-424 | CF₃ | CN | F | Br |
| A-425 | CN | CN | F | Br |
| A-426 | H | H | Cl | Br |
| A-427 | F | H | Cl | Br |
| A-428 | Cl | H | Cl | Br |
| A-429 | CF₃ | H | Cl | Br |
| A-430 | CN | H | Cl | Br |
| A-431 | H | F | Cl | Br |
| A-432 | F | F | Cl | Br |
| A-433 | Cl | F | Cl | Br |
| A-434 | CF₃ | F | Cl | Br |
| A-435 | CN | F | Cl | Br |
| A-436 | H | Cl | Cl | Br |
| A-437 | F | Cl | Cl | Br |
| A-438 | Cl | Cl | Cl | Br |
| A-439 | CF₃ | Cl | Cl | Br |
| A-440 | CN | Cl | Cl | Br |
| A-441 | H | CF₃ | Cl | Br |
| A-442 | F | CF₃ | Cl | Br |
| A-443 | Cl | CF₃ | Cl | Br |
| A-444 | CF₃ | CF₃ | Cl | Br |
| A-445 | CN | CF₃ | Cl | Br |
| A-446 | H | CN | Cl | Br |
| A-447 | F | CN | Cl | Br |
| A-448 | Cl | CN | Cl | Br |
| A-449 | CF₃ | CN | Cl | Br |
| A-450 | CN | CN | Cl | Br |
| A-451 | H | H | CF₃ | Br |
| A-452 | F | H | CF₃ | Br |
| A-453 | Cl | H | CF₃ | Br |
| A-454 | CF₃ | H | CF₃ | Br |
| A-455 | CN | H | CF₃ | Br |
| A-456 | H | F | CF₃ | Br |
| A-457 | F | F | CF₃ | Br |
| A-458 | Cl | F | CF₃ | Br |
| A-459 | CF₃ | F | CF₃ | Br |
| A-460 | CN | F | CF₃ | Br |
| A-461 | H | Cl | CF₃ | Br |
| A-462 | F | Cl | CF₃ | Br |
| A-463 | Cl | Cl | CF₃ | Br |
| A-464 | CF₃ | Cl | CF₃ | Br |
| A-465 | CN | Cl | CF₃ | Br |
| A-466 | H | CF₃ | CF₃ | Br |
| A-467 | F | CF₃ | CF₃ | Br |
| A-468 | Cl | CF₃ | CF₃ | Br |
| A-469 | CF₃ | CF₃ | CF₃ | Br |
| A-470 | CN | CF₃ | CF₃ | Br |

TABLE A-continued

| Line | $X^1$ | $X^2$ | $X^3$ | $R^3$ |
|---|---|---|---|---|
| A-471 | H | CN | $CF_3$ | Br |
| A-472 | F | CN | $CF_3$ | Br |
| A-473 | Cl | CN | $CF_3$ | Br |
| A-474 | $CF_3$ | CN | $CF_3$ | Br |
| A-475 | CN | CN | $CF_3$ | Br |
| A-476 | H | H | CN | Br |
| A-477 | F | H | CN | Br |
| A-478 | Cl | H | CN | Br |
| A-479 | $CF_3$ | H | CN | Br |
| A-480 | CN | H | CN | Br |
| A-481 | H | F | CN | Br |
| A-482 | F | F | CN | Br |
| A-483 | Cl | F | CN | Br |
| A-484 | $CF_3$ | F | CN | Br |
| A-485 | CN | F | CN | Br |
| A-486 | H | Cl | CN | Br |
| A-487 | F | Cl | CN | Br |
| A-488 | Cl | Cl | CN | Br |
| A-489 | $CF_3$ | Cl | CN | Br |
| A-490 | CN | Cl | CN | Br |
| A-491 | H | $CF_3$ | CN | Br |
| A-492 | F | $CF_3$ | CN | Br |
| A-493 | Cl | $CF_3$ | CN | Br |
| A-494 | $CF_3$ | $CF_3$ | CN | Br |
| A-495 | CN | $CF_3$ | CN | Br |
| A-496 | H | CN | CN | Br |
| A-497 | F | CN | CN | Br |
| A-498 | Cl | CN | CN | Br |
| A-499 | $CF_3$ | CN | CN | Br |
| A-500 | CN | CN | CN | Br |
| A-501 | H | H | H | $CH_3$ |
| A-502 | F | H | H | $CH_3$ |
| A-503 | Cl | H | H | $CH_3$ |
| A-504 | $CF_3$ | H | H | $CH_3$ |
| A-505 | CN | H | H | $CH_3$ |
| A-506 | H | F | H | $CH_3$ |
| A-507 | F | F | H | $CH_3$ |
| A-508 | Cl | F | H | $CH_3$ |
| A-509 | $CF_3$ | F | H | $CH_3$ |
| A-510 | CN | F | H | $CH_3$ |
| A-511 | H | Cl | H | $CH_3$ |
| A-512 | F | Cl | H | $CH_3$ |
| A-513 | Cl | Cl | H | $CH_3$ |
| A-514 | $CF_3$ | Cl | H | $CH_3$ |
| A-515 | CN | Cl | H | $CH_3$ |
| A-516 | H | $CF_3$ | H | $CH_3$ |
| A-517 | F | $CF_3$ | H | $CH_3$ |
| A-518 | Cl | $CF_3$ | H | $CH_3$ |
| A-519 | $CF_3$ | $CF_3$ | H | $CH_3$ |
| A-520 | CN | $CF_3$ | H | $CH_3$ |
| A-521 | H | CN | H | $CH_3$ |
| A-522 | F | CN | H | $CH_3$ |
| A-523 | Cl | CN | H | $CH_3$ |
| A-524 | $CF_3$ | CN | H | $CH_3$ |
| A-525 | CN | CN | H | $CH_3$ |
| A-526 | H | H | F | $CH_3$ |
| A-527 | F | H | F | $CH_3$ |
| A-528 | Cl | H | F | $CH_3$ |
| A-529 | $CF_3$ | H | F | $CH_3$ |
| A-530 | CN | H | F | $CH_3$ |
| A-531 | H | F | F | $CH_3$ |
| A-532 | F | F | F | $CH_3$ |
| A-533 | Cl | F | F | $CH_3$ |
| A-534 | $CF_3$ | F | F | $CH_3$ |
| A-535 | CN | F | F | $CH_3$ |
| A-536 | H | Cl | F | $CH_3$ |
| A-537 | F | Cl | F | $CH_3$ |
| A-538 | Cl | Cl | F | $CH_3$ |
| A-539 | $CF_3$ | Cl | F | $CH_3$ |
| A-540 | CN | Cl | F | $CH_3$ |
| A-541 | H | $CF_3$ | F | $CH_3$ |
| A-542 | F | $CF_3$ | F | $CH_3$ |
| A-543 | Cl | $CF_3$ | F | $CH_3$ |
| A-544 | $CF_3$ | $CF_3$ | F | $CH_3$ |
| A-545 | CN | $CF_3$ | F | $CH_3$ |
| A-546 | H | CN | F | $CH_3$ |
| A-547 | F | CN | F | $CH_3$ |
| A-548 | Cl | CN | F | $CH_3$ |
| A-549 | $CF_3$ | CN | F | $CH_3$ |
| A-550 | CN | CN | F | $CH_3$ |
| A-551 | H | H | Cl | $CH_3$ |
| A-552 | F | H | Cl | $CH_3$ |
| A-553 | Cl | H | Cl | $CH_3$ |
| A-554 | $CF_3$ | H | Cl | $CH_3$ |
| A-555 | CN | H | Cl | $CH_3$ |
| A-556 | H | F | Cl | $CH_3$ |
| A-557 | F | F | Cl | $CH_3$ |
| A-558 | Cl | F | Cl | $CH_3$ |
| A-559 | $CF_3$ | F | Cl | $CH_3$ |
| A-560 | CN | F | Cl | $CH_3$ |
| A-561 | H | Cl | Cl | $CH_3$ |
| A-562 | F | Cl | Cl | $CH_3$ |
| A-563 | Cl | Cl | Cl | $CH_3$ |
| A-564 | $CF_3$ | Cl | Cl | $CH_3$ |
| A-565 | CN | Cl | Cl | $CH_3$ |
| A-566 | H | $CF_3$ | Cl | $CH_3$ |
| A-567 | F | $CF_3$ | Cl | $CH_3$ |
| A-568 | Cl | $CF_3$ | Cl | $CH_3$ |
| A-569 | $CF_3$ | $CF_3$ | Cl | $CH_3$ |
| A-570 | CN | $CF_3$ | Cl | $CH_3$ |
| A-571 | H | CN | Cl | $CH_3$ |
| A-572 | F | CN | Cl | $CH_3$ |
| A-573 | Cl | CN | Cl | $CH_3$ |
| A-574 | $CF_3$ | CN | Cl | $CH_3$ |
| A-575 | CN | CN | Cl | $CH_3$ |
| A-576 | H | H | $CF_3$ | $CH_3$ |
| A-577 | F | H | $CF_3$ | $CH_3$ |
| A-578 | Cl | H | $CF_3$ | $CH_3$ |
| A-579 | $CF_3$ | H | $CF_3$ | $CH_3$ |
| A-580 | CN | H | $CF_3$ | $CH_3$ |
| A-581 | H | F | $CF_3$ | $CH_3$ |
| A-582 | F | F | $CF_3$ | $CH_3$ |
| A-583 | Cl | F | $CF_3$ | $CH_3$ |
| A-584 | $CF_3$ | F | $CF_3$ | $CH_3$ |
| A-585 | CN | F | $CF_3$ | $CH_3$ |
| A-586 | H | Cl | $CF_3$ | $CH_3$ |
| A-587 | F | Cl | $CF_3$ | $CH_3$ |
| A-588 | Cl | Cl | $CF_3$ | $CH_3$ |
| A-589 | $CF_3$ | Cl | $CF_3$ | $CH_3$ |
| A-590 | CN | Cl | $CF_3$ | $CH_3$ |
| A-591 | H | $CF_3$ | $CF_3$ | $CH_3$ |
| A-592 | F | $CF_3$ | $CF_3$ | $CH_3$ |
| A-593 | Cl | $CF_3$ | $CF_3$ | $CH_3$ |
| A-594 | $CF_3$ | $CF_3$ | $CF_3$ | $CH_3$ |
| A-595 | CN | $CF_3$ | $CF_3$ | $CH_3$ |
| A-596 | H | CN | $CF_3$ | $CH_3$ |
| A-597 | F | CN | $CF_3$ | $CH_3$ |
| A-598 | Cl | CN | $CF_3$ | $CH_3$ |
| A-599 | $CF_3$ | CN | $CF_3$ | $CH_3$ |
| A-600 | CN | CN | $CF_3$ | $CH_3$ |
| A-601 | H | H | CN | $CH_3$ |
| A-602 | F | H | CN | $CH_3$ |
| A-603 | Cl | H | CN | $CH_3$ |
| A-604 | $CF_3$ | H | CN | $CH_3$ |
| A-605 | CN | H | CN | $CH_3$ |
| A-606 | H | F | CN | $CH_3$ |
| A-607 | F | F | CN | $CH_3$ |
| A-608 | Cl | F | CN | $CH_3$ |
| A-609 | $CF_3$ | F | CN | $CH_3$ |
| A-610 | CN | F | CN | $CH_3$ |
| A-611 | H | Cl | CN | $CH_3$ |
| A-612 | F | Cl | CN | $CH_3$ |
| A-613 | Cl | Cl | CN | $CH_3$ |
| A-614 | $CF_3$ | Cl | CN | $CH_3$ |
| A-615 | CN | Cl | CN | $CH_3$ |
| A-616 | H | $CF_3$ | CN | $CH_3$ |
| A-617 | F | $CF_3$ | CN | $CH_3$ |
| A-618 | Cl | $CF_3$ | CN | $CH_3$ |
| A-619 | $CF_3$ | $CF_3$ | CN | $CH_3$ |
| A-620 | CN | $CF_3$ | CN | $CH_3$ |
| A-621 | H | CN | CN | $CH_3$ |
| A-622 | F | CN | CN | $CH_3$ |
| A-623 | Cl | CN | CN | $CH_3$ |
| A-624 | $CF_3$ | CN | CN | $CH_3$ |
| A-625 | CN | CN | CN | $CH_3$ |
| A-626 | H | H | H | CN |

TABLE A-continued

| Line | $X^1$ | $X^2$ | $X^3$ | $R^3$ |
|---|---|---|---|---|
| A-627 | F | H | H | CN |
| A-628 | Cl | H | H | CN |
| A-629 | $CF_3$ | H | H | CN |
| A-630 | CN | H | H | CN |
| A-631 | H | F | H | CN |
| A-632 | F | F | H | CN |
| A-633 | Cl | F | H | CN |
| A-634 | $CF_3$ | F | H | CN |
| A-635 | CN | F | H | CN |
| A-636 | H | Cl | H | CN |
| A-637 | F | Cl | H | CN |
| A-638 | Cl | Cl | H | CN |
| A-639 | $CF_3$ | Cl | H | CN |
| A-640 | CN | Cl | H | CN |
| A-641 | H | $CF_3$ | H | CN |
| A-642 | F | $CF_3$ | H | CN |
| A-643 | Cl | $CF_3$ | H | CN |
| A-644 | $CF_3$ | $CF_3$ | H | CN |
| A-645 | CN | $CF_3$ | H | CN |
| A-646 | H | CN | H | CN |
| A-647 | F | CN | H | CN |
| A-648 | Cl | CN | H | CN |
| A-649 | $CF_3$ | CN | H | CN |
| A-650 | CN | CN | H | CN |
| A-651 | H | H | F | CN |
| A-652 | F | H | F | CN |
| A-653 | Cl | H | F | CN |
| A-654 | $CF_3$ | H | F | CN |
| A-655 | CN | H | F | CN |
| A-656 | H | F | F | CN |
| A-657 | F | F | F | CN |
| A-658 | Cl | F | F | CN |
| A-659 | $CF_3$ | F | F | CN |
| A-660 | CN | F | F | CN |
| A-661 | H | Cl | F | CN |
| A-662 | F | Cl | F | CN |
| A-663 | Cl | Cl | F | CN |
| A-664 | $CF_3$ | Cl | F | CN |
| A-665 | CN | Cl | F | CN |
| A-666 | H | $CF_3$ | F | CN |
| A-667 | F | $CF_3$ | F | CN |
| A-668 | Cl | $CF_3$ | F | CN |
| A-669 | $CF_3$ | $CF_3$ | F | CN |
| A-670 | CN | $CF_3$ | F | CN |
| A-671 | H | CN | F | CN |
| A-672 | F | CN | F | CN |
| A-673 | Cl | CN | F | CN |
| A-674 | $CF_3$ | CN | F | CN |
| A-675 | CN | CN | F | CN |
| A-676 | H | H | Cl | CN |
| A-677 | F | H | Cl | CN |
| A-678 | Cl | H | Cl | CN |
| A-679 | $CF_3$ | H | Cl | CN |
| A-680 | CN | H | Cl | CN |
| A-681 | H | F | Cl | CN |
| A-682 | F | F | Cl | CN |
| A-683 | Cl | F | Cl | CN |
| A-684 | $CF_3$ | F | Cl | CN |
| A-685 | CN | F | Cl | CN |
| A-686 | H | Cl | Cl | CN |
| A-687 | F | Cl | Cl | CN |
| A-688 | Cl | Cl | Cl | CN |
| A-689 | $CF_3$ | Cl | Cl | CN |
| A-690 | CN | Cl | Cl | CN |
| A-691 | H | $CF_3$ | Cl | CN |
| A-692 | F | $CF_3$ | Cl | CN |
| A-693 | Cl | $CF_3$ | Cl | CN |
| A-694 | $CF_3$ | $CF_3$ | Cl | CN |
| A-695 | CN | $CF_3$ | Cl | CN |
| A-696 | H | CN | Cl | CN |
| A-697 | F | CN | Cl | CN |
| A-698 | Cl | CN | Cl | CN |
| A-699 | $CF_3$ | CN | Cl | CN |
| A-700 | CN | CN | Cl | CN |
| A-701 | H | H | $CF_3$ | CN |
| A-702 | F | H | $CF_3$ | CN |
| A-703 | Cl | H | $CF_3$ | CN |
| A-704 | $CF_3$ | H | $CF_3$ | CN |
| A-705 | CN | H | $CF_3$ | CN |
| A-706 | H | F | $CF_3$ | CN |
| A-707 | F | F | $CF_3$ | CN |
| A-708 | Cl | F | $CF_3$ | CN |
| A-709 | $CF_3$ | F | $CF_3$ | CN |
| A-710 | CN | F | $CF_3$ | CN |
| A-711 | H | Cl | $CF_3$ | CN |
| A-712 | F | Cl | $CF_3$ | CN |
| A-713 | Cl | Cl | $CF_3$ | CN |
| A-714 | $CF_3$ | Cl | $CF_3$ | CN |
| A-715 | CN | Cl | $CF_3$ | CN |
| A-716 | H | $CF_3$ | $CF_3$ | CN |
| A-717 | F | $CF_3$ | $CF_3$ | CN |
| A-718 | Cl | $CF_3$ | $CF_3$ | CN |
| A-719 | $CF_3$ | $CF_3$ | $CF_3$ | CN |
| A-720 | CN | $CF_3$ | $CF_3$ | CN |
| A-721 | H | CN | $CF_3$ | CN |
| A-722 | F | CN | $CF_3$ | CN |
| A-723 | Cl | CN | $CF_3$ | CN |
| A-724 | $CF_3$ | CN | $CF_3$ | CN |
| A-725 | CN | CN | $CF_3$ | CN |
| A-726 | H | H | CN | CN |
| A-727 | F | H | CN | CN |
| A-728 | Cl | H | CN | CN |
| A-729 | $CF_3$ | H | CN | CN |
| A-730 | CN | H | CN | CN |
| A-731 | H | F | CN | CN |
| A-732 | F | F | CN | CN |
| A-733 | Cl | F | CN | CN |
| A-734 | $CF_3$ | F | CN | CN |
| A-735 | CN | F | CN | CN |
| A-736 | H | Cl | CN | CN |
| A-737 | F | Cl | CN | CN |
| A-738 | Cl | Cl | CN | CN |
| A-739 | $CF_3$ | Cl | CN | CN |
| A-740 | CN | Cl | CN | CN |
| A-741 | H | $CF_3$ | CN | CN |
| A-742 | F | $CF_3$ | CN | CN |
| A-743 | Cl | $CF_3$ | CN | CN |
| A-744 | $CF_3$ | $CF_3$ | CN | CN |
| A-745 | CN | $CF_3$ | CN | CN |
| A-746 | H | CN | CN | CN |
| A-747 | F | CN | CN | CN |
| A-748 | Cl | CN | CN | CN |
| A-749 | $CF_3$ | CN | CN | CN |
| A-750 | CN | CN | CN | CN |

The compounds of the formula I and the compositions according to the invention, respectively, are suitable as fungicides. They are distinguished by an outstanding effectiveness against a broad spectrum of phytopathogenic fungi, including soil-borne fungi, which derive especially from the following classes or are closely related to any of them: Ascomycota (*Ascomycetes*), for example, but not limited to the genus *Cocholiobolus, Colletotrichum, Fusarium, Microdochium, Penicillium, Phoma, Magnaporte, Zymoseptoria,* and *Pseudocercosporella*; Basdiomycota (*Basidiomycetes*), for example, but not limited to the genus *Phakospora, Puccinia, Rhizoctonia, Sphacelotheca, Tilletia, Typhula,* and *Ustilago*; Chytridiomycota (Chytridiomycetes), for example, but not limited to the genus *Chytridiales,* and *Synchytrium*; Deuteromycetes (syn. Fungi imperfecti), for example, but not limited to the genus *Ascochyta, Diplodia, Erysiphe, Fusarium, Phomopsis,* and *Pyrenophora*; Peronosporomycetes (syn. Oomycetes), for example but not limited to the genus *Peronospora, Pythium, Phytophthora*; Plasmodiophoromycetes, for example but not limited to the genus *Plasmodiophora*; Zygomycetes, for example, but not limited to the genus *Rhizopus*.

The compounds I and the compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants; Preferably, compounds of the formula I and compositions thereof, respectively, are used for controlling a multitude of fungi on field crops, such as potatoes, sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans, carots or squashes.

Particularly the compounds of the formula I and the compositions according to the invention are important in the control of phytopathogenic fungi on soybeans, cereals and corn and on the plant propagation material, such as seeds, and the crop material of these crops.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the Mexican wild potato *Solanum bulbocastanum*) or T4-lysozym (e.g. potato cultivars capable of synthesizing these proteins with increased resistance against bacteria such as *Erwinia amyylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The compounds I and compositions thereof, respectively, are particularly suitable for controlling the following plant diseases:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporiodes*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri* Black Foot Disease) and ornamentals; *Dematophora* (teleomorph: *Rosellinia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. amplenia*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohilum* (syn. *Helminthosporium*) spp. on corn (e.g. *E.*

*turcicum*); *Fusarium* (teleomorph: *Gibberella*) spp. (wilt, root or stem rot) on various plants, such as *F. gramineaurum* or *F. culmorum* (root rot, scab or head blight) on cereals (e.g. wheat or barley), *F. oxysporum* on tomatoes, *F. solani* (f. sp. glycines now syn. *F. virguliforme*) and *F. tucumaniae* and *F. brasiliense* each causing sudden death syndrome on soybeans, and *F. verticilliodes* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grainstaining complex on rice; *Guignarda bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemlleia* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microspharea diffusa* (powdery mildew) on soybeans; *Monilinia* spp., e.g. *M. laxa, M. fruticola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici, Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. vitcola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans*: late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or, rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septoria* spp. on various plants, e.g. *S. glycines* (brown spot) on soybeans, *S. tritici* (*Septoria* blotch) on wheat and S. (syn. *Stagonospora*) *nodorum* (*Stagonospora* blotch) on cereals; *Uncinula* (syn. *Erysiphe*) *necator* (powdery mildew, anamorph: *Oidium tucker*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reilana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compounds I and compositions thereof, respectively, are also suitable for controlling harmful fungi in the protection of stored products or harvest and in the protection of materials.

The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocysgs* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichoderma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compounds I and compositions thereof, respectively, may be used for improving the health of a plant. The invention also relates to a method for improving plant health by treating a plant, its propagation material and/or the locus where the plant is growing or is to grow with an effective amount of compounds I and compositions thereof, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. They are likewise subject matter of the present invention.

The compounds I are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I as such or a composition comprising at least one compound I prophylactically either at or before planting or transplanting.

The invention also relates to agrochemical compositions comprising an auxiliary and at least one compound I according to the invention.

An agrochemical composition comprises a fungicidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzyl alcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methyl pyrrolidone, fatty acid dimethyl amides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.)

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:
i) Water-soluble concentrates (SL, LS)
10-60 wt % of a compound I and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible concentrates (DC)
5-25 wt % of a compound I and 1-10 wt % dispersant (e.g. polyvinyl pyrrolidone) are dissolved in organic solvent (e.g. cyclohexanone) ad 100 wt %. Dilution with water gives a dispersion.

iii) Emulsifiable concentrates (EC)
15-70 wt % of a compound I and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)
5-40 wt % of a compound I and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)
In an agitated ball mill, 20-60 wt % of a compound I are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinyl alcohol) is added.

vi) Water-dispersible granules and water-soluble granules (WG, SG)
50-80 wt % of a compound I are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-dispersible powders and water-soluble powders (WP, SP, WS)
50-80 wt % of a compound I are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)
In an agitated ball mill, 5-25 wt % of a compound I are comminuted with addition of 3-10 wt % dispersants (e.g. sodium lignosulfonate), 1-5 wt % thickener (e.g. carboxymethyl cellulose) and water ad 100 wt % to give a fine suspension of the active substance. Dilution with water gives a stable suspension of the active substance.

ix) Microemulsion (ME)
5-20 wt % of a compound I are added to 5-30 wt % organic solvent blend (e.g. fatty acid dimethyl amide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

x) Microcapsules (CS)
An oil phase comprising 5-50 wt % of a compound I, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable powders (DP, DS)

1-10 wt % of a compound I are ground finely and mixed intimately with solid carrier (e.g. finely divided kaolin) ad 100 wt %.

xii) Granules (GR, FG)

0.5-30 wt % of a compound I is ground finely and associated with solid carrier (e.g. silicate) ad 100 wt %. Granulation is achieved by extrusion, spray-drying or fluidized bed.

xiii) Ultra-low volume liquids (UL)

1-50 wt % of a compound I are dissolved in organic solvent (e.g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, onto plant propagation material, especially seeds, include dressing, coating, pelleting, dusting, and soaking as well as in-furrow application methods. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

A pesticide is generally a chemical or biological agent (such as pestidal active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e.g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

Mixing the compounds I or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of pesticides II, or component 2) (e.g. pesticidally-active substances), in conjunction with which the compounds I can be used, is intended to illustrate the possible combinations but does not limit them:

A) Respiration Inhibitors

Inhibitors of complex III at $Q_o$ site (e.g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)pyrazol-3-yl]oxymethyl]phenyl]-4-methyl-tetrazol-5-one instead of 1-[3-chloro-2-[[[1-(4-chlorophenyl)-1H-pyrazol-3-yl]oxy]methyl]phenyl]-1,4-dihydro-4-methyl-5H-tetrazol-5-one (A.1.23), (Z,2E)-5-[1-(2,4-dichlorophenyl)-1H-pyrazol-3-yl]oxy-2-(methoxyimino)-N,3-dimethyl-pent-3-enamide (A.1.24), (Z,2E)-5-[1-(4-chlorophenyl)-1H-pyrazol-3-yl]oxy-2-(methoxyimino)-N,3-dimethyl-pent-3-enamide (A.1.25), (Z,2E)-5-[1-(4-chloro-2-fluoro-phenyl)pyrazol-3-yl]oxy-2-methoxyimino-N,3-dimethyl-pent-3-enamide (A.1.26), 1-[3-bromo-2-[[1-(4-chlorophenyl)pyrazol-3-yl]oxymethyl]phenyl]-4-methyl-tetrazol-5-one (A.1.27), 1-[2-[[1-(4-chlorophenyl)pyrazol-3-yl]oxymethyl]-3-methyl-phenyl]-4-methyl-tetrazol-5-one (A.1.28), 1-[2-[[1-(4-chlorophenyl)pyrazol-3-yl]oxymethyl]-3-fluoro-phenyl]-4-methyl-tetrazol-5-one (A.1.29), 1-[2-[[1-(2,4-dichlorophenyl)pyrazol-3-yl]oxymethyl]-3-fluoro-phenyl]-4-methyl-tetrazol-5-one (A.1.30), 1-[2-[[4-(4-chlorophenyl)thiazol-2-yl]oxymethyl]-3-methyl-phenyl]-4-methyl-tetrazol-5-one (A.1.31), 1-[3-chloro-2-[[4-(p-tolyl)thiazol-2-yl]oxymethyl]phenyl]-4-methyl-tetrazol-5-one (A.1.32), 1-[3-cyclopropyl-2-[[2-methyl-4-(1-methylpyrazol-3-yl)phenoxy]methyl]phenyl]-4-methyl-tetrazol-5-one (A.1.33);

inhibitors of complex III at $Q_i$ site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate (A.2.3), [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate (A.2.4), [(3S,6S,7R,8R)-8-benzyl-3-[(3-isobutoxycarbonyloxy-4-methoxy-pyridine-2-carbonyl)amino]6-methyl-4,9-dioxo-1,5-dioxonan-7-yl]2-methylpropanoate (A2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7), (3S,6S,7R,8R)-8-benzyl-3-[3-[(isobutyryloxy)methoxy]-4-methoxypicolinamido]-6-methyl-4,9-dioxo-1,5-dioxonan-7-yl isobutyrate (A.2.8);

inhibitors of complex II (e.g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N-(1,1,3-trimethylindan-4-yl)pyrazole-4-carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methylethyl]-3-(difluoromethyl)-1-methyl-pyrazole-4-carboxamide (A.3.27);

other respiration inhibitors (e.g. complex I, uncouplers): diflumetorim (A.4.1), (5,8-difluoroquinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol Biosynthesis Inhibitors (SBI Fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S,3R)-3-(2-chlorophenyl)-2-(2,4-difluorophenyl)-oxiranylmethyl]-5-thio-cyanato-1H-[1,2,4]triazolo (B.1.31), 2-[rel-(2S;3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluorometh-yl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)-phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)-phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenyhl)isoxazol-4-yl]-(3-pyridyl)methanol (B.1.50);

Delta14-reductase inhibitors: aldimorph (B.2.1), dodemorph (B.2.2), dodemorphacetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of Cell Division and Cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of Amino Acid and Protein Synthesis methionine synthesis inhibitors (anilino-pyrimidines): cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal Transduction Inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofosmethyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenyhethanesulfonyl)-but-2-yl) carbamic acid-(4-fluorophenyl) ester (G.3.8);

compounds affecting cell membrane permeability and fatty acides: propamocarb (G.4.1);

fatty acid amide hydrolase inhibitors: oxathiapiprolin (G.5.1), 2-{3-[2-{[3,5-bis(difluoromethyl-1H-pyrazol-1-yl]acetyl}piperidin-4-yl]-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl me-thanesulfonate (G.5.3);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds (e.g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methyl-benzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadinetriacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (1.1.1), polyoxin B (1.1.2);

melanin synthesis inhibitors: pyroquilon (1.2.1), tricyclazole (1.2.2), carpropamid (1.2.3), dicyclomet (1.2.4), fenoxanil (1.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown Mode of Action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquatmethylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothalisopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yhpiperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclopropylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyl-tetrazol-5-yl)-phenyl-methylene]amino]oxymethyl]-2-pyridyl]carbamate (K.1.42), 2-[2-[(7,8-difluoro-2-methyl-3-quinolyhoxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxazepine (K.1.48);

M) Growth Regulators abscisic acid (M.1.1), amidochlor, ancymidol, 6-benzylaminopurine, brassinolide, butralin, chlormequat, chlormequat chloride, choline chloride, cyclanilide, daminozide, dikegulac, dime-thipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat, mepiquat chloride, naphthaleneacetic acid, N-6-benzyladenine, paclobutrazol, prohexadione, prohexadione-calcium, prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor (N.1.1), alachlor, butachlor, dimethachlor, dimethenamid (N.1.2), flufenacet (N.1.3), mefenacet (N.1.4), metolachlor (N.1.5), metazachlor (N.1.6), napropamide, naproanilide, pethoxamid, pretilachlor, propachlor, thenylchlor;

amino acid derivatives: bilanafos, glyphosate (N.2.1), glufosinate (N.2.2), sulfosate (N.2.3);

aryloxyphenoxypropionates: clodinafop (N.3.1), cyhalofop-butyl, fenoxaprop (N.3.2), fluazifop (N.3.3), haloxyfop (N.3.4), metamifop, propaquizafop, quizalofop, quizalofop-P-tefuryl;

Bipyridyls: diquat, paraquat (N.4.1);

(thio)carbamates: asulam, butylate, carbetamide, desmedipham, dimepiperate, eptam (EPTC), esprocarb, molinate, orbencarb, phenmedipham (N.5.1), prosulfocarb, pyributicarb, thiobencarb, triallate;

cyclohexanediones: butroxydim, clethodim (N.6.1), cycloxydim (N.6.2), profoxydim (N.6.3), sethoxydim (N.6.4), tepraloxydim (N.6.5), tralkoxydim;

dinitroanilines: benfluralin, ethalfluralin, oryzalin, pendimethalin (N.7.1), prodiamine (N.7.2), trifluralin (N.7.3);

diphenyl ethers: acifluorfen (N.8.1), aclonifen, bifenox, diclofop, ethoxyfen, fomesafen, lactofen, oxyfluorfen;

hydroxybenzonitriles: bomoxynil (N.9.1), dichlobenil, ioxynil;

imidazolinones: imazamethabenz, imazamox (N.10.1), imazapic (N.10.2), imazapyr (N.10.3), imazaquin (N.10.4), imazethapyr (N.10.5);

phenoxy acetic acids: clomeprop, 2,4-dichlorophenoxyacetic acid (2,4-D) (N.11.1), 2,4-DB, dichlorprop, MCPA, MCPA-thioethyl, MCPB, Mecoprop;

pyrazines: chloridazon (N.11.1), flufenpyr-ethyl, fluthiacet, norflurazon, pyridate;

pyridines: aminopyralid, clopyralid (N.12.1), diflufenican, dithiopyr, fluridone, fluroxypyr (N.12.2), picloram (N.12.3), picolinafen (N.12.4), thiazopyr;

sulfonyl ureas: amidosulfuron, azimsulfuron, bensulfuron (N.13.1), chlorimuron-ethyl (N.13.2), chlorsulfuron, cinosulfuron, cyclosulfamuron (N.13.3), ethoxysulfuron, flazasulfuron, flucetosulfuron, flupyrsulfuron, foramsulfuron, halosulfuron, imazosulfuron, iodosulfuron (N.13.4), mesosulfuron (N.13.5), metazosulfuron, metsulfuron-methyl (N.13.6), nicosulfuron (N.13.7), oxasulfuron, primisulfuron, prosulfuron, pyrazosulfuron, rimsulfuron (N.13.8), sulfometuron, sulfosulfuron, thifensulfuron, triasulfuron, tribenuron, trifloxysulfuron, triflusulfuron (N.13.9), tritosulfuron, 1-((2-chloro-6-propyl-imidazo[1,2-b]pyridazin-3-yl) sulfonyl)-3-(4,6-dimethoxy-pyrimidin-2-yl)urea;

triazines: ametryn, atrazine (N.14.1), cyanazine, dimethametryn, ethiozin, hexazinone (N.14.2), metamitron, metribuzin, prometryn, simazine, terbuthylazine, terbutryn, triaziflam, trifludimoxazin (N14.3);

ureas: chlorotoluron, daimuron, diuron (N.15.1), fluometuron, isoproturon, linuron, methabenzthiazuron, tebuthiuron;

other acetolactate synthase inhibitors: bispyribac-sodium, cloransulam-methyl, diclosulam, florasulam (N.16.1), flucarbazone, flumetsulam, metosulam, ortho-sulfamuron, penoxsulam, propoxycarbazone, pyribambenz-propyl, pyribenzoxim, pyriftalid, pyriminobacmethyl, pyrimisulfan, pyrithiobac, pyroxasulfone (N.16.2), pyroxsulam;

others: amicarbazone, aminotriazole, anilofos, beflubutamid, benazolin, bencarbazone, benfluresate, benzofenap, bentazone (N.17.1), benzobicyclon, bicyclopyrone, bromacil, bromobutide, butafenacil, butamifos, cafenstrole, carfentrazone, cinidon-ethyl (N.17.2), chlorthal, cinmethylin (N.17.3), clomazone (N.17.4), cumyluron, cyprosulfamide, dicamba (N.17.5), difenzoquat, diflufenzopyr (N.17.6), *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac (N.17.7), quinmerac (N.17.8), mesotrione (N.17.9), methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil (N.17.10), sulcotrione (N.17.11), sulfentrazone, terbacil, tefuryltrione, tembotrione, thiencarbazone, topramezone (N.17.12), (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoropyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

O) Insecticides organo(thio)phosphates: acephate (O.1.1), azamethiphos (O.1.2), azinphos-methyl (O. 1.3), chlorpyrifos (O.1.4), chlorpyrifos-methyl (O.1.5), chlorfenvinphos (O.1.6), diazinon (O.1.7), dichlorvos (O.1.8), dicrotophos (O.1.9), dimethoate (O.1.10), disulfoton (O.1.11), ethion (O.1.12), fenitrothion (O.1.13), fenthion (O.1.14), isoxathion (O.1.15), malathion (O.1.16), methamidophos (O.1.17), methidathion (O.1.18), methyl-parathion (O.1.19), mevinphos (O.1.20), monocrotophos (O.1.21), oxydemeton-methyl (O.1.22), paraoxon (O.1.23), parathion (O.1.24), phenthoate (O.1.25), phosalone (O.1.26), phosmet (O.1.27), phosphamidon (O.1.28), phorate (O.1.29), phoxim (O.1.30), pirimiphos-methyl (O.1.31), profenofos (O.1.32), prothiofos (O.1.33), sulprophos (O.1.34), tetrachlorvinphos (O.1.35), terbufos (O.1.36), triazophos (O.1.37), trichlorfon (O.1.38);

carbamates: alanycarb (O.2.1), aldicarb (O.2.2), bendiocarb (O.2.3), benfuracarb (O.2.4), carbaryl (O.2.5), carbofuran (O.2.6), carbosulfan (O.2.7), fenoxycarb (O.2.8), furathiocarb (O.2.9), methiocarb (O.2.10), methomyl (O.2.11), oxamyl (O.2.12), pirimicarb (O.2.13), propoxur (O.2.14), thiodicarb (O.2.15), triazamate (O.2.16);

pyrethroids: allethrin (O.3.1), bifenthrin (O.3.2), cyfluthrin (O.3.3), cyhalothrin (O.3.4), cyphenothrin (O.3.5), cypermethrin (O.3.6), alpha-cypermethrin (O.3.7), betacypermethrin (O.3.8), zeta-cypermethrin (O.3.9), deltamethrin (O.3.10), esfenvalerate (O.3.11), etofenprox (O.3.11), fenpropathrin (O.3.12), fenvalerate (O.3.13), imiprothrin (O.3.14), lambda-cyhalothrin (O.3.15), permethrin (O.3.16), prallethrin (O.3.17), pyrethrin I and II (O.3.18), resmethrin (O.3.19), silafluofen (O.3.20), tau-fluvalinate (O.3.21), tefluthrin (O.3.22), tetramethrin (O.3.23), tralomethrin (O.3.24), transfluthrin (O.3.25), profluthrin (O.3.26), dimefluthrin (O.3.27);

insect growth regulators: a) chitin synthesis inhibitors: benzoylureas: chlorfluazuron (O.4.1), cyramazin (O.4.2), diflubenzuron (O.4.3), flucycloxuron (O.4.4), flufenoxuron (O.4.5), hexaflumuron (O.4.6), lufenuron (O.4.7), novaluron (O.4.8), teflubenzuron (O.4.9), triflumuron (O.4.10); buprofezin (O.4.11), diofenolan (O.4.12), hexythiazox (O.4.13), etoxazole (O.4.14), clofentazine (O.4.15); b) ecdysone antagonists: halofenozide (O.4.16), methoxyfenozide (O.4.17), tebufenozide (O.4.18), azadirachtin (O.4.19); c) juvenoids: pyriproxyfen (O.4.20), methoprene (O.4.21), fenoxycarb (O.4.22); d) lipid biosynthesis inhibitors: spirodiclofen (O.4.23), spiromesifen (O.4.24), spirotetramat (O.4.24);

nicotinic receptor agonists/antagonists compounds: clothianidin (O.5.1), dinotefuran (O.5.2), flupyradifurone (O.5.3), imidacloprid (O.5.4), thiamethoxam (O.5.5), nitenpyram (O.5.6), acetamiprid (O.5.7), thiacloprid (O.5.8), 1-2-chloro-thiazol-5-ylmethyl)-2-nitrimino-3,5-dimethyl-[1,3,5]triazinane (O.5.9);

GABA antagonist compounds: endosulfan (O.6.19, ethiprole (O.6.2), fipronil (O.6.3), vaniliprole (O.6.4), pyrafluprole (O.6.5), pyriprole (O.6.6), 5-amino-1-(2,6-dichloro-4-methyl-phenyl)-4-sulfinamoyl-1H-pyrazole-3-carbothioic acid amide (O.6.7);

macrocyclic lactone insecticides: abamectin (O.7.1), emamectin (O.7.2), milbemectin (O.7.3), lepimectin (O.7.4), spinosad (O.7.5), spinetoram (O.7.6);

mitochondrial electron transport inhibitor (METI) I acaricides: fenazaquin (O.8.1), pyridaben (O.8.2), tebufenpyrad (O.8.3), tolfenpyrad (O.8.4), flufenerim (O.8.5);

METI II and III compounds: acequinocyl (O.9.1), fluacyprim (O.9.2), hydramethylnon (O.9.3);

Uncouplers: chlorfenapyr (O.10.1);

oxidative phosphorylation inhibitors: cyhexatin (O.11.1), diafenthiuron (O.11.2), fenbutatin oxide (O.11.3), propargite (O.11.4);

moulting disruptor compounds: cryomazine (O.12.1);

mixed function oxidase inhibitors: piperonyl butoxide (O.13.1);

sodium channel blockers: indoxacarb (O.14.1), metaflumizone (O.14.2);

ryanodine receptor inhibitors: chlorantraniliprole (O.15.1), cyantraniliprole (O.15.2), flubendiamide (O.15.3), N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide (O.15.4); N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide (O.15.5); N-[4-chloro-2-[(di-2-propyl-lambda-4-sulfanylidene) carbamoyl]-6-methyl-phenyl]-2-(3-chloro-2-pyridyl)-5-(trifluoromethyl)pyrazole-3-carboxamide (O.15.6); N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide (O.15.7); N-[4,6-di-chloro-2-[(diethyl-lambda-4-sulfanylidene) carbamoyl]-phenyl]-2-(3-chloro-2-pyridyl)-5-(di-fluoromethyl)pyrazole-3-carboxamide (O.15.8); N-[4,6-di-bromo-2-[(di-2-propyl-lambda-4-sulfanylidene) carbamoyl]-phenyl]-2-(3-chloro-2-pyridyl)-5-(trifluoromethyl)pyrazole-3-carboxamide (O.15.9); N-[4-chloro-2-[(di-2-propyl-lambda-4-sulfanylidene) carbamoyl]-6-cyano-phenyl]-2-(3-chloro-2-pyridyl)-5-(trifluoromethyl)pyrazole-3-carboxamide (O.15.10); N-[4,6-dibromo-2-[(diethyl-lambda-4-sulfanylidene) carbamoyl]-phenyl]-2-(3-chloro-2-pyridyl)-5-(trifluoromethyl)pyrazole-3-carboxamide (O.15.11);

others: benclothiaz (O.16.1), bifenazate (O.16.2), artap (O.16.3), flonicamid (O.16.4), pyridalyl (O.16.5), pymetrozine (O.16.6), sulfur (O.16.7), thiocyclam (O.16.8), cyenopyrafen (O.16.9), flupyrazofos (O.16.10), cyflumetofen (O.16.11), amidoflumet (O.16.12), imicyafos (O.16.13), bistrifluron (O.16.14), pyrifluquinazon (O.16.15) and 1,1'-[(3S,4R,4aR,6S, 6aS,12R,12aS,12bS)-4-[[(2-cyclopropylacetypoxy] methyl]-1,3,4,4a,5,6,6a,12,12a,12b-decahydro-12-hydroxy-4,6a,12b-trimethyl-11-oxo-9-(3-pyridinyl)-2H, 11H-naphtho[2,1-b]pyrano[3,4-e]pyran-3,6-diyl] cyclopropaneacetic acid ester (O.16.16).

The active substances referred to as component 2, their preparation and their activity e.g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296, 272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

The present invention furthermore relates to agrochemical mixtures comprising at least one compound I (component 1) and at least one further active substance useful for plant protection, e.g. selected from the groups A) to O) (component 2), in particular one further fungicide, e.g. one or more fungicide from the groups A) to K), as described above, and if desired one suitable solvent or solid carrier. Those mixtures are of particular interest, since many of them at the same application rate show higher efficiencies against harmful fungi. Furthermore, combating harmful fungi with a mixture of compounds I and at least one fungicide from groups A) to K), as described above, is more efficient than combating those fungi with individual compounds I or individual fungicides from groups A) to K).

By applying compounds I together with at least one active substance from groups A) to O) a synergistic effect can be obtained, i.e. more than simple addition of the individual effects is obtained (synergistic mixtures).

This can be obtained by applying the compounds I and at least one further active substance simultaneously, either jointly (e.g. as tank-mix) or seperately, or in succession, wherein the time interval between the individual applications is selected to ensure that the active substance applied first still occurs at the site of action in a sufficient amount at the time of application of the further active substance(s). The order of application is not essential for working of the present invention.

When applying compound I and a pesticide II sequentially the time between both applications may vary e.g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day.

In the binary mixtures and compositions according to the invention the weight ratio of the component 1) and the component 2) generally depends on the properties of the active components used, usually it is in the range of from 1:100 to 100:1, regularly in the range of from 1:50 to 50:1, preferably in the range of from 1:20 to 20:1, more preferably in the range of from 1:10 to 10:1, even more preferably in the range of from 1:4 to 4:1 and in particular in the range of from 1:2 to 2:1.

According to a further embodiment of the binary mixtures and compositions thereof, the weight ratio of the component 1) and the component 2) usually is in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to a further embodiment of the binary mixtures and compositions thereof, the weight ratio of the component 1) and the component 2) usually is in the range of from 1:1 to 1:1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

In the ternary mixtures, i.e. compositions according to the invention comprising the component 1) and component 2) and a compound III (component 3), the weight ratio of component 1) and component 2) depends on the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1, and the weight ratio of component 1) and component 3) usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:4 to 4:1.

Any further active components are, if desired, added in a ratio of from 20:1 to 1:20 to the component 1).

These ratios are also suitable for inventive mixtures applied by seed treatment.

Preference is also given to mixtures comprising as component 2) at least one active substance selected from group A), which is particularly selected from (A.1.1), (A.1.4), (A.1.8), (A.1.9), (A.1.12), (A.1.13), (A.1.14), (A.1.17), (A.1.19), (A.1.21), (A.2.1), (A.2.2), (A.2.8), (A.3.2), (A.3.3), (A.3.4), (A.3.7), (A.3.8), (A.3.9), (A.3.12), (A.3.14), (A.3.15), (A.3.16), (A.3.19), (A.3.20), (A.3.21), (A.3.22), (A.3.23), (A.3.24), (A.3.25), (A.3.26), (A.3.27); (A.4.5), (A.4.6), (A.4.8), (A.4.9), (A.4.11), (A.1.23), (A.1.24), (A.1.25), (A.1.26), (A.1.27), (A.1.28), (A.1.29), (A.1.30), (A.1.31), (A.1.32), and (A.1.33).

Preference is given to mixtures comprising as component 2) at least one active substance selected from group B), which is particularly selected from (B.1.4), (B.1.5), diniconazole (B.1.6), (B.1.8), (B.1.10), (B.1.11), (B.1.12), (B.1.17), (B.1.18), (B.1.21), (B.1.22), (B.1.23), (B.1.25), (B.1.26), (B.1.27), (B.1.28), (B.1.29), uni (B.1.31), (B.1.32), (B.1.33), (B.1.34), (B.1.35), (B.1.36), (B.1.37), (B.1.38), (B.1.39), (B.1.40), (B.1.41), (B.1.42), (B.1.44), (B.1.46), (B.1.49) and (B.1.50; (B.2.2), (B.2.4), (B.2.5), (B.2.6), piperalin (B.2.7), (B.2.8); and (B.3.1).

Preference is given to mixtures comprising as component 2) at least one active substance selected from group C), which is particularly selected from (C.1.4), C.1.5), (C.1.6), and (C.2.4).

Preference is given to mixtures comprising as component 2) at least one active substance selected from group D), which is particularly selected from (D1.1), (D1.2), (D1.4), (D1.5); (D2.2), (D2.4), (D2.5), (D2.6) and (D2.7);

Preference is also given to mixtures comprising as component 2) at least one active substance selected from group E), which is particularly selected from (E.1.1), (E.1.2), and (E.1.3);

Preference is also given to mixtures comprising as component 2) at least one active substance selected from group F), which is particularly selected from (F.1.2), (F.1.4), (F.1.5), (F.1.6) and (F.2.1).

Preference is also given to mixtures as component 2) at least one active substance selected from group G), which is particularly selected from (G.3.1), (G.3.2), (G.3.3), (G.3.4), (G.3.5), (G.3.6), (G.4.1) and (G.5.1).

Preference is also given to mixtures comprising as component 2) at least one active substance selected from group H), which is and particularly selected from (H.1.2), (H.1.3), copper oxychloride (H.1.4), (H.1.5), (H.1.6); (H.2.2), (H.2.5), (H.2.7), (H.3.2), (H.3.3), (H.3.4), (H.3.5), (H.3.6), (H.3.12); (H.4.2), (H.4.6), dithianon (H.4.9) and (H.4.10).

Preference is also given to mixtures comprising as component 2) at least one active substance selected from group I), which is particularly selected from (I.2.3) and (I.2.5).

Preference is also given to mixtures comprising as component 2) at least one active substance selected from group J), which is particularly selected from (J.1.1), (J.1.2), (J.1.3), (J.1.4), (J.1.6), (J.1.7), (J.1.8) and (J.1.9).

Preference is also given to mixtures comprising as component 2) at least one active substance selected from group K), which is particularly selected from (K.1.4), (K.1.5), (K.1.8), (K.1.12), (K.1.14), (K.1.15), (K.1.19) and (K.1.22).

Accordingly, the present invention furthermore relates to mixtures comprising one compound of the formula I (component 1) and one pesticide II (component 2), wherein pesticide II is selected from the column "Co. 2" of the lines B-1 to B-580 of Table B.

A further embodiment relates to the mixtures B-1 to B-580 listed in Table B, where a row of Table B corresponds in each case to a fungicidal mixture comprising as active components one of the in the present specification individualized compounds of formula I, i.e. compounds I-1 to I-890 as defined in table A (component 1 in column "Co.1") and the respective pesticide II from groups A) to O) (component 2) stated in the row in question.

Another embodiment relates to the mixtures B-1 to B-580 listed in Table B, where a row of Table B corresponds in each case to a fungicidal mixture comprising as active components one of the compounds Ex-1 to Ex-7 of formula I as defined below in table I (component 1 in column "Co.1") and the respective pesticide II from groups A) to O) (component 2) stated in the row in question.

Preferably, the compositions described in Table B comprise the active components in synergistically effective amounts.

TABLE B

Mixtures comprising as active components one indiviualized compound of the fomula I (in column Co. 1), in particular compounds I-1 to I-890 as defined in table A, or more particularly compounds Ex-1 to Ex-7, as defined below in table I, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-1 | (I) | (A.1.1) |
| B-2 | (I) | (A.1.2) |
| B-3 | (I) | (A.1.3) |
| B-4 | (I) | (A.1.4) |
| B-5 | (I) | (A.1.5) |
| B-6 | (I) | (A.1.6) |
| B-7 | (I) | (A.1.7) |
| B-8 | (I) | (A.1.8) |
| B-9 | (I) | (A.1.9) |
| B-10 | (I) | (A.1.10) |
| B-11 | (I) | (A.1.11) |
| B-12 | (I) | (A.1.12) |
| B-13 | (I) | (A.1.13) |
| B-14 | (I) | (A.1.14) |
| B-15 | (I) | (A.1.15) |
| B-16 | (I) | (A.1.16) |
| B-17 | (I) | (A.1.17) |
| B-18 | (I) | (A.1.18) |
| B-19 | (I) | (A.1.19) |
| B-20 | (I) | (A.1.20) |
| B-21 | (I) | (A.1.21) |
| B-22 | (I) | (A.1.22) |

TABLE B-continued

Mixtures comprising as active components one indiviualized compound of the fomula I (in column Co. 1), in particular compounds I-1 to I-890 as defined in table A, or more particularly compounds Ex-1 to Ex-7, as defined below in table I, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-23 | (I) | (A.1.23) |
| B-24 | (I) | (A.1.24) |
| B-25 | (I) | (A.1.25) |
| B-26 | (I) | (A.1.26) |
| B-27 | (I) | (A.1.27) |
| B-28 | (I) | (A.1.28) |
| B-29 | (I) | (A.1.29) |
| B-30 | (I) | (A.1.30) |
| B-31 | (I) | (A.1.31) |
| B-32 | (I) | (A.1.32) |
| B-33 | (I) | (A.1.33) |
| B-34 | (I) | (A.2.1) |
| B-35 | (I) | (A.2.2) |
| B-36 | (I) | (A.2.3) |
| B-37 | (I) | (A.2.4) |
| B-38 | (I) | (A.2.5) |
| B-39 | (I) | (A.2.6) |
| B-40 | (I) | (A.2.7) |
| B-41 | (I) | (A.2.8) |
| B-42 | (I) | (A.3.1) |
| B-43 | (I) | (A.3.2) |
| B-44 | (I) | (A.3.3) |
| B-45 | (I) | (A.3.4) |
| B-46 | (I) | (A.3.5) |
| B-47 | (I) | (A.3.6) |
| B-48 | (I) | (A.3.7) |
| B-49 | (I) | (A.3.8) |
| B-50 | (I) | (A.3.9) |
| B-51 | (I) | (A.3.10) |
| B-52 | (I) | (A.3.11) |
| B-53 | (I) | (A.3.12) |
| B-54 | (I) | (A.3.13) |
| B-55 | (I) | (A.3.14) |
| B-56 | (I) | (A.3.15) |
| B-57 | (I) | (A.3.16) |
| B-58 | (I) | (A.3.17) |
| B-59 | (I) | (A.3.18) |
| B-60 | (I) | (A.3.19) |
| B-61 | (I) | (A.3.20) |
| B-62 | (I) | (A.3.21) |
| B-63 | (I) | (A.3.22) |
| B-64 | (I) | (A.3.23) |
| B-65 | (I) | (A.3.24) |
| B-66 | (I) | (A.3.25) |
| B-67 | (I) | (A.3.26) |
| B-68 | (I) | (A.3.27) |
| B-69 | (I) | (A.4.1) |
| B-70 | (I) | (A.4.2) |
| B-71 | (I) | (A.4.3) |
| B-72 | (I) | (A.4.4) |
| B-73 | (I) | (A.4.5) |
| B-74 | (I) | (A.4.6) |
| B-75 | (I) | (A.4.7) |
| B-76 | (I) | (A.4.8) |
| B-77 | (I) | (A.4.9) |
| B-78 | (I) | (A.4.10) |
| B-79 | (I) | (A.4.11) |
| B-80 | (I) | (A.4.12) |
| B-81 | (I) | (B.1.1) |
| B-82 | (I) | (B.1.2) |
| B-83 | (I) | (B.1.3) |
| B-84 | (I) | (B.1.4) |
| B-85 | (I) | (B.1.5) |
| B-86 | (I) | (B.1.6) |
| B-87 | (I) | (B.1.7) |
| B-88 | (I) | (B.1.8) |
| B-89 | (I) | (B.1.9) |
| B-90 | (I) | (B.1.10) |
| B-91 | (I) | (B.1.11) |
| B-92 | (I) | (B.1.12) |
| B-93 | (I) | (B.1.13) |

TABLE B-continued

Mixtures comprising as active components one indiviualized compound of the fomula I (in column Co. 1), in particular compounds I-1 to I-890 as defined in table A, or more particularly compounds Ex-1 to Ex-7, as defined below in table I, and as component 2) (in column Co. 2) one pesticide from groups A) to O) [which is coded e.g. as (A.1.1) for azoxystrobin as defined above].

| Mixt. | Co. 1 | Co. 2 |
| --- | --- | --- |
| B-94 | (I) | (B.1.14) |
| B-95 | (I) | (B.1.15) |
| B-96 | (I) | (B.1.16) |
| B-97 | (I) | (B.1.17) |
| B-98 | (I) | (B.1.18) |
| B-99 | (I) | (B.1.19) |
| B-100 | (I) | (B.1.20) |
| B-101 | (I) | (B.1.21) |
| B-102 | (I) | (B.1.22) |
| B-103 | (I) | (B.1.23) |
| B-104 | (I) | (B.1.24) |
| B-105 | (I) | (B.1.25) |
| B-106 | (I) | (B.1.26) |
| B-107 | (I) | (B.1.27) |
| B-108 | (I) | (B.1.28) |
| B-109 | (I) | (B.1.29) |
| B-110 | (I) | (B.1.30) |
| B-111 | (I) | (B.1.31) |
| B-112 | (I) | (B.1.32) |
| B-113 | (I) | (B.1.33) |
| B-114 | (I) | (B.1.34) |
| B-115 | (I) | (B.1.35) |
| B-116 | (I) | (B.1.36) |
| B-117 | (I) | (B.1.37) |
| B-118 | (I) | (B.1.38) |
| B-119 | (I) | (B.1.39) |
| B-120 | (I) | (B.1.40) |
| B-121 | (I) | (B.1.41) |
| B-122 | (I) | (B.1.42) |
| B-123 | (I) | (B.1.43) |
| B-124 | (I) | (B.1.44) |
| B-125 | (I) | (B.1.45) |
| B-126 | (I) | (B.1.46) |
| B-127 | (I) | (B.1.47) |
| B-128 | (I) | (B.1.48) |
| B-129 | (I) | (B.1.49) |
| B-130 | (I) | (B.1.50) |
| B-131 | (I) | (B.1.51) |
| B-132 | (I) | (B.2.1) |
| B-133 | (I) | (B.2.2) |
| B-134 | (I) | (B.2.3) |
| B-135 | (I) | (B.2.4) |
| B-136 | (I) | (B.2.5) |
| B-137 | (I) | (B.2.6) |
| B-138 | (I) | (B.2.7) |
| B-139 | (I) | (B.2.8) |
| B-140 | (I) | (B.3.1) |
| B-141 | (I) | (C.1.1) |
| B-142 | (I) | (C.1.2) |
| B-143 | (I) | (C.1.3) |
| B-144 | (I) | (C.1.4) |
| B-145 | (I) | (C.1.5) |
| B-146 | (I) | (C.1.6) |
| B-147 | (I) | (C.1.7) |
| B-148 | (I) | (C.2.1) |
| B-149 | (I) | (C.2.2) |
| B-150 | (I) | (C.2.3) |
| B-151 | (I) | (C.2.4) |
| B-152 | (I) | (C.2.5) |
| B-153 | (I) | (C.2.6) |
| B-154 | (I) | (C.2.7) |
| B-155 | (I) | (D.1.1) |
| B-156 | (I) | (D.1.2) |
| B-157 | (I) | (D.1.3) |
| B-158 | (I) | (D.1.4) |
| B-159 | (I) | (D.1.5) |
| B-160 | (I) | (D.1.6) |
| B-161 | (I) | (D.2.1) |
| B-162 | (I) | (D.2.2) |
| B-163 | (I) | (D.2.3) |
| B-164 | (I) | (D.2.4) |
| B-165 | (I) | (D.2.5) |
| B-166 | (I) | (D.2.6) |
| B-167 | (I) | (D.2.7) |
| B-168 | (I) | (E.1.1) |
| B-169 | (I) | (E.1.2) |
| B-170 | (I) | (E.1.3) |
| B-171 | (I) | (E.2.1) |
| B-172 | (I) | (E.2.2) |
| B-173 | (I) | (E.2.3) |
| B-174 | (I) | (E.2.4) |
| B-175 | (I) | (E.2.5) |
| B-176 | (I) | (E.2.6) |
| B-177 | (I) | (E.2.7) |
| B-178 | (I) | (E.2.8) |
| B-179 | (I) | (F.1.1) |
| B-180 | (I) | (F.1.2) |
| B-181 | (I) | (F.1.3) |
| B-182 | (I) | (F.1.4) |
| B-183 | (I) | (F.1.5) |
| B-184 | (I) | (F.1.6) |
| B-185 | (I) | (F.2.1) |
| B-186 | (I) | (G.1.1) |
| B-187 | (I) | (G.1.2) |
| B-188 | (I) | (G.1.3) |
| B-189 | (I) | (G.1.4) |
| B-190 | (I) | (G.2.1) |
| B-191 | (I) | (G.2.2) |
| B-192 | (I) | (G.2.3) |
| B-193 | (I) | (G.2.4) |
| B-194 | (I) | (G.2.5) |
| B-195 | (I) | (G.2.6) |
| B-196 | (I) | (G.2.7) |
| B-197 | (I) | (G.3.1) |
| B-198 | (I) | (G.3.2) |
| B-199 | (I) | (G.3.3) |
| B-200 | (I) | (G.3.4) |
| B-201 | (I) | (G.3.5) |
| B-202 | (I) | (G.3.6) |
| B-203 | (I) | (G.3.7) |
| B-204 | (I) | (G.3.8) |
| B-205 | (I) | (G.4.1) |
| B-206 | (I) | (G.5.1) |
| B-207 | (I) | (G.5.2) |
| B-208 | (I) | (G.5.3) |
| B-209 | (I) | (H.1.1) |
| B-210 | (I) | (H.1.2) |
| B-211 | (I) | (H.1.3) |
| B-212 | (I) | (H.1.4) |
| B-213 | (I) | (H.1.5) |
| B-214 | (I) | (H.1.6) |
| B-215 | (I) | (H.2.1) |
| B-216 | (I) | (H.2.2) |
| B-217 | (I) | (H.2.3) |
| B-218 | (I) | (H.2.4) |
| B-219 | (I) | (H.2.5) |
| B-220 | (I) | (H.2.6) |
| B-221 | (I) | (H.2.7) |
| B-222 | (I) | (H.2.8) |
| B-223 | (I) | (H.2.9) |
| B-224 | (I) | (H.3.1) |
| B-225 | (I) | (H.3.2) |
| B-226 | (I) | (H.3.3) |
| B-227 | (I) | (H.3.4) |
| B-228 | (I) | (H.3.5) |
| B-229 | (I) | (H.3.6) |
| B-230 | (I) | (H.3.7) |
| B-231 | (I) | (H.3.8) |
| B-232 | (I) | (H.3.9) |
| B-233 | (I) | (H.3.10) |
| B-234 | (I) | (H.3.11) |
| B-235 | (I) | (H.4.1) |

TABLE B-continued

Mixtures comprising as active components one indiviualized compound of the fomula I (in column Co. 1), in particular compounds I-1 to I-890 as defined in table A, or more particularly compounds Ex-1 to Ex-7, as defined below in table I, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-236 | (I) | (H.4.2) |
| B-237 | (I) | (H.4.3) |
| B-238 | (I) | (H.4.4) |
| B-239 | (I) | (H.4.5) |
| B-240 | (I) | (H.4.6) |
| B-241 | (I) | (H.4.7) |
| B-242 | (I) | (H.4.8) |
| B-243 | (I) | (H.4.9) |
| B-244 | (I) | (H.4.10) |
| B-245 | (I) | (I.1.1) |
| B-246 | (I) | (I.1.2) |
| B-247 | (I) | (I.2.1) |
| B-248 | (I) | (I.2.2) |
| B-249 | (I) | (I.2.3) |
| B-250 | (I) | (I.2.4) |
| B-251 | (I) | (I.2.5) |
| B-252 | (I) | (J.1.1) |
| B-253 | (I) | (J.1.2) |
| B-254 | (I) | (J.1.3) |
| B-255 | (I) | (J.1.4) |
| B-256 | (I) | (J.1.5) |
| B-257 | (I) | (J.1.6) |
| B-258 | (I) | (J.1.7) |
| B-259 | (I) | (J.1.8) |
| B-260 | (I) | (J.1.9) |
| B-261 | (I) | (K.1.1) |
| B-262 | (I) | (K.1.2) |
| B-263 | (I) | (K.1.3) |
| B-264 | (I) | (K.1.4) |
| B-265 | (I) | (K.1.5) |
| B-266 | (I) | (K.1.6) |
| B-267 | (I) | (K.1.7) |
| B-268 | (I) | (K.1.8) |
| B-269 | (I) | (K.1.9) |
| B-270 | (I) | (K.1.10) |
| B-271 | (I) | (K.1.11) |
| B-272 | (I) | (K.1.12) |
| B-273 | (I) | (K.1.13) |
| B-274 | (I) | (K.1.14) |
| B-275 | (I) | (K.1.15) |
| B-276 | (I) | (K.1.16) |
| B-277 | (I) | (K.1.17) |
| B-278 | (I) | (K.1.18) |
| B-279 | (I) | (K.1.19) |
| B-280 | (I) | (K.1.20) |
| B-281 | (I) | (K.1.21) |
| B-282 | (I) | (K.1.22) |
| B-283 | (I) | (K.1.23) |
| B-284 | (I) | (K.1.24) |
| B-285 | (I) | (K.1.25) |
| B-286 | (I) | (K.1.26) |
| B-287 | (I) | (K.1.27) |
| B-288 | (I) | (K.1.28) |
| B-289 | (I) | (K.1.29) |
| B-290 | (I) | (K.1.30) |
| B-291 | (I) | (K.1.31) |
| B-292 | (I) | (K.1.32) |
| B-293 | (I) | (K.1.33) |
| B-294 | (I) | (K.1.34) |
| B-295 | (I) | (K.1.35) |
| B-296 | (I) | (K.1.36) |
| B-297 | (I) | (K.1.37) |
| B-298 | (I) | (K.1.38) |
| B-299 | (I) | (K.1.39) |
| B-300 | (I) | (K.1.40) |
| B-301 | (I) | (K.1.41) |
| B-302 | (I) | (K.1.42) |
| B-303 | (I) | (K.1.43) |
| B-304 | (I) | (K.1.44) |
| B-305 | (I) | (K.1.45) |
| B-306 | (I) | (K.1.46) |
| B-307 | (I) | (K.1.47) |
| B-308 | (I) | (K.1.48) |
| B-309 | (I) | (M.1.1) |
| B-310 | (I) | (M.1.2) |
| B-311 | (I) | (M.1.3) |
| B-312 | (I) | (M.1.4) |
| B-313 | (I) | (M.1.5) |
| B-314 | (I) | (M.1.6) |
| B-315 | (I) | (M.1.7) |
| B-316 | (I) | (M.1.8) |
| B-317 | (I) | (M.1.9) |
| B-318 | (I) | (M.1.10) |
| B-319 | (I) | (M.1.11) |
| B-320 | (I) | (M.1.12) |
| B-321 | (I) | (M.1.13) |
| B-322 | (I) | (M.1.14) |
| B-323 | (I) | (M.1.15) |
| B-324 | (I) | (M.1.16) |
| B-325 | (I) | (M.1.17) |
| B-326 | (I) | (M.1.18) |
| B-327 | (I) | (M.1.19) |
| B-328 | (I) | (M.1.20) |
| B-329 | (I) | (M.1.21) |
| B-330 | (I) | (M.1.22) |
| B-331 | (I) | (M.1.23) |
| B-332 | (I) | (M.1.24) |
| B-333 | (I) | (M.1.25) |
| B-334 | (I) | (M.1.26) |
| B-335 | (I) | (M.1.27) |
| B-336 | (I) | (M.1.28) |
| B-337 | (I) | (M.1.29) |
| B-338 | (I) | (M.1.30) |
| B-339 | (I) | (M.1.31) |
| B-340 | (I) | (M.1.32) |
| B-341 | (I) | (M.1.33) |
| B-342 | (I) | (M.1.34) |
| B-343 | (I) | (M.1.35) |
| B-344 | (I) | (M.1.36) |
| B-345 | (I) | (M.1.37) |
| B-346 | (I) | (M.1.38) |
| B-347 | (I) | (M.1.39) |
| B-348 | (I) | (M.1.40) |
| B-349 | (I) | (M.1.41) |
| B-350 | (I) | (M.1.42) |
| B-351 | (I) | (M.1.43) |
| B-352 | (I) | (M.1.44) |
| B-353 | (I) | (M.1.45) |
| B-354 | (I) | (M.1.46) |
| B-355 | (I) | (M.1.47) |
| B-356 | (I) | (M.1.48) |
| B-357 | (I) | (M.1.49) |
| B-358 | (I) | (M.1.50) |
| B-359 | (I) | (N.1.1) |
| B-360 | (I) | (N.1.2) |
| B-361 | (I) | (N.1.3) |
| B-362 | (I) | (N.1.4) |
| B-363 | (I) | (N.1.5) |
| B-364 | (I) | (N.2.1) |
| B-365 | (I) | (N.2.2) |
| B-366 | (I) | (N.2.3) |
| B-367 | (I) | (N.3.1) |
| B-368 | (I) | (N.3.2) |
| B-369 | (I) | (N.3.3) |
| B-370 | (I) | (N.3.4) |
| B-371 | (I) | (N.4.1) |
| B-372 | (I) | (N.5.1) |
| B-373 | (I) | (N.6.1) |
| B-374 | (I) | (N.6.2) |
| B-375 | (I) | (N.6.3) |
| B-376 | (I) | (N.6.4) |
| B-377 | (I) | (N.6.5) |

TABLE B-continued

Mixtures comprising as active components one indiviualized compound of the fomula I (in column Co. 1), in particular compounds I-1 to I-890 as defined in table A, or more particularly compounds Ex-1 to Ex-7, as defined below in table I, and as component 2) (in column Co. 2) one pesticide from groups A) to O) [which is coded e.g. as (A.1.1) for azoxystrobin as defined above].

| Mixt. | Co. 1 | Co. 2 |
|---|---|---|
| B-378 | (I) | (N.7.1) |
| B-379 | (I) | (N.7.2) |
| B-380 | (I) | (N.7.3) |
| B-381 | (I) | (N.8.1) |
| B-382 | (I) | (N.9.1) |
| B-383 | (I) | (N.10.1) |
| B-384 | (I) | (N.10.2) |
| B-385 | (I) | (N.10.3) |
| B-386 | (I) | (N.10.4) |
| B-387 | (I) | (N.10.5) |
| B-388 | (I) | (N.11.1) |
| B-389 | (I) | (N.12.1) |
| B-390 | (I) | (N.12.2) |
| B-391 | (I) | (N.12.3) |
| B-392 | (I) | (N.12.4) |
| B-393 | (I) | (N.13.1) |
| B-394 | (I) | (N.13.2) |
| B-395 | (I) | (N.13.3) |
| B-396 | (I) | (N.13.4) |
| B-397 | (I) | (N.13.5) |
| B-398 | (I) | (N.13.6) |
| B-399 | (I) | (N.13.7) |
| B-400 | (I) | (N.13.8) |
| B-401 | (I) | (N.13.9) |
| B-402 | (I) | (N.14.1) |
| B-403 | (I) | (N.14.2) |
| B-404 | (I) | (N.14.3) |
| B-405 | (I) | (N.15.1) |
| B-406 | (I) | (N.16.1) |
| B-407 | (I) | (N.16.2) |
| B-408 | (I) | (N.17.1) |
| B-409 | (I) | (N.17.2) |
| B-410 | (I) | (N.17.3) |
| B-411 | (I) | (N.17.4) |
| B-412 | (I) | (N.17.5) |
| B-413 | (I) | (N.17.6) |
| B-414 | (I) | (N.17.7) |
| B-415 | (I) | (N.17.8) |
| B-416 | (I) | (N.17.9) |
| B-417 | (I) | (N.17.10) |
| B-418 | (I) | (N.17.11) |
| B-419 | (I) | (N.17.12) |
| B-420 | (I) | (O.1.1) |
| B-421 | (I) | (O.1.2) |
| B-422 | (I) | (O.1.3) |
| B-423 | (I) | (O.1.4) |
| B-424 | (I) | (O.1.5) |
| B-425 | (I) | (O.1.6) |
| B-426 | (I) | (O.1.7) |
| B-427 | (I) | (O.1.8) |
| B-428 | (I) | (O.1.9) |
| B-429 | (I) | (O.1.10) |
| B-430 | (I) | (O.1.11) |
| B-431 | (I) | (O.1.12) |
| B-432 | (I) | (O.1.13) |
| B-433 | (I) | (O.1.14) |
| B-434 | (I) | (O.1.15) |
| B-435 | (I) | (O.1.16) |
| B-436 | (I) | (O.1.17) |
| B-437 | (I) | (O.1.18) |
| B-438 | (I) | (O.1.19) |
| B-439 | (I) | (O.1.20) |
| B-440 | (I) | (O.1.21) |
| B-441 | (I) | (O.1.22) |
| B-442 | (I) | (O.1.23) |
| B-443 | (I) | (O.1.24) |
| B-444 | (I) | (O.1.25) |
| B-445 | (I) | (O.1.26) |
| B-446 | (I) | (O.1.27) |
| B-447 | (I) | (O.1.28) |
| B-448 | (I) | (O.1.29) |
| B-449 | (I) | (O.1.30) |
| B-450 | (I) | (O.1.31) |
| B-451 | (I) | (O.1.32) |
| B-452 | (I) | (O.1.33) |
| B-453 | (I) | (O.1.34) |
| B-454 | (I) | (O.1.35) |
| B-455 | (I) | (O.1.36) |
| B-456 | (I) | (O.1.37) |
| B-457 | (I) | (O.1.38) |
| B-458 | (I) | (O.2.1) |
| B-459 | (I) | (O.2.2) |
| B-460 | (I) | (O.2.3) |
| B-461 | (I) | (O.2.4) |
| B-462 | (I) | (O.2.5) |
| B-463 | (I) | (O.2.6) |
| B-464 | (I) | (O.2.7) |
| B-465 | (I) | (O.2.8) |
| B-466 | (I) | (O.2.9) |
| B-467 | (I) | (O.2.10) |
| B-468 | (I) | (O.2.11) |
| B-469 | (I) | (O.2.12) |
| B-470 | (I) | (O.2.13) |
| B-471 | (I) | (O.2.14) |
| B-472 | (I) | (O.2.15) |
| B-473 | (I) | (O.2.16) |
| B-474 | (I) | (O.3.1) |
| B-475 | (I) | (O.3.2) |
| B-476 | (I) | (O.3.3) |
| B-477 | (I) | (O.3.4) |
| B-478 | (I) | (O.3.5) |
| B-479 | (I) | (O.3.6) |
| B-480 | (I) | (O.3.7) |
| B-481 | (I) | (O.3.8) |
| B-482 | (I) | (O.3.9) |
| B-483 | (I) | (O.3.10) |
| B-484 | (I) | (O.3.11) |
| B-485 | (I) | (O.3.12) |
| B-486 | (I) | (O.3.13) |
| B-487 | (I) | (O.3.14) |
| B-488 | (I) | (O.3.15) |
| B-489 | (I) | (O.3.16) |
| B-490 | (I) | (O.3.17) |
| B-491 | (I) | (O.3.18) |
| B-492 | (I) | (O.3.19) |
| B-493 | (I) | (O.3.20) |
| B-494 | (I) | (O.3.21) |
| B-495 | (I) | (O.3.22) |
| B-496 | (I) | (O.3.23) |
| B-497 | (I) | (O.3.24) |
| B-498 | (I) | (O.3.25) |
| B-499 | (I) | (O.3.26) |
| B-500 | (I) | (O.3.27) |
| B-501 | (I) | (O.4.1) |
| B-502 | (I) | (O.4.2) |
| B-503 | (I) | (O.4.3) |
| B-504 | (I) | (O.4.4) |
| B-505 | (I) | (O.4.5) |
| B-506 | (I) | (O.4.6) |
| B-507 | (I) | (O.4.7) |
| B-508 | (I) | (O.4.8) |
| B-509 | (I) | (O.4.9) |
| B-510 | (I) | (O.4.10) |
| B-511 | (I) | (O.4.11) |
| B-512 | (I) | (O.4.12) |
| B-513 | (I) | (O.4.13) |
| B-514 | (I) | (O.4.14) |
| B-515 | (I) | (O.4.15) |
| B-516 | (I) | (O.4.16) |
| B-517 | (I) | (O.4.17) |
| B-518 | (I) | (O.4.18) |
| B-519 | (I) | (O.4.19) |

TABLE B-continued

Mixtures comprising as active components one indiviualized compound of the fomula I (in column Co. 1), in particular compounds I-1 to I-890 as defined in table A, or more particularly compounds Ex-1 to Ex-7, as defined below in table I, and as component 2) (in column Co. 2) one pesticide from groups A) to O) [which is coded e.g. as (A.1.1) for azoxystrobin as defined above].

| Mixt. | Co. 1 | Co. 2 |
| --- | --- | --- |
| B-520 | (I) | (O.4.20) |
| B-521 | (I) | (O.4.21) |
| B-522 | (I) | (O.4.22) |
| B-523 | (I) | (O.4.23) |
| B-524 | (I) | (O.4.24) |
| B-525 | (I) | (O.5.1) |
| B-526 | (I) | (O.5.2) |
| B-527 | (I) | (O.5.3) |
| B-528 | (I) | (O.5.4) |
| B-529 | (I) | (O.5.5) |
| B-530 | (I) | (O.5.6) |
| B-531 | (I) | (O.5.7) |
| B-532 | (I) | (O.5.8) |
| B-533 | (I) | (O.5.9) |
| B-534 | (I) | (O.6.1) |
| B-535 | (I) | (O.6.2) |
| B-536 | (I) | (O.6.3) |
| B-537 | (I) | (O.6.4) |
| B-538 | (I) | (O.6.5) |
| B-539 | (I) | (O.6.6) |
| B-540 | (I) | (O.6.7) |
| B-541 | (I) | (O.7.1) |
| B-542 | (I) | (O.7.2) |
| B-543 | (I) | (O.7.3) |
| B-544 | (I) | (O.7.4) |
| B-545 | (I) | (O.7.5) |
| B-546 | (I) | (O.7.6) |
| B-547 | (I) | (O.8.1) |
| B-548 | (I) | (O.8.2) |
| B-549 | (I) | (O.8.3) |
| B-550 | (I) | (O.8.4) |
| B-551 | (I) | (O.8.5) |
| B-552 | (I) | (O.9.1) |
| B-553 | (I) | (O.9.2) |
| B-554 | (I) | (O.9.3) |
| B-555 | (I) | (O.10.1) |
| B-556 | (I) | (O.11.1) |
| B-557 | (I) | (O.11.2) |
| B-558 | (I) | (O.11.3) |
| B-559 | (I) | (O.11.4) |
| B-560 | (I) | (O.12.1) |
| B-561 | (I) | (O.13.1) |
| B-562 | (I) | (O.14.1) |
| B-563 | (I) | (O.14.2) |
| B-564 | (I) | (O.15.1) |
| B-565 | (I) | (O.15.2) |
| B-566 | (I) | (O.15.3) |
| B-567 | (I) | (O.15.4) |
| B-568 | (I) | (O.15.5) |
| B-569 | (I) | (O.15.6) |
| B-570 | (I) | (O.15.7) |
| B-571 | (I) | (O.15.8) |
| B-572 | (I) | (O.15.9) |
| B-573 | (I) | (O.15.10) |
| B-574 | (I) | (O.15.11) |
| B-575 | (I) | (O.16.1) |
| B-576 | (I) | (O.16.2) |
| B-577 | (I) | (O.16.3) |
| B-578 | (I) | (O.16.4) |
| B-579 | (I) | (O.16.5) |
| B-580 | (I) | (O.16.6) |

The mixtures of active substances can be prepared as compositions comprising besides the active ingredients at least one inert ingredient (auxiliary) by usual means, e.g. by the means given for the compositions of compounds I.

Concerning usual ingredients of such compositions reference is made to the explanations given for the compositions containing compounds I.

I. SYNTHESIS EXAMPLES

I.1 Preparation of 1-[2-[(5,6-dimethyl-3-pyridyl)oxy]-6-fluoro-phenyl]ethanone

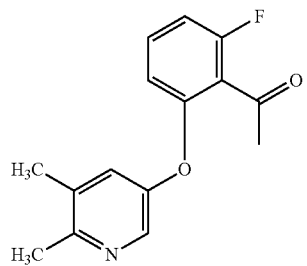 [SMILES: CC(=O)c1c(F)cccc1Oc1cnc(C)c(C)c1]

To a solution of 5,6-dimethyl-3-hydroxypyridine (3.00 g, 1.0 eq; prepared as described in Journal of Medicinal Chemistry, 36(2), 249-55; 1993) in NMP (100 mL) was added potassium carbonate (7.40 g, 2.2 eq) and the mixture was stirred at rt for 15 minutes. It was added 2,6-difluoroacetophenon (4.14 g, 1.1 eq) and the mixture was warmed to 100° C. and stirred overnight. After cooling to ambient temperature, water was added and the product was extracted into MTBE. The combined organic extracts were washed with water and brine, successively, and dried over $Na_2SO_4$. Removal of the solvent under reduced pressure afforded a residue that was further purified by column chromatography. The title compound was isolated as light brown oil (1.40 g, 44%).

$t_R$=0.749 min; $^1$H NMR (400 MHz, $CDCl_3$, 298 K): δ[ppm]=8.12 (s, 1H), 7.30-7.25 (m, 1H), 7.10 (s, 1H), 6.88 (t, 1H), 6.60 (d, 1H), 2.57 (s, 3H), 2.45 (s, 3H), 2.25 (s, 3H).

I.2 Preparation of 1-[2-[(5,6-dimethyl-3-pyridyl)oxy]-6-fluoro-phenyl]ethanol

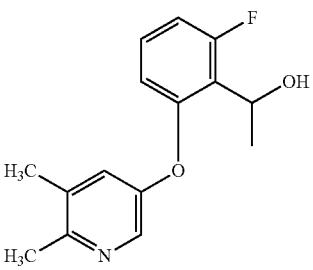 [SMILES: Cc1cc(Oc2cccc(F)c2C(C)O)cnc1C]

A cold (0° C.) solution of the ketone obtained from above (200 mg, 1.0 eq) in MeOH (6 mL) was treated with sodium borohydride (15.0 mg, 0.5 eq) and stirred for 1 h at this temperature. When HPLC indicated complete conversion, the reaction was quenched by careful addition of water and the product was extracted into MTBE. The organic extracts were combined, washed with water and dried over $Na_2SO_4$. The solvent was removed under reduced pressure and purification of the crude product yielded the title compound as colorless oil (190 mg, 96%).

$t_R$=0.707 min; $^1$H NMR (400 MHz, $CDCl_3$, 298 K): δ[ppm]=8.18 (s, 1H), 7.20-7.10 (m, 2H), 6.85 (t, 1H), 6.55 (d, 1H), 5.30 (m, 1H), 2.50 (s, 3H), 2.25 (s, 3H), 1.62 (d, 3H).

I.3 Preparation of 5-[3-fluoro-2-[1-(m-tolyl-methoxy)ethyl]phenoxy]-2,3-dimethyl-pyridine

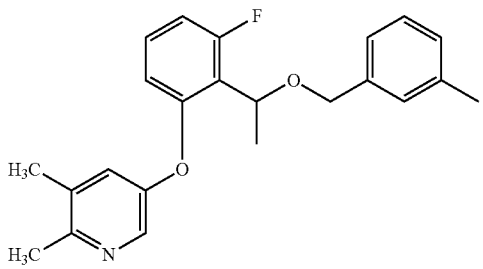

The alcohol prepared as described above (150 mg, 1.0 eq) was dissolved in NMP (4 mL) and cooled to 0° C. before NaH (25.7 mg, 60% suspension in mineral oil, 1.1 eq) was added and the mixture slowly warmed to rt. After 0.5 h, 3-methylbenzyl chloride (88.8 mg, 1.1 eq) was added and stirring was continued overnight, before the reaction was quenched with water. The agueous layer was extracted with MTBE and the combined organic extracts were washed with brine, dried over $Na_2SO_4$ and freed from solvent under reduced pressure. Purification of the crude product by column chromatography afforded the title compound as yellow oil (75.0 mg, 32.2%).

$t_R$=1.056 min; $^1$H NMR (400 MHz, $CDCl_3$, 298 K): δ[ppm]=8.10 (s, 1H), 7.25-7.02 (m, 5H), 6.97 (s, 1H), 6.90 (t, 1H), 6.62 (d, 1H), 5.10 (m, 1H), 4.65 (d, 1H), 4.42 (d, 1H), 4.30 (d, 1H), 2.45 (s, 3H), 2.38 (s, 3H), 2.22 (s, 3H), 1.62 (d, 3H).

With due modification of the starting compounds, the procedures shown in the synthesis examples below were used to obtain further compounds I. The resulting compounds, together with physical data, are listed in Table I below.

Table I:

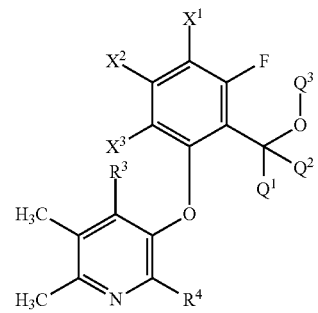

# means conntection to O atom.

| No. | $R^3$ | $R^4$ | $X^1$ | $X^2$ | $X^3$ | $Q^1$ | $Q^2$ | $Q^3$ | $^1$H-NMR (δ in ppm); HPLC-MS* (El ($M^+$ + H) $R_t$ [min], Mp (° C.) |
|---|---|---|---|---|---|---|---|---|---|
| I-1 | H | H | H | H | H | $CH_3$ | H | #-benzyl | $M^+$ + H 352.2 $R_t$ = 1.004 min |
| I-2 | H | H | H | H | H | $CH_3$ | H | #-(3-methylbenzyl) | $M^+$ + H 366.3 $R_t$ = 1.056 min |
| I-3 | H | H | H | H | H | $CH_3$ | H | #-(4-methylbenzyl) | $M^+$ + H 366.1 $R_t$ = 1.035 min |
| I-4 | H | H | H | H | H | $CH_3$ | H | #-(2-methylbenzyl) | $M^+$ + H 366.3 $R_t$ = 1.047 min |

-continued
| No. | R³ | R⁴ | X¹ | X² | X³ | Q¹ | Q² | Q³ | ¹H-NMR (δ in ppm); HPLC-MS* (EI (M⁺ + H) R$_t$ [min], Mp (° C.) |
|---|---|---|---|---|---|---|---|---|---|
| I-5 | H | H | H | H | H | CH₃ | H | 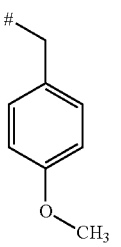 | M⁺ + H 382.2<br>R$_t$ = 1.006 min |
| I-6 | H | H | H | H | H | CH₃ | H | 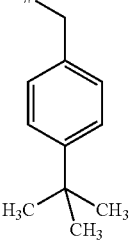 | M⁺ + H 408.4<br>R$_t$ = 1.19 min |
| I-7 | H | H | H | H | H | CH₃ | H | 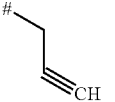 | M⁺ + H 300.1<br>R$_t$ = 0.858 min |
| I-8 | H | CN | H | H | H | CH₃ | H | 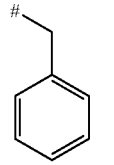 | M⁺ + H 377.1<br>R$_t$ = 1.365 |
| I-9 | H | Cl | H | H | H | CH₃ | H | 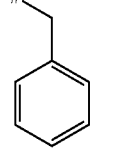 | M⁺ + H 260.0<br>R$_t$ = 1.053 |
| I-10 | H | H | H | H | H | CH₃ | H | 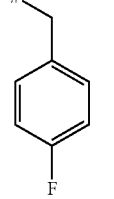 | M⁺ + H 370.4<br>R$_t$ = 0.999 min |
| I-11 | H | H | H | H | H | CH₃ | H | 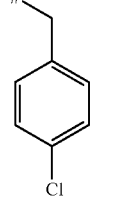 | M⁺ + H 386.1<br>R$_t$ = 1.044 min |

| No. | R³ | R⁴ | X¹ | X² | X³ | Q¹ | Q² | Q³ | ¹H-NMR (δ in ppm); HPLC-MS* (EI (M⁺ + H) R_t [min], Mp (° C.) |
|---|---|---|---|---|---|---|---|---|---|
| I-12 | H | H | H | H | H | CH₃ | H | #—CH₂—C₆H₄—CF₃ (para) | M⁺ + H 420.1 R_t = 1.088 min |
| I-13 | H | H | H | H | H | CH₃ | H | #—CH₂—(2-thienyl)-5-Cl | M⁺ + H 392 R_t = 1.039 min |
| I-14 | H | H | H | H | H | CH₃ | H | #—CH₂—C₆H₃—3,4-F₂ | M⁺ + H 388.1 R_t = 1.028 min |
| I-15 | H | H | H | H | H | CH₃ | H | #—C₆H₄—F (para) | M⁺ + H 356 R_t = 0.93 min |
| I-16 | H | H | H | H | H | CH₃ | H | C₂H₅ | M⁺ + H 290.1 R_t = 0.856 min |
| I-17 | H | H | H | H | H | CH₃ | H | #—CH₂-cyclopropyl | M⁺ + H 316.1 R_t = 0.932 min |
| I-18 | H | H | H | H | H | CH₃ | H | #—CH₂—CH=CH—Cl | M⁺ + H 336.1 R_t = 0.956 min |
| I-19 | H | H | H | H | H | CH₃ | H | #—CH₂CH₂CH₂—O—CH₃ | M⁺ + H 334.2 R_t = 0.871 min |

-continued
| No. | R³ | R⁴ | X¹ | X² | X³ | Q¹ | Q² | Q³ | ¹H-NMR (δ in ppm); HPLC-MS* (EI (M⁺ + H) $R_t$ [min], Mp (° C.) |
|---|---|---|---|---|---|---|---|---|---|
| I-20 | H | H | H | H | H | CH₃ | H | 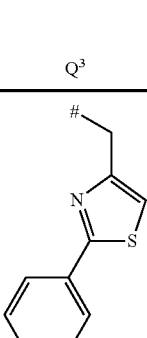 | M⁺ + H 434.9 $R_t$ = 1.046 min |
| I-21 | H | H | H | H | H | CH₃ | H | 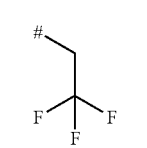 | M⁺ + H 344 $R_t$ = 0.922 min |
| I-22 | H | H | H | H | H | CH₃ | H | 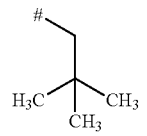 | M⁺ + H 332.1 $R_t$ = 1.083 min |
| I-23 | H | H | H | H | H | CH₃ | H | 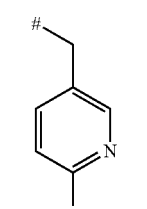 | M⁺ + H 387 $R_t$ = 0.938 min |
| I-24 | H | H | H | H | H | CH₃ | CH₃ | C₂H₅ | M⁺ + H 304.1 $R_t$ = 0.911 min |
| I-25 | H | H | H | H | H | CH₃ | H | 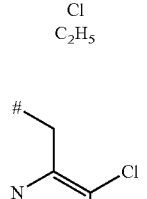 | M⁺ + H 440.9 $R_t$ = 1.118 min |
| I-26 | H | H | H | H | H | CH₃ | H | 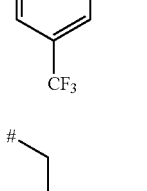 | M⁺ + H 408.1 $R_t$ = 1.008 min |
| I-27 | H | H | H | H | H | CH₃ | H | 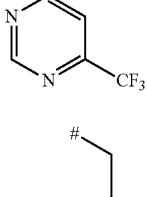 | M⁺ + H 418.2 $R_t$ = 0.973 min |

-continued
| No. | R³ | R⁴ | X¹ | X² | X³ | Q¹ | Q² | Q³ | ¹H-NMR (δ in ppm); HPLC-MS* (EI (M⁺ + H) R_t [min], Mp (° C.) |
|---|---|---|---|---|---|---|---|---|---|
| I-28 | H | CH₃ | H | H | H | CH₃ | H | 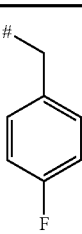 | M⁺ + H 384.0<br>R_t = 1.004 min |
| I-29 | H | H | F | H | H | CH₃ | H | 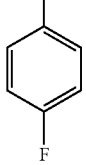 | M⁺ + H 387.9<br>R_t = 1.01 min |
| I-30 | H | H | H | H | H | CF₃ | H | 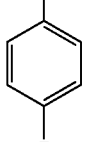 | M⁺ + H 424.1<br>R_t = 1.03 min |
| I-31 | H | H | H | F | H | CH₃ | H | 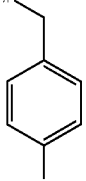 | M⁺ + H 388.1<br>R_t = 1.041 min |
| I-32 | H | H | H | F | H | CH₃ | H | CH₃ | M⁺ + H 294.1<br>R_t = 0.849 min |
| I-33 | H | H | H | H | H | CH₃ | H | 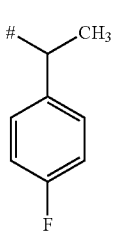 | M⁺ + H 384<br>R_t = 1.046 min |
| I-34 | H | H | H | H | H | CH₃ | H | 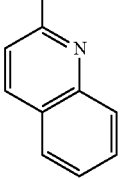 | M⁺ + H 403.1<br>R_t = 0.797 min |

-continued

| No. | R³ | R⁴ | X¹ | X² | X³ | Q¹ | Q² | Q³ | ¹H-NMR (δ in ppm); HPLC-MS* (EI $(M^+ + H)$ $R_t$ [min], Mp (° C.) |
|---|---|---|---|---|---|---|---|---|---|
| I-35 | H | Cl | H | H | H | CH₃ | H | 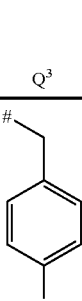 | $M^+ + H$ 404.1 $R_t = 1.438$ min |
| I-36 | H | CH₃ | H | H | H | CH₃ | CH₃ | C₂H₅ | $M^+ + H$ 318.1 $R_t = 0.884$ min |
| I-37 | H | CH₃ | H | H | H | CH₃ | CH₃ | 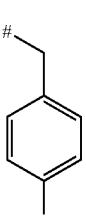 | $M^+ + H$ 398.2 $R_t = 1.029$ min |

HPLC-MS: HPLC-column Kinetex XB C18 1.7µ (50 × 2.1 mm); eluent: acetonitrile/water + 0.1% TFA (5 gradient from 5:95 to 100:0 in 1.5 min at 60° C., flow gradient from 0.8 to 1.0 ml/min in 1.5 min).
MS: Quadrupol Electrospray Ionisation, 80 V (positive mode).

II. BIOLOGICAL TRIALS

Microtest

The active compounds were formulated separately as a stock solution having a concentration of 10000 ppm in dimethyl sulfoxide.

Example 1—Activity Against the Grey Mold Botrytis cinerea in the Microtiterplate Test The stock solutions were mixed according to the ratio, pipetted onto a micro titer plate (MTP) and diluted with water to the stated concentrations. A spore suspension of Botrci cinerea in a DOB medium solution was then added. The plates were placed in a water vapor-saturated chamber at a temperature of 18° C. Using an absorption photometer, the MTPs were measured at 405 nm 9 days after the inoculation.

In this test, the samples which had been treated with 31 ppm of the active substance from examples I-5, I-10, I-11, I-12, I-13, I-14, I-17, I-18, I-20, I-22, I-26, I-27, I-29, I-30 and I-37 respectively, showed up to at most 19% growth of the pathogen.

Example 2—Activity Against Rice Blast Pyricularia oryzae in the Microtiterplate Test The stock solutions were mixed according to the ratio, pipetted onto a micro titer plate (MTP) and diluted with water to the stated concentrations. A spore suspension of Pyricularia oryzae in a DOB medium solution was then added. The plates were placed in a water vapor-saturated chamber at a temperature of 18° C. Using an absorption photometer, the MTPs were measured at 405 nm 9 days after the inoculation.

In this test, the samples which had been treated with 31 ppm of the active substance from examples I-2, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-33, I-34, I-35, I-36 and I-37 respectively, showed up to at most 6% growth of the pathogen.

Example 3—Activity Against Leaf Blotch on Wheat Caused by Septona tritici

The stock solutions were mixed according to the ratio, pipetted onto a micro titer plate (MTP) and diluted with water to the stated concentrations. A spore suspension of Septoria tritici in a DOB medium solution was then added. The plates were placed in a water vapor-saturated chamber at a temperature of 18° C. Using an absorption photometer, the MTPs were measured at 405 nm 9 days after the inoculation.

In this test, the samples which had been treated with 31 ppm of the active substance from examples I-25, I-30 and I-37 respectively, showed up to at most 19% growth of the pathogen.

Example 4—Activity Against Early Blight Caused by Alternaria solani

The stock solutions were mixed according to the ratio, pipetted onto a micro titer plate (MTP) and diluted with water to the stated concentrations. A spore suspension of Alternaria solani in a DOB medium solution was then added. The plates were placed in a water vapor-saturated chamber at a temperature of 18° C. Using an absorption photometer, the MTPs were measured at 405 nm 9 days after the inoculation.

In this test, the samples which had been treated with 31 ppm of the active substance from examples I-2, I-5, I-6, I-7, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36 and I-37 respectively, showed up to at most 17% growth of the pathogen.

Example 5—Activity Against Wheat Leaf Spots Caused by *Leptosphaeria nodorum*

The stock solutions were mixed according to the ratio, pipetted onto a micro titer plate (MTP) and diluted with water to the stated concentrations. A spore suspension of *Leptosphaeria nodorum* in a DOB medium solution was then added. The plates were placed in a water vapor-saturated chamber at a temperature of 18° C. Using an absorption photometer, the MTPs were measured at 405 nm 9 days after the inoculation.

In this test, the samples which had been treated with 31 ppm of the active substance from examples I-17, I-18, I-19, I-23, I-24, I-28 I-30, I-36 and I-37 respectively, showed up to at most 20% growth of the pathogen.

The measured parameters were compared to the growth of the active compound-free control variant (100%) and the fungus-free and active compound-free blank value to determine the relative growth in % of the pathogens in the respective active compounds.

III. COMPARATIVE EXAMPLES

Microtest

The active compounds were formulated separately as a stock solution having a concentration of 10000 ppm in dimethyl sulfoxide.

Example 1—Activity Against the Grey Mold *Botrytis cinerea* in the Microtiterplate Test The stock solutions were mixed according to the ratio, pipetted onto a micro titer plate (MTP) and diluted with water to the stated concentrations. A spore suspension of *Botrci cinerea* in a DOB medium solution was then added. The plates were placed in a water vapor-saturated chamber at a temperature of 18° C. Using an absorption photometer, the MTPs were measured at 405 nm 9 days after the inoculation.

| Compound | Structure | Growth (%) at 31 ppm |
|---|---|---|
| State of the art | 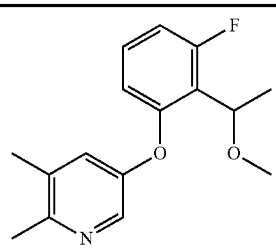 | 58 |
| I-16 | 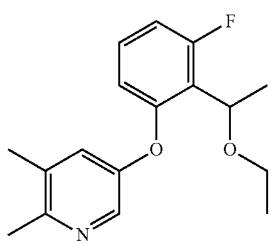 [SMILES: CCOC(C)c1c(F)cccc1Oc1cnc(C)c(C)c1] | 34 |

Example 2—Activity Against Wheat Leaf Spots Caused by *Leptosphaeria nodorum*

The stock solutions were mixed according to the ratio, pipetted onto a micro titer plate (MTP) and diluted with water to the stated concentrations. A spore suspension of *Leptosphaeria nodorum* in a DOB medium solution was then added. The plates were placed in a water vapor-saturated chamber at a temperature of 18° C. Using an absorption photometer, the MTPs were measured at 405 nm 9 days after the inoculation.

| Compound | Structure | Growth (%) at 31 ppm |
|---|---|---|
| State of the art | 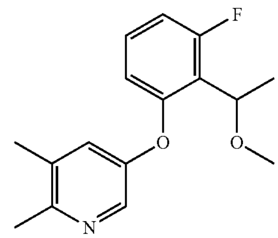 [SMILES: COC(C)c1c(F)cccc1Oc1cnc(C)c(C)c1] | 68 |
| I-16 | 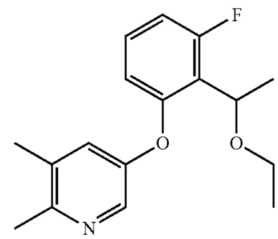 [SMILES: CCOC(C)c1c(F)cccc1Oc1cnc(C)c(C)c1] | 40 |

The invention claimed is:
1. A compound of the formula I

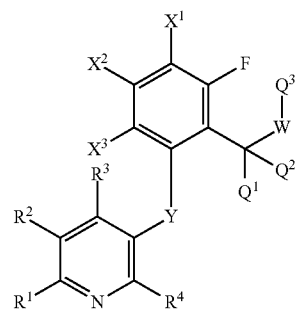

wherein
$R^1$ is $CH_3$;
$R^2$ is $CH_3$;
$R^3$ is selected from the group consisting of H, halogen, OH, CN, $NO_2$, SH, $NH_2$, $NH(C_1-C_4$-alkyl), $N(C_1-C_4$-alkyl$)_2$, $NH$—$SO_2$—$R^{31}$, $C_1-C_6$-alkyl, $C_2-C_6$-alkenyl, $C_2-C_6$-alkynyl, $C_1-C_6$-alkoxy, $C_3-C_6$-cycloalkyl, five- or six-membered heteroaryl and aryl; wherein the heteroaryl contains one, two or three heteroatoms selected from the group consisting of N, O and S; wherein
$R^{31}$ is $C_1-C_4$-alkyl, $C_1-C_4$-halogenalkyl, aryl or heteroaryl that is unsubstituted or substituted by 1, 2, 3, 4 or 5 substituents $R^{311}$ independently selected from $C_1-C_4$-alkyl;

and wherein the aliphatic moieties of $R^3$ are unsubstituted or substituted with identical or different groups $R^{3a}$ which independently of one another are selected from the group consisting of:
$R^{3a}$ is halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl or phenoxy, wherein the phenyl and phenoxy group is unsubstituted or carries 1, 2, 3, 4 or 5 substituents $R^{31a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

and wherein the cycloalkyl, heteroaryl and aryl moieties of $R^3$ are unsubstituted or substituted with 1, 2, 3, 4, 5 or up to the maximum number of identical or different groups $R^{3b}$ which independently of one another are selected from the group consisting of:
$R^{3b}$ halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

$R^4$ is selected from the group consisting of H, halogen, OH, CN, $NO_2$, SH, $NH_2$, $NH(C_1$-$C_4$-alkyl), $N(C_1$-$C_4$-alkyl)$_2$, $NH$—$SO_2$—$R^{41}$, $C_1$-$C_6$-alkyl, $C_2$-$C_6$-alkenyl, $C_2$-$C_6$-alkynyl, $C_1$-$C_6$-alkoxy, $C_3$-$C_6$-cycloalkyl, five- or six-membered heteroaryl and aryl; wherein the heteroaryl contains one, two or three heteroatoms selected from the group consisting of N, O and S; wherein
$R^{41}$ is $C_1$-$C_4$-alkyl, $C_1$-$C_4$-halogenalkyl, aryl or heteroaryl that is unsubstituted or substituted by 1, 2, 3, 4 or 5 substituents $R^{411}$ independently selected from $C_1$-$C_4$-alkyl;

and wherein the aliphatic moieties of $R^4$ are unsubstituted or substituted with identical or different groups $R^{4a}$ which independently of one another are selected from the group consisting of:
$R^{4a}$ is halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl or phenoxy, wherein the phenyl and phenoxy group is unsubstituted or carries 1, 2, 3, 4 or 5 substituents $R^{41a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

and wherein the cycloalkyl, heteroaryl and aryl moieties of $R^4$ are unsubstituted or substituted with 1, 2, 3, 4, 5 or up to the maximum number of identical or different groups $R^{4b}$ which independently of one another are selected from the group consisting of:
$R^{4b}$ is halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy or $C_1$-$C_6$-alkylthio;

Y is O or S(O)n wherein
n is 0, 1 or 2;

$Q^1$ is selected from the group consisting of $C_1$-$C_6$-alkyl, $C_2$-$C_6$-alkenyl, $C_2$-$C_6$-alkynyl, $C_3$-$C_6$-cycloalkyl, five- or six-membered heteroaryl and aryl; wherein the heteroaryl contains one, two or three heteroatoms selected from the group consisting of N, O and S;
wherein the aliphatic moieties of $Q^1$ are unsubstituted or substituted with identical or different groups $Q^{1a}$ which independently of one another are selected from the group consisting of:
$Q^{1a}$ is halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl or phenoxy, wherein the phenyl and phenoxy group is unsubstituted or carries 1, 2, 3, 4 or 5 substituents $Q^{11a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the cycloalkyl, heteroaryl and aryl moieties of $Q^1$ are unsubstituted or substituted with 1, 2, 3, 4, 5 or up to the maximum number of identical or different groups $Q^{1b}$ which independently of one another are selected from the group consisting of:
$Q^{1b}$ is halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy or $C_1$-$C_6$-alkylthio;

$Q^2$ is selected from the group consisting of H, $C_1$-$C_6$-alkyl, $C_2$-$C_6$-alkenyl, $C_2$-$C_6$-alkynyl, $C_3$-$C_6$-cycloalkyl, five- or six-membered heteroaryl and aryl; wherein the heteroaryl contains one, two or three heteroatoms selected from the group consisting of N, O and S;
wherein the aliphatic moieties of $Q^2$ are unsubstituted or substituted with identical or different groups $Q^{2a}$ which independently of one another are selected from the group consisting of:
$Q^{2a}$ is halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl or phenoxy, wherein the phenyl and phenoxy group is unsubstituted or substituted with 1, 2, 3, 4 or 5 substituents $Q^{12}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy;

wherein the cycloalkyl, heteroaryl and aryl moieties of $Q^2$ are unsubstituted or substituted with 1, 2, 3, 4, 5 or up to the maximum number of identical or different groups $Q^{2b}$ which independently of one another are selected from the group consisting of:
$Q^{2b}$ is halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy or $C_1$-$C_6$-alkylthio;

$Q^1$ and $Q^2$ together with the carbon atoms to which they are bound form a three- to seven-membered saturated or partially unsaturated ring, wherein the ring may further contain 1, 2, 3 or 4 heteroatoms selected from the group consisting of N—$R^N$, O and S
wherein $R^N$ is selected from the group consisting of H, $C_1$-$C_4$-alkyl and $SO_2R^Q$;
wherein
$R^Q$ is selected from the group consisting of $C_1$-$C_4$-alkyl, $C_1$-$C_4$-halogenalkyl, unsubstituted aryl and heteroaryl that is substituted by 1, 2, 3, 4 or 5 substituents $R^{Q1}$ independently selected from $C_1$-$C_4$-alkyl;

and wherein S may be in the form of its oxide SO or $SO_2$; and wherein in each case one or two $CH_2$ groups of the carbo- or heterocycle may be replaced by a group independently selected from C(=O) and C(=S);

and wherein the ring is unsubstituted or substituted with 1, 2, 3, 4, 5 or up to the maximum number of identical or different groups $Q^{QR}$ which independently of one another are selected from the group consisting of:
halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy or $C_1$-$C_6$-alkylthio;

$Q^3$ is selected from the group consisting of H, $C_1$-$C_6$-alkyl, $C_2$-$C_6$-alkenyl, $C_2$-$C_6$-alkynyl, $C_3$-$C_6$-cycloalkyl, five- or six-membered heteroaryl and aryl; wherein the heteroaryl contains one, two or three heteroatoms selected from the group consisting of N, O and S;

wherein the aliphatic moieties of $Q^3$ are unsubstituted or substituted with identical or different groups $Q^{3a}$ which independently of one another are selected from the group consisting of H, $C_1$-$C_6$-alkyl, $C_2$-$C_6$-alkenyl, $C_2$-$C_6$-alkynyl, $C_3$-$C_6$-cycloalkyl, five- or six-membered heteroaryl and aryl; wherein the heteroaryl contains one, two or three heteroatoms selected from the group consisting of N, O and S;

wherein the aliphatic moieties of $Q^3$ are unsubstituted or substituted with identical or different groups $Q^{3a}$ which independently of one another are selected from:

$Q^{3a}$ is halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy or five- to ten-membered heterocycle, heteroaryl, heterocycloxy, or heteryloxy; wherein the heterocycle or heteroaryl contains one, two or three heteroatoms selected from the group consisting of N, O and S; wherein the phenyl, phenoxy, heterocycle and heteroaryl groups are unsubstituted or substituted with 1, 2, 3, 4 or 5 substituents $Q^{13a}$ selected from the group consisting of halogen, OH, $C_1$-$C_4$-alkyl, $C_1$-$C_4$-halogenalkyl, $C_1$-$C_4$-alkoxy, $C_1$-$C_4$-halogenalkoxy, CR'=NOR"; phenyl, phenoxy and five- to ten-membered heterocycle and heteroaryl; wherein the heterocycle or heteroaryl contains one, two or three heteroatoms selected from the group consisting of N, O and S; and wherein the phenyl, phenoxy, heterocycle and heteroaryl groups are unsubstituted or substituted with 1, 2, 3, 4 or 5 substituents $Q^{113a}$ selected from the group consisting of halogen, OH, $C_1$-$C_4$-alkyl, $C_1$-$C_4$-halogenalkyl, $C_1$-$C_4$-alkoxy, CN, CR'=NOR" and $C_1$-$C_4$-halogenalkoxy;

wherein the cycloalkyl, heteroaryl and aryl moieties of $Q^3$ are unsubstituted or substituted with 1, 2, 3, 4, 5 or up to the maximum number of identical or different groups $Q^{3b}$ which independently of one another are selected from the group consisting of:

$Q^{3b}$ is halogen, OH, CN, $C_1$-$C_6$-alkoxy, $C_3$-$C_6$-cycloalkyl, $C_3$-$C_6$-halogencycloalkyl, $C_1$-$C_4$-halogenalkoxy, $C_1$-$C_6$-alkylthio, phenyl, phenoxy or five- to ten-membered heterocycle, heteroaryl, heterocycloxy, or heteryloxy; wherein the heterocycle or heteroaryl contains one, two or three heteroatoms selected from the group consisting of N, O and S; wherein the phenyl, phenoxy, heterocycle and heteroaryl groups are unsubstituted or substituted with 1, 2, 3, 4 or 5 substituents $Q^{13b}$ selected from the group consisting of halogen, OH, $C_1$-$C_4$-alkyl, $C_1$-$C_4$-halogenalkyl, $C_1$-$C_4$-alkoxy, $C_1$-$C_4$-halogenalkoxy, CR'=NOR"; phenyl, phenoxy and five- to ten-membered heterocycle and heteroaryl; wherein the heterocycle or heteroaryl contains one, two or three heteroatoms selected from the group consisting of N, O and S; and wherein the phenyl, phenoxy, heterocycle and heteroaryl groups are unsubstituted or substituted with 1, 2, 3, 4 or 5 substituents $Q^{113b}$ selected from the group consisting of halogen, OH, $C_1$-$C_4$-alkyl, $C_1$-$C_4$-halogenalkyl, $C_1$-$C_4$-alkoxy, CN, CR'=NOR" and $C_1$-$C_4$-halogenalkoxy; and wherein R' and R" are independently unsubstituted or substituted by R''' which is independently selected from the group consisting of halogen, OH, CN, $NO_2$, SH, $NH_2$, $NH(C_1$-$C_4$-alkyl), $N(C_1$-$C_4$-alkyl)$_2$, $C_1$-$C_6$-alkyl, $C_1$-$C_6$-halogenalkyl, $C_2$-$C_6$-alkenyl, $C_2$-$C_6$-halogenalkenyl, $C_2$-$C_6$-alkynyl, $C_2$-$C_6$-halogenalkynyl, $C_1$-$C_6$-alkoxy, $C_1$-$C_6$-halogenalkoxy, $C_3$-$C_6$-cycloalkyl, $C_3$-$C_6$-halogencycloalkyl and phenyl;

W is O or S;

$X^1$ is selected from the group consisting of H, halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

$X^2$ is selected from the group consisting of H, halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

$X^3$ is selected from the group consisting of H, halogen, OH, CN, $C_1$-$C_4$-alkyl, $C_1$-$C_4$-alkoxy, $C_1$-$C_4$-halogenalkyl, $C_3$-$C_6$-cycloalkyl, $C_3$-$C_6$-halogencycloalkyl, $C_1$-$C_4$-halogenalkoxy and $C_1$-$C_6$-alkylthio;

and N-oxides and agriculturally acceptable salts thereof with the proviso that if $X^1$, $X^2$ and $X^3$ are H $Q^3$ is not H or $CH_3$.

2. The compound of claim 1, wherein $R^3$ is selected from the group consisting of H, halogen, $C_1$-$C_6$-alkyl, $C_2$-$C_6$-alkenyl, $C_2$-$C_6$-alkynyl, $C_1$-$C_6$-alkoxy, and $C_3$-$C_6$-cycloalkyl, wherein the aliphatic moieties of $R^3$ are unsubstituted or substituted with identical or different groups $R^{3a}$ which independently of one another are selected from the group consisting of:

halogen, phenyl or phenoxy, wherein the phenyl and phenoxy group is unsubstituted or carries 1, 2, 3, 4 or 5 substituents $R^{31a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein the cycloalkyl, heteroaryl and aryl moieties of $R^3$ are unsubstituted or substituted with 1, 2, 3, 4, 5 or up to the maximum number of identical or different groups $R^{3b}$ which independently of one another are selected from:

halogen.

3. The compound of claim 1, wherein $R^4$ is selected from the group consisting of H, halogen, $C_1$-$C_6$-alkyl, $C_2$-$C_6$-alkenyl, $C_2$-$C_6$-alkynyl, $C_1$-$C_6$-alkoxy, and $C_3$-$C_6$-cycloalkyl, wherein the aliphatic moieties of $R^3$ are unsubstituted or substituted with identical or different groups $R^{2a}$ which independently of one another are selected from the group consisting of halogen, phenyl and phenoxy, wherein the phenyl and phenoxy group is unsubstituted or carries 1, 2, 3, 4 or 5 substituents $R^{31a}$ selected from the group consisting of halogen, OH, $C_1$-$C_4$-alkyl, $C_1$-$C_4$-halogenalkyl, $C_1$-$C_4$-alkoxy and $C_1$-$C_4$-halogenalkoxy; and wherein the cycloalkyl, heteroaryl and aryl moieties of $R^3$ are unsubstituted or substituted with 1, 2, 3, 4, 5 or up to the maximum number of identical or different groups $R^{3b}$ which independently of one another are selected from:

halogen.

4. The compound of claim 1, wherein Y and W are O.

5. The compound of 1, wherein $Q^1$ is selected from the group consisting of $C_1$-$C_6$-alkyl, $C_1$-$C_6$-haloalkyl, and $C_2$-$C_6$-alkenyl;

$Q^2$ is selected from the group consisting of $C_1$-$C_6$-alkyl, $C_1$-$C_6$-haloalkyl, and $C_2$-$C_6$-alkenyl;

Q$^1$ and Q$^2$ together with the carbon atom to which they are bound form a three- to seven-membered saturated carbo- or heterocycle, wherein the ring may further contain 1, 2, 3 or 4 heteroatoms selected from O and wherein in each case one or two CH$_2$ groups of the carbo- or heterocycle may be replaced by a group independently selected from C(=O) and C(=S); and wherein the ring is unsubstituted or substituted with 1, 2, 3, 4, 5 or up to the maximum number of identical or different groups R$^{QR}$ which independently of one another are selected from the group consisting of:

Q$^{QR}$ halogen, OH, CN, C$_1$-C$_4$-alkyl, C$_1$-C$_4$-alkoxy, C$_1$-C$_4$-halogenalkyl, C$_3$-C$_6$-cycloalkyl, C$_3$-C$_6$-halogencycloalkyl, C$_1$-C$_4$-halogenalkoxy and C$_1$-C$_6$-alkylthio.

6. The compound of claim 1, wherein
Q$^3$ is selected from the group consisting of C$_1$-C$_6$-alkyl, C$_1$-C$_6$-haloalkyl, and C$_2$-C$_6$-alkenyl.

7. The compound of claim 1, wherein
X$^1$ is selected from the group consisting of H, halogen, C$_1$-C$_4$-alkyl, and C$_1$-C$_4$-halogenalkyl.

8. The compound of claim 1, wherein
X$^2$ is selected from the group consisting of H, halogen, C$_1$-C$_4$-alkyl, and C$_1$-C$_4$-halogenalkyl.

9. A composition comprising one compound of formula I, as defined in claim 1, an N-oxide or an agriculturally acceptable salt thereof.

10. The composition of claim 9, further comprising an additional active substance.

11. A method for combating phytopathogenic fungi, comprising treating the fungi or materials, plants, soil or seeds to be protected against fungal attack with an effective amount of at least one compound of formula I, as defined in claim 1.

12. A seed coated with at least one compound of the formula I, as defined in claim 1, and/or an agriculturally acceptable salt thereof in an amount of from 0.1 to 10 kg per 100 kg of seed.

13. A method for combating phytopathogenic fungi, comprising treating the fungi or materials, plants, the soil or seeds to be protected against fungal attack with an effective amount of the composition of claim 9.

14. The method of claim 11, wherein
R$^3$ is selected from the group consisting of H, halogen, C$_1$-C$_6$-alkyl, C$_2$-C$_6$-alkenyl, C$_2$-C$_6$-alkynyl, C$_1$-C$_6$-alkoxy, and C$_3$-C$_6$-cycloalkyl, wherein the aliphatic moieties of R$^3$ are unsubstituted or substituted with identical or different groups R$^{3a}$ which independently of one another are selected from the group consisting of:
halogen, phenyl or phenoxy, wherein the phenyl and phenoxy group is unsubstituted or carries 1, 2, 3, 4 or 5 substituents R$^{31a}$ selected from the group consisting of halogen, OH, C$_1$-C$_4$-alkyl, C$_1$-C$_4$-halogenalkyl, C$_1$-C$_4$-alkoxy and C$_1$-C$_4$-halogenalkoxy; and
wherein the cycloalkyl, heteroaryl and aryl moieties of R$^3$ are unsubstituted or substituted with 1, 2, 3, 4, 5 or up to the maximum number of identical or different groups R$^{3b}$ which independently of one another are selected from:
halogen.

15. The method of claim 11, wherein
R$^4$ is selected from the group consisting of H, halogen, C$_1$-C$_6$-alkyl, C$_2$-C$_6$-alkenyl, C$_2$-C$_6$-alkynyl, C$_1$-C$_6$-alkoxy, and C$_3$-C$_6$-cycloalkyl, wherein the aliphatic moieties of R$^3$ are unsubstituted or substituted with identical or different groups R$^{2a}$ which independently of one another are selected from the group consisting of halogen, phenyl and phenoxy, wherein the phenyl and phenoxy group is unsubstituted or carries 1, 2, 3, 4 or 5 substituents R$^{31a}$ selected from the group consisting of halogen, OH, C$_1$-C$_4$-alkyl, C$_1$-C$_4$-halogenalkyl, C$_1$-C$_4$-alkoxy and C$_1$-C$_4$-halogenalkoxy; and
wherein the cycloalkyl, heteroaryl and aryl moieties of R$^3$ are unsubstituted or substituted with 1, 2, 3, 4, 5 or up to the maximum number of identical or different groups R$^{3b}$ which independently of one another are selected from:
halogen.

16. The method of claim 11, wherein Y and W are O.

17. The method of claim 11, wherein
Q$^1$ is selected from the group consisting of C$_1$-C$_6$-alkyl, C$_1$-C$_6$-haloalkyl, and C$_2$-C$_6$-alkenyl;
Q$^2$ is selected from the group consisting of C$_1$-C$_6$-alkyl, C$_1$-C$_6$-haloalkyl, and C$_2$-C$_6$-alkenyl;
Q$^1$ and Q$^2$ together with the carbon atom to which they are bound form a three- to seven-membered saturated carbo- or heterocycle, wherein the ring may further contain 1, 2, 3 or 4 heteroatoms selected from O and wherein in each case one or two CH$_2$ groups of the carbo- or heterocycle may be replaced by a group independently selected from C(=O) and C(=S); and wherein the ring is unsubstituted or substituted with 1, 2, 3, 4, 5 or up to the maximum number of identical or different groups Q$^{QR}$ which independently of one another are selected from the group consisting of:
halogen, OH, CN, C$_1$-C$_4$-alkyl, C$_1$-C$_4$-alkoxy, C$_1$-C$_4$-halogenalkyl, C$_3$-C$_6$-cycloalkyl, C$_3$-C$_6$-halogencycloalkyl, C$_1$-C$_4$-halogenalkoxy and C$_1$-C$_6$-alkylthio.

18. The method of claim 11, wherein
Q$^3$ is selected from the group consisting of C$_1$-C$_6$-alkyl, C$_1$-C$_6$-haloalkyl, and C$_2$-C$_6$-alkenyl.

19. The method of claim 11, wherein
X$^1$ is selected from the group consisting of H, halogen, C$_1$-C$_4$-alkyl, and C$_1$-C$_4$-halogenalkyl.

20. The method of claim 11, wherein
X$^2$ is selected from the group consisting of H, halogen, C$_1$-C$_4$-alkyl, and C$_1$-C$_4$-halogenalkyl.

* * * * *